US011878060B2

(12) United States Patent
Dominy et al.

(10) Patent No.: US 11,878,060 B2
(45) Date of Patent: Jan. 23, 2024

(54) MRNA-MEDIATED IMMUNIZATION METHODS

(71) Applicant: NOVARTIS AG, Basel (CH)

(72) Inventors: John Dominy, Belmont, MA (US); Robert Dunn, San Diego, CA (US); Scott Glaser, San Diego, CA (US); Mark Keating, Weston, MA (US); Carla Klattenhoff, Arlington, MA (US); Igor Splawski, Winchester, MA (US)

(73) Assignee: Novartis AG, Basel (CH)

( * ) Notice: Subject to any disclaimer, the term of this patent is extended or adjusted under 35 U.S.C. 154(b) by 539 days.

(21) Appl. No.: 16/323,319

(22) PCT Filed: Aug. 4, 2017

(86) PCT No.: PCT/IB2017/054801
§ 371 (c)(1),
(2) Date: Feb. 5, 2019

(87) PCT Pub. No.: WO2018/029586
PCT Pub. Date: Feb. 15, 2018

(65) Prior Publication Data

US 2021/0283262 A1 Sep. 16, 2021

Related U.S. Application Data

(60) Provisional application No. 62/399,544, filed on Sep. 26, 2016, provisional application No. 62/371,834, filed on Aug. 7, 2016.

(51) Int. Cl.
*A61K 47/54* (2017.01)
*C07K 16/28* (2006.01)
*C07K 16/22* (2006.01)

(52) U.S. Cl.
CPC .......... *A61K 47/549* (2017.08); *A61K 47/543* (2017.08); *C07K 16/22* (2013.01); *C07K 16/28* (2013.01); *C07K 16/2803* (2013.01); *C07K 16/2851* (2013.01); *C07K 2317/24* (2013.01)

(58) Field of Classification Search
CPC .... A61K 47/549; A61K 47/543; C07K 16/22; C07K 16/28; C07K 16/2803; C07K 16/2851; C07K 2317/24
See application file for complete search history.

(56) References Cited

U.S. PATENT DOCUMENTS

2014/0303232 A1* 10/2014 Baryza ................ C07D 213/79
558/275

FOREIGN PATENT DOCUMENTS

| | | | | | |
|---|---|---|---|---|---|
| CN | 1966684 | A | | 5/2007 | |
| WO | 94/27435 | A1 | | 12/1994 | |
| WO | WO-9427435 | A1 | * | 12/1994 | ............ A61K 39/00 |
| WO | 2011/076807 | A2 | | 6/2011 | |
| WO | 2012/006369 | A2 | | 1/2012 | |
| WO | 2012/030901 | A1 | | 3/2012 | |
| WO | 2013090648 | A1 | | 6/2013 | |
| WO | 2013/151663 | A1 | | 10/2013 | |
| WO | 2014/136086 | A1 | | 9/2014 | |
| WO | 2015/095340 | A1 | | 6/2015 | |
| WO | 2015/095346 | A1 | | 6/2015 | |
| WO | 2015/095351 | A1 | | 6/2015 | |
| WO | WO-2015135035 | A2 | * | 9/2015 | .............. A61P 35/00 |
| WO | 2016/010840 | A1 | | 1/2016 | |
| WO | 2016/037053 | A1 | | 3/2016 | |

OTHER PUBLICATIONS

Y. Yao, et al. "Identification and Comparative Functional Characterization of a New Human Riboflavin Transporter hRFT3 Expressed in the Brain," J. Nutr. 140: 1220-1226, 2010. (Year: 2010).*

* cited by examiner

*Primary Examiner* — Michael P Cohen
(74) *Attorney, Agent, or Firm* — Linyu L. Mitra

(57) ABSTRACT

The present disclosure is directed to methods of immunization and methods for generating antibodies using compositions comprising cationic lipids and polynucleotide molecules, such as polyribonucleotide molecules, e.g., mRNA, which code for immunogens (e.g., a target protein or a fragment thereof).

13 Claims, 8 Drawing Sheets

Specification includes a Sequence Listing.

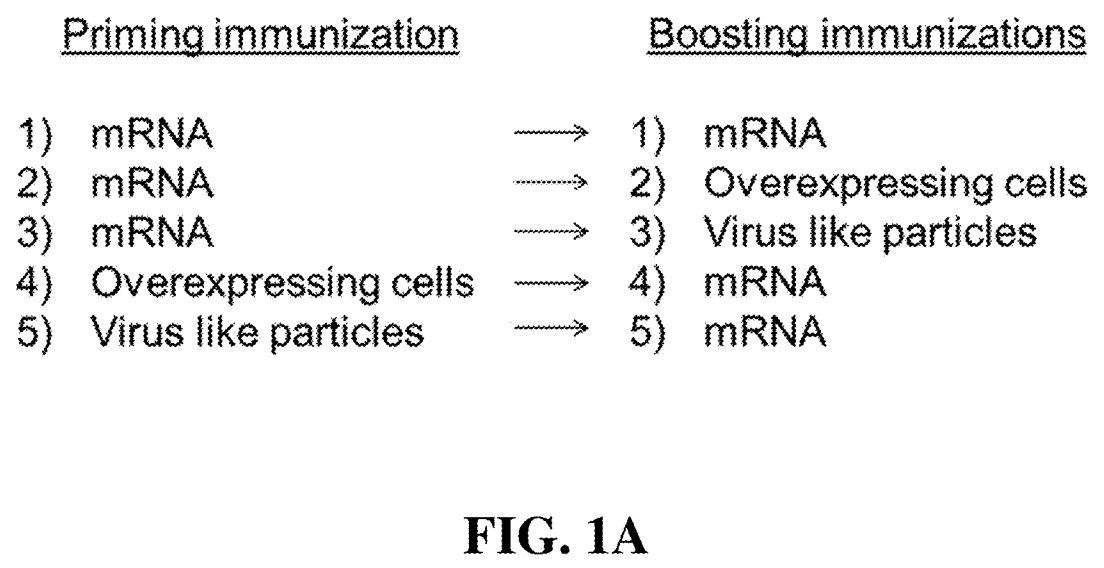

| Priming immunization | | Boosting immunizations |
|---|---|---|
| 1) mRNA | → | 1) mRNA |
| 2) mRNA | → | 2) Overexpressing cells |
| 3) mRNA | → | 3) Virus like particles |
| 4) Overexpressing cells | → | 4) mRNA |
| 5) Virus like particles | → | 5) mRNA |

FIG. 1A

MRNA-MEDIATED IMMUNIZATION METHODS

This application is a 371 U.S. national phase application of international application number PCT/IB2017/054801 filed 4 Aug. 2017, which application claims priority to U.S. provisional patent application Ser. No. 62/371,834 filed 7 Aug. 2016 and 62/399,544 filed 26 Sep. 2016; each of which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Aug. 3, 2017, is named PAT057169-WO-PCT_SL.txt and is 146,992 bytes in size.

FIELD

The present disclosure is in the field of immunology. In particular, this disclosure is directed to methods of immunization using compositions comprising cationic lipids and polynucleotide molecules, such as polyribonucleotide molecules, e.g., mRNA, which code for immunogens (e.g., a target protein or a fragment thereof). This disclosure is also directed to methods for producing antibodies (e.g., monoclonal antibodies) from immunized animals (e.g., non-human animals) for the purposes of making therapeutic antibodies, as well as to the antibodies themselves.

BACKGROUND

Therapeutic monoclonal antibody development in vivo is often limited by the ability to produce a high quality antigen that can be used for immunization. Ideally, the antigen should be a highly purified protein with an intact structural conformation and have enough sequence variation from the animal host strain as to break immunological tolerance and induce a robust humoral response. For many target proteins intended for use as antigens, however, meeting these requirements is not possible due to such issues as inherently poor biophysical properties of the protein that proscribe overexpression/purification, cytotoxicity in host production cells, and poor immunogenicity of the target protein's amino acid sequence.

Traditional methods of animal immunization have employed two general strategies for the generation of antibodies. The first involves repeated injections of full length protein antigen in purified format in the presence of an adjuvant to enhance the immune response. For small to medium-sized soluble proteins, this procedure can be a successful method for the generation of monoclonal antibodies against an antigen in its native conformation. For very large proteins, transmembrane proteins, proteins with unusual post translational modifications, or proteins with poor solubility, this method is of very limited utility, as obtaining pure native, full length protein in the quantities needed for immunization is difficult. The second strategy entails immunization of animals with a DNA construct which encodes the antigen of interest. This strategy allows for the expression of difficult to purify proteins in their native state in situ. It suffers, however, from a relatively low antibody titer generation, which can ultimately correlate with a low yield of monoclonal hybridoma production (Howard et al. *Making and using antibodies: A Practical Handbook,* $2^{nd}$ Edition CRC Press, 2013).

SUMMARY

The present disclosure is directed to a method for eliciting an immune response in an animal (e.g., non-human animal), comprising the steps of: (a) mixing at least one cationic lipid with a polynucleotide, such as polyribonucleotide (e.g., mRNA), coding for an antigenic determinant, thereby forming a cationic lipid-polynucleotide complex; and (b) administering the lipid-polynucleotide complex to the animal. The present disclosure is further directed to a genetic immunization method wherein the polynucleotide is a polyribonucleotide molecule such as an mRNA molecule which codes for an immunogen (e.g., a target protein or a fragment thereof). The present disclosure is further directed to a method for producing antibodies (e.g., polyclonal or monoclonal antibodies) comprising the use of genetic immunization method described herein, and further comprising the step of isolating the antibodies from the immunized animal.

The present disclosure is also directed to a method for producing monoclonal antibodies comprising the steps of: (a) mixing at least one cationic lipid with a polynucleotide, thereby forming a lipid-polynucleotide complex, wherein the polynucleotide comprises an mRNA sequence coding for an immunogen; (b) administering the lipid-polynucleotide complex to at least one mouse; (c) removing antibody-producing cells such as lymphocytes (e.g., B-lymphocytes) or splenocytes from the immunized mice; (d) fusing the B-lymphocytes from the immunized mice with myeloma cells, thereby producing hybridomas; (e) cloning the hybridomas; (f) selecting positive clones which produce anti-immunogen antibody; (g) culturing the anti-immunogen antibody-producing clones; and (h) isolating anti-immunogen antibodies from the cultures. In certain aspects, the methods provided herein for producing antibodies comprise further steps to determine the amino acid sequence of the heavy chain variable region and light chain variable region of such antibodies as well as the corresponding encoding nucleic acid sequences. In particular aspects, the methods provided herein for producing antibodies comprise further steps to generate a chimeric antibody or humanized antibody of the anti-immunogen antibody.

The present disclosure is also directed to a method in which immune tissues are collected from animals immunized with mRNA containing cationic lipid nanoparticles (LNPs) and B cells are selectively isolated. The B cells are directly screened for the production of an antibody with the desired properties and the antibody is directly cloned and expressed recombinantly, bypassing the need for generation of hybridomas.

The mRNA encapsulated LNPs of the present disclosure may also be used for the purpose of generating a recombinant antibody library from the immune tissues of an immunized host animal (e.g., rodents (e.g., mice and rats), rabbits, chickens, cows, camelids, pigs, sheep, goats, sharks, and non-human primates, etc.). This library can then be subsequently screened in a heterologous host system, such as phage or yeast display for the desired properties.

The methods of polynucleotide-based, e.g., mRNA-based, immunization of the present disclosure have addressed many of the issues associated with the above-described difficulties inherent in antigen production and/or antibody generation. Among other things, said methods dispense with the need to directly express and purify the target protein antigen. An animal host's own cellular machinery is used to make the target protein and present it to the immune system. For eukaryotic target proteins, this has the added advantage of permitting the addition of eukaryotic-specific post-translational modifications and protein processing. In particular, unpurified mRNA that is used for immunization has a highly inflammatory character, due in part to the presence of double stranded RNA entities in the preparation. Double-stranded RNA can present pathogen-associated molecular patterns that are recognized by receptors comprising the innate immune system, most notably the toll-like receptors. Without being bound by any particular theory, it is believed that this serves as an adjuvant to boost the humoral response against the target protein and result in high titer antibody production.

Monoclonal antibody development for an immunogen, e.g., a target protein or a fragment thereof, can be expedited in particular through the immunization of animals with mRNAs which encode said target protein or a fragment thereof. This method offers considerable advantages for proteins against which it has historically been technically challenging to develop specific antibodies, such as transmembrane proteins (e.g., multi-pass transmembrane proteins), for example, G-protein coupled receptors (GPCRs), as there is no need to heterologously produce and purify the target protein. Without being bound by any particular theory, it is believed that host defense mechanisms elicited by the adjuvant-like properties of the mRNA result in a fast development of sera titers and make it a superior choice over DNA immunization or other conventional methods of immunization (e.g., recombinant protein immunization).

Non-limiting embodiments of the present disclosure are described in the following aspects:

Aspect 1. A method for producing antibodies (e.g., monoclonal antibodies) against a target protein, comprising the steps of: (a) mixing at least one cationic lipid with a polyribonucleotide such as an messenger RNA (mRNA) coding for the target protein or a fragment thereof, thereby forming a cationic lipid-polyribonucleotide complex (e.g., mRNA-LNP complex); (b) administering the lipid-polyribonucleotide complex to a non-human animal; and (c) obtaining antibodies that specifically bind to the target protein from the animal.

Aspect 2. A method for producing antibodies (e.g., monoclonal antibodies) against a target protein, comprising the steps of: (a) administering a lipid-polyribonucleotide complex (e.g., mRNA-LNP complex) to a non-human animal, wherein the complex comprises at least one cationic lipid with a polyribonucleotide, such as mRNA, coding for the target protein or a fragment thereof, thereby inducing an immune response to the target protein; and (b) obtaining antibodies produced by the animal that specifically bind to the target protein.

Aspect 3. The method of aspect 1 or 2, wherein the target protein is a transmembrane protein.

Aspect 4. The method of aspect 3, wherein the transmembrane protein is selected from the following:

(i) a G protein coupled receptor (GPCR);

(ii) a single pass transmembrane protein receptor;

(iii) a Tumor Necrosis Factor Receptor Superfamily (TNFRSF) member;

(iv) an interleukin (IL) receptor;

(v) an ion channel;

(vi) a solute carrier;

(vii) an immune receptor; and (viii) a multi-pass transmembrane protein.

Aspect 5. The method of aspect 3 or 4, wherein the transmembrane protein is a multi-pass transmembrane protein such as a G protein coupled receptor (GPCR).

Aspect 6. The method of aspect 5, wherein the GPCR is RXFP1, TSHR, APJ, GPR40, GPR64, GPR4, or GPR15.

Aspect 7. The method of aspect 3 or 4, wherein the transmembrane protein is a single pass transmembrane protein receptor such as GP130 or a multi-pass transmembrane protein such as SLC52A2.

Aspect 8. The method of aspect 3 or 4, wherein the transmembrane protein is an interleukin (IL) receptor, such as IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, or IL-36 receptor.

Aspect 9. The method of aspect 3 or 4, wherein the transmembrane protein is a tumor necrosis factor receptor superfamily (TNFRSF) member selected from the group consisting of the following: TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, and TNFRSF27.

Aspect 10. The method of aspect 3 or 4, wherein the transmembrane protein is an ion channel such as TMEM16A.

Aspect 11. The method of aspect 3 or 4, wherein the transmembrane protein is a solute carrier.

Aspect 12. The method of aspect 1 or 2, wherein the target protein is selected from the following: ACKR1, ACKR2, ACKR3, ACKR4, ADCYAP1R1, ADGRA1, ADGRA2, ADGRA3, ADGRB1, ADGRB2, ADGRB3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADORA1, ADORA2A, ADORA2B, ADGRA3, ADRA1A, ADRA1B, ADRA1D, ADRA2A, ADRA2B, ADRA2C, ADRB1, ADRB2, ADRB3, AGTR1, AGTR2, APLNR/APJ, ASGR1, ASGR2, AVPR1A, AVPR1B, AVPR2, BDKRB1, BDKRB2, BRS3, BRS3, C3AR1, C5AR1, C5AR2, CALCR, CALCRL, CASR, CCKAR, CCKBR, CCR1, CCR10, CCR2, CCR3, CCR4, CCR5, CCR6, CCR7, CCR8, CCR9, CCRL2, CELSR1, CELSR2, CELSR3, CHRM1, CHRM2, CHRM3, CHRM4, CHRM5, CMKLR1, CNR1, CNR2, CRHR1, CRHR2, CX3CR1, CXCR1, CXCR2, CXCR3, CXCR4, CXCR5, CXCR6, CYSLTR1, CYSLTR2, DRD1, DRD2, DRD3, DRD4, DRD5, EDNRA, EDNRB, F2R, F2RL1, F2RL2, F2RL3, FFAR1, FFAR2, FFAR3, FFAR4, FPR1, FPR2, FPR2, FPR3, FSHR, FZD1, FZD10, FZD2, FZD3, FZD4, FZD5, FZD6, FZD7, FZD8, FZD9, GABBR1, GABBR2, GALR1, GALR2, GALR3, GCGR, GHRHR, GHSR, GIPR, GLP1R, GLP2R, GNRHR, GNRHR2, GPBAR1, GPER1, GPR1, GPR4, GPR12, GPR15, GPR17, GPR18, GPR19, GPR20, GPR21, GPR22, GPR25, GPR26, GPR27, GPR3, GPR31, GPR32, GPR33, GPR34, GPR35, GPR37, GPR37L1, GPR39, GPR40, GPR42, GPR42, GPR45, GPR50, GPR52, GPR55, GPR6, GPR61, GPR62, GPR63, GPR65, GPR68, GPR75, GPR78, GPR79, GPR82, GPR83, GPR84, GPR85, GPR87, GPR88, GPR101, GPR107, GPR132, GPR135, GPR137, GPR139, GPR141, GPR142, GPR143, GPR146, GPR148, GPR149, GPR15, GPR150, GPR151, GPR152, GPR153, GPR156, GPR157, GPR158, GPR160, GPR161, GPR162, GPR171, GPR173, GPR174, GPR176, GPR179, GPR182, GPR183, GPRC5A, GPRC5B, GPRC5C, GPRC5D, GPRC6A, GRM1, GRM2, GRM3, GRM4, GRM5, GRM6, GRM7, GRM8, GRPR, HCAR1, HCAR2, HCAR3, HCRTR1, HCRTR2, HRH1, HRH2, HRH3, HRH4, HTR1A, HTR1B, HTR1D, HTR1E, HTR1F, HTR2A, HTR2B, HTR2C, HTR4, HTR5A, HTR5BP, HTR6, HTR7, KISS1R, LGR3, LGR4, LGR5, LGR6, LHCGR, LPAR1, LPAR2, LPAR3, LPAR4, LPAR5, LPAR6, LTB4R, LTB4R2, MAS1, MAS1L, MC1R, MC2R, MC3R, MC4R, MC5R, MCHR1, MCHR2, MLNR, MRGPRD, MRGPRE, MRGPRF, MRGPRG, MRGPRX1, MRGPRX2, MRGPRX3, MRGPRX4, MTNR1A, MTNR1B, NMBR, NMUR1, NMUR2, NPBWR1, NPBWR2, NPFFR1, NPFFR2, NPSR1, NPY1R, NPY2R, NPY4R, NPY5R, NPY6R, NTSR1, NTSR2, OPN3, OPN4, OPN5, OPRD1, OPRK1, OPRL1, OPRM1, OR51E1, OXER1, OXGR1, OXTR, P2RY1, P2RY10, P2RY11, P2RY12, P2RY13, P2RY14, P2RY2, P2RY4, P2RY6, P2RY8, PRLHR, PROKR1, PROKR2, PTAFR, PTGDR, PTGDR2, PTGER1, PTGER2, PTGER3, PTGER4, PTGFR, PTGIR, PTH1R, PTH2R, QRFPR, RXFP1, RXFP2, RXFP3, RXFP4, S1PR1, S1PR2, S1PR3, S1PR4, S1PR5, SCTR, SMO, SSTR1, SSTR2, SSTR3, SSTR4, SSTR5, SUCNR1, TAAR1, TAAR2, TAAR3, TAAR4P, TAAR5, TAAR6, TAAR8, TAAR9, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TBXA2R, TPRA1, TRHR, TSHR, UTS2R, VIPR1, VIPR2, XCR1, TCR-α, TCR-β, CD3, ζ-chain accessory, CD4, CD8, SIGIRR (Single Ig And TIR Domain Containing), mannose receptor (MR), asialoglycoprotein receptor family (e.g., asialoglycoprotein receptor macrophage galactose-type lectin (MGL)), DC-SIGN (CLEC4L), langerin (CLEC4K), myeloid DAP12-associating lectin (MDL)-1 (CLEC5A), dectin 1/CLEC7A, DNGR1/CLEC9A, Myeloid C-type lectin-like receptor (MICL) (CLEC12A), CLEC2 (also called CLEC1B), CLEC12B, DCIR/CLEC4A, Dectin 2/CLEC6A, Blood DC antigen 2 (BDCA2) (CLEC4C), macrophage-inducible C-type lectin (CLEC4E), TLR1, TLR2, TLR3, TLR4, TLR5, TLR6, TLR7, TLR8, TLR9, TLR10, TLR11, TLR12, TLR13, FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαR1 (CD89), Fcα/μR, FcRn, CD27, CD40, OX40, GITR, CD137, PD-1, CTLA-4, PD-L1, TIGIT, T-cell immunoglobulin domain and mucin domain 3 (TIM3), V-domain Ig suppressor of T cell activation (VISTA), CD28, CD122, ICOS, A2AR, B7-H3, B7-H4, B and T lymphocyte attenuator (BILA), Indoleamine 2,3-dioxygenase (IDO), killer-cell immunoglobulin-like receptor (KIR), lymphocyte activation gene-3 (LAGS), FAM159B, HLA-A, HLA-B, HLA-C, HLA-DPA1, HLA-DPB1, HLA-DQA1, HLA-DQB1, HLA-DRA, HLA-DRB1, gp130, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, IL-36 receptor, FGFR1, FGFR2, FGFR3, FGFR4, TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF100, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, TNFRSF27, SCN1A, SCN1B, SCN2A, SCN2B, SCN3A, SCN3B, SCN4A, SCN5A, SCN7A, SCN8A, SCN9A, SCN10A, SCN11A, CACNA1A, CACNA1B, CACNA1C, CACNA1D, CACNA1E, CACNA1F, CACNA1G, CACNA1H, CACNA1I, CACNA1S, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, MCOLN1, MCOLN2, MCOLN3, PKD1, PKD2, PKD2L1, PKD2L2, TRPV1, TRPV2, TRPV3, TRPV4, TRPV5, TRPV6, CATSPER1, CATSPER2, CATSPER3, CATSPER4, TPCN1, TPCN2, CNGA1, CNGA2, CNGA3, CNGA4, CNGB1, CNGB3, HCN1, HCN2, HCN3, HCN4, KCNMA1, KCNN1, KCNN2, KCNN3, KCNN4, KCNT1, KCNT2, KCNU1, KCNA1, KCNA2, KCNA3, KCNA4, KCNA5, KCNA6, KCNA7, KCNA10, KCNB1, KCNB2, KCNC1, KCNC2, KCNC3, KCNC4, KCND1, KCND2, KCND3, KCNF1, KCNG1, KCNG2, KCNG3, KCNG4, KCNH1, KCNH2, KCNH3, KCNH4, KCNH5, KCNH6, KCNH7, KCNH8, KCNQ1, KCNA2, KCNA3, KCNA4, KCNA5, KCNS1, KCNS2, KCNS3, KCNV1, KCNV2, KCNJ1, KCNJ2, KCNJ3, KCNJ4, KCNJ5, KCNJ6, KCNJ8, KCNJ9, KCNJ10, KCNJ11, KCNJ12, KCNJ13, KCNJ14, KCNJ15, KCNJ16, KCNJ18, KCNK1, KCNK2, KCNK3, KCNK4, KCNK5, KCNK6, KCNK7, KCNK9, KCNK10, KCNK12, KCNK13, KCNK15, KCNK16, KCNK17, KCNK18, HVCN1, HTR3A, HTR3B, HTR3C, HTR3D, HTR3E, CHRNA1, CHRNA2, CHRNA3, CHRNA4, CHRNA5, CHRNA6, CHRNA7, CHRNA9, CHRNA10, CHRNB1, CHRNB2, CHRNB3, CHRNB4, CHRND, CHRNE, CHRNG, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GRIA1, GRIA2, GRIA3, GRIA4, GRID1, GRID2, GRIK1, GRIK2, GRIK3, GRIK4, GRIK5, GRIN1, GRIN2A, GRIN2B, GRIN2C, GRIN2D, GRIN3A, GRIN3B, GLRA1, GLRA2, GLRA3, GLRA4, P2RX1, P2RX2, P2RX3, P2RX4, P2RX5, P2RX6, P2RX7, ZACN, ASIC1, ASIC2, ASIC3, ASIC4, AQP1, AQP2, AQP3, AQP4, AQP5, AQP6, AQP7, AQP8, AQP9, AQP10, AQP11, AQP12A, AQP12B, MIP, CLCN1, CLCN2, CLCN3, CLCN4, CLCN5, CLCN6, CLCN7, CLCNKA, CLCNKB, Cystic fibrosis transmembrane conductance regulator (CFTR), ANO1, ANO2, ANO3, ANO4, ANO5, ANO6, ANO7, ANO8, ANO9, ANO10, BEST1, BEST2, BEST3, BEST4, CLIC1, CLIC2, CLIC3, CLIC4, CLIC5, CLIC6, GJA1, GJA3, GJA4, GJA5, GJA6P, GJA8, GJA9, GJA10, GJB1, GJB2, GJB3, GJB4, GJB5, GJB6, GJB7, GJC1, GJC2, GJC3, GJD2, GJD3, GJD4, GJE1, ITPR1, ITPR2, ITPR3, PANX1, PANX2, PANX3, RYR1, RYR2, RYR3, NALCN, SCNN1A, SCNN1B, SCNN1D, SCNN1G, TEM16A, ADAMTS7, ANGPTL3, ANGPTL4, ANGPTL8, LPL, GDF15, galectin-1, galectin-2, galectin-3, galectin-4, galectin-7, galectin-8, galectin-9, galectin-10, galectin-12, galectin-13, matrix gla protein (MGP), PRNP, DGAT1, GPAT3, DMC1, BLM, BRCA2, members of the human endogenous retrovirus type K (HERV-K) family, ectonucleoside triphosphate diphosphohydrolase 1 (ENTPD1), ectonucleoside triphosphate diphosphohydrolase 2 (ENTPD2), SLC1A1, SLC1A2, SLC1A3, SLC1A4, SLC1A5, SLC1A6, SLC1A7, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, SLC2A14, SLC3A1, SLC3A2, SLC4A1, SLC4A2, SLC4A3, SLC4A4, SLC4A5, SLC4A6, SLC4A7, SLC4A8, SLC4A9, SLC4A10, SLC4A11, SLC5A1, SLC5A2, SLC5A3, SLC5A4, SLC5A5, SLC5A6, SLC5A7, SLC5A8, SLC5A9, SLC5A10, SLC5A11, SLC5A12, SLC6A1, SLC6A2, SLC6A3, SLC6A4, SLC6A5, SLC6A6, SLC6A7, SLC6A8, SLC6A9, SLC6A10, SLC6A11, SLC6A12, SLC6A13, SLC6A14, SLC6A15, SLC6A16, SLC6A17, SLC6A18, SLC6A19, SLC6A20, SLC7A5, SLC7A6, SLC7A7, SLC7A8, SLC7A9, SLC7A10, SLC7A11, SLC7A13, SLC7A14, SLC8A1, SLC8A2, SLC8A3, SLC9A1, SLC9A2, SLC9A3, SLC9A4, SLC9A5, SLC9A6, SLC9A7, SLC9A8, SLC9A9, SLC9A10, SLC9A11, SLC9B1, SLC9B2, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14, SLC17A1, SLC17A2, SLC17A3, SLC17A4, SLC17A5, SLC17A6, SLC17A7, SLC17A8, SLC17A9, SLC18A1, SLC18A2, SLC18A3, SLC19A1, SLC19A2, SLC19A3, SLC20A1, SLC20A2, SLCO1A2, SLCO1B1, SLCO1B3, SLCO1C1, SLCO2A1, SLCO2B1, SLCO3A1, SLCO4A1, SLCO4C1, SLCO5A1, SLCO6A1, SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A18AS, SLC22A19, SLC22A20, SLC22A23, SLC22A24, SLC22A25, SLC22A31, SLC23A1, SLC23A2, SLC23A3, SLC23A4, SLC24A1, SLC24A2, SLC24A3, SLC24A4, SLC24A5, SLC24A6, SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, SLC25A46, SLC26A1, SLC26A2, SLC26A3, SLC26A4, SLC26A5, SLC26A6, SLC26A7, SLC26A8, SLC26A9, SLC26A10, SLC26A11, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC30A1, SLC30A2, SLC30A3, SLC30A4, SLC30A5, SLC30A6, SLC30A7, SLC30A8, SLC30A9, SLC30A10, SLC31A1, SLC31A2, SLC32A1, SLC33A1, SLC34A1, SLC34A2, SLC34A3, SLC35A1, SLC35A2, SLC35A3, SLC35A4, SLC35A5, SLC3561, SLC35B2, SLC35B3, SLC35B4, SLC35C1, SLC35C2, SLC35D1, SLC35D2, SLC35D3, SLC35E1, SLC35E2, SLC35E3, SLC35E4, SLC35F1, SLC35F2, SLC35F3, SLC35F4, SLC35F5, SLC35G1, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A2, SLC38A3, SLC38A4, SLC38A5, SLC38A6, SLC38A7, SLC38A8, SLC38A9, SLC38A10, SLC38A11, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14, SLC40A1, SLC41A1, SLC41A2, SLC41A3, RhAG, RhBG, RhCG, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, HCP-1, MFSD5, MFSD10, SLC50A1, OSTα, OSTβ, SLC52A1, SLC52A2, and SLC52A3.

Aspect 13. The method of aspect 1 or 2 wherein the target antigen is difficult to express or difficult to raise antibodies against.

Aspect 14. The method of aspect 13, wherein expression of the target protein leads to cytotoxicity or increases in cytotoxicity in host production cells.

Aspect 15. The method of aspect 13, wherein the target protein, when expressed recombinantly and/or purified, exhibits poor yield, stability, solubility, and/or functional activity.

Aspect 16. The method of any one of the preceding aspects wherein said polyribonucleotide of the complex comprises one or more of the following: a consensus Kozak sequence; a 7-methylguanosine cap on the 5' end of the mRNA; a polyadenosine (polyA) tail found at the 3' terminus of the mRNA transcript; and 5'- and 3'-untranslated regions (UTRs).

Aspect 17. The method of any one of the preceding aspects, wherein said administering is parenteral.

Aspect 18. The method of any one of the preceding aspects, wherein said administering is intravenous.

Aspect 19. The method of any one of the preceding aspects, wherein said administering is intramuscular.

Aspect 20. The method of any one of the preceding aspects, wherein said administering is subcutaneous.

Aspect 21. The method of any one of aspects 1-16, wherein said administering is intranasal.

Aspect 22. The method of any one of the preceding aspects, wherein said target protein is RXFP1 or a fragment thereof.

Aspect 23. The method of any one of the preceding aspects, wherein said complex comprises a polyribonucleotide comprising the nucleotide sequence of SEQ ID NO:4, or any one of SEQ ID NOs: 2, 4, and 37.

Aspect 24. The method of any one of the preceding aspects, wherein said target protein is SLC52A2 or a fragment thereof.

Aspect 25. The method of any one of the preceding aspects, wherein said complex comprises a polyribonucleotide comprising the nucleotide sequence of SEQ ID NO:7, or any one of SEQ ID NOs: 5, 7, and 40.

Aspect 26. The method of any one of the preceding aspects, wherein said target protein is ANGPTL8 or a fragment thereof.

Aspect 27. The method of any one of the preceding aspects, wherein said complex comprises a polyribonucleotide comprising the nucleotide sequence of SEQ ID NO:10, or any one of SEQ ID NOs: 8, 10, and 43.

Aspect 28. The method of any one of the preceding aspects, wherein said target protein is TSHR or a fragment thereof.

Aspect 29. The method of any one of the preceding aspects, wherein said complex comprises a polyribonucleotide comprising the nucleotide sequence of SEQ ID NO:16, or any one of SEQ ID NOs: 14, 16, and 46.

Aspect 30. The method of any one of the preceding aspects, wherein said target protein is APJ or a fragment thereof.

Aspect 31. The method of any one of the preceding aspects, wherein said complex comprises a polyribonucleotide comprising the nucleotide sequence of SEQ ID NO:19, or any one of SEQ ID NOs: 17, 19, and 49.

Aspect 32. The method of any one of the preceding aspects, wherein said target protein is gp130 or a fragment thereof.

Aspect 33. The method of any one of the preceding aspects, wherein said complex comprises a polyribonucleotide comprising the nucleotide sequence of SEQ ID NO:22, or any one of SEQ ID NOs: 20, 22, and 52.

Aspect 34, The method of any one of the preceding aspects, wherein said target protein is Galectin 3 or a fragment thereof.

Aspect 35. The method of any one of the preceding aspects, wherein said complex comprises a polyribonucleotide comprising the nucleotide sequence of SEQ ID NO:55, or any one of SEQ ID NOs: 26, 55, and 56.

Aspect 36. The method of any one of aspects 1-35, wherein said complex has a diameter of approximately 30-150 nm.

Aspect 37. The method of any one of aspects 1-35, wherein the complex comprises helper lipids.

Aspect 38. The method of any one of aspects 1-35, wherein the complex comprises any combination of (i) cationic lipid, (ii) a helper lipid, for example cholesterol, (iii) a neutral lipid, for example DSPC, and (iv) a stealth lipid, for example S010, S024, S027, S031, or S033.

Aspect 39. The method of any one of aspects 1-38, wherein the animal is administered with 5 μg, 10 μg, 12.5 μg, 20 μg, 25 μg, 30 μg, 40 μg, 50 μg, 60 μg, 70 μg, 80 μg, 90 μg, 100 μg, 110 μg, 120 μg, 130 μg, 140 μg or 150 μg polyribonucleotide.

Aspect 40. The method of any one of aspects 1-39, wherein the cationic lipid is selected from the group consisting of: N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy) propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N, N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy) propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP).

Aspect 41. The method of aspect 40, wherein the cationic lipid is DOTAP or DLTAP.

Aspect 42. The method of any one of aspects 1-41 further comprising the step of generating hybridomas producing antibodies that specifically bind the target antigen.

Aspect 43. The method of any one of aspects 1-42 further comprising the step of purifying antibodies that specifically bind to the target protein.

Aspect 44. The method of any one of aspects 1-43, further comprising the step of generating chimeric or humanized antibodies derived from the purified antibodies that specifically bind the target protein.

Aspect 45. The method of any one of aspects 1-44, wherein said method produces higher antibody titer in sera from a first bleed or a second bleed relative to a method comprising immunization with cDNA, protein or peptide, a viral particle, or whole cell.

Aspect 46. The method of any one of aspects 1-44, wherein said method produces a higher number of hybridomas producing target protein-specific antibodies than a method comprising immunization with cDNA, protein or peptide, a viral particle, or whole cell.

Aspect 47. The method of any one of aspects 1-46, wherein the target protein is a human target protein, and the non-human animal is a mouse, rat, rabbit, sheep, cat, dog, camelid, shark, monkey, pig, or horse.

Aspect 48. A hybridoma producing an antibody that specifically binds to the target protein, wherein the hybridoma is obtainable by the method of any one of aspects 1-47.

Aspect 49. A mixture of polyclonal antibodies, which specifically bind to the target protein, wherein the mixture is obtainable from the method of any one of aspects 1-47.

Aspect 50. An isolated monoclonal antibody which specifically binds to the target protein, wherein the monoclonal antibody is obtainable by the method of any one of aspects 1-47.

Aspect 51. A method for eliciting an immune response to a target protein in a non-human animal, comprising the steps of: administering a lipid-polynucleotide complex to the animal, wherein the lipid-polynucleotide complex comprises a cationic lipid and an mRNA coding for a target protein, wherein the target protein is of a species different than the animal.

Aspect 52. The method of aspect 51 wherein said complex comprises one or more of the following: a consensus Kozak sequence; a 7-methylguanosine cap on the 5' end of the mRNA; a polyadenosine (polyA) tail found at the 3' terminus of the mRNA transcript; and 5'- and 3'-untranslated regions (UTRs).

Aspect 53. The method of aspect 51, wherein said administering is parenteral.

Aspect 54. The method of aspect 51, wherein said administering is intravenous.

Aspect 55. The method of aspect 51, wherein said administering is intramuscular.

Aspect 56. The method of aspect 51, wherein said administering is subcutaneous.

Aspect 57. The method of aspect 51, wherein said administering is intranasal.

Aspect 58. The method of any one of aspects 51-57, wherein said target protein is RXFP1.

Aspect 59. The method of any one of aspects 51-57, wherein said complex comprises a polyribonucleotide comprising the nucleotide sequence of SEQ ID NO:4, or any one of SEQ ID NOs: 2, 4, and 37.

Aspect 60. The method of any one of aspects 51-57, wherein said target protein is SLC52A2.

Aspect 61. The method of any one of aspects 51-57, wherein said complex comprises a polyribonucleotide comprising the nucleotide sequence of SEQ ID NO:7, or any one of SEQ ID NOs: 5, 7, and 40.

Aspect 62. The method of any one of aspects 51-57, wherein said target protein is ANGPTL8.

Aspect 63. The method of any one of aspects 51-57, wherein said complex comprises a polyribonucleotide comprising the nucleotide sequence of SEQ ID NO:10, or any one of SEQ ID NOs: 8, 10, and 43.

Aspect 64. The method of any one of aspects 51-57, wherein said target protein is TSHR.

Aspect 65. The method of any one of aspects 51-57, wherein said complex comprises a polyribonucleotide comprising the nucleotide sequence of SEQ ID NO:16, or any one of SEQ ID NOs: 14, 16, and 46.

Aspect 66. The method of any one of aspects 51-57, wherein said target protein is APJ.

Aspect 67. The method of any one of aspects 51-57, wherein said complex comprises a polyribonucleotide comprising the nucleotide sequence of SEQ ID NO:19, or any one of SEQ ID NOs: 17, 19, and 49.

Aspect 68. The method of any one of aspects 51-57, wherein said target protein is GP130.

Aspect 69. The method of any one of aspects 51-57, wherein said complex comprises a polyribonucleotide comprising the nucleotide sequence of SEQ ID NO: 22, or any one of SEQ ID NOs: 20, 22, and 52.

Aspect 70. The method of aspect 51, wherein said target protein is Galectin 3.

Aspect 71. The method of aspect 51, wherein said complex comprises SEQ ID NO:55, or any one of SEQ ID NOs: 26, 55, and 56.

Aspect 72. The method of any one of aspects 51-71, which further comprises the step of obtaining antibodies, which specifically binds the target protein, or an antibody-producing cell, from the animal.

Aspect 73. The method of any one of aspects 51-72, wherein the target protein is a human target protein, and the non-human animal is a mouse, rat, rabbit, sheep, cat, dog, camelid, shark, monkey, pig, or horse.

Aspect 74. The method of any one of aspects 51-73, wherein the complex comprises any combination of (i) cationic lipid, (ii) a helper lipid, for example cholesterol, (iii) a neutral lipid, for example DSPC, and (iv) a stealth lipid, for example S010, S024, S027, S031, or S033.

Aspect 75. The method of any one of aspects 51-74, wherein the animal is administered with 5 μg, 10 μg, 12.5 μg, 20 μg, 25 μg, 30 μg, 40 μg, 50 μg, 60 μg, 70 μg, 80 μg, 90 μg, 100 μg, 110 μg, 120 μg, 130 μg, 140 μg or 150 μg polyribonucleotide (e.g., mRNA).

Aspect 76. The method of any one of aspects 51-75, wherein the cationic lipid is selected from the group consisting of: N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy) propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N, N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy) propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP).

Aspect 77. The method of aspect 76, wherein the cationic lipid is DOTAP or DLTAP.

Aspect 78. The method of any one of aspects 51-77, wherein the target protein is selected from the following:

ACKR1, ACKR2, ACKR3, ACKR4, ADCYAP1R1, ADGRA1, ADGRA2, ADGRA3, ADGRB1, ADGRB2, ADGRB3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADORA1, ADORA2A, ADORA2B, ADORA3, ADRA1A, ADRA1B, ADRA1D, ADRA2A, ADRA2B, ADRA2C, ADRB1, ADRB2, ADRB3, AGTR1, AGTR2, APLNR/APJ, ASGR1, ASGR2, AVPR1A, AVPR1B, AVPR2, BDKRB1, BDKRB2, BRS3, BRS3, C3AR1, C5AR1, C5AR2, CALCR, CALCRL, CASR, CCKAR, CCKBR, CCR1, CCR10, CCR2, CCR3, CCR4, CCR5, CCR6, CCR7, CCR8, CCR9, CCRL2, CELSR1, CELSR2, CELSR3, CHRM1, CHRM2, CHRM3, CHRM4, CHRM5, CMKLR1, CNR1, CNR2, CRHR1, CRHR2, CX3CR1, CXCR1, CXCR2, CXCR3, CXCR4, CXCR5, CXCR6, CYSLTR1, CYSLTR2, DRD1, DRD2, DRD3, DRD4, DRD5, EDNRA, EDNRB, F2R, F2RL1, F2RL2, F2RL3, FFAR1, FFAR2, FFAR3, FFAR4, FPR1, FPR2, FPR2, FPR3, FSHR, FZD1, FZD10, FZD2, FZD3, FZD4, FZD5, FZD6, FZD7, FZD8, FZD9, GABBR1, GABBR2, GALR1, GALR2, GALR3, GCGR, GHRHR, GHSR, GIPR, GLP1R, GLP2R, GNRHR, GNRHR2, GPBAR1, GPER1, GPR1, GPR4, GPR12, GPR15, GPR17, GPR18, GPR19, GPR20, GPR21, GPR22, GPR25, GPR26, GPR27, GPR3, GPR31, GPR32, GPR33, GPR34, GPR35, GPR37, GPR37L1, GPR39, GPR40, GPR42, GPR42, GPR45, GPR50, GPR52, GPR55, GPR6, GPR61, GPR62, GPR63, GPR65, GPR68, GPR75, GPR78, GPR79, GPR82, GPR83, GPR84, GPR85, GPR87, GPR88, GPR101, GPR107, GPR132, GPR135, GPR137, GPR139, GPR141, GPR142, GPR143, GPR146, GPR148, GPR149, GPR15, GPR150, GPR151, GPR152, GPR153, GPR156, GPR157, GPR158, GPR160, GPR161, GPR162, GPR171, GPR173, GPR174, GPR176, GPR179, GPR182, GPR183, GPRC5A, GPRC5B, GPRC5C, GPRC5D, GPRC6A, GRM1, GRM2, GRM3, GRM4, GRM5, GRM6, GRM7, GRM8, GRPR, HCAR1, HCAR2, HCAR3, HCRTR1, HCRTR2, HRH1, HRH2, HRH3, HRH4, HTR1A, HTR1B, HTR1D, HTR1E, HTR1F, HTR2A, HTR2B, HTR2C, HTR4, HTR5A, HTR5BP, HTR6, HTR7, KISS1R, LGR3, LGR4, LGR5, LGR6, LHCGR, LPAR1, LPAR2, LPAR3, LPAR4, LPAR5, LPAR6, LTB4R, LTB4R2, MAS1, MAS1L, MC1R, MC2R, MC3R, MC4R, MC5R, MCHR1, MCHR2, MLNR, MRGPRD, MRGPRE, MRGPRF, MRGPRG, MRGPRX1, MRGPRX2, MRGPRX3, MRGPRX4, MTNR1A, MTNR1B, NMBR, NMUR1, NMUR2, NPBWR1, NPBWR2, NPFFR1, NPFFR2, NPSR1, NPY1R, NPY2R, NPY4R, NPY5R, NPY6R, NTSR1, NTSR2, OPN3, OPN4, OPN5, OPRD1, OPRK1, OPRL1, OPRM1, OR51E1, OXER1, OXGR1, OXTR, P2RY1, P2RY10, P2RY11, P2RY12, P2RY13, P2RY14, P2RY2, P2RY4, P2RY6, P2RY8, PRLHR, PROKR1, PROKR2, PTAFR, PTGDR, PTGDR2, PTGER1, PTGER2, PTGER3, PTGER4, PTGFR, PTGIR, PTH1R, PTH2R, QRFPR, RXFP1, RXFP2, RXFP3, RXFP4, S1PR1, S1PR2, S1PR3, S1PR4, S1PR5, SCTR, SMO, SSTR1, SSTR2, SSTR3, SSTR4, SSTR5, SUCNR1, TAAR1, TAAR2,

TAAR3, TAAR4P, TAAR5, TAAR6, TAAR8, TAAR9, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TBXA2R, TPRA1, TRHR, TSHR, UTS2R, VIPR1, VIPR2, XCR1, TCR-α, TCR-β, CD3, ζ-chain accessory, CD4, CD8, SIGIRR (Single Ig And TIR Domain Containing), mannose receptor (MR), asialoglycoprotein receptor family (e.g., asialoglycoprotein receptor macrophage galactose-type lectin (MGL)), DC-SIGN (CLEC4L), langerin (CLEC4K), myeloid DAP12-associating lectin (MDL)-1 (CLEC5A), dectin 1/CLEC7A, DNGR1/CLEC9A, Myeloid C-type lectin-like receptor (MICL) (CLEC12A), CLEC2 (also called CLEC1B), CLEC12B, DCIR/CLEC4A, Dectin 2/CLEC6A, Blood DC antigen 2 (BDCA2) (CLEC4C), macrophage-inducible C-type lectin (CLEC4E), TLR1, TLR2, TLR3, TLR4, TLR5, TLR6, TLR7, TLR8, TLR9, TLR10, TLR11, TLR12, TLR13, FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαR1 (CD89), Fcα/μR, FcRn, CD27, CD40, OX40, GITR, CD137, PD-1, CTLA-4, PD-L1, TIGIT, T-cell immunoglobulin domain and mucin domain 3 (TIM3), V-domain Ig suppressor of T cell activation (VISTA), CD28, CD122, ICOS, A2AR, B7-H3, B7-H4, B and T lymphocyte attenuator (BILA), Indoleamine 2,3-dioxygenase (IDO), killer-cell immunoglobulin-like receptor (KIR), lymphocyte activation gene-3 (LAGS), FAM159B, HLA-A, HLA-B, HLA-C, HLA-DPA1, HLA-DPB1, HLA-DQA1, HLA-DQB1, HLA-DRA, HLA-DRB1, gp130, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, IL-36 receptor, FGFR1, FGFR2, FGFR3, FGFR4, TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, TNFRSF27, SCN1A, SCN1B, SCN2A, SCN2B, SCN3A, SCN3B, SCN4A, SCN5A, SCN7A, SCN8A, SCN9A, SCN10A, SCN11A, CACNA1A, CACNA1B, CACNA1C, CACNA1D, CACNA1E, CACNA1F, CACNA1G, CACNA1H, CACNA1I, CACNA1S, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, MCOLN1, MCOLN2, MCOLN3, PKD1, PKD2, PKD2L1, PKD2L2, TRPV1, TRPV2, TRPV3, TRPV4, TRPV5, TRPV6, CATSPER1, CATSPER2, CATSPER3, CATSPER4, TPCN1, TPCN2, CNGA1, CNGA2, CNGA3, CNGA4, CNGB1, CNGB3, HCN1, HCN2, HCN3, HCN4, KCNMA1, KCNN1, KCNN2, KCNN3, KCNN4, KCNT1, KCNT2, KCNU1, KCNA1, KCNA2, KCNA3, KCNA4, KCNA5, KCNA6, KCNA7, KCNA10, KCNB1, KCNB2, KCNC1, KCNC2, KCNC3, KCNC4, KCND1, KCND2, KCND3, KCNF1, KCNG1, KCNG2, KCNG3, KCNG4, KCNH1, KCNH2, KCNH3, KCNH4, KCNH5, KCNH6, KCNH7, KCNH8, KCNQ1, KCNA2, KCNA3, KCNA4, KCNQ5, KCNS1, KCNS2, KCNS3, KCNV1, KCNV2, KCNJ1, KCNJ2, KCNJ3, KCNJ4, KCNJ5, KCNJ6, KCNJ8, KCNJ9, KCNJ10, KCNJ11, KCNJ12, KCNJ13, KCNJ14, KCNJ15, KCNJ16, KCNJ18, KCNK1, KCNK2, KCNK3, KCNK4, KCNK5, KCNK6, KCNK7, KCNK9, KCNK10, KCNK12, KCNK13, KCNK15, KCNK16, KCNK17, KCNK18, HVCN1, HTR3A, HTR3B, HTR3C, HTR3D, HTR3E, CHRNA1, CHRNA2, CHRNA3, CHRNA4, CHRNA5, CHRNA6, CHRNA7, CHRNA9, CHRNA10, CHRNB1, CHRNB2, CHRNB3, CHRNB4, CHRND, CHRNE, CHRNG, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GRIA1, GRIA2, GRIA3, GRIA4, GRID1, GRID2, GRIK1, GRIK2, GRIK3, GRIK4, GRIK5, GRIN1, GRIN2A, GRIN2B, GRIN2C, GRIN2D, GRIN3A, GRIN3B, GLRA1, GLRA2, GLRA3, GLRA4, P2RX1, P2RX2, P2RX3, P2RX4, P2RX5, P2RX6, P2RX7, ZACN, ASIC1, ASIC2, ASIC3, ASIC4, AQP1, AQP2, AQP3, AQP4, AQP5, AQP6, AQP7, AQP8, AQP9, AQP10, AQP11, AQP12A, AQP12B, MIP, CLCN1, CLCN2, CLCN3, CLCN4, CLCN5, CLCN6, CLCN7, CLCNKA, CLCNKB, Cystic fibrosis transmembrane conductance regulator (CFTR), ANO1, ANO2, ANO3, ANO4, ANO5, ANO6, ANO7, ANO8, ANO9, ANO10, BEST1, BEST2, BEST3, BEST4, CLIC1, CLIC2, CLIC3, CLIC4, CLIC5, CLIC6, GJA1, GJA3, GJA4, GJA5, GJA6P, GJA8, GJA9, GJA10, GJB1, GJB2, GJB3, GJB4, GJB5, GJB6, GJB7, GJC1, GJC2, GJC3, GJD2, GJD3, GJD4, GJE1, ITPR1, ITPR2, ITPR3, PANX1, PANX2, PANX3, RYR1, RYR2, RYR3, NALCN, SCNN1A, SCNN1B, SCNN1D, SCNN1G, TEM16A, ADAMTS7, ANGPTL3, ANGPTL4, ANGPTL8, LPL, GDF15, galectin-1, galectin-2, galectin-3, galectin-4, galectin-7, galectin-8, galectin-9, galectin-10, galectin-12, galectin-13, matrix gla protein (MGP), PRNP, DGAT1, GPAT3, DMC1, BLM, BRCA2, members of the human endogenous retrovirus type K (HERV-K) family, ectonucleoside triphosphate diphosphohydrolase 1 (ENTPD1), ectonucleoside triphosphate diphosphohydrolase 2 (ENTPD2), SLC1A1, SLC1A2, SLC1A3, SLC1A4, SLC1A5, SLC1A6, SLC1A7, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, SLC2A14, SLC3A1, SLC3A2, SLC4A1, SLC4A2, SLC4A3, SLC4A4, SLC4A5, SLC4A6, SLC4A7, SLC4A8, SLC4A9, SLC4A10, SLC4A11, SLC5A1, SLC5A2, SLC5A3, SLC5A4, SLC5A5, SLC5A6, SLC5A7, SLC5A8, SLC5A9, SLC5A10, SLC5A11, SLC5A12, SLC6A1, SLC6A2, SLC6A3, SLC6A4, SLC6A5, SLC6A6, SLC6A7, SLC6A8, SLC6A9, SLC6A10, SLC6A11, SLC6A12, SLC6A13, SLC6A14, SLC6A15, SLC6A16, SLC6A17, SLC6A18, SLC6A19, SLC6A20, SLC7A5, SLC7A6, SLC7A7, SLC7A8, SLC7A9, SLC7A10, SLC7A11, SLC7A13, SLC7A14, SLC8A1, SLC8A2, SLC8A3, SLC9A1, SLC9A2, SLC9A3, SLC9A4, SLC9A5, SLC9A6, SLC9A7, SLC9A8, SLC9A9, SLC9A10, SLC9A11, SLC9B1, SLC9B2, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14, SLC17A1, SLC17A2, SLC17A3, SLC17A4, SLC17A5, SLC17A6, SLC17A7, SLC17A8, SLC17A9, SLC18A1, SLC18A2, SLC18A3, SLC19A1, SLC19A2, SLC19A3, SLC20A1, SLC20A2, SLCO1A2, SLCO1B1, SLCO1B3, SLCO1C1, SLCO2A1, SLCO2B1, SLCO3A1, SLCO4A1, SLCO4C1, SLCO5A1, SLCO6A1, SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A18AS, SLC22A19, SLC22A20, SLC22A23, SLC22A24, SLC22A25, SLC22A31, SLC23A1, SLC23A2, SLC23A3, SLC23A4, SLC24A1, SLC24A2, SLC24A3, SLC24A4, SLC24A5, SLC24A6, SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, SLC25A46, SLC26A1, SLC26A2, SLC26A3, SLC26A4, SLC26A5, SLC26A6, SLC26A7, SLC26A8, SLC26A9, SLC26A10, SLC26A11, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC30A1, SLC30A2, SLC30A3, SLC30A4, SLC30A5, SLC30A6, SLC30A7, SLC30A8, SLC30A9, SLC30A10, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E3, SLC35E4, SLC35F1, SLC35F2, SLC35F3, SLC35F4, SLC35F5, SLC35G1, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A2, SLC38A3, SLC38A4, SLC38A5, SLC38A6, SLC38A7, SLC38A8, SLC38A9, SLC38A10, SLC38A11, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14, SLC40A1, SLC41A1, SLC41A2, SLC41A3, RhAG, RhBG, RhCG, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, HCP-1, MFSD5, MFSD10, SLC50A1, OSTα, OSTβ, SLC52A1, SLC52A2, and SLC52A3.

Aspect 79. The method of any one of the preceding aspects, wherein the step of obtaining antibodies that specifically bind to the target protein comprises obtaining antibody-producing cells from the animal, generating hybridomas with the antibody-producing cells, selecting hybridomas that produce the antibodies that specifically bind to the target protein, and isolating the antibodies produced by the hybridoma.

Aspect 80. The method of aspect 79, further comprising the step of determining the nucleic acid sequence encoding the antibody that specifically binds to the target protein.

Aspect 81. The method of aspect 72, 79, or 80, wherein the antibody-producing cells are lymphocytes, splenocytes, or peripheral blood mononuclear cells (PBMCs).

Aspect 82. The method of any one of the preceding aspects, further comprising the step of generating a chimeric antibody or humanized antibody based on the antibody that specifically binds to the target protein, wherein the chimeric antibody or humanized antibody is capable of binding to the target protein with comparable affinity.

Aspect 83. The method of any one of the preceding aspects, wherein the animal has been genetically modified to produce human antibodies.

Aspect 84. The method of any one of the preceding aspects, wherein the polyribonucleotide of the complex comprises pseudouridine.

Aspect 85. The method of any one of the preceding aspects, wherein the polyribonucleotide of the complex comprises:

(a) one or more of the following modified nucleotides for cytidine: 5-formylcytidine, 5-methylcytidine, 5-methoxycytidine, 5-hydroxycytidine, and 5-hydroxymethylcytidine;

(b) one or more of the following modified nucleotides for uridine: 5-formyluridine, 5-methyluridine, 5-methoxyuridine, 5-carboxymethylesteruridine, pseudouridine, and N1-methylpseudouridine;

(c) N6-methyladenosine as a modified nucleotide for adenosine: and/or (d) thienoguanosine as a modified nucleotide for guanosine.

Aspect 86. The method of any one of the preceding aspects, wherein the complex comprises two or more different polyribonucleotides, such as mRNAs, encoding two or more different target proteins which are capable of binding to each other.

Aspect 87. The method of any one of the preceding aspects, wherein said complex comprises a polyribonucleotide comprising a sequence that is at least 80%, 85%, 90%, 91%, 92%, 93%, 94%, 95%, 96%, 97%, 98%, or 99% identical to any one of the sequences in Tables 1-7, e.g., SEQ ID NOs: 2, 4, 37, 5, 7, 40, 8, 10, 43, 14, 16, 46, 17, 19, 49, 20, 22, 52, 26, 55, or 56.

BRIEF DESCRIPTION OF THE DRAWINGS

FIGS. 1A-1D depict an exemplary RXFP1 immunization strategy and resulting FACS-based sera response.

FIG. 1A is a schematic of an exemplary immunization strategy for human RXFP1.

FIG. 1B depicts FACS-based sera responses from animals 10 days after the priming immunization, illustrating the rapid induction of target-specific titers by mRNA immunization compared to the more traditional immunization formats of whole cells overexpressing human RXFP1 (BaF/3) or virus like particles overexpressing human RXFP1 (VLP-300.19).

FIG. 1C depicts final sera responses of immunized mice prior to final boost and initiation of hybridoma fusion. Eight mice were selected for fusion and boosted with 100 ug of the indicated immunogen.

FIG. 1D depicts sample FACS profiles of three anti-human RXFP1 hybridoma clones obtained from the immunization campaign. 207 RXFP1 specific clones were obtained in total.

DETAILED DESCRIPTION

Figure 1B:
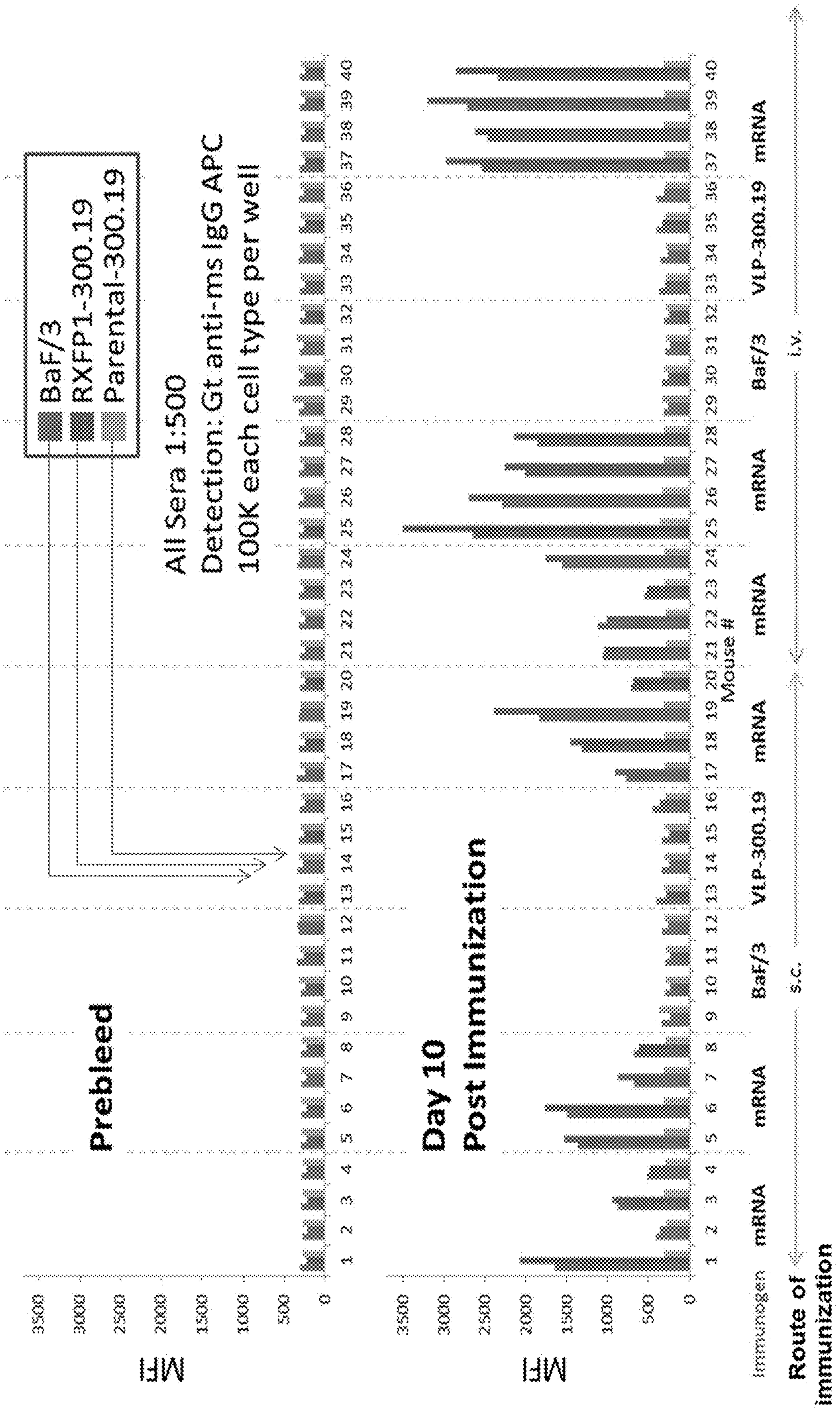

The present disclosure is directed to methods of immunization using compositions comprising cationic lipids and polynucleotide molecules, such as polyribonucleotide molecules, e.g., mRNA, which code for immunogens (e.g., target proteins or fragments thereof). This disclosure is also directed to methods for producing polyclonal and monoclonal antibodies from genetically immunized animals, as well as to the antibodies produced by the immunization methods provided herein, including chimeric and humanized variants of such antibodies. This disclosure is also directed hybridomas obtained by the immunization methods (e.g., mRNA-LNP immunization methods) provided herein.

The present disclosure is directed to a method for eliciting an immune response in an animal (e.g., non-human animal such as mouse, rat, or rabbit), comprising the steps of: (a) mixing at least one cationic lipid with a polynucleotide coding for an antigenic determinant, thereby forming a cationic lipid-polynucleotide complex (e.g., mRNA-LNP complex); and (b) administering the lipid-polynucleotide complex to the animal. The present disclosure is further directed to a genetic immunization method wherein the polynucleotide is an mRNA molecule which codes for an immunogen (e.g., transmembrane protein (e.g., multi-pass transmembrane protein) such as a GPCR. mRNA has been found to be a superior polynucleotide for quickly raising antibodies to challenging and complex protein targets (e.g., multi-pass transmembrane proteins such as GPCRs).

The present disclosure is further directed to a method for producing polyclonal antibodies comprising the use of the genetic immunization method described above, and further comprising the step of isolating the polyclonal antibodies from the immunized animal.

The present disclosure is also directed to a method for producing monoclonal antibodies comprising the steps of: (a) administering to a non-human animal (e.g., mouse) a composition comprising at least one cationic lipid and a polynucleotide (e.g., polyribonucleotide), wherein the polynucleotide comprises an mRNA sequence coding for an immunogen; and (b) obtaining antibodies which specifically bind to the immunogen. In specific aspects, the step of obtaining antibodies which specifically bind to the immunogen comprises one or more of the following steps: (a) obtaining antibody-producing cells such as lymphocytes (e.g., B-lymphocytes) or splenocytes, from the immunized animal; (b) fusing the antibody-producing cells from the immunized animal with myeloma cells, thereby producing hybridomas; (c) cloning the hybridomas; (d) selecting positive clones which produce anti-immunogen antibody (i.e., antibody which specifically binds to the immunogen); (e) culturing the anti-immunogen antibody-producing clones; and (f) isolating anti-immunogen antibodies from the cultures.

The present disclosure is also directed to a method for producing monoclonal antibodies comprising the steps of: (a) mixing at least one cationic lipid with a polynucleotide (e.g., polyribonucleotide), thereby forming a lipid-polynucleotide complex, wherein the polynucleotide comprises an mRNA sequence coding for an immunogen; (b) administering the lipid-polynucleotide complex to at least one mouse; (c) removing antibody-producing cells such as lymphocytes (e.g., B-lymphocytes) or splenocytes, from the immunized mice; (d) using the B-lymphocytes from the immunized mice with myeloma cells, thereby producing hybridomas; (e) cloning the hybridomas; (f) selecting positive clones which produce anti-immunogen antibody; (g) culturing the anti-immunogen antibody-producing clones; and (h) isolating anti-immunogen antibodies from the cultures.

Various formulations of cationic lipids have been used to transfect cells in vitro (for example, WO 91/17424; WO 91/16024; U.S. Pat. Nos. 4,897,355; 4,946,787; 5,049,386; and 5,208,036). Cationic lipids have also been used to introduce foreign polynucleotides into frog and rat cells in vivo (see, e.g., Holt et al., *Neuron* 4:203-214 (1990); Hazinski et al., *Am. J. Respr. Cell. Mol. Biol.* 4: 206-209 (1991)). In specific embodiments provided herein, cationic lipids are used, generally, to deliver or to introduce biologically active substances (for example, see WO 91/17424; WO 91/16024; and WO 93/03709). In specific aspects described herein, cationic liposomes can provide an efficient carrier for the introduction of foreign polynucleotides such as polyribonucleotides (e.g., mRNA) into host cells for genetic immunization.

Various cationic lipids well-known in the prior art can be used in the compositions and methods provided herein. One well-known cationic lipid is N-[1-(2,3-dioleoyloxy)propyl]-N,N,N-trimethylammonium chloride (DOTMA). DOTMA, alone or in a 1:1 combination with dioleoylphosphatidylethanolamine (DOPE) can be formulated into liposomes using standard techniques. Feigner et al. (*Proc. Natl. Acad. Sci. U.S.A.* 84:7413-7417 (1987)), which is hereby incorporated by reference in its entirety, have shown that such liposomes provide efficient delivery of nucleic acids to cultured cells. A DOTMA:DOPE (1:1) formulation is sold under the name LIPOFECTIN™ (GIBCO/BRL: Life Technologies, Inc., Gaithersburg, Md.). Another commercially available cationic lipid is 1,2-bis(oleoyloxy)-3-3-(trimethylammonia)propane (DOTAP), which differs from DOTMA in that the oleoyl moieties are linked via ester bonds, not ether bonds, to the propylamine. DOTAP is believed to be more readily degraded by target cells.

Related groups of known compounds differ from DOTMA and DOTAP in that one of the methyl groups of the trimethylammonium group is replaced by a hydroxyethyl group. Compounds of this type are similar to the Rosenthal Inhibitor of phospholipase A (Rosenthal et al., *J. Biol. Chem.* 235:2202-2206 (1960), which has stearoyl esters linked to the propylamine core. The dioleoyl analogs of the Rosenthal Inhibitor (RI) are commonly abbreviated as DORI-ether and DORI-ester, depending upon the linkage of the fatty acid moieties to the propylamine core. The hydroxy group can be used as a site for further functionalization, for example, by esterification to carboxyspermine.

Another class of known compounds has been described by Behr et al. (Proc. Natl. Acad. Sci. USA 86:6982-6986 (1989); EPO Publication 0 394 111), in which carboxyspermine has been conjugated to two types of lipids, resulting in dipalmitoylphosphatidylethanolamine 5-carboxyspermylamide (DDPES).

Both DOGS and DPPES have been used to coat plasmids, forming a lipid aggregate complex that provides efficient transfection. The compounds are claimed to be more efficient and less toxic than DOTMA for transfection of certain cell lines. DOGS is available commercially as TRANSFECTAM™ (Promega, Madison, Wis.).

A cationic cholesterol derivative (DC-Chol) has been synthesized and formulated into liposomes in combination with DOPE (Gao et al., *Biochim. Biophys. Res. Comm.* 179:280-285 (1991)). Liposomes formulated with DC-Chol provide more efficient transfection and lower toxicity than DOTMA-containing liposomes for certain cell lines.

Lipopolylysine is formed by conjugating polylysine to DOPE. This compound has been reported to be especially effective for transfection in the presence of serum (Zhou et al., *Biochim. Biophys. Res. Comm.* 165:8-14 (1991)). Thus, lipopolylysine may be an effective carrier for immunization.

Other non-limiting examples of lipids (e.g., cationic lipids, helper lipids, and stealth lipids) which can be used in the methods and compositions provided herein include those described in WO2015/095346, WO2015/095340, WO2016/037053, WO2014/136086, and WO2011/076807, each of which is hereby incorporated by reference in its entirety.

In certain aspects, cationic lipids for the compositions and methods described herein include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment, the cationic lipid for the compositions and methods provided herein is DOTAP or DLTAP. These compounds are useful either alone, or in combination with other lipid aggregate-forming components (such as DOPE or cholesterol) for formulation into liposomes or other lipid aggregates. Such aggregates are cationic and able to complex with anionic macromolecules such as DNA or RNA.

The methods of mRNA-based immunization provided herein have addressed many of the issues associated with the above-described difficulties inherent in antigen production and/or antibody generation. Among other things, said methods dispense with the need to directly express and purify the target protein antigen. An animal host's own cellular machinery is used to make the target protein and present it to the immune system. For eukaryotic target proteins, this has the added advantage of permitting the addition of eukaryotic-specific post-translational modifications and protein processing. Without being bound to any particular theory, the unpurified mRNA that is used for immunization has a highly inflammatory character due in part to the presence of double stranded RNA entities in the preparation. In specific aspects, this serves as an adjuvant to boost the humoral response against the target protein.

In particular aspects provided herein, monoclonal antibody development for a target protein can be expedited through the immunization of animals with mRNAs which encode said target protein. This method offers considerable advantages for proteins against which it has historically been technically challenging to develop specific antibodies, such as G-protein coupled receptors, as there is no need to heterologously produce and purify the target protein. Host defense mechanisms elicited by the adjuvant-like properties of the mRNA result in a fast development of sera titers.

In certain aspects, hybridoma fusions using antibody-producing cells obtained from animals immunized with the encapsulated mRNA-based immunization methods provided herein have been highly productive. The encapsulated mRNAs are potent and highly immunogenic, which can shorten an immunization schedule and require fewer animals. All manner of proteins can be generated as antigens with the present methods, e.g., soluble, membrane bound, complexed/heteromeric, etc., regardless of complexity. Expression should result in the native confirmation of the antigen.

The present methods provided herein also can result in the co-expression of multiple chains for complexed protein (e.g., IgGs, receptor complexes). In specific aspects of the mRNA-based immunization methods provided herein, expressed antigens are immunogenically clean, i.e, have no contaminants which would alter the specificity of the humoral response or infectious pathogens, since they are synthetic.

In particular aspects, the present methods describe a stable method of antigen generation and reagent storage, as the lipid encapsulated mRNAs of the present invention are capable of remaining stable at 4° C. for months. Furthermore, there is no IMPACT (Infectious Microbe PCR Amplification Test) pathogen testing required, as the mRNAs are all synthetic.

Terminology

"Cloning Vector" means plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

"Expression vector" is a vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

"Expression" is the cellular process by which a polypeptide is produced from a structural gene. The process involves transcription of a gene into messenger RNA (mRNA) and the translation of such mRNA into polypeptide(s). "Expression" can also include where applicable, but not limited to, for example, transcription, translation, folding, modification and processing. "Expression products" include RNA transcribed from a gene, and polypeptides obtained by translation of mRNA transcribed from a gene. In specific aspects, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

An "exogenous" nucleic acid is a nucleic acid (e.g., a modified synthetic mRNA described herein) that has been introduced by a process involving human intervention into a biological system such as a cell or organism in which it is not normally found, or in which it is found in lower amounts. A factor (e.g. a modified synthetic mRNA described herein) is exogenous if it is introduced into an immediate precursor cell or a progeny cell that inherits the substance. In contrast, an "endogenous" is a factor or expression product that is native to the biological system or cell (e.g., endogenous expression of a gene).

"Isolated" means, in the case of a nucleic acid or polypeptide, a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

"Isolated cells" are cells that have been removed from an organism in which they originally found, or descendants of such cells. Optionally the cell has been cultured in vitro, e.g., in the presence of other cells. Optionally, the cell is later introduced into a second organism or re-introduced into the organism from which it (or the cell or population of cells from which it descended) was isolated.

"Modified" means a changed state or structure of a molecule described herein. Molecules may be modified in many ways including chemically, structurally, and functionally. In one embodiment, the mRNA molecules described herein are modified by the introduction of natural and non-natural nucleosides and/or nucleotides. Modified may also mean any alteration which is different from the wild type. A "modified" RNA is an RNA molecule produced in vitro, which comprise at least one modified nucleoside.

A "modified nucleoside" is a ribonucleoside that encompasses modification(s) relative to the standard guanine (G), adenine (A), cytidine (C), and uridine (U) nucleosides. Such modifications can include, for example, modifications normally introduced post-transcriptionally to mammalian cell mRNA, and artificial chemical modifications, as known to one of skill in the art. In one aspect, the following are non-limiting examples of modified nucleotides: 5-formylcytidine, 5-methylcytidine, 5-methoxycytidine, 5-hydroxycytidine, 5-hydroxymethylcytidine, 5-formyluridine, 5-methyluridine, 5-methoxyuridine, 5-carboxymethylesteruridine, pseudouridine, N1-methylpseudouridine, N6-methyladenosine, and thienoguanosine.

"Added co-transcriptionally" means the addition of a feature, e.g., a 5' methylguanosine cap or other modified nucleoside, to a modified synthetic mRNA of the invention during transcription of the RNA molecule (i.e., the modified RNA is not fully transcribed prior to the addition of the 5' cap).

"Contacting" a cell means contacting with a factor (e.g., a modified synthetic mRNA described herein), optionally, including subjecting a cell to a transfection system. Where such a cell is in vivo, contacting the cell with a modified synthetic mRNA described herein includes administering a modified synthetic mRNA described herein in a formulation, such as a pharmaceutical composition, to a subject by an appropriate administration route, such that the compound contacts the cell in vivo.

In general, a "recombinant host" may be any prokaryotic or eukaryotic microorganism or cell which contains the desired cloned genes in an expression vector or cloning vector. This term is also meant to include those microorganisms that have been genetically engineered to contain the desired gene(s) in the chromosome or genome of that organism.

"Recombinant vector" is any cloning vector or expression vector which contains the desired cloned gene(s).

A "host" means any prokaryotic or eukaryotic microorganism or cell that is the recipient of a replicable expression vector or cloning vector. A host also includes prokaryotic or eukaryotic microorganisms or cells that can be genetically engineered by well-known techniques to contain desired gene(s) on its chromosome or genome. For examples of such hosts, see Maniatis et al., *Molecular Cloning: A Laboratory Manual*, Cold Spring Harbor Laboratory, Cold Spring Harbor, N.Y. (1982).

A "promoter" is a DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

"Gene" is a DNA sequence that contains information needed for expressing a polypeptide or protein.

"Structural gene" is a nucleotide, e.g., DNA, sequence that is transcribed into messenger RNA (mRNA) that is then translated into a sequence of amino acids characteristic of a specific polypeptide.

"Transfection" refers to the transformation of a host cell with polynucleotides, e.g., DNA or RNA. The recombinant host cell expresses protein which is encoded by the transfected polynucleotide, e.g., DNA or RNA. In specific aspects, "transfection" means the use of methods, such as chemical methods, to introduce exogenous nucleic acids, such as the modified synthetic mRNA described herein into a host cell, such as a eukaryotic cell. As used herein, the term "transfection" does not encompass viral-based methods of introducing exogenous nucleic acids into a cell. Non-limiting methods of transfection include physical treatments (e.g., electroporation, nanoparticles, magnetofection), and chemical-based transfection methods. Chemical-based transfection methods include, but are not limited to, cyclodextrin, polymers, liposomes, and nanoparticles.

An "epitope" is the part of a non-immunoglobulin antigen to which the variable region of an antibody binds. An "antigenic determinant" is a protein or peptide which contains one or more epitopes. An "immunogen" is a protein or peptide which is capable of eliciting an immune response due to the presence of one or more epitopes. The terms "antigen," "antigenic determinant," and "immunogen" are used synonymously herein. In specific aspects, epitopes usually consist of chemically active surface groupings of molecules such as amino acids or sugar side chains and may have specific three dimensional structural characteristics, as well as specific charge characteristics. In particular aspects, conformational and nonconformational epitopes are distinguished in that the binding to the former but not the latter is lost in the presence of denaturing solvents. In certain aspects, an epitope may be a linear epitope comprising contiguous amino acid sequences of a fragment or portion of an antigen. In certain aspects, an epitope may be a conformational epitope comprising noncontiguous amino acid sequences of an antigen.

A "transfection reagent" is an agent that induces uptake of polynucleotides such as DNA or RNA into a host cell. In specific aspects, also encompassed are agents that enhance uptake e.g., by at least 50-90%, compared to a modified synthetic mRNA described herein administered in the absence of such a reagent. In one embodiment, a cationic or non-cationic lipid molecule useful for preparing a pharmaceutical composition or for co-administration with a modified synthetic mRNA described herein is used as a transfection reagent. In other embodiments, the modified synthetic mRNA described herein comprises a chemical linkage to attach e.g., a ligand, a peptide group, a lipophilic group, a targeting moiety etc. In other embodiments, the transfection reagent comprises a charged lipid, an emulsion, a liposome, a cationic or non-cationic lipid, an anionic lipid, or a penetration enhancer as known in the art or described herein.

"Innate immune response" or "interferon response" means a cellular defense response initiated by a cell in response to recognition of infection by a foreign organism, such as a virus or bacteria or a product of such an organism, e.g., an RNA lacking the modifications characteristic of RNAs produced in the subject cell. The innate immune response protects against viral and bacterial infection by inducing the death of cells that detect exogenous nucleic acids.

A "therapeutically effective amount" or "effective amount" is the amount of the subject compound or combination that will elicit the biological or medical response of a tissue, system, animal or human that is being sought by the researcher, veterinarian, medical doctor or other clinician.

"Primers" are also nucleic acid sequences. PCR primers are typically oligonucleotides of fairly short length (e.g., 8-30 nucleotides) that are used in polymerase chain reactions. PCR primers and hybridization probes can readily be developed and produced by those of skill in the art, using sequence information from the target sequence. See, Sambrook et al. (1989) Molecular Cloning: A Laboratory Manual (Cold Spring Harbor Labs Press).

"Selectively binds to" or "specifically binds to" means the specific binding of one protein to another (e.g., an antibody, fragment thereof, or binding partner to a target protein), wherein the level of binding, as measured by any standard assay (e.g., an immunoassay), is statistically significantly higher than the background control for the assay.

A "conserved" nucleotide or amino acid is a residue of a polynucleotide sequence or polypeptide sequence, respectively, which occurs unaltered in the same position of two or more sequences being compared. Nucleotides or amino acids that are relatively conserved are those that are conserved amongst more related sequences than nucleotides or amino acids appearing elsewhere in the sequences. Two or more sequences are "completely conserved" if they are 100% identical to one another. In some embodiments, two or more sequences are "highly conserved" if they are at least 90% identical, to one another. In some embodiments, two or more bases are "conserved" if they are identical, to one another. Conservation of sequence may apply to the entire length of an oligonucleotide or polypeptide or may apply to a portion, region or feature thereof. In the context of polypeptides, the following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Delivery" means the act or manner of delivering a compound, substance, entity, moiety, cargo or payload.

A "delivery agent" is any substance which facilitates, at least in part, the in vivo delivery of a nucleic acid molecule to targeted cells.

A "formulation" includes at least a modified nucleic acid molecule and a delivery agent.

"Homology" means the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25% identical. The term "homologous" necessarily refers to a comparison between at least two sequences (polynucleotide or polypeptide sequences). Two polynucleotide sequences are considered to be homologous if the polypeptides they encode are at least about 50% identical for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical for at least one stretch of at least about 20 amino acids.

"Identity" means the overall relatedness between polymeric molecules, e.g., between oligonucleotide molecules (e.g., DNA molecules and/or RNA molecules) or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. Two non-limiting examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information.

The term "cationic liposome(s)" or "cationic lipid(s)" are structures that are made of positively charged lipids, which are capable of interacting with negatively charged DNA and cell membranes.

The term "lipid nanoparticle" or "LNP" refers to a particle that comprises a plurality of (i.e. more than one) lipid molecules physically associated with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The term "nucleic acid" is used herein interchangeably with the term "polynucleotide" and refers to deoxyribonucleotides (DNA) or ribonucleotides (RNA) or polyribonucleotides, including messenger RNA (mRNA), and polymers thereof in either single- or double-stranded form. The term encompasses nucleic acids containing known nucleotide analogs or modified backbone residues or linkages, which are synthetic, naturally occurring, and non-naturally occurring, which have similar properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "sample" is a subset of its tissues, cells or component parts (e.g., body fluids). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

"Synthetic" means produced, prepared, and/or manufactured by human intervention. Synthesis of polynucleotides or polypeptides or other molecules described herein may be chemical or enzymatic.

As used herein, "pseudouridine" refers to the C-glycoside isomer of the nucleoside uridine.

As used herein, "purify," "purified," "purification" means to make substantially pure or clear from unwanted components, material defilement, admixture or imperfection.

The term "antibody" as used herein means a whole antibody and any antigen-binding fragment (i.e., "antigen-binding portion") or single chain thereof. A whole antibody is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" or "antigen-binding fragment" of an antibody, as used herein, refers to one or more fragments of an intact antibody that retain the ability to specifically bind to a given antigen. Antigen-binding functions of an antibody can be performed by fragments of an intact antibody. Examples of binding fragments encompassed within the term antigen-binding portion or antigen-binding fragment of an antibody include a Fab fragment, a monovalent fragment consisting of the VL, VH, CL and CH1 domains; a $F(ab)_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain or a VL domain; and an isolated complementarity determining region (CDR). In certain aspects, the CDRs of an antibody can be determined according to (i) the Kabat numbering system (Kabat et al. (1971) Ann. NY Acad. Sci. 190:382-391 and, Kabat et al. (1991) Sequences of Proteins of Immunological Interest Fifth Edition, U.S. Department of Health and Human Services, NIH Publication No. 91-3242); or (ii) the Chothia numbering scheme (see, e.g., Chothia and Lesk, 1987, J. Mol. Biol., 196:901-917; Al-Lazikani et al, 1997, J. Mol. Biol., 273:927-948; Chothia et al., 1992, J. Mol. Biol., 227:799-817; Tramontano A et al., 1990, J. Mol. Biol. 215(1): 175-82; and U.S. Pat. No. 7,709,226); or (iii) the ImMunoGeneTics (IMGT) numbering system, for example, as described in Lefranc, M.-P., 1999, The Immunologist, 7: 132-136 and Lefranc, M.-P. et al, 1999, Nucleic Acids Res., 27:209-212 ("IMGT CDRs"); or (iv) MacCallum et al, 1996, J. Mol. Biol., 262:732-745. See also, e.g., Martin, A., "Protein Sequence and Structure Analysis of Antibody Variable Domains," in Antibody Engineering, Kontermann and Diibel, eds., Chapter 31, pp. 422-439, Springer-Verlag, Berlin (2001).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more antigen-binding portions or fragments of an antibody. These antibody fragments are obtained using conventional techniques known to those of skill in the art, and the fragments are screened for utility in the same manner as are intact antibodies.

Antigen-binding fragments can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen-binding portions of antibodies can be grafted into scaffolds based on polypeptides such as Fibronectin type III (Fn3) (see U.S. Pat. No. 6,703,199, which describes fibronectin polypeptide monobodies).

Antigen-binding fragments can be incorporated into single chain molecules comprising a pair of tandem Fv segments (VH-CH1-VH-CH1) which, together with complementary light chain polypeptides, form a pair of antigen-binding regions (Zapata et al. (1995) Protein Eng. 8(10):1057-1062; and U.S. Pat. No. 5,641,870).

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. As used herein, the term "high affinity" for an antibody or antigen-binding fragments thereof (e.g., a Fab fragment) generally refers to an antibody, or antigen-binding fragment, having a $K_D$ of $10^{-9}$M or less.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. In certain aspects, human antibodies, such as human monoclonal antibodies, may be produced by a hybridoma which includes an immortalized cell fused to a B cell obtained from a transgenic non-human animal, e.g., a transgenic mouse, having a genome comprising a human heavy chain transgene and a human light chain transgene.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but are not limited to XOMA technology disclosed in U.S. Pat. No. 5,766,886.

The term "hybridoma" refers to an immortalized cell derived from the fusion of an antibody-producing cell, such as B lymphoblasts, with a fusion partner, such as a myeloma cell. In specific aspects, the antibody-producing cell used to generate a hybridoma is obtained from an animal immunized with an antigen, for example, immunized according to the mRNA-based immunization methods described herein.

The term "isolated antibody" refers to an antibody that is substantially free of other antibodies having different antigenic specificities and/or different amino acid sequence. In particular aspects, an isolated antibody that specifically binds an antigen may, however, have cross-reactivity to other antigens. In specific aspects, an isolated antibody may be substantially free of other cellular material and/or chemicals.

The term "isotype" refers to the antibody class (e.g., IgM, IgE, IgG such as $IgG_1$, $IgG_2$, or $IgG_4$) that is provided by the heavy chain constant region genes. Isotype also includes modified versions of one of these classes, where modifications have been made to alter the Fc function, for example, to enhance or reduce effector functions or binding to Fc receptors. The term "monoclonal antibody" is a well known term of art that refers to an antibody obtained from a population of homogenous or substantially homogeneous antibodies displaying binding specificity and affinity for a particular epitope. The term "monoclonal" is not limited to any particular method for making the antibody. Generally, a population of monoclonal antibodies can be generated by cells, a population of cells, or a cell line. In particular aspects, a monoclonal antibody can be a chimeric antibody or a humanized antibody. In particular aspects, a monoclonal antibody is a monovalent antibody or multivalent (e.g., bivalent) antibody.

As used herein, the term "polyclonal antibodies" refers to a heterologous antibody population comprising a variety of different antibodies that react against a specific antigen, but the different antibodies recognize different epitopes within the antigen.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, the term, "optimized" means that a nucleotide sequence has been altered to encode an amino acid sequence using codons that are preferred in the production cell or organism, generally a eukaryotic cell. In certain aspects, the optimized nucleotide sequence is engineered to retain completely or as much as possible the amino acid sequence originally encoded by the starting nucleotide sequence, which is also known as the "parental" sequence. In particular aspects, optimized sequences described herein have been engineered to have codons that are preferred in mammalian cells, such as murine cells. In other aspects, optimized expression of sequences in other eukaryotic cells or prokaryotic cells is also envisioned herein.

I. Target Proteins/Antigenic Determinants

Provided herein are methods for inducing an immune response to a target protein (e.g. human protein, such as human transmembrane protein, e.g., human GPCR) or a fragment thereof in an animal (e.g., non-human animal), wherein the animal is administered a composition comprising a complex comprising a lipid and a polynucleotide, such as polyribonucleotide (e.g., mRNA), encoding the target protein or a fragment thereof, and related methods of producing antibodies against such target protein. The methods provided herein are useful to produce antibodies (e.g., monoclonal antibodies) against, or to induce an immune response to, any target protein of interest (e.g., transmembrane protein). In specific aspects, the target proteins are human target proteins and the immunized animals used in the methods described herein are non-human animals.

In specific aspects, provided herein are methods for producing antibodies to a target protein (e.g. human protein, such as human transmembrane protein, e.g., human GPCR) or a fragment thereof in an animal (e.g., non-human animal), using a composition comprising a complex comprising a lipid and a polyribonucleotide, such as mRNA, encoding the target protein or a fragment thereof, wherein the target protein is (i) a G protein coupled receptor (GPCR); (ii) a single pass transmembrane protein receptor; (iii) a Tumor Necrosis Factor Receptor Superfamily (TNFRSF) member; (iv) an interleukin (IL) receptor; (v) an ion channel; (vi) a solute carrier; (vii) an immune receptor; or (viii) a multipass transmembrane protein.

In specific aspects, provided herein are methods for producing antibodies to a target protein (e.g. human protein, such as human transmembrane protein, e.g., human GPCR) or a fragment thereof in an animal (e.g., non-human animal), using a composition comprising a complex comprising a lipid and a polyribonucleotide, such as mRNA, encoding the target protein or a fragment thereof, wherein the target protein is selected from the following: ACKR1, ACKR2, ACKR3, ACKR4, ADCYAP1R1, ADGRA1, ADGRA2, ADGRA3, ADGRB1, ADGRB2, ADGRB3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADORA1, ADORA2A, ADORA2B, ADGRA3, ADRA1A, ADRA1B, ADRA1D, ADRA2A, ADRA2B, ADRA2C, ADRB1, ADRB2, ADRB3, AGTR1, AGTR2, APLNR/APJ, ASGR1, ASGR2, AVPR1A, AVPR1B, AVPR2, BDKRB1, BDKRB2, BRS3, BRS3, C3AR1, C5AR1, C5AR2, CALCR, CALCRL, CASR, CCKAR, CCKBR, CCR1, CCR10, CCR2, CCR3, CCR4, CCR5, CCR6, CCR7, CCR8, CCR9, CCRL2, CELSR1, CELSR2, CELSR3, CHRM1, CHRM2, CHRM3, CHRM4, CHRM5, CMKLR1, CNR1, CNR2, CRHR1, CRHR2, CX3CR1, CXCR1, CXCR2, CXCR3, CXCR4, CXCR5, CXCR6, CYSLTR1, CYSLTR2, DRD1, DRD2, DRD3, DRD4, DRD5, EDNRA, EDNRB, F2R, F2RL1, F2RL2, F2RL3, FFAR1, FFAR2, FFAR3, FFAR4, FPR1, FPR2, FPR2, FPR3, FSHR, FZD1, FZD10, FZD2, FZD3, FZD4, FZD5, FZD6, FZD7, FZD8, FZD9, GABBR1, GABBR2, GALR1, GALR2, GALR3, GCGR, GHRHR, GHSR, GIPR, GLP1R, GLP2R, GNRHR, GNRHR2, GPBAR1, GPER1, GPR1, GPR4, GPR12, GPR15, GPR17, GPR18, GPR19, GPR20, GPR21, GPR22, GPR25, GPR26, GPR27, GPR3, GPR31, GPR32, GPR33, GPR34, GPR35, GPR37, GPR37L1, GPR39, GPR40, GPR42, GPR42, GPR45, GPR50, GPR52, GPR55, GPR55, GPR6, GPR61, GPR62, GPR63, GPR65, GPR68, GPR75, GPR78, GPR79, GPR82, GPR83, GPR84, GPR85, GPR87, GPR88, GPR101, GPR107, GPR132, GPR135, GPR137, GPR139, GPR141, GPR142, GPR143, GPR146, GPR148, GPR149, GPR15, GPR150, GPR151, GPR152, GPR153, GPR156, GPR157, GPR158, GPR160, GPR161, GPR162, GPR171, GPR173, GPR174, GPR176, GPR179, GPR182, GPR183, GPRC5A, GPRC5B, GPRC5C, GPRC5D, GPRC6A, GRM1, GRM2, GRM3, GRM4, GRM5, GRM6, GRM7, GRM8, GRPR, HCAR1, HCAR2, HCAR3, HCRTR1, HCRTR2, HRH1, HRH2, HRH3, HRH4, HTR1A, HTR1B, HTR1D, HTR1E, HTR1F, HTR2A, HTR2B, HTR2C, HTR4, HTR5A, HTR5BP, HTR6, HTR7, KISS1R, LGR3, LGR4, LGR5, LGR6, LHCGR, LPAR1, LPAR2, LPAR3, LPAR4, LPAR5, LPAR6, LTB4R, LTB4R2, MAS1, MAS1L, MC1R, MC2R, MC3R, MC4R, MC5R, MCHR1, MCHR2, MLNR, MRGPRD, MRGPRE, MRGPRF, MRGPRG, MRGPRX1, MRGPRX2, MRGPRX3, MRGPRX4, MTNR1A, MTNR1B, NMBR, NMUR1, NMUR2, NPBWR1, NPBWR2, NPFFR1, NPFFR2, NPSR1, NPY1R, NPY2R, NPY4R, NPY5R, NPY6R, NTSR1, NTSR2, OPN3, OPN4, OPN5, OPRD1, OPRK1, OPRL1, OPRM1, OR51E1, OXER1, OXGR1, OXTR, P2RY1, P2RY10, P2RY11, P2RY12, P2RY13, P2RY14, P2RY2, P2RY4, P2RY6, P2RY8, PRLHR, PROKR1, PROKR2, PTAFR, PTGDR, PTGDR2, PTGER1, PTGER2, PTGER3, PTGER4, PTGFR, PTGIR, PTH1R, PTH2R, QRFPR, RXFP1, RXFP2, RXFP3, RXFP4, S1PR1, S1PR2, S1PR3, S1PR4, S1PR5, SCTR, SMO, SSTR1, SSTR2, SSTR3, SSTR4, SSTR5, SUCNR1, TAAR1, TAAR2, TAAR3, TAAR4P, TAAR5, TAAR6, TAAR8, TAAR9, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TBXA2R, TPRA1, TRHR, TSHR, UTS2R, VIPR1, VIPR2, XCR1, TCR-α, TCR-β, CD3, ζ-chain accessory, CD4, and CD8, mannose receptor (MR), asialoglycoprotein receptor family (e.g., asialoglycoprotein receptor macrophage galactose-type lectin (MGL)), DC-SIGN (CLEC4L), langerin (CLEC4K), myeloid DAP12-associating lectin (MDL)-1 (CLEC5A), dectin 1/CLEC7A, DNGR1/CLEC9A, Myeloid C-type lectin-like receptor (MICL) (CLEC12A), CLEC2 (also called CLEC1B), CLEC12B, DCIR/CLEC4A, Dectin 2/CLEC6A, Blood DC antigen 2 (BDCA2) (CLEC4C), macrophage-inducible C-type lectin (CLEC4E), TLR1, TLR2, TLR3, TLR4, TLR5, TLR6, TLR7, TLR8, TLR9, TLR10, TLR11, TLR12, TLR13, FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαR1 (CD89), Fcα/μR, FcRn, CD27, CD40, OX40, GITR, CD137, PD-1, CTLA-4, PD-L1, TIGIT, T-cell immunoglobulin domain and mucin domain 3 (TIM3), V-domain Ig suppressor of T cell activation (VISTA), CD28, CD122, ICOS, A2AR, B7-H3, B7-H4, B and T lymphocyte attenuator (BILA), Indoleamine 2,3-dioxygenase (IDO), killer-cell immunoglobulin-like receptor (KIR), lymphocyte activation gene-3 (LAGS), FAM159B, HLA-A, HLA-B, HLA-C, HLA-DPA1, HLA-DPB1, HLA-DQA1, HLA-DQB1, HLA-DRA, HLA-DRB1, gp130, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, IL-36 receptor, FGFR1, FGFR2, FGFR3, FGFR4, TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, TNFRSF27, SCN1A, SCN1B, SCN2A, SCN2B, SCN3A, SCN3B, SCN4A, SCN5A, SCN7A, SCN8A, SCN9A, SCN10A, SCN11A, CACNA1A, CACNA1B, CACNA1C, CACNA1D, CACNA1E, CACNA1F, CACNA1G, CACNA1H, CACNA1I, CACNA1S, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, MCOLN1, MCOLN2, MCOLN3, PKD1, PKD2, PKD2L1, PKD2L2, TRPV1, TRPV2, TRPV3, TRPV4, TRPV5, TRPV6, CATSPER1, CATSPER2, CATSPER3, CATSPER4, TPCN1, TPCN2, CNGA1, CNGA2, CNGA3, CNGA4, CNGB1, CNGB3, HCN1, HCN2, HCN3, HCN4, KCNMA1, KCNN1, KCNN2, KCNN3, KCNN4, KCNT1, KCNT2, KCNU1, KCNA1, KCNA2, KCNA3, KCNA4, KCNA5, KCNA6, KCNA7, KCNA10, KCNB1, KCNB2, KCNC1, KCNC2, KCNC3, KCNC4, KCND1, KCND2, KCND3, KCNF1, KCNG1, KCNG2, KCNG3, KCNG4, KCNH1, KCNH2, KCNH3, KCNH4, KCNH5, KCNH6, KCNH7, KCNH8, KCNQ1, KCNA2, KCNA3, KCNA4, KCNA5, KCNS1, KCNS2, KCNS3, KCNV1, KCNV2, KCNJ1, KCNJ2, KCNJ3, KCNJ4, KCNJ5, KCNJ6, KCNJ8, KCNJ9, KCNJ10, KCNJ11, KCNJ12, KCNJ13, KCNJ14, KCNJ15, KCNJ16, KCNJ18, KCNK1, KCNK2, KCNK3, KCNK4, KCNK5, KCNK6, KCNK7, KCNK9, KCNK10, KCNK12, KCNK13, KCNK15, KCNK16, KCNK17, KCNK18, HVCN1, HTR3A, HTR3B, HTR3C, HTR3D, HTR3E, CHRNA1, CHRNA2, CHRNA3, CHRNA4, CHRNA5, CHRNA6, CHRNA7, CHRNA9, CHRNA10, CHRNB1, CHRNB2, CHRNB3, CHRNB4, CHRND, CHRNE, CHRNG, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GRIA1, GRIA2, GRIA3, GRIA4, GRID1, GRID2, GRIK1, GRIK2, GRIK3, GRIK4, GRIK5, GRIN1, GRIN2A, GRIN2B, GRIN2C, GRIN2D, GRIN3A, GRIN3B, GLRA1, GLRA2, GLRA3, GLRA4, P2RX1, P2RX2, P2RX3, P2RX4, P2RX5, P2RX6, P2RX7, ZACN, ASIC1, ASIC2, ASIC3, ASIC4, AQP1, AQP2, AQP3, AQP4, AQP5, AQP6, AQP7, AQP8, AQP9, AQP10, AQP11, AQP12A, AQP12B, MIP, CLCN1, CLCN2, CLCN3, CLCN4, CLCN5, CLCN6, CLCN7, CLCNKA, CLCNKB, Cystic fibrosis transmembrane conductance regulator (CFTR), ANO1/TMEM16a, ANO2, ANO3, ANO4, ANO5, ANO6, ANO7, ANO8, ANO9, ANO10, BEST1, BEST2, BEST3, BEST4, CLIC1, CLIC2, CLIC3, CLIC4, CLIC5, CLIC6, GJA1, GJA3, GJA4, GJA5, GJA6P, GJA8, GJA9, GJA10, GJB1, GJB2, GJB3, GJB4, GJB5, GJB6, GJB7, GJC1, GJC2, GJC3, GJD2, GJD3, GJD4, GJE1, ITPR1, ITPR2, ITPR3, PANX1, PANX2, PANX3, RYR1, RYR2, RYR3, NALCN, SCNN1A, SCNN1B, SCNN1D, SCNN1G, ADAMTS7, ANGPTL3, ANGPTL4, ANGPTL8, LPL, GDF15, galectin-1, galectin-2, galectin-3, galectin-4, galectin-7, galectin-8, galectin-9, galectin-10, galectin-12, galectin-13, matrix gla protein (MGP), PRNP, DGAT1, GPAT3, DMC1, BLM, BRCA2, members of the human endogenous retrovirus type K (HERV-K) family, ectonucleoside triphosphate diphosphohydrolase 1 (ENTPD1), ectonucleoside triphosphate diphosphohydrolase 2 (ENTPD2), SLC1A1, SLC1A2, SLC1A3, SLC1A4, SLC1A5, SLC1A6, SLC1A7, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, SLC2A14, SLC3A1, SLC3A2, SLC4A1, SLC4A2, SLC4A3, SLC4A4, SLC4A5, SLC4A6, SLC4A7, SLC4A8, SLC4A9, SLC4A10, SLC4A11, SLC5A1, SLC5A2, SLC5A3, SLC5A4, SLC5A5, SLC5A6, SLC5A7, SLC5A8, SLC5A9, SLC5A10, SLC5A11, SLC5A12, SLC6A1, SLC6A2, SLC6A3, SLC6A4, SLC6A5, SLC6A6, SLC6A7, SLC6A8, SLC6A9, SLC6A10, SLC6A11, SLC6A12, SLC6A13, SLC6A14, SLC6A15, SLC6A16, SLC6A17, SLC6A18, SLC6A19, SLC6A20, SLC7A5, SLC7A6, SLC7A7, SLC7A8, SLC7A9, SLC7A10, SLC7A11, SLC7A13, SLC7A14, SLC8A1, SLC8A2, SLC8A3, SLC9A1, SLC9A2, SLC9A3, SLC9A4, SLC9A5, SLC9A6, SLC9A7, SLC9A8, SLC9A9, SLC9A10, SLC9A11, SLC9B1, SLC9B2, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14, SLC17A1, SLC17A2, SLC17A3, SLC17A4, SLC17A5, SLC17A6, SLC17A7, SLC17A8, SLC17A9, SLC18A1, SLC18A2, SLC18A3, SLC19A1, SLC19A2, SLC19A3, SLC20A1, SLC20A2, SLCO1A2, SLCO1B1, SLCO1B3, SLCO1C1, SLCO2A1, SLCO2B1, SLCO3A1, SLCO4A1, SLCO4C1, SLCO5A1, SLCO6A1, SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A18AS, SLC22A19, SLC22A20, SLC22A23, SLC22A24, SLC22A25, SLC22A31, SLC23A1, SLC23A2, SLC23A3, SLC23A4, SLC24A1, SLC24A2, SLC24A3, SLC24A4, SLC24A5, SLC24A6, SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, SLC25A46, SLC26A1, SLC26A2, SLC26A3, SLC26A4, SLC26A5, SLC26A6, SLC26A7, SLC26A8, SLC26A9, SLC26A10, SLC26A11, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC30A1, SLC30A2, SLC30A3, SLC30A4, SLC30A5, SLC30A6, SLC30A7, SLC30A8, SLC30A9, SLC30A10, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E3, SLC35E4, SLC35F1, SLC35F2, SLC35F3, SLC35F4, SLC35F5, SLC35G1, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A2, SLC38A3, SLC38A4, SLC38A5, SLC38A6, SLC38A7, SLC38A8, SLC38A9, SLC38A10, SLC38A11, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14, SLC40A1, SLC41A1, SLC41A2, SLC41A3, RhAG, RhBG, RhCG, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, HCP-1, MFSD5, MFSD10, SLC50A1, OSTα, OSTβ, SLC52A1, SLC52A2, and SLC52A3.

In specific aspects, the methods provided herein are effective at producing antibodies against target proteins that are transmembrane proteins, such as transmembrane receptors, and target proteins that are difficult to raise antibodies against or that are difficult to express, for example, those that are difficult due to cytotoxicity, yield, solubility, aggregation and/or stability issues.

In certain aspects, target proteins (e.g., human target proteins) described herein include integral membrane proteins (IMPs), which are classified as Type I, type II, single-anchor type II, C-terminal anchor, and polytopic (e.g., see Ott and Lingappa, 2002, J. Cell Sci., 115(Pt 10):2003-2009). In specific aspects, target proteins (e.g., human target proteins) described herein are single pass transmembrane proteins. In specific aspects, target proteins (e.g., human target proteins) described herein are multi-pass transmembrane proteins.

G Protein Coupled Receptor (GPCR):

In specific aspects, complexes for use in the methods provided herein comprise a lipid and a polynucleotide (e.g., mRNA) encoding a target protein, wherein the target protein (e.g., human target protein) is a GPCR (e.g., human GPCR). GPCRs, also known as seven-transmembrane (7TM) domain receptors and G protein-linked receptors (GPLR). The two main signal transduction pathways involving GPCRs are the cAMP signal pathway and the phosphatidylinositol signal pathway.

Classes of GPCRs include class A (Rhodopsin-like), B (Secretin receptor family), C (Metabotropic glutamate/pheromone), D (Fungal mating pheromone receptors), E (Cyclic AMP receptors) and F (Frizzled/Smoothened).

Non-limiting examples of target proteins which are GPCRs (Class A, B, C, Class Frizzled, and other 7 transmembrane proteins) include:

ACKR1, ACKR2, ACKR3, ACKR4, ADCYAP1R1, ADGRA1, ADGRA2, ADGRA3, ADGRB1, ADGRB2, ADGRB3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADORA1, ADORA2A, ADORA2B, ADORA3, ADRA1A, ADRA1B, ADRA1D, ADRA2A, ADRA2B, ADRA2C, ADRB1, ADRB2, ADRB3, AGTR1, AGTR2, APLNR/APJ, AVPR1A, AVPR1B, AVPR2, BDKRB1, BDKRB2, BRS3, BRS3, C3AR1, C5AR1, C5AR2, CALCR, CALCRL, CASR, CCKAR, CCKBR, CCR1, CCR10, CCR2, CCR3, CCR4, CCR5, CCR6, CCR7, CCR8, CCR9, CCRL2, CELSR1, CELSR2, CELSR3, CHRM1, CHRM2, CHRM3, CHRM4, CHRM5, CMKLR1, CNR1, CNR2, CRHR1, CRHR2, CX3CR1, CXCR1, CXCR2, CXCR3, CXCR4, CXCR5, CXCR6, CYSLTR1, CYSLTR2, DRD1, DRD2, DRD3, DRD4, DRD5, EDNRA, EDNRB, F2R, F2RL1, F2RL2, F2RL3, FFAR1, FFAR2, FFAR3, FFAR4, FPR1, FPR2, FPR2, FPR3, FSHR, FZD1, FZD10, FZD2, FZD3, FZD4, FZD5, FZD6, FZD7, FZD8, FZD9, GABBR1, GABBR2, GALR1, GALR2, GALR3, GCGR, GHRHR, GHSR, GIPR, GLP1R, GLP2R, GNRHR, GNRHR2, GPBAR1, GPER1, GPR1, GPR4, GPR12, GPR15, GPR17, GPR18, GPR19, GPR20, GPR21, GPR22, GPR25, GPR26, GPR27, GPR3, GPR31, GPR32, GPR33, GPR34, GPR35, GPR37, GPR37L1, GPR39, GPR40, GPR42, GPR42, GPR45, GPR50, GPR52, GPR55, GPR6, GPR61, GPR62, GPR63, GPR65, GPR68, GPR75, GPR78, GPR79, GPR82, GPR83, GPR84, GPR85, GPR87, GPR88, GPR101, GPR107, GPR132, GPR135, GPR137, GPR139, GPR141, GPR142, GPR143, GPR146, GPR148, GPR149, GPR15, GPR150, GPR151, GPR152, GPR153, GPR156, GPR157, GPR158, GPR160, GPR161, GPR162, GPR171, GPR173, GPR174, GPR176, GPR179, GPR182, GPR183, GPRC5A, GPRC5B, GPRC5C, GPRC5D, GPRC6A, GRM1, GRM2, GRM3, GRM4, GRM5, GRM6, GRM7, GRM8, GRPR, HCAR1, HCAR2, HCAR3, HCRTR1, HCRTR2, HRH1, HRH2, HRH3, HRH4, HTR1A, HTR1B, HTR1D, HTR1E, HTR1F, HTR2A, HTR2B, HTR2C, HTR4, HTR5A, HTR5BP, HTR6, HTR7, KISS1R, LGR4, LGR5, LGR6, LHCGR, LPAR1, LPAR2, LPAR3, LPAR4, LPAR5, LPAR6, LTB4R, LTB4R2, MAS1, MAS1L, MC1R, MC2R, MC3R, MC4R, MC5R, MCHR1, MCHR2, MLNR, MRGPRD, MRGPRE, MRGPRF, MRGPRG, MRGPRX1, MRGPRX2, MRGPRX3, MRGPRX4, MTNR1A, MTNR1B, NMBR, NMUR1, NMUR2, NPBWR1, NPBWR2, NPFFR1, NPFFR2, NPSR1, NPY1R, NPY2R, NPY4R, NPY5R, NPY6R, NTSR1, NTSR2, OPN3, OPN4, OPN5, OPRD1, OPRK1, OPRL1, OPRM1, OR51E1, OXER1, OXGR1, OXTR, P2RY1, P2RY10, P2RY11, P2RY12, P2RY13, P2RY14, P2RY2, P2RY4, P2RY6, P2RY8, PRLHR, PROKR1, PROKR2, PTAFR, PTGDR, PTGDR2, PTGER1, PTGER2, PTGER3, PTGER4, PTGFR, PTGIR, PTH1R, PTH2R, QRFPR, RXFP1, RXFP2, RXFP3, RXFP4, S1PR1, S1PR2, S1PR3, S1PR4, S1PR5, SCTR, SMO, SSTR1, SSTR2, SSTR3, SSTR4, SSTR5, SUCNR1, TAAR1, TAAR2, TAAR3, TAAR4P, TAAR5, TAAR6, TAAR8, TAAR9, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TBXA2R, TPRA1, TRHR, TSHR, UTS2R, VIPR1, VIPR2, and XCR1.

Transmembrane and Membrane-Associated Immune Receptors:

In specific aspects, complexes for use in the methods provided herein comprise a lipid and a polynucleotide (e.g., mRNA) encoding a target protein, wherein the target protein is an immune receptor, such as pattern recognition receptors (PRRs), Toll-like receptors (TLRs), killer activated and killer inhibitor receptors (KARs and KIRs), complement receptors, Fc receptors, B cell receptors and T cell receptors (e.g., TCR-α, TCR-β, CD3, ζ-chain accessory, CD4, and CD8), and major histocompatibility complexes.

Non-limiting examples of pattern recognition receptors (PRRs) include mannose receptor (MR), asialoglycoprotein receptor family (e.g., asialoglycoprotein receptor macrophage galactose-type lectin (MGL)), DC-SIGN (CLEC4L), langerin (CLEC4K), myeloid DAP12-associating lectin (MDL)-1 (CLEC5A), dectin 1/CLEC7A, DNGR1/CLEC9A, Myeloid C-type lectin-like receptor (MICL) (CLEC12A), CLEC2 (also called CLEC1B), CLEC12B, and DC immunoreceptor (DCIR) subfamily (e.g., DCIR/CLEC4A, Dectin 2/CLEC6A, Blood DC antigen 2 (BDCA2) (CLEC4C), and macrophage-inducible C-type lectin (CLEC4E)).

In specific aspects, complexes for use in the methods provided herein comprise a lipid and a polynucleotide (e.g., mRNA) encoding a target protein, wherein the target protein is a Toll-like receptor (TLR). TLRs are a class of proteins that play a key role in the innate immune system. They are single, membrane-spanning, non-catalytic receptors usually expressed in cells such as macrophages and dendritic cells that recognize structurally conserved molecules derived from microbes, and activate immune cell responses. Non-limiting examples of TLRs include TLR1, TLR2, TLR3, TLR4, TLR5, TLR6, TLR7, TLR8, TLR9, TLR10, TLR11, TLR12, and TLR13.

Non-limiting examples of Fc receptors (e.g., Fc-gamma receptors, Fc-alpha receptors, and Fc-epsilon receptors) include polymeric immunoglobulin receptor (pIgR), FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαR1 (CD89), Fcα/μR, and FcRn.

In specific aspects, complexes for use in the methods provided herein comprise a lipid and a polynucleotide (e.g., mRNA) encoding a target protein, wherein the target protein is an immune receptor selected from the following: CD27, CD40, OX40, GITR, CD137, PD-1, CTLA-4, PD-L1, TIGIT, T-cell immunoglobulin domain and mucin domain 3 (TIM3), V-domain Ig suppressor of T cell activation (VISTA), CD28, CD122, ICOS, A2AR, B7-H3, B7-H4, B and T lymphocyte attenuator (BTLA), Indoleamine 2,3-dioxygenase (IDO), killer-cell immunoglobulin-like receptor (KIR), and lymphocyte activation gene-3 (LAGS).

In specific aspects, complexes for use in the methods provided herein comprise a lipid and a polynucleotide (e.g., mRNA) encoding a target protein, wherein the target protein is a part of the major histocompatibility complex I or II (MHC I or II) or MHC in complex with a peptide fragment. MHC proteins are a part of the acquired immune system and play a role in the presentation of processed peptide fragments to T cells and eliciting humoral immune system activation. Non-limiting examples of MHC proteins include HLA-A, HLA-B, HLA-C, HLA-DPA1, HLA-DPB1, HLA-DQA1, HLA-DQB1, HLA-DRA, and HLA-DRB1.

Cytokine Receptors:

In specific aspects, complexes for use in the methods provided herein comprise a lipid and a polynucleotide (e.g., mRNA) encoding a target protein, wherein the target protein is a cytokine receptor (e.g., interleukin (IL) receptor or fibroblast growth factor (FGF) receptors). Non-limiting examples of cytokine receptors include receptors for nerve growth factor (NGF), myostatin (GDF-8), growth differentiation factors (GDFs), granulocyte-macrophage colony-stimulating factor (GM-CSF), granulocyte colony-stimulating factor (G-CSF), platelet derived growth factors (PDGF), erythropoietin (EPO), thrombopoietin (TPO), Epidermal growth factor (EGF), fibroblast growth factors (FGF), vascular endothelial growth factors (VEGF), tissue inhibitor or metalloproteinase (TIMP), matrix metalloproteinases (MMPs), macrophage stimulating factor (MSF), ciliary neurotrophic factor (CNTF), cardiotrophin, oncostatin M, leukemia inhibitory factor (LIF), transforming growth factor (TGF)-alpha and -beta, interferon (IFN)-beta and -gamma, and tumor necrosis factor (TNF) alpha. In a specific embodiment, complexes for use in the methods provided herein comprising a lipid and a polynucleotide (e.g., mRNA) encoding a target protein, wherein the target protein is gp130, which is a shared receptor utilized by several related cytokines, including IL-6, IL-11, IL-27, Leukemia Inhibitory Factor (LIF), Oncostatin M (OSM), Ciliary Neurotrophic Factor (CNTF), Cardiotrophin 1 (CT-1) and Cardiotrophin-like Cytokine (CLC).

In specific aspects, complexes for use in the methods provided herein comprise a lipid and a polynucleotide (e.g., mRNA) encoding a target protein, wherein the target protein is an interleukin (IL) receptor. Non-limiting examples of IL receptors include IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, and IL-36 receptor.

In specific aspects, complexes for use in the methods provided herein comprise a lipid and a polynucleotide (e.g., mRNA) encoding a target protein, wherein the target protein is a fibroblast growth factor (FGF) receptor (FGFR). Non-limiting examples of FGF receptors include FGFR1, FGFR2, FGFR3, and FGFR4.

In specific aspects, complexes for use in the methods provided herein comprise a lipid and a polynucleotide (e.g., mRNA) encoding a target protein, wherein the target protein is a tumor necrosis factor receptor superfamily (TNFRSF) member. Non-limiting examples of TNFRSF members include TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, and TNFRSF27.

Ion Channels:

In specific aspects, complexes for use in the methods provided herein comprise a lipid and a polynucleotide (e.g., mRNA) encoding a target protein, wherein the target protein is an ion channel.

There are over 300 types of ion channels, and they can be classified by the nature of their gating, the species of ions passing through those gates, the number of gates (pores) and localization of proteins. For example, voltage-gated ion channels include, but are not limited to, voltage-gated sodium channels, voltage-gated calcium channels, voltage-gated potassium channels ($K_v$), hyperpolarization-activated cyclic nucleotide-gated channels, voltage-gated proton channels. Ligand-gated ion channels, include, but are not limited to, cation-permeable “nicotinic” Acetylcholine receptor, ionotropic glutamate-gated receptors and ATP-gated P2X receptors, and the anion-permeable γ-aminobutyric acid-gated GABA receptor. Classification of ion channels by type of ions include, but are not limited to, chloride channels, potassium channels (e.g., ATP-sensitive potassium ion channels), sodium channels (e.g., NaVs, ENaCs, CaVs), calcium channels, proton channels, and non-selective cation channels.

Non-limiting examples of voltage-gated sodium channels include SCN1A, SCN1B, SCN2A, SCN2B, SCN3A, SCN3B, SCN4A, SCN5A, SCN7A, SCN8A, SCN9A, SCN10A and SCN11A.

Non-limiting examples of voltage-gated calcium channels include CACNA1A, CACNA1B, CACNA1C, CACNA1D, CACNA1E, CACNA1F, CACNA1G, CACNA1H, CACNA1I and CACNA1S.

Non-limiting examples of transient receptor potential cation channels include TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, MCOLN1, MCOLN2, MCOLN3, PKD1, PKD2, PKD2L1, PKD2L2, TRPV1, TRPV2, TRPV3, TRPV4, TRPV5 and TRPV6.

Non-limiting examples of CatSper channels include CATSPER1, CATSPER2, CATSPER3 and CATSPER4.

Non-limiting examples of two-pore channels include TPCN1 and TPCN2.

Non-limiting examples of cyclic nucleotide-regulated channels include CNGA1, CNGA2, CNGA3, CNGA4, CNGB1, CNGB3, HCN1, HCN2, HCN3 and HCN4.

Non-limiting examples of calcium-activated Potassium channels include KCNMA1, KCNN1, KCNN2, KCNN3, KCNN4, KCNT1, KCNT2, and KCNU1.

Non-limiting examples of voltage-gated Potassium channels include KCNA1, KCNA2, KCNA3, KCNA4, KCNA5, KCNA6, KCNA7, KCNA10, KCNB1, KCNB2, KCNC1, KCNC2, KCNC3, KCNC4, KCND1, KCND2, KCND3, KCNF1, KCNG1, KCNG2, KCNG3, KCNG4, KCNH1, KCNH2, KCNH3, KCNH4, KCNH5, KCNH6, KCNH7, KCNH8, KCNQ1, KCNA2, KCNA3, KCNA4, KCNA5, KCNS1, KCNS2, KCNS3, KCNV1 and KCNV2.

Non-limiting examples of inwardly rectifying Potassium channels include KCNJ1, KCNJ2, KCNJ3, KCNJ4, KCNJ5, KCNJ6, KCNJ8, KCNJ9, KCNJ10, KCNJ11, KCNJ12, KCNJ13, KCNJ14, KCNJ15, KCNJ16 and KCNJ18.

Non-limiting examples of two-P Potassium channels include KCNK1, KCNK2, KCNK3, KCNK4, KCNK5, KCNK6, KCNK7, KCNK9, KCNK10, KCNK12, KCNK13, KCNK15, KCNK16, KCNK17 and KCNK18.

Non-limiting examples of Hydrogen voltage-gated ion channels include HVCN1.

Non-limiting examples of ionotropic 5-HT (serotonin) receptors include HTR3A, HTR3B, HTR3C, HTR3D and HTR3E.

Non-limiting examples of nicotinic acetylcholine receptors include CHRNA1, CHRNA2, CHRNA3, CHRNA4, CHRNA5, CHRNA6, CHRNA7, CHRNA9, CHRNA10, CHRNB1, CHRNB2, CHRNB3, CHRNB4, CHRND, CHRNE and CHRNG.

Non-limiting examples of GABA(A) receptors include GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2 and GABRR3.

Non-limiting examples of ionotropic Glutamate receptors include GRIA1, GRIA2, GRIA3, GRIA4, GRID1, GRID2, GRIK1, GRIK2, GRIK3, GRIK4, GRIK5, GRIN1, GRIN2A GRIN2B, GRIN2C, GRIN2D, GRIN3A and GRIN3B.

Non-limiting examples of Glycine receptors include GLRA1, GLRA2, GLRA3 and GLRA4

Non-limiting examples of ionotropic Purinergic receptors include P2RX1, P2RX2, P2RX3, P2RX4, P2RX5, P2RX6 and P2RX7.

Non-limiting examples of Zinc-activated channels include ZACN.

Non-limiting examples of Acid-sensing (proton-gated) ion channels include ASIC1, ASIC2, ASIC3, ASIC4.

Non-limiting examples of Aquaporins include AQP1, AQP2, AQP3, AQP4, AQP5, AQP6, AQP7, AQP8, AQP9, AQP10, AQP11, AQP12A, AQP12B and MIP.

Non-limiting examples of voltage-sensitive Chloride channels include CLCN1, CLCN2, CLCN3, CLCN4, CLCN5, CLCN6, CLCN7, CLCNKA and CLCNKB.

Non-limiting examples of Cystic fibrosis transmembrane conductance regulators include CFTR.

Non-limiting examples of Calcium activated chloride channels (CaCC) include ANO1, ANO2, ANO3, ANO4, ANO5, ANO6, ANO7, ANO8, ANO9, ANO10, BEST1, BEST2, BEST3 and BEST4.

Non-limiting examples of Chloride intracelluar channels include CLIC1, CLIC2, CLIC3, CLIC4, CLIC5 and CLIC6.

Non-limiting examples of Gap junction proteins (connexins) include GJA1, GJA3, GJA4, GJA5, GJA6P, GJA8, GJA9, GJA10, GJB1, GJB2, GJB3, GJB4, GJB5, GJB6, GJB7, GJC1, GJC2, GJC3, GJD2, GJD3, GJD4 and GJE1.

Non-limiting examples of IP3 receptors include ITPR1, ITPR2 and ITPR3.

Non-limiting examples of Pannexins include PANX1, PANX2 and PANX3.

Non-limiting examples of Ryanodine receptors include RYR1, RYR2 and RYR3.

A non-limiting example of non-selective Sodium leak channels includes NALCN.

Non-limiting examples of nonvoltage-gated Sodium channels include SCNN1A, SCNN1B, SCNN1 D and SCNN1G.

Solute Carrier Proteins:

In specific aspects, complexes for use in the methods provided herein comprise a lipid and a polynucleotide (e.g., mRNA) encoding a target protein, wherein the target protein is a solute carrier. Solute carrier proteins are integral membrane proteins that are characterized by their ability to transport a solute from one side of the lipid membrane to the other. This group of proteins includes secondary active transporters, which translocate solutes against an electrochemical gradient, and facilitative transporters, which translocate solutes in the direction of their electrochemical gradient. Solute carriers are organized into 52 families which encompass over 300 proteins. The 52 families and non-limiting example members thereof are indicated below:

(1) The high-affinity glutamate and neutral amino acid transporter family, non-limiting examples include: SLC1A1, SLC1A2, SLC1A3, SLC1A4, SLC1A5, SLC1A6, and SLC1A7;

(2) The facilitative glucose (GLUT) transporter family, non-limiting examples include: SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, and SLC2A14;

(3) The heavy subunits of heterodimeric amino acid family, non-limiting examples include: SLC3A1, and SLC3A2;

(4) The bicarbonate family. Examples include: SLC4A1, SLC4A2, SLC4A3, SLC4A4, SLC4A5, SLC4A6, SLC4A7, SLC4A8, SLC4A9, SLC4A10, and SLC4A11;

(5) The sodium glucose cotransporter family. Examples include: SLC5A1, SLC5A2, SLC5A3, SLC5A4, SLC5A5, SLC5A6, SLC5A7, SLC5A8, SLC5A9, SLC5A10, SLC5A11, and SLC5A12;

(6) The sodium- and chloride-dependent sodium:neurotransmitter symporter family. Examples include: SLC6A1, SLC6A2, SLC6A3, SLC6A4, SLC6A5, SLC6A6, SLC6A7, SLC6A8, SLC6A9, SLC6A10, SLC6A11, SLC6A12, SLC6A13, SLC6A14, SLC6A15, SLC6A16, SLC6A17, SLC6A18, SLC6A19, and SLC6A20;

(7) The cationic amino acid transporter/glycoprotein-associated family, non-limiting examples include: (i) cationic amino acid transporters (SLC7A1, SLC7A2, SLC7A3, SLC7A4) and (ii) glycoprotein-associated/light or catalytic subunits of heterodimeric amino acid transporters (SLC7A5, SLC7A6, SLC7A7, SLC7A8, SLC7A9, SLC7A10, SLC7A11, SLC7A13, SLC7A14);

(8) The Na+/Ca2+ exchanger family, non-limiting examples include: SLC8A1, SLC8A2, and SLC8A3;

(9) The Na+/H+ exchanger family, non-limiting examples include: SLC9A1, SLC9A2, SLC9A3, SLC9A4, SLC9A5, SLC9A6, SLC9A7, SLC9A8, SLC9A9, SLC9A10, SLC9A11, SLC9B1, and SLC9B2;

(10) The sodium bile salt cotransport family, non-limiting examples include: SLC10A1, SLC10A2, SLC10A3, SLC10A4, SLC10A5, SLC10A6, and SLC10A7;

(11) The proton coupled metal ion transporter family, non-limiting examples include: SLC11A1 and SLC11A2;

(12) The electroneutral cation-Cl cotransporter family, non-limiting examples include: SLC12A1, SLC12A1, SLC12A2, SLC12A3, SLC12A4, SLC12A5, SLC12A6, SLC12A7, SLC12A8, and SLC12A9;

(13) The Na+-SO42−/carboxylate cotransporter family; non-limiting examples include: SLC13A1, SLC13A2, SLC13A3, SLC13A4, and SLC13A5;

(14) The urea transporter family, non-limiting examples include: SLC14A1 and SLC14A2;

(15) The proton oligopeptide cotransporter family, non-limiting examples include: SLC15A1, SLC15A2, SLC15A3, and SLC15A4;

(16) The monocarboxylate transporter family, non-limiting examples include: SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, and SLC16A14;

(17) The vesicular glutamate transporter family, non-limiting examples include: SLC17A1, SLC17A2, SLC17A3, SLC17A4, SLC17A5, SLC17A6, SLC17A7, SLC17A8, and SLC17A9;

(18) The vesicular amine transporter family, non-limiting examples include: SLC18A1, SLC18A2, and SLC18A3;

(19) The folate/thiamine transporter family, non-limiting examples include: SLC19A1, SLC19A2, and SLC19A3;

(20) The type III Na+-phosphate cotransporter family, non-limiting examples include: SLC20A1 and SLC20A2;

(21) The organic anion transporter family; non-limiting examples include: (i) subfamily 1 SLCO1A2, SLCO1B1, SLCO1B3, and SLCO1C1; (ii) subfamily 2, SLCO2A1 and SLCO2B1; (iii) subfamily 3, SLCO3A1; (iv) subfamily 4, SLCO4A1, SLCO4C1; (v) subfamily 5, SLCO5A1; and (vi) subfamily 6, SLCO6A1;

(22) The organic cation/anion/zwitterion transporter family, non-limiting examples include: SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A18AS, SLC22A19, SLC22A20, SLC22A23, SLC22A24, SLC22A25, and SLC22A31.

(23) The Na+-dependent ascorbic acid transporter family, non-limiting examples include: SLC23A1, SLC23A2, SLC23A3, and SLC23A4.

(24) The Na+/(Ca2+-K+) exchanger family, non-limiting examples include: SLC24A1, SLC24A2, SLC24A3, SLC24A4, SLC24A5, and SLC24A6;

(25) The mitochondrial carrier family, non-limiting examples include: SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, and SLC25A46;

(26) The multifunctional anion exchanger family, non-limiting examples include: SLC26A1, SLC26A2, SLC26A3, SLC26A4, SLC26A5, SLC26A6, SLC26A7, SLC26A8, SLC26A9, SLC26A10, and SLC26A11;

(27) The fatty acid transport protein family, non-limiting examples include: SLC27A1, SLC27A2, SLC27A3, SLC27A4, SLC27A5, and SLC27A6;

(28) The Na+-coupled nucleoside transport family, non-limiting examples include: SLC28A1, SLC28A2, and SLC28A3;

(29) The facilitative nucleoside transporter family, non-limiting examples include: SLC29A1, SLC29A2, SLC29A3, and SLC29A4;

(30) The zinc efflux family, non-limiting examples include: SLC30A1, SLC30A2, SLC30A3, SLC30A4, SLC30A5, SLC30A6, SLC30A7, SLC30A8, SLC30A9, and SLC30A10;

(31) The copper transporter family, non-limiting examples include: SLC31A1 and SLC31A2;

(32) The vesicular inhibitory amino acid transporter family, a non-limiting example includes: SLC32A1.

(33) The acetyl-CoA transporter family, a non-limiting example includes: SLC33A1;

(34) The type II Na+-phosphate cotransporter family, non-limiting examples include: SLC34A1, SLC34A2, and SLC34A3;

(35) The nucleoside-sugar transporter family, non-limiting examples include: (i) subfamily A, SLC35A1, SLC35A2, SLC35A3, SLC35A4, SLC35A5; (ii) subfamily B, SLC35B1, SLC35B2, SLC35B3, SLC35B4; (iii) subfamily C, SLC35C1, SLC35C2; (iv) subfamily D, SLC35D1, SLC35D2, SLC35D3; (v) subfamily E, SLC35E1, SLC35E2, SLC35E3, SLC35E4; (vi) subfamily F, SLC35F1, SLC35F2, SLC35F3, SLC35F4, SLC35F5; (vii) subfamily G, SLC35G1, SLC35G3, SLC35G4, SLC35G5, SLC35G6;

(36) The proton-coupled amino acid transporter family, non-limiting examples include: SLC36A1, SLC36A2, SLC36A3, and SLC36A4;

(37) The sugar-phosphate/phosphate exchanger family, non-limiting examples include: SLC37A1, SLC37A2, SLC37A3, and SLC37A4;

(38) The system A & N, sodium-coupled neutral amino acid transporter family, non-limiting examples include: SLC38A1, SLC38A2, SLC38A3, SLC38A4, SLC38A5, SLC38A6, SLC38A7, SLC38A8, SLC38A9, SLC38A10, and SLC38A11;

(39) The metal ion transporter family, non-limiting examples include: SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, and SLC39A14;

(40) The basolateral iron transporter family, a non-limiting example includes: SLC40A1;

(41) The MgtE-like magnesium transporter family, non-limiting examples include: SLC41A1, SLC41A2, and SLC41A3;

(42) The ammonia transporter family, non-limiting examples include: RhAG, RhBG, and RhCG;

(43) The Na+-independent, system-L like amino acid transporter family; non-limiting examples include: SLC43A1, SLC43A2, and SLC43A3;

(44) The choline-like transporter family; non-limiting examples include: SLC44A1, SLC44A2, SLC44A3, SLC44A4, and SLC44A5;

(45) The putative sugar transporter family, non-limiting examples include: SLC45A1, SLC45A2, SLC45A3, and SLC45A4;

(46) The folate transporter family; non-limiting examples include: SLC46A1, SLC46A2, and SLC46A3;

(47) The multidrug and toxin extrusion family; non-limiting examples include: SLC47A1 and SLC47A2;

(48) The heme transporter family, a non-limiting example includes: HCP-1;

(49) Transporters of the major facilitator superfamily, non-limiting examples include MFSD5 and MFSD10;

(50) Sugar efflux transporters of the SWEET family, a non-limiting example includes SLC50A1;

(51) Transporters of steroid-derived molecules, non-limiting examples include OSTα and OSTβ;

(52) Riboflavin transporter family RFVT/SLC52, non-limiting examples include SLC52A1, SLC52A2, and SLC52A3.

Difficult to Express Target Proteins:

In specific aspects, conventional methods for producing antibodies, e.g., immunizing animals with a purified recombinant protein, may not be effective for difficult to express target proteins. Many factors can contribute to expression issues, such as cytotoxicity in host production cells, inherently poor biophysical properties (e.g., size, solubility, conformation, post-translational modifications (such as glycosylation) of the protein that proscribe overexpression/purification. Non-limiting examples of characteristics of difficult-to-express proteins include, but are not limited to, large proteins (e.g., proteins with a molecular weight 150 kDa), transmembrane proteins, proteins with unusual post translational modifications, or proteins with poor solubility, unstable proteins, secreted proteins that do not contain a signal peptide, membrane associated proteins, intrinsically disordered proteins and proteins with a short half-life.

Non-limiting examples of target proteins such as soluble target proteins, which may be difficult to express, for use in the methods provided herein include: ADAMTS7, ANGPTL3, ANGPTL4, ANGPTL8, LPL, GDF15, Galectin-1, Galectin-2, Galectin-3, matrix gla protein (MGP), PRNP, DGAT1, GPAT3, DMC1, BLM, and BRCA2.

Characteristics of difficult-to-express proteins can be assessed using methods described in the art, for example, solubility assays (e.g., dynamic light scattering, liquid chromatography mass spectrometry), stability assays (e.g., Differential scanning fluorimetry, Differential scanning calorimetry, circular dicroism), NMR, and chromatography. In certain aspects, a difficult-to-express protein may be more susceptible to aggregation (e.g., at least 5% aggregation, or at least 10% aggregation, or at least 20% aggregation, or at least 30% aggregation, or at least 40% aggregation, or at least 50% aggregation, or least 60% aggregation), for example, when kept in solution at room temperature or at 4° C. for a period of more than a week, more than several weeks, more than a month, more than several months (e.g., 3 months, 4 months or 5 months), or more than 6 months or 1 year.

In particular aspects, a difficult-to-express protein has a positive charge. In certain aspects, a difficult-to-express protein has a negative charge. In certain aspects, a difficult-to-express protein is hydrophobic.

In certain aspects, a difficult-to-express protein has a short half-life, for example, a half-life of less than 24 hours, less than 20 hours, less than 15 hours, less than 12 hours, less than 10 hours, less than 8 hours, less than 6 hours, less than 4 hours, less than 2 hours, or less than 1 hour.

In certain embodiments, target proteins described herein include positively charged proteins, negatively charged proteins, hydrophobic proteins, and glycoproteins.

In certain embodiments, target proteins described herein include enzymes, such as secreted and membrane associated enzymes.

II. Cationic Liposomes

Any of the cationic lipids known in the prior art may be employed in the practice of the claimed invention. See, for example, Feigner et al. (*Proc. Natl. Acad. Sci. U.S.A.* 84:7413-7417 (1987)); Feigner et al. (*Focus* 11:21-25 (1989)); Feigner ("Cationic Liposome-Mediated Transfection with Lipofectin™ Reagent," in *Gene Transfer and Expression Protocols Vol.* 7, Murray, E. J., Ed., Humana Press, New Jersey, pp. 81-89 (1991)); WO 91/17424; WO 91/16024; U.S. Pat. Nos. 4,897,355; 4,946,787; 5,049,386; 5,208,036; Behr et al. (*Proc. Natl. Acad. Sci. USA* 86:6982-6986 (1989); EPO Publication 0 394 111); Gao et al. (*Biochim. Biophys. Res. Comm.* 179:280-285 (1991)); Zhou et al., (*Biochim. Biophys. Res. Comm.* 165:8-14 (1991)); and Gebeychu et al. (co-owned U.S. application Ser. No. 07/937,508; filed Aug. 28, 1992), the contents of which are fully incorporated by reference.

Other non-limiting examples of lipids (e.g., cationic lipids, neutral lipids, helper lipids, and stealth lipids) which can be used in the methods and compositions provided herein include those described in WO2016/037053, WO2016/010840, WO2015/095346, WO2015/095340, WO2016/037053, WO2014/136086, and WO2011/076807, each of which is hereby incorporated by reference in its entirety. In a specific aspect, cationic lipids suitable for the methods described herein include Lipid A, Lipid B, and Lipid C having the following chemical structure (which are described in more detail in WO2015/095346 and WO2015/095340):

Chemical structure of Lipid A

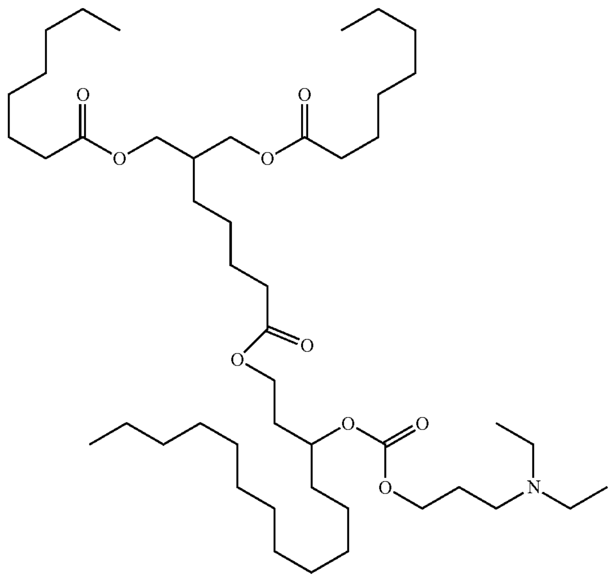

Chemical structure Lipid B

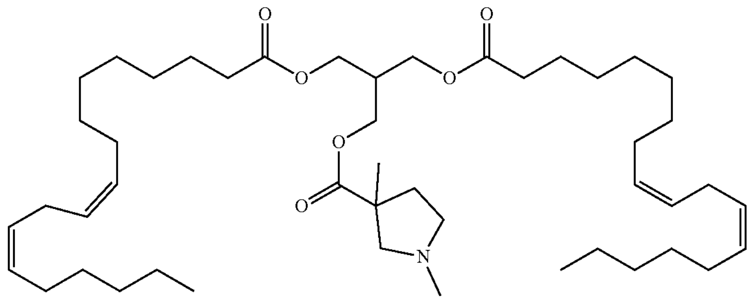

Chemical structure Lipid C

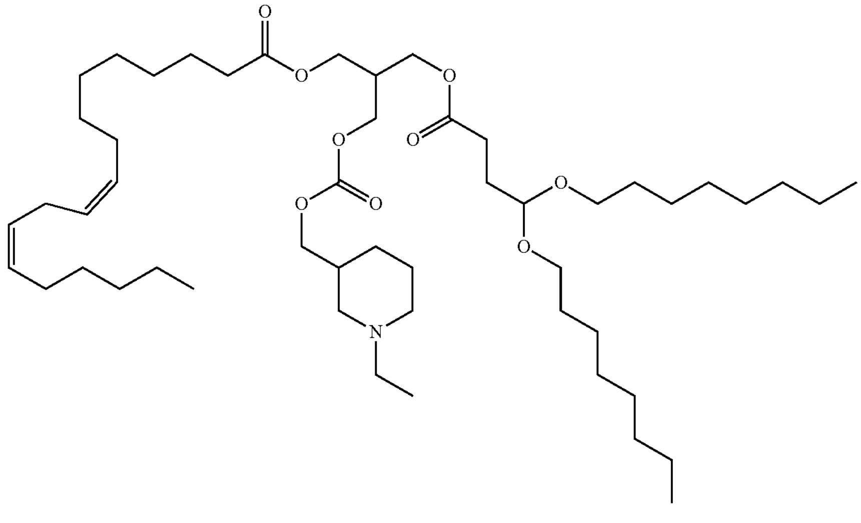

In certain aspects, cationic lipids for the compositions and methods described herein include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment, the cationic lipid for the compositions and methods provided herein is DOTAP or DLTAP.

In specific embodiments, cationic lipids for the compositions and methods described herein include N-[1-(2,3-dioleoyloxy)propyl]-N,N,N-trimethylammonium chloride (DOTMA). DOTMA, alone or in a 1:1 combination with dioleoylphosphatidylethanolamine (DOPE) can be formulated into liposomes using standard techniques. A DOTMA: DOPE (1:1) formulation is sold under the name LIPOFECTIN™ (GIBCO/BRL: Life Technologies, Inc., Gaithersburg, Md.). In a particular embodiment, a commercially available cationic lipid is 1,2-bis(oleoyloxy)-3-3-(trimethylammonia)propane (DOTAP), which differs from DOTMA in that the oleoyl moieties are linked via ester bonds, not ether bonds, to the propylamine.

In particular embodiments, a related group of cationic lipids for the compositions and methods described herein differ from DOTMA and DOTAP in that one of the methyl groups of the trimethylammonium group is replaced by a hydroxyethyl group. Compounds of this type are similar to the Rosenthal Inhibitor of phospholipase A (Rosenthal et al., supra), which has stearoyl esters linked to the propylamine core. The dioleoyl analogs of the Rosenthal Inhibitor (RI) are commonly abbreviated as DORI-ether and DORI-ester, depending upon the linkage of the fatty acid moieties to the propylamine core. The hydroxy group can be used as a site for further functionalization, for example, by esterification to carboxyspermine.

In certain embodiments, another class of cationic lipids for the compositions and methods described herein include, carboxyspermine that has been conjugated to two types of lipids, resulting in 5-carboxylspermylglycine dioctadecylamide (DOGS). DOGS is available commercially as TRANSFECTAM™ (Promega, Madison, Wis.).

Another class of known compounds has been described by Behr et al. (*Proc. Natl. Acad. Sci. USA* 86:6982-6986 (1989); EPO Publication 0 394 111), in which carboxyspermine has been conjugated to two types of lipids, resulting in dipalmitoylphosphatidylethanolamine 5-carboxyspermylamide (DDPES).

In specific aspects, another cationic lipid for the compositions and methods described herein is a cholesterol derivative (DC-Chol) which has been synthesized and formulated into liposomes in combination with DOPE. In another specific embodiment, a cationic lipid for the compositions and methods described herein is lipopolylysine, which is formed by conjugating polylysine to DOPE.

Further non-limiting examples of cationic lipids for the compositions and methods provided herein include the following, as well as those described in WO2015/095346: 2-(10-dodecyl-3-ethyl-8,14-dioxo-7,9,13-trioxa-3-azaoctadecan-18-yl)propane-1,3-diyl dioctanoate; 2-(9-dodecyl-2-methyl-7,13-dioxo-6,8,12-trioxa-2-azaheptadecan-17-yl) propane-1,3-diyl dioctanoate; 2-(9-dodecyl-2-methyl-7,13-dioxo-6,8,12-trioxa-2-azapentadecan-15-yl)propane-1,3-diyl dioctanoate; 2-(10-dodecyl-3-ethyl-8,14-dioxo-7,9,13-trioxa-3-azahexadecan-16-yl)propane-1,3-diyl dioctanoate; 2-(8-dodecyl-2-methyl-6,12-dioxo-5,7,11-trioxa-2-azaheptadecan-17-yl)propane-1,3-diyl dioctanoate; 2-(10-dodecyl-3-ethyl-8,14-dioxo-7,9,13-trioxa-3-azanonadecan-19-yl) propane-1,3-diyl dioctanoate; 2-(9-dodecyl-2-methyl-7,13-dioxo-6,8,12-trioxa-2-azaoctadecan-18-yl)propane-1,3-diyl dioctanoate; 2-(8-dodecyl-2-methyl-6,12-dioxo-5,7,11-trioxa-2-azaoctadecan-18-yl)propane-1,3-diyl dioctanoate; 2-(10-dodecyl-3-ethyl-8,14-dioxo-7,9,13-trioxa-3-azaicosan-20-yl)propane-1,3-diyl dioctanoate; 2-(9-dodecyl-2-methyl-7,13-dioxo-6,8,12-trioxa-2-azanonadecan-19-yl) propane-1,3-diyl dioctanoate; 3-(((3-(diethylamino) propoxy)carbonyl)oxy)pentadecyl 4,4-bis(octyloxy) butanoate; 3-(((3-(diethylamino)propoxy)carbonyl)oxy) pentadecyl 4,4-bis((2-ethylhexyl)oxy)butanoate; 3-(((3-(diethylamino)propoxy)carbonyl)oxy)pentadecyl 4,4-bis ((2-propylpentyl)oxy)butanoate; 3-(((3-(ethyl(methyl) amino)propoxy)carbonyl)oxy)pentadecyl 4,4-bis((2-propylpentyl)oxy)butanoate; 3-(((3-(dimethylamino) propoxy)carbonyl)oxy)pentadecyl 4,4-bis((2-propylpentyl) oxy)butanoate; 3-(((3-(diethylamino)propoxy)carbonyl) oxy)pentadecyl 6,6-bis(octyloxy)hexanoate; 3-(((3-(diethylamino)propoxy)carbonyl)oxy)pentadecyl 6,6-bis (hexyloxy)hexanoate; 3-(((3-(diethylamino)propoxy) carbonyl)oxy)pentadecyl 6,6-bis((2-ethylhexyl)oxy) hexanoate; 3-(((3-(diethylamino)propoxy)carbonyl)oxy) pentadecyl 8,8-bis(hexyloxy)octanoate; 3-(((3-(diethylamino)propoxy)carbonyl)oxy)pentadecyl 8,8-dibutoxyoctanoate; 3-(((3-(diethylamino)propoxy)carbonyl) oxy)pentadecyl 8,8-bis((2-propylpentyl)oxy)octanoate; 3-(((3-(ethyl(methyl)amino)propoxy)carbonyl)oxy)pentadecyl 8,8-bis((2-propylpentyl)oxy)octanoate; 3-(((3-(dimethylamino)propoxy)carbonyl)oxy)pentadecyl 8,8-bis((2-propylpentyl)oxy)octanoate; 3-(((3-(dimethylamino) propoxy)carbonyl)oxy)pentadecyl 3-octylundecanoate; 3-(((3-(dimethylamino)propoxy)carbonyl)oxy)pentadecyl 3-octylundec-2-enoate; 3-(((3-(dimethylamino)propoxy) carbonyl)oxy)pentadecyl 7-hexyltridec-6-enoate; 3-(((3-(dimethylamino)propoxy)carbonyl)oxy)pentadecyl 9-pentyltetradecanoate; 3-(((3-(dimethylamino)propoxy) carbonyl)oxy)pentadecyl 9-pentyltetradec-8-enoate; 3-(((3-(dimethylamino)propoxy)carbonyl)oxy)pentadecyl 5-heptyldodecanoate; 3-(((3-(dimethylamino)propoxy)carbonyl)oxy)tridecyl 5-heptyldodecanoate; 3-(((3-(dimethylamino)propoxy)carbonyl)oxy)undecyl 5-heptyldodecanoate; 1,3-bis(octanoyloxy)propan-2-yl (3-(((2-(dimethylamino)ethoxy)carbonyl)oxy)pentadecyl) succinate; 1,3-bis(octanoyloxy)propan-2-yl (3-(((3-(dimethylamino)propoxy)carbonyl)oxy)pentadecyl) succinate; 1-(3-(((3-(dimethylamino)propoxy)carbonyl)oxy)pentadecyl) 10-octyl decanedioate; 1-(3-(((3-(diethylamino)propoxy) carbonyl)oxy)pentadecyl) 10-octyl decanedioate; 1-(3-(((3-(ethyl(methyl)amino)propoxy)carbonyl)oxy)pentadecyl) 10-octyl decanedioate; 1-(3-(((3-(diethylamino)propoxy) carbonyl)oxy)pentadecyl) 10-(2-ethylhexyl) decanedioate; 1-(3-(((3-(ethyl(methyl)amino)propoxy)carbonyl)oxy)pentadecyl) 10-(2-ethylhexyl) decanedioate; 3-(((3-(dimethylamino)propoxy)carbonyl)oxy)pentadecyl 10-(octanoyloxy) decanoate; 8-dodecyl-2-methyl-6,12-dioxo-5,7,11-trioxa-2-azanonadecan-19-yl decanoate; 3-(((3-(diethylamino) propoxy)carbonyl)oxy)pentadecyl 10-(octanoyloxy) decanoate; 3-(((3-(ethyl(methyl)amino)propoxy)carbonyl) oxy)pentadecyl 10-(octanoyloxy)decanoate; (9Z,12Z)-3-(((3-(dimethylamino)propoxy)carbonyl)oxy) pentadecyloctadeca-9,12-dienoate; (9Z,12Z)-3-(((3-(diethylamino)propoxy)carbonyl)oxy)pentadecyl octadeca-9,12-dienoate; (9Z,12Z)-3-(((3-(ethyl(methyl)amino) propoxy)carbonyl)oxy)pentadecyl octadeca-9,12-dienoate; (9Z,12Z)-3-(((2-(dimethylamino)ethoxy)carbonyl)oxy)pentadecyl octadeca-9,12-dienoate; 1-((9Z,12Z)-octadeca-9,12-dienoyloxy)pentadecan-3-yl 1,4-dimethylpiperidine-4-carboxylate; 2-(((3-(diethylamino)propoxy)carbonyl)oxy) tetradecyl 4,4-bis((2-ethylhexyl)oxy)butanoate; (9Z,12Z)-(12Z,15Z)-3-((3-(dimethylamino)propanoyl)oxy)henicosa-12,15-dien-1-yl octadeca-9,12-dienoate; (12Z,15Z)-3-((4-(dimethylamino)butanoyl)oxy)henicosa-12,15-dien-1-yl 3-octylundecanoate; (12Z,15Z)-3-((4-(dimethylamino)butanoyl)oxy)henicosa-12,15-dien-1-yl 5-heptyldodecanoate; (12Z,15Z)-3-((4-(dimethylamino)butanoyl)oxy)henicosa-12,15-dien-1-yl 7-hexyltridecanoate; (12Z,15Z)-3-((4-(dimethylamino)butanoyl)oxy)henicosa-12,15-dien-1-yl 9-pentyltetradecanoate; (12Z,15Z)-1-((((9Z,12Z)-octadeca-9,12-dien-1-yloxy)carbonyl)oxy)henicosa-12,15-dien-3-yl 3-(dimethylamino)propanoate; (13Z,16Z)-4-(((2-(dimethylamino)ethoxy)carbonyl)oxy)docosa-13,16-dien-1-yl 2,2-bis (heptyloxy)acetate; (13Z,16Z)-4-(((3-(diethylamino) propoxy)carbonyl)oxy)docosa-13,16-dien-1-yl 2,2-bis (heptyloxy)acetate; 2,2-bis(heptyloxy)ethyl 3-((3-ethyl-10-((9Z,12Z)-octadeca-9,12-dien-1-yl)-8,15-dioxo-7,9,14-trioxa-3-azaheptadecan-17-yl)disulfanyl)propanoate; (13Z,16Z)-4-(((3-(dimethylamino)propoxy)carbonyl)oxy) docosa-13,16-dien-1-yl heptadecan-9-yl succinate; (9Z,12Z)-2-(((11Z,14Z)-2-((3-(dimethylamino)propanoyl)oxy) icosa-11,14-dien-1-yl)oxy)ethyl octadeca-9,12-dienoate; (9Z,12Z)-3-(((3-(dimethylamino)propoxy)carbonyl)oxy)-13-(octanoyloxy)tridecyl octadeca-9,12-dienoate; 3-(((3-(dimethylamino)propoxy)carbonyl)oxy)-13-(octanoyloxy) tridecyl 3-octylundecanoate; 3-(((3-(dimethylamino) propoxy)carbonyl)oxy)-13-hydroxytridecyl 5-heptyldodecanoate; 3-(((3-(dimethylamino)propoxy)carbonyl)oxy)-13-(octanoyloxy)tridecyl 5-heptyldodecanoate; 3-(((3-(dimethylamino)propoxy)carbonyl)oxy)-13-(octanoyloxy)tridecyl 7-hexyltridecanoate; 3-(((3-(dimethylamino)propoxy)carbonyl)oxy)-13-hydroxytridecyl 9-pentyltetradecanoate; 3-(((3-(dimethylamino)propoxy) carbonyl)oxy)-13-(octanoyloxy)tridecyl 9-pentyltetradecanoate; 1-(3-(((3-(dimethylamino)propoxy) carbonyl)oxy)-13-(octanoyloxy)tridecyl) 10-octyl decanedioate; 3-(((3-(dimethylamino)propoxy)carbonyl)oxy)-13-(octanoyloxy)tridecyl 10-(octanoyloxy)decanoate; (9Z,12Z)-3-(((3-(dimethylamino)propoxy)carbonyl)oxy)-5-octyltridecyl octadeca-9,12-dienoate; 3-(((3-(dimethylamino)propoxy)carbonyl)oxy)-5-octyltridecyl decanoate; 5-(((3-(dimethylamino)propoxy)carbonyl)oxy)-7-octylpentadecyl octanoate; (9Z,12Z)-5-(((3-(dimethylamino)propoxy)carbonyl)oxy)-7-octylpentadecyl octadeca-9,12-dienoate; 9-(((3-(dimethylamino)propoxy)carbonyl) oxy)-11-octylnonadecyl octanoate; 9-(((3-(dimethylamino) propoxy)carbonyl)oxy)-11-octylnonadecyl decanoate; (9Z,12Z)-9-(((3-(dimethylamino)propoxy)carbonyl)oxy) nonadecyl octadeca-9,12-dienoate; 9-(((3-(dimethylamino) propoxy)carbonyl)oxy)nonadecyl hexanoate; 9-(((3-(dimethylamino)propoxy)carbonyl)oxy)nonadecyl 3-octylundecanoate; 9-((4-(dimethylamino)butanoyl)oxy) nonadecyl hexanoate; 9-((4-(dimethylamino)butanoyl)oxy) nonadecyl 3-octylundecanoate; (9Z,9'Z,12Z,12'Z)-2-((4-(((3-(dimethylamino)propoxy)carbonyl)oxy)hexadecanoyl) oxy)propane-1,3-diyl bis(octadeca-9,12-dienoate); (9Z,9'Z,12Z,12'Z)-2-((4-(((3-(diethylamino)propoxy)carbonyl)oxy) hexadecanoyl)oxy)propane-1,3-diyl bis(octadeca-9,12-dienoate); (9Z,9'Z,12Z,12'Z,15Z,15'Z)-2-((4-(((3-(dimethylamino)propoxy)carbonyl)oxy) hexadecanoyl)oxy) propane-1,3-diyl bis(octadeca-9,12,15-trienoate); (Z)-2-((4-(((3-(dimethylamino)propoxy)carbonyl)oxy)hexadecanoyl) oxy)propane-1,3-diyl dioleate; 2-((4-(((3-(diethylamino) propoxy)carbonyl)oxy)hexadecanoyl)oxy)propane-1,3-diyl ditetradecanoate; 2-((4-(((3-(dimethylamino)propoxy)carbonyl)oxy)hexadecanoyl)oxy)propane-1,3-diyl ditetradecanoate; 2-((4-(((3-(ethyl(methyl)amino)propoxy)carbonyl) oxy)hexadecanoyl)oxy)propane-1,3-diyl ditetradecanoate; 2-((4-(((3-(dimethylamino)propoxy)carbonyl)oxy)hexadecanoyl)oxy)propane-1,3-diyl didodecanoate; 2-((4-(((3-(diethylamino)propoxy)carbonyl)oxy)hexadecanoyl)oxy)propane-1,3-diyl didodecanoate; 2-((4-(((3-(ethyl(methyl) amino)propoxy)carbonyl)oxy)hexadecanoyl)oxy)propane-1,3-diyl didodecanoate; 2-((4-(((3-(diethylamino)propoxy) carbonyl)oxy)hexadecanoyl)oxy)propane-1,3-diyl bis (decanoate); 2-((4-(((3-(ethyl(methyl)amino)propoxy) carbonyl)oxy)hexadecanoyl)oxy)propane-1,3-diyl bis (decanoate); 2-((4-(((3-(diethylamino)propoxy)carbonyl) oxy)hexadecanoyl)oxy)propane-1,3-diyl dioctanoate; 2-((4-(((3-(ethyl(methyl)amino)propoxy)carbonyl)oxy) hexadecanoyl)oxy)propane-1,3-diyl dioctanoate; 2-(((13Z,16Z)-4-(((3-(dimethylamino)propoxy)carbonyl)oxy) docosa-13,16-dienoyl)oxy)propane-1,3-diyl dioctanoate; 2-(((13Z,16Z)-4-(((3-(diethylamino)propoxy)carbonyl)oxy) docosa-13,16-dienoyl)oxy)propane-1,3-diyl dioctanoate; (9Z,9'Z,12Z,12'Z)-2-((2-(((3-(diethylamino)propoxy)carbonyl)oxy)tetradecanoyl)oxy)propane-1,3-diyl bis(octadeca-9,12-dienoate); (9Z,9'Z,12Z,12'Z)-2-((2-(((3-(dimethylamino) propoxy)carbonyl)oxy)dodecanoyl)oxy)propane-1,3-diyl bis(octadeca-9,12-dienoate); (9Z,9'Z,12Z,12'Z)-2-((2-(((3-(dimethylamino)propoxy)carbonyl)oxy)tetradecanoyl)oxy) propane-1.3-diyl bis(octadeca-9,12-dienoate); (9Z,9'Z,12Z,12'Z)-2-((2-(((3-(diethylamino)propoxy)carbonyl)oxy) dodecanoyl)oxy)propane-1,3-diyl bis(octadeca-9,12-dienoate); 2-((2-(((3-(diethylamino)propoxy)carbonyl)oxy) tetradecanoyl)oxy)propane-1,3-diyl dioctanoate; 4.4-bis (octyloxy)butyl 4-(((3-(dimethylamino)propoxy)carbonyl) oxy)hexadecanoate; 4,4-bis(octyloxy)butyl 2-(((3-(diethylamino)propoxy)carbonyl)oxy)dodecanoate; (9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yloctadeca-9,12-dienoate; 2-((4-(((3-(diethylamino)propoxy)carbonyl)oxy)-11-(octanoyloxy) undecanoyl)oxy)propane-1,3-diyl dioctanoate; (9Z,9'Z,12Z,12'Z)-2-(9-dodecyl-2-methyl-7,12-dioxo-6,8,13-trioxa-2-azatetradecan-14-yl)propane-1,3-diylbis(octadeca-9,12-dienoate); 3-(((3-(dimethylamino)propoxy)carbonyl)oxy) pentadecyl 4,4-bis(octyloxy)butanoate; 3-(((3-(piperidin-1-yl)propoxy)carbonyl)oxy)pentadecyl 6,6-bis(octyloxy) hexanoate; 3-(((3-(piperazin-1-yl)propoxy)carbonyl)oxy) pentadecyl 6,6-bis(octyloxy) hexanoate; 3-(((4-(diethylamino)butoxy)carbonyl)oxy)pentadecyl 6,6-bis (octyloxy)hexanoate; 3-(((3-(4-methylpiperazin-1-yl) propoxy)carbonyl)oxy)pentadecyl 6,6-bis(octyloxy) hexanoate; 3-((((1-methylpiperidin-4-yl)methoxy)carbonyl) oxy)pentadecyl 6,6-bis(octyloxy)hexanoate; 3-(((3-morpholinopropoxy)carbonyl)oxy)pentadecyl 6,6-bis (octyloxy)hexanoate; 3-(((2-(diethylamino)ethoxy) carbonyl)oxy)pentadecyl 6,6-bis(octyloxy)hexanoate; 3-(((3-(dimethylamino)propoxy)carbonyl)oxy)pentadecyl 6,6-bis(octyloxy)hexanoate; 3-(((3-(diethylamino)propoxy) carbonyl)oxy)pentadecyl 6,6-bis((2-propylpentyl)oxy) hexanoate; 3-(((3-(dimethylamino)propoxy)carbonyl)oxy) pentadecyl 6,6-bis((2-propylpentyl)oxy)hexanoate LXR420: 3-(((3-(dimethylamino)propoxy)carbonyl)oxy) pentadecyl 6,6-bis((3-ethylpentyl)oxy)hexanoate; (2R)-1-((6,6-bis(octyloxy)hexanoyl)oxy)pentadecan-3-yl 1-methylpyrrolidine-2-carboxylate; (2S)-1-((6,6-bis(octyloxy) hexanoyl)oxy)pentadecan-3-yl 1-methylpyrrolidine-2-carboxylate; (2R)-1-((6,6-bis(octyloxy)hexanoyl)oxy) pentadecan-3-ylpyrrolidine-2-carboxylate; 1-((6,6-bis (octyloxy)hexanoyl)oxy)pentadecan-3-yl 1,3-dimethylpyrrolidine-3-carboxylate; 3-((3-(1-methylpiperidin-4-yl)propanoyl)oxy)pentadecyl 6,6-bis(octyloxy)hexanoate; 1-((6,6-bis(octyloxy)hexanoyl)oxy)pentadecan-3-yl 1,4-dimethylpiperidine-4-carboxylate; 3-((5-(diethylamino)pentanoyl)oxy)pentadecyl 6,6-bis(octyloxy)hexanoate; 3-(((3-(diethylamino)propoxy)carbonyl)oxy)pentadecyl 5-(4,6-diheptyl-1,3-dioxan-2-yl)pentanoate; 3-(((3-(diethylamino)propoxy)carbonyl)oxy)undecyl 6,6-bis(octyloxy)hexanoate; 3-(((3-(diethylamino)propoxy)carbonyl)oxy)tridecyl 6,6-bis(octyloxy)hexanoate; (12Z,15Z)-3-(((3-(diethylamino)propoxy)carbonyl)oxy)henicosa-12,15-dien-1-yl 6,6-bis(octyloxy)hexanoate; 6-((6,6-bis(octyloxy)hexanoyl)oxy)-4-(((3-(diethylamino)propoxy)carbonyl)oxy)hexyl octanoate; 4,4-bis(octyloxy)butyl 5-(((3-(diethylamino)propoxy)carbonyl)oxy)heptadecanoate; 4,4-bis(octyloxy)butyl (3-(diethylamino)propyl) pentadecane-1,3-diyl dicarbonate; 2-(5-((4-((1,4-dimethylpiperidine-4-carbonyl)oxy)hexadecyl)oxy)-5-oxopentyl)propane-1,3-diyl dioctanoate; 2-(5-((4-((1,3-dimethylpyrrolidine-3-carbonyl)oxy)hexadecyl)oxy)-5-oxopentyl)propane-1,3-diyl dioctanoate; 2-(5-oxo-5-((4-(((S)-pyrrolidine-2-carbonyl)oxy)hexadecyl)oxy)pentyl)propane-1,3-diyl dioctanoate; 2-(5-((4-(((((S)-1-methylpyrrolidin-3-yl)oxy)carbonyl)oxy)hexadecyl)oxy)-5-oxopentyl)propane-1,3-diyl dioctanoate; 2-(5-((4-(((((R)-1-methylpyrrolidin-3-yl)oxy)carbonyl)oxy)hexadecyl)oxy)-5-oxopentyl)propane-1,3-diyl dioctanoate; 2-(5-((4-((((1-ethylpiperidin-3-yl)methoxy)carbonyl)oxy)hexadecyl)oxy)-5-oxopentyl)propane-1,3-diyl dioctanoate; 2-(5-((4-((((1-methylpiperidin-4-yl)oxy)carbonyl)oxy)hexadecyl)oxy)-5-oxopentyl)propane-1,3-diyl dioctanoate; 2-(10-dodecyl-3-ethyl-8,15-dioxo-7,9,14-trioxa-3-azanonadecan-19-yl)propane-1,3-diyl dioctanoate; 2-(11-dodecyl-3-ethyl-9,15-dioxo-8,10,14-trioxa-3-azanonadecan-19-yl)propane-1,3-diyl dioctanoate; 2-(5-((3-(((3-(1H-imidazol-1-yl)propoxy)carbonyl)oxy)pentadecyl)oxy)-5-oxopentyl)propane-1,3-diyl dioctanoate; 2-(5-oxo-5-((3-(((3-(piperidin-1-yl)propoxy)carbonyl)oxy)pentadecyl)oxy)pentyl)propane-1,3-diyl dioctanoate; and 2-(12-dodecyl-3-ethyl-8,14-dioxo-7,9,13-trioxa-3-azaoctadecan-18-yl)propane-1,3-diyl dioctanoate.

In specific aspects, these cationic lipid compounds are useful either alone, or in combination with other lipid aggregate-forming components (such as DOPE or cholesterol) for formulation into liposomes or other lipid aggregates. Such aggregates are cationic and able to complex with anionic macromolecules such as DNA or RNA.

"Neutral lipids" suitable for use in a lipid composition and methods described herein include, for example, a variety of neutral, uncharged or zwitterionic lipids. Examples of neutral phospholipids suitable for use in the present invention include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

"Helper lipids" are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for the compositions and methods described herein include, but are not limited to, cholesterol, 5-heptadecylresorcinol, and cholesterol hemisuccinate. Non-limiting examples of helper lipids for the compositions and methods described herein include those described in WO2015/095346, WO2015/095340, WO2016/037053, WO2014/136086, and WO2011/076807, each of which is hereby incorporated by reference in its entirety.

Stealth lipids are lipids that increase the length of time for which the nanoparticles can exist in vivo (e.g. in the blood). Stealth lipids suitable for the compositions and methods described herein include, but are not limited to, stealth lipids having a hydrophilic head group linked to a lipid moiety. Non-limiting examples of stealth lipids for the compositions and methods described herein include those described in WO2015/095346, WO2015/095340, WO2016/037053, WO2014/136086, and WO2011/076807, each of which is hereby incorporated by reference in its entirety. In a certain aspect, examples of stealth lipids include compounds of formula (XI), as described in WO2011/076807, and compounds listed in Table 1 of WO2016/010840. In particular aspects, other stealth lipids suitable for use in a lipid composition described herein and information about the biochemistry of such lipids can be found in Romberg et al., Pharmaceutical Research, Vol. 25, No. 1, 2008, p. 55-71 and Hoekstra et al., Biochimica et Biophysica Acta 1660 (2004) 41-52.

In one aspect, a suitable stealth lipid comprises a group selected from PEG (sometimes referred to as poly(ethylene oxide) and polymers based on poly(oxazoline), poly(vinyl alcohol), poly(glycerol), poly(N-vinylpyrrolidone), polyaminoacids and poly [N-(2-hydroxypropyl) methacrylamide], and additional suitable PEG lipids disclosed, e.g., in WO 2006/007712.

In specific aspects, non-limiting examples of suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. In further aspects, the dialkylglycerol or dialkylglycamide group can further comprise one or more substituted alkyl groups. In further aspects described herein, a PEG conjugate can be selected from PEG-dilaurylglycerol, PEG-dimyristylglycerol (PEG-DMG) (catalog #GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl]carbamoyl-[omega]-methyl-poly (ethylene glycol), PEG-DMB (3,4-Ditetradecoxylbenzyl-

[omega]-methyl-poly(ethylene glycol) ether), I,2-dimyristoyl-sn-glycero-3-phosphoethanolamine-N-[methoxy(polyethylene glycol)-2000] (catalog #880150P from Avanti Polar Lipids, Alabaster, Ala., USA). In one aspect, the stealth lipid is S010, S024, S027, S031, or S033 (as described in WO2016/037053, e.g., Table 1). In another aspect, the stealth lipid is S024 (as described in WO2016/037053, e.g., Table 1).

III. Composition of the mRNA Molecule

In a specific embodiment, the polynucleotide to be used for the immunization methods of the invention is polyribonucleotide-based such as mRNA-based. This mRNA molecule should be able to directly encode and facilitate translation of the target protein(s) against which an antibody response is desired. As such, the molecule should contain several components. In specific aspects, the first component is the open reading frame corresponding to the amino acid sequence of a protein(s), for example, a human target protein or fragment thereof. The native codon sequence may be used or, alternatively, codon optimization may be performed for the host species (such as mouse or rabbit) to increase translational efficiency and ultimately protein expression levels of the target. Additional modifications may be made to the open reading frame to enhance protein expression/trafficking. For secreted or membrane proteins, this may include the use of heterologous signal peptides such as the secretion signal from interleukin 2 (IL-2). In a specific example for secreted proteins, an mRNA molecule may include a heterologous signal peptide, such as the signal peptide of human IL-2 or IgG kappa.

In specific aspects, a second component is a consensus Kozak sequence. An exemplary Kozak DNA sequence is provided: GCCACCATG (SEQ ID NO: 1), wherein the nucleotides ATG represent the initiator methionine. An exemplary Kozak RNA sequence is provided: GCCACCAUG (SEQ ID NO: 11), wherein the nucleotides AUG represent the initiator methionine. Other non-limiting examples of a Kozak sequence include, as encoded by either RNA or DNA: (GCC)GCCRCCAUGG (SEQ ID NO: 12), AGNNAUGN (SEQ ID NO: 13), ANNAUGG (SEQ IDNO: 23), ACCAUGG (SEQ ID NO: 24), GACACCAUGG (SEQ ID NO: 25), GCCRCCATGG (SEQ ID NO: 57), CAAACATG (SEQ ID NO: 58), AAAAAATGTCT (SEQ ID NO: 28), AAAAAAATGRNA (SEQ ID NO: 29), NTAAAAATGRCT (SEQ ID NO: 30), TAAAAAATGAAN (SEQ ID NO: 31), GNCAAAATGG (SEQ ID NO: 32), NNNANNATGNC (SEQ ID NO: 33), and AACAATGGC (SEQ ID NO: 34), where “N” denotes any nucleotide (e.g., A, G, C or T in the context of DNA and A, G, C, or U in the context of RNA), and “R” denotes A or G. It is widely known that the inclusion of a Kozak sequence 5' of the open reading frame enhances translation in a eukaryotic host.

In specific aspects, a third component is a 7-methylguanosine cap on the 5' end of an mRNA. This cap is essential for the recruitment of eukaryotic initiation factor elF4E and assembly of a mature ribosome. The methylguanosine cap can be added enzymatically or chemically following generation of the mRNA transcript.

In specific aspects, a fourth component is a polyadenosine (polyA) tail found at the 3' terminus of an mRNA transcript. A polyA tract is known to prolong the half-life of an mRNA in cells as well as to promote efficient ribosome assembly and protein translation. In a specific embodiment, an mRNA for the compositions and methods described herein comprises a polyA tail of 120 nucleotides (SEQ ID NO: 59). In certain embodiments, an mRNA for the compositions and methods described herein comprises a polyA tail having 60-120 nucleotides. In particular embodiments, an mRNA for the compositions and methods described herein comprises a polyA tail of 60 nucleotides, 70 nucleotides, 80 nucleotides, 90 nucleotides, 100 nucleotides, 110 nucleotides, or 120 nucleotides. Inclusion of the polyA tract may be done through in vitro transcription or by enzymatic polyadenylation using poly(A) polymerase.

In specific aspects, a fifth component of an mRNA molecule is the inclusion of 5'- and 3'-untranslated regions (UTRs). In specific embodiments, the 5' UTR is derived from tobacco etch virus and the 3' UTR is a tandem repeat of the 3' UTR found in human β-globin. It is widely accepted that the presence of UTRs can enhance the translation of a mRNA as well as increase its half-life within a cell (see, e.g., R. L. Tanguay and D. R. Gallie Molecular and Cellular Biology 1996 vol 16 no1 pp 146-156).

Sufficient quantities of such RNA molecules may be obtained using in vitro transcription, followed by RNA purification. The technique of transcribing cloned DNA sequences in vitro using DNA-dependent RNA polymerases is well-known in the art (for example, see Sambrook et al., *Molecular Cloning: A Laboratory Manual,* 2nd Edition, Cold Spring Harbor Laboratory Press, 1989). Either naturally occurring ribonucleotides, such as uracil, guanine, cytosine, adenine, pseudouracil, or modified ribonucleotides may be used for mRNA synthesis so long as they still support appropriate codon recognition and protein translation. In this invention, guanine, cytosine, adenine, and pseudouracil were used for mRNA synthesis. In specific aspects, the use of pseudouracil instead of uracil permits more accurate estimates of mRNA size during quality control assessments on a BioAnalyzer (as described below).

IV. Use of the Lipid/Polynucleotide Complex

According to the present disclosure, in specific aspects, the lipid/polynucleotide complex is used to carry out an in vivo transfection. Transfected cells express the protein encoded by the polynucleotide (e.g., polyribonucleotide such as mRNA), and may express or present the foreign protein, for example, on the cell surface. As a result, the host animal (e.g., non-human host animal) mounts an immune response to the foreign protein, or immunogen.

Synthetic mRNA is transcribed in vitro using plasmid DNA template, rNTPs and T7 RNA polymerase. A 7-methylguanosine cap structure (Cap1) is enzymatically added to 5' end of mRNA to promote efficient translation. Capped mRNA is formulated into cationic lipid nanoparticles (LNPs) to protect mRNA from degradation and enhance cytoplasmic delivery. mRNA LNPs are stable at 4° C. for 3-4 months and are ready to use for immunization. In specific aspects, cationic lipid-polynucleotide complexes are formed by mixing a cationic lipid solution with an equal volume of polynucleotide solution. The cationic lipid and polynucleotides can be dissolved in any sterile physiologically-compatible aqueous carrier. In specific embodiments, cationic lipid and polynucleotides are dissolved in sterile saline (150 mM NaCl). The solutions are mixed at ambient temperatures. In certain embodiments, the solutions are mixed at 25° C. After mixing, the cationic lipid-polynucleotide complexes are incubated at room temperature, for example, for 15 to 45 minutes.

Administration of lipid/polynucleotide complexes of the methods described herein may be by parenteral, intravenous, intramuscular, subcutaneous, intranasal, or any other suitable means. In mice, intravenous administration of mRNA LNPs has been found to be superior to subcutaneous delivery (see FIG. 1B). The specific dosage administered may be dependent upon the age, weight, kind of current treatment, if any, and nature of the immunogen which will be expressed. The initial dose may be followed by booster dosages to enhance the immunogenic response. Immunization with mRNA LNPs can also be alternated with other immunogen formats (see FIG. 1C).

Because immunization generates the production of immunogen-specific antibodies in the host, the present disclosure is also directed to methods of producing immunogen-specific antibodies. Polyclonal antibodies may be isolated and purified from host animals using procedures well-known in the art (for example, see Harlow et al., *Antibodies: A Laboratory Manual*, Cold Spring Harbor Laboratory Press, 1988).

This disclosure is also directed to the use of mRNA LNP-based immunization to produce monoclonal antibodies. According to this method, non-human animals (e.g., mice) are injected with a lipid/mRNA complex, and antibody-producing cells (e.g., B-lymphocytes or splenocytes) are isolated from the immunized animal (e.g., mice). Monoclonal antibodies are produced by any method known in the art, for example, following the procedure of Kohler and Milstein (Nature 256:495-497 (1975) (for example, see Harlow et al., supra). Briefly, monoclonal antibodies can be produced by immunizing animals (e.g., mice) with a cationic lipid-mRNA complex, verifying the presence of antibody production by removing a serum sample, removing the spleen to obtain B-lymphocytes, fusing the B-lymphocytes with myeloma cells to produce hybridomas, cloning the hybridomas, selecting positive clones which produce anti-immunogen antibody, culturing the anti-immunogen antibody-producing clones, and isolating anti-immunogen antibodies from the hybridoma cultures.

V. RNA Modifications

Polyribonucleotides such as mRNA for the compositions and methods described herein can include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation, dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages.

In specific aspects, polyribonucleotides such as mRNA described herein can further comprise a 5' cap. In some embodiments of the aspects described herein, the modified synthetic mRNA comprises a 5' cap comprising a modified guanine nucleotide that is linked to the 5' end of an RNA molecule using a 5'-5' triphosphate linkage. The term "5' cap" is also intended to encompass other 5' cap analogs including, e.g., 5' diguanosine cap, tetraphosphate cap analogs having a methylene-bis(phosphonate) moiety (see e.g., Rydzik, A M et al. (2009) Org Biomol Chem 7(22):4763-76), dinucleotide cap analogs having a phosphorothioate modification (see e.g., Kowalska, J. et al. (2008) RNA 14(6):1119-1131), cap analogs having a sulfur substitution for a non-bridging oxygen (see e.g., Grudzien-Nogalska, E. et al., (2007) RNA 13(10): 1745-1755), N7-benzylated dinucleoside tetraphosphate analogs (see e.g., Grudzien, E. et al. (2004) RNA 10(9):1479-1487), or anti-reverse cap analogs (see e.g., Jemielity, J. et al., (2003) RNA 9(9): 1108-1122 and Stepinski, J. et al. (2001) RNA 7(10):1486-1495). In one such embodiment, the 5' cap analog is a 5' diguanosine cap. In some embodiments, the modified synthetic mRNA of the invention does not comprise a 5' triphosphate.

The 5' cap is important for recognition and attachment of an mRNA to a ribosome to initiate translation. The 5' cap also protects modified synthetic mRNA described herein from 5' exonuclease mediated degradation.

Polyribonucleotides such as mRNA described herein can further comprise a 5' and/or 3' untranslated region (UTR). Untranslated regions are regions of the RNA before the start codon (5') and after the stop codon (3'), and are therefore not translated by the translation machinery. Modification of an RNA molecule with one or more untranslated regions can improve the stability of an mRNA, since the untranslated regions can interfere with ribonucleases and other proteins involved in RNA degradation. In addition, modification of an RNA with a 5' and/or 3' untranslated region can enhance translational efficiency by binding proteins that alter ribosome binding to an mRNA. Modification of an RNA with a 3' UTR can be used to maintain a cytoplasmic localization of the RNA, permitting translation to occur in the cytoplasm of the cell. In one embodiment, the modified synthetic mRNA of the invention does not comprise a 5' or 3' UTR. In another embodiment, the modified synthetic mRNA of the invention comprises either a 5' or 3' UTR. In another embodiment, the modified synthetic mRNA of the invention comprises both a 5' and a 3' UTR. In one embodiment, the 5' and/or 3' UTR is selected from an mRNA known to have high stability in the cell (e.g., a murine alpha-globin 3' UTR). In some embodiments, the 5' UTR, the 3' UTR, or both comprise one or more modified nucleosides.

In some embodiments, polyribonucleotides such as mRNA described herein further comprise a Kozak sequence. The "Kozak sequence" refers to a sequence on eukaryotic mRNA having the consensus (gcc)gccRccAUGG (SEQ ID NO: 12), where R is a purine (adenine or guanine) three bases upstream of the start codon (AUG), which is followed by another 'G.' The Kozak consensus sequence is recognized by the ribosome to initiate translation of a polypeptide. Typically, initiation occurs at the first AUG codon encountered by the translation machinery that is proximal to the 5' end of the transcript. However, in some cases, this AUG codon can be bypassed in a process called leaky scanning. The presence of a Kozak sequence near the AUG codon will strengthen that codon as the initiating site of translation, such that translation of the correct polypeptide occurs. Furthermore, addition of a Kozak sequence to a modified synthetic mRNA described herein can promote more efficient translation, even if there is no ambiguity regarding the start codon. Thus, in some embodiments, the modified synthetic mRNA described herein further comprise a Kozak consensus sequence at the desired site for initiation of translation to produce the correct length polypeptide. In some such embodiments, the Kozak sequence comprises one or more modified nucleosides.

In some embodiments, modified synthetic mRNA described herein further comprise a "poly (A) tail", which refers to a 3' homopolymeric tail of adenine nucleotides, which can vary in length (e.g., at least 5 adenine nucleotides) and can be up to several hundred adenine nucleotides). The inclusion of a 3' poly(A) tail can protect the modified synthetic mRNA of the invention from degradation in the cell, and also facilitates extra-nuclear localization to enhance translation efficiency. In some embodiments, the poly(A) tail comprises between 1 and 500 adenine nucleotides (SEQ ID NO: 60); in other embodiments the poly(A) tail comprises at least 5 adenine nucleotides or more. In one embodiment, the poly(A) tail comprises between 1 and 150 adenine nucleotides. In one embodiment, the poly(A) tail comprises between 60 and 120 adenine nucleotides. In another embodiment, the poly(A) tail comprises between 90 and 120 adenine nucleotides. In some such embodiments, the poly(A) tail comprises one or more modified nucleosides.

The following are representative examples of target protein antigens that are amenable to production and expression according to the mRNA immunization methods provided herein. Generation of their mRNAs and immunization of host animals with the same demonstrate proof of concept for said methods, as described herein.

I. RXFP1

RXFP1, or relaxin/insulin-like family peptide receptor 1, is a 757 amino acid class A G protein coupled receptor (GPCR) which contains a leucine-rich repeat N-terminal extracellular domain. Phylogenetically, it is a part of the same receptor subfamily which includes follicle stimulating hormone, luteinizing hormone, and thyroid stimulating hormone receptors. The endogenous ligand of RXFP1 is the protein hormone relaxin. RXFP1 and its ligand have been implicated in the control of menstruation and some of the physiological responses associated with pregnancy and parturition. In patients suffering from acute decompensated heart failure, a phase III clinical trial (RELAX-AHF) has shown that 48 h of recombinant relaxin infusion during hospitalization significantly reduced 6 month mortality.

Establishing cell lines with high levels of RXFP1 expression is difficult due to cytotoxicity. Like many GPCRs, expression of purified, full length recombinant protein is also technically prohibitive.

For the generation of human RXFP1 mRNA, the native human nucleotide sequence for the RXFP1 open reading frame (e.g., accession numbers NM 021634.3/NP 067647.2) was subjected to codon optimization using GeneArt®'s codon optimization algorithm for mice (see Table 1). In addition to changing codon sequences on the basis of mouse biases, sequences were altered to remove BamHI, RsrII, and BspQI restriction sites as these would be employed for subsequent subcloning and mRNA synthesis.

TABLE 1

Exemplary RXFP1 Polynucleotide and Polypeptide Sequences

| SEQ ID NO: and features | Sequence |
|---|---|
| SEQ ID NO: 1 Consensus Kozak sequence (DNA) | GCCACCATG |
| SEQ ID NO: 11 Consensus Kozak sequence (RNA) | GCCACCAUG<br>U = Uridine and/or pseudouridine |
| SEQ ID NO: 35 RXFP1 native DNA sequence corresponding to Protein Accession # NP_067647.2 | GTGCGTGTGTGTAAAGAAGGAGATTAGGACATTTAGAGAAGGAGGGCGGGGAGGAGA<br>GATCCTGAGAATAGAAAGGAGGAAAGAAAAAAAGAGGAATGGAAAGAGACAGAGAAA<br>GGAAATGGGAGTGGAAGGAGGGAGGACTGCTTTGTAACTGCTAAGATTGCAGACAGAA<br>ATAGCACACAACCACTGTGAGCTGTATGCGATTCAGAAACCAAGACCAAATTTTGCTCAC<br>TTTCATTAATCAGTTGCTCAGATAGAAGGAAATGACATCTGGTTCTGTCTTCTTCTACATC<br>TTAATTTTTGGAAAATATTTTTCTCATGGGGGTGGACAGGATGTCAAGTGCTCCCTTGGC<br>TATTTCCCCTGTGGGAACATCACAAAGTGCTTGCCTCAGCTCCTGCACTGTAACGGTGTG<br>GACGACTGCGGGAATCAGGCCGATGAGGACAACTGTGGAGACAACAATGGATGGTCTC<br>TGCAATTTGACAAATATTTTGCCAGTTACTACAAAATGACTTCCCAATATCCTTTTGAGGC<br>AGAAACACCTGAATGTTTGGTCGGTTCTGTGCCAGTGCAATGTCTTTGCCAAGGTCTGGA<br>GCTTGACTGTGATGAAACCAATTTACGAGCTGTTCCATCGGTTTCTTCAAATGTGACTGCA<br>ATGTCACTTCAGTGGAACTTAATAAGAAAGCTTCCTCCTGATTGCTTCAAGAATTATCATG<br>ATCTTCAGAAGCTGTACCTGCAAAACAATAAGATTACATCCATCTCCATCTATGCTTTCAG<br>AGGACTGAATAGCCTTACTAAACTGTATCTCAGTCATAACAGAATAACCTTCCTGAAGCC<br>GGGTGTTTTTGAAGATCTTCACAGACTAGAATGGCTGATAATTGAAGATAATCACCTCAG<br>TCGAATTTCCCCACCAACATTTTATGGACTAAATTCTCTTATTCTCTTAGTCCTGATGAATA<br>ACGTCCTCACCCGTTTACCTGATAAACCTCTCTGTCAACACATGCCAAGACTACATTGGCT<br>GGACCTTGAAGGCAACCATATCCATAATTTAAGAAATTTGACTTTTATTTCCTGCAGTAAT<br>TTAACTGTTTTAGTGATGAGGAAAAACAAAATTAATCACTTAAATGAAAATACTTTTGCAC<br>CTCTCCAGAAACTGGATGAATTGGATTTAGGAAGTAATAAGATTGAAAATCTTCCACCGC<br>TTATATTCAAGGACCTGAAGGAGCTGTCACAATTGAATCTTTCCTATAATCCAATCCAGAA<br>AATTCAAGCAAACCAATTTGATTATCTTGTCAAACTCAAGTCTCTCAGCCTAGAAGGGATT<br>GAAATTTCAAATATCCAACAAAGGATGTTTAGACCTCTTATGAATCTCTCTCACATATATT<br>TTAAGAAATTCCAGTACTGTGGGTATGCACCACATGTTCGCAGCTGTAAACCAAACACTG<br>ATGGAATTTCATCTCTAGAGAATCTCTTGGCAAGCATTATTCAGAGAGTATTTGTCTGGG<br>TTGTATCTGCAGTTACCTGCTTTGGAAACATTTTTGTCATTTGCATGCGACCTTATATCAG<br>GTCTGAGAACAAGCTGTATGCCATGTCAATCATTTCTCTCTGCTGTGCCGACTGCTTAATG<br>GGAATATATTTATTCGTGATCGGAGGCTTTGACCTAAAGTTTCGTGGAGAATACAATAAG<br>CATGCGCAGCTGTGGATGGAGAGTACTCATTGTCAGCTTGTAGGATCTTTGGCCATTCTG<br>TCCACAGAAGTATCAGTTTTACTGTTAACATTTCTGACATTGGAAAAATACATCTGCATTG<br>TCTATCCTTTTAGATGTGTGAGACCTGGAAAATGCAGAACAATTACAGTTCTGATTCTCAT<br>TTGGATTACTGGTTTTATAGTGGCTTTCATTCCATTGAGCAATAAGGAATTTTTCAAAAAC<br>TACTATGGCACCAATGGAGTATGCTTCCCTCTTCATTCAGAAGATACAGAAAGTATTGGA<br>GCCCAGATTTATTCAGTGGCAATTTTTCTTGGTATTAATTTGGCCGCATTTATCATCATAG<br>TTTTTTCCTATGGAAGCATGTTTTATAGTGTTCATCAAAGTGCCATAACAGCAACTGAAAT<br>ACGGAATCAAGTTAAAAAAGAGATGATCCTTGCCAAACGTTTTTTCTTTATAGTATTTACT<br>GATGCATTATGCTGGATACCCATTTTTGTAGTGAAATTTCTTTCACTGCTTCAGGTAGAAA<br>TACCAGGTACCATAACCTCTTGGGTAGTGATTTTTATTCTGCCCATTAACAGTGCTTTGAA<br>CCCAATTCTCTATACTCTGACCACAAGACCATTTAAAGAAATGATTCATCGGTTTTGGTAT |

TABLE 1-continued

Exemplary RXFP1 Polynucleotide and Polypeptide Sequences

| SEQ ID NO: and features | Sequence |
|---|---|
| | AACTACAGACAAAGAAAATCTATGGACAGCAAAGGTCAGAAAACATATGCTCCATCATT<br>CATCTGGGTGGAAATGTGGCCACTGCAGGAGATGCCACCTGAGTTAATGAAGCCGGACC<br>TTTTCACATACCCCTGTGAAATGTCACTGATTTCTCAATCAACGAGACTCAATTCCTATTCA<br>TGACTGACTCTGAAATTCATTTCTTCGCAGAGAATACTGTGGGGGTGCTTCATGAGGGAT<br>TTACTGGTATGAAATGAATACCACAAAATTAATTTATAATAATAGCTAAGATAAATATTTT<br>ACAAGGACATGAGGAAAAATAAAAATGACTAATGCTCTTACAAAGGGAAGTAATTATAT<br>CAATAATGTATATATATTAGTAGACATTTTGCATAAGAAATTAAGAGAAATCTACTTCAGT<br>AACATTCATTCATTTTTCTAACATGCATTTATTGAGTACCCACTACTATGTGCATAGCATTG<br>CAATATAGTCCTGGAAGTAGACAGTGCAGAACCTTTCAATCTGTAGATGGTGTTTAATGA<br>CAAAAGACTATACAAAGTCCATCTGCAGTTCCTAGTTTAAAGTAGAGCTTTACCTGTCAT<br>GTGCATCAGCAAGAATCATAGGCACTTTTAAATAAAGGTTTAAAGTTTTGGAATACTCAG<br>TGTATTTGCATCATAGAAAATGTCTGACTGTTTGCAAAATAATATTCTGTTTTAAGAATCC<br>ATCTTACCTCTCTTTAAGTTTCCATACACTTGAGAGCCAACACAACATATTTATTACTAAAA<br>AGATGCTTTGCTAGAAACTCAAAAACAGCACTTCTTTTGGCACTTCCTGCCCAGTTTTCTC<br>TTTGCTTTAAATGAACATCATCATATGGAATTGGAATAGGAGAGTATGAGTACGGCAGA<br>GAAGTGGATCAGAAAAACTAGAATGAGGATAAACATTTACATTAGTGGAAACTCCTGAA<br>ATAAATCCTTGTATTGTCAGTTAACTGATTTTCAACAAGGATGCCAAGACAAAAAGGCTT<br>TTCAACAAACCGTGCTGTTTTAAGAACAGACCTAAGTGGTTTAATTCACCCACTTTAGATG<br>GGTGAATGTTATGGTGTGTGAAATATCTCAGTAAAGCAGTTAAAAGGAAAAAGAGCTGG<br>AATGCACTGATTCAGGAACTTAATTTCAGGAAGGAAAGGTCTGTATGTACACATTTCACT<br>TTAAGCAGAAAATCTTTCTTCAAGAAATGACTTTACTTTCTCTTTGCACTGCCAGCACGTG<br>AGATACTAACTTTTTAACTAGTTGTTCTTCTCTAGTCTCTACGTTATTAGAATTTTTTGCTTT<br>CATAATGTGAAACCTTTAAGCAGGAGAAGAAAATGTTTTCAGATAGTTTCAAATACACCA<br>AAAATGTTTGAAACACAAAAATACTGGAATCAAACCATAATGCACTTATTGAATATATAG<br>TTGTATAGATTTGTTCTGAAAATAAATTATCTGAAATTTAACTATTAAAAAAAAAAAAAAA<br>AAAAAAAAAA |
| SEQ ID NO: 2<br>Native mRNA<br>sequence<br>corresponding to<br>Protein Accession #<br>NP_067647.2 | GUGCGUGUGUGUAAAGAAGGAGAUUAGGACAUUUAGAGAAGGAGGG<br>CGGGGAGGAGAGAUCCUGAGAAUAGAAAGGAGGAAAGAAAAAAAGA<br>GGAAUGGAAAGAGACAGAGAAAGGAAAUGGGAGUGGAAGGAGGGAG<br>GACUGCUUUGUAACUGCUAAGAUUGCAGACAGAAAUAGCACACAACC<br>ACUGUGAGCUGUAUGCGAUUCAGAAACCAAGACCAAAUUUUGCUCA<br>CUUUCAUUAAUCAGUUGCUCAGAUAGAAGGAAAUGACAUCUGGUUC<br>UGUCUUCUUCUACAUCUUAAUUUUGGAAAAUAUUUUUCUCAUGGG<br>GGUGGACAGGAUGUCAAGUGCUCCCUUGGCUAUUUCCCCUGUGGG<br>AACAUCACAAAGUGCUUGCCUCAGCUCCUGCACUGUAACGGUGUGG<br>ACGACUGCGGGAAUCAGGCCGAUGAGGACAACUGUGGAGACAACAA<br>UGGAUGGUCUCUGCAAUUUGACAAAUAUUUUGCCAGUUACUACAAAA<br>UGACUUCCCAAUAUCCUUUUGAGGCAGAAACACCUGAAUGUUUGGU<br>CGGUUCUGUGCCAGUGCAAUGUCUUUGCCAAGGUCUGGAGCUUGA<br>CUGUGAUGAAACCAAUUUACGAGCUGUUCCAUCGGUUUCUUCAAAU<br>GUGACUGCAAUGUCACUUCAGUGGAACUUAAUAAGAAAGCUUCCUC<br>CUGAUUGCUUCAAGAAUUAUCAUGAUCUUCAGAAGCUGUACCUGCA<br>AAACAAUAAGAUUACAUCCAUCUCCAUCUAUGCUUUCAGAGGACUGA<br>AUAGCCUUACUAAACUGUAUCUCAGUCAUAACAGAAUAACCUUCCUG<br>AAGCCGGGUGUUUUUGAAGAUCUUCACAGACUAGAAUGGCUGAUAA<br>UUGAAGAUAAUCACCUCAGUCGAAUUUCCCCACCAACAUUUUAUGGA<br>CUAAAUUCUCUUAUUCUCUUAGUCCUGAUGAAUAACGUCCUCACCC<br>GUUUACCUGAUAAACCUCUCUGUCAACACAUGCCAAGACUACAUUGG<br>CUGGACCUUGAAGGCAACCAUAUCCAUAAUUUAAGAAAUUUGACUUU<br>UAUUUCCUGCAGUAAUUUAACUGUUUUAGUGAUGAGGAAAAACAAAA<br>UUAAUCACUUAAAUGAAAAUACUUUUGCACCUCUCCAGAAACUGGAU<br>GAAUUGGAUUUAGGAAGUAAUAAGAUUGAAAAUCUUCCACCGCUUAU<br>AUUCAAGGACCUGAAGGAGCUGUCACAAUUGAAUCUUUCCUAUAAUC<br>CAAUCCAGAAAAUUCAAGCAAACCAAUUUGAUUAUCUUGUCAAACUC<br>AAGUCUCUCAGCCUAGAAGGGAUUGAAAUUUCAAAUAUCCAACAAAG<br>GAUGUUUAGACCUCUUAUGAAUCUCUCUCACAUAUAUUUUAAGAAAU<br>UCCAGUACUGUGGGUAUGCACCACAUGUUCGCAGCUGUAAACCAAA<br>CACUGAUGGAAUUUCAUCUCUAGAGAAUCUCUUGGCAAGCAUUAUU<br>CAGAGAGUAUUUGUCUGGGUUGUAUCUGCAGUUACCUGCUUUGGAA<br>ACAUUUUUGUCAUUUGCAUGCGACCUUAUAUCAGGUCUGAGAACAA<br>GCUGUAUGCCAUGUCAAUCAUUUCUCUCUGCUGUGCCGACUGCUUA<br>AUGGGAAUAUAUUUAUUCGUGAUCGGAGGCUUUGACCUAAAGUUUC<br>GUGGAGAAUACAAUAAGCAUGCGCAGCUGUGGAUGGAGAGUACUCA<br>UUGUCAGCUUGUAGGAUCUUUGGCCAUUCUGUCCACAGAAGUAUCA<br>GUUUUACUGUUAACAUUUCUGACAUUGGAAAAAUACAUCUGCAUUGU<br>CUAUCCUUUUAGAUGUGUGAGACCUGGAAAAUGCAGAACAAUUACA<br>GUUCUGAUUCUCAUUUGGAUUACUGGUUUUAUAGUGGCUUUCAUUC<br>CAUUGAGCAAUAAGGAAUUUUUCAAAAACUACUAUGGCACCAAUGGA<br>GUAUGCUUCCCUCUUCAUUCAGAAGAUACAGAAAGUAUUGGAGCCC<br>AGAUUUAUUCAGUGGCAAUUUUUCUUGGUAUUAAUUUGGCCGCAUU<br>UAUCAUCAUAGUUUUUUCCUAUGGAAGCAUGUUUUAUAGUGUUCAU<br>CAAAGUGCCAUAACAGCAACUGAAAUACGGAAUCAAGUUAAAAAAGA<br>GAUGAUCCUUGCCAAACGUUUUUUCUUUAUAGUAUUUACUGAUGCA<br>UUAUGCUGGAUACCCAUUUUUGUAGUGAAAUUUCUUUCACUGCUUC |

TABLE 1-continued

| Exemplary RXFP1 Polynucleotide and Polypeptide Sequences | |
|---|---|
| SEQ ID NO: and features | Sequence |
| | AGGUAGAAAUACCAGGUACCAUAACCUCUUGGGUAGUGAUUUUUAU<br>UCUGCCCAUUAACAGUGCUUUGAACCCAAUUCUCUAUACUCUGACCA<br>CAAGACCAUUUAAAGAAAUGAUUCAUCGGUUUUGGUAUAACUACAGA<br>CAAAGAAAAUCUAUGGACAGCAAAGGUCAGAAAACAUAUGCUCCAUC<br>AUUCAUCUGGGUGGAAAUGUGGCCACUGCAGGAGAUGCCACCUGAG<br>UUAAUGAAGCCGGACCUUUUCACAUACCCCUGUGAAAUGUCACUGA<br>UUUCUCAAUCAACGAGACUCAAUUCCUAUUCAUGACUGACUCUGAAA<br>UUCAUUUCUUCGCAGAGAAUACUGUGGGGGUGCUUCAUGAGGGAUU<br>UACUGGUAUGAAAUGAAUACCACAAAAUUAAUUUAUAAUAAUAGCUA<br>AGAUAAAUAUUUUACAAGGACAUGAGGAAAAAUAAAAAUGACUAAUG<br>CUCUUACAAAGGGAAGUAAUUAUAUCAAUAAUGUAUAUAUAUUAGUA<br>GACAUUUUGCAUAAGAAAUUAAGAGAAAUCUACUUCAGUAACAUUCA<br>UUCAUUUUUCUAACAUGCAUUUAUUGAGUACCCACUACUAUGUGCAU<br>AGCAUUGCAAUAUAGUCCUGGAAGUAGACAGUGCAGAACCUUUCAA<br>UCUGUAGAUGGUGUUUAAUGACAAAAGACUAUACAAAGUCCAUCUGC<br>AGUUCCUAGUUUAAAGUAGAGCUUUACCUGUCAUGUGCAUCAGCAA<br>GAAUCAUAGGCACUUUUAAAUAAAGGUUUAAAGUUUUGGAAUACUCA<br>GUGUAUUUGCAUCAUAGAAAAUGUCUGACUGUUUGCAAAAUAAUAUU<br>CUGUUUUAAGAAUCCAUCUUACCUCUCUUUAAGUUUCCAUACACUUG<br>AGAGCCAACACAACAUAUUUAUUACUAAAAAGAUGCUUUGCUAGAAA<br>CUCAAAAACAGCACUUCUUUUGGCACUUCCUGCCCAGUUUUCUCUU<br>UGCUUUAAAUGAACAUCAUCAUAUGGAAUUGGAAUAGGAGAGUAUGA<br>GUACGGCAGAGAAGUGGAUCAGAAAAACUAGAAUGAGGAUAAACAUU<br>UACAUUAGUGGAAACUCCUGAAAUAAAUCCUUGUAUUGUCAGUUAAC<br>UGAUUUUCAACAAGGAUGCCAAGACAAAAAGGCUUUUCAACAAACCG<br>UGCUGUUUUAAGAACAGACCUAAGUGGUUUAAUUCACCCACUUUAG<br>AUGGGUGAAUGUUAUGGUGUGUGAAAUAUCUCAGUAAAGCAGUUAA<br>AAGGAAAAAGAGCUGGAAUGCACUGAUUCAGGAACUUAAUUUCAGGA<br>AGGAAAGGUCUGUAUGUACACAUUUCACUUUAAGCAGAAAAUCUUUC<br>UUCAAGAAAUGACUUUACUUUCUCUUUGCACUGCCAGCACGUGAGA<br>UACUAACUUUUUAACUAGUUGUUCUUCUCUAGUCUCUACGUUAUUA<br>GAAUUUUUUGCUUUCAUAAUGUGAAACCUUUAAGCAGGAGAAGAAAA<br>UGUUUUCAGAUAGUUUCAAAUACACCAAAAAUGUUUGAAACACAAAA<br>AUACUGGAAUCAAACCAUAAUGCACUUAUUGAAUAUAUAGUUGUAUA<br>GAUUUGUUCUGAAAAUAAAUUAUCUGAAAUUUAACUAUUAAAAAAAAA<br>AAAAAAAAAAAAAAAA<br>U = Uridine and/or pseudouridine |
| SEQ ID NO: 3<br>Translated human RXFP1 from coding sequence (CDS) of the DNA construct of SEQ ID NO: 2 | MTSGSVFFYILIFGKYFSHGGGQDVKCSLGYFPCGNITKCLPQLLHCNGV<br>DDCGNQADEDNCGDNNGWSLQFDKYFASYYKMTSQYPFEAETPECLVG<br>SVPVQCLCQGLELDCDETNLRAVPSVSSNVTAMSLQWNLIRKLPPDCFK<br>NYHDLQKLYLQNNKITSISIYAFRGLNSLTKLYLSHNRITFLKPGVFEDLHRL<br>EWLIIEDNHLSRISPPTFYGLNSLILLVLMNNVLTRLPDKPLCQHMPRLHWL<br>DLEGNHIHNLRNLTFISCSNLTVLVMRKNKINHLNENTFAPLQKLDELDLGS<br>NKIENLPPLIFKDLKELSQLNLSYNPIQKIQANQFDYLVKLKSLSLEGIEISNI<br>QQRMFRPLMNLSHIYFKKFQYCGYAPHVRSCKPNTDGISSLENLLASIIQR<br>VFVWVVSAVTCFGNIFVICMRPYIRSENKLYAMSIISLCCADCLMGIYLFVIG<br>GFDLKFRGEYNKHAQLWMESTHCQLVGSLAILSTEVSVLLLTFLTLEKYICI<br>VYPFRCVRPGKCRTITVLILIWITGFIVAFIPLSNKEFFKNYYGTNGVCFPLH<br>SEDTESIGAQIYSVAIFLGINLAAFIIIVFSYGSMFYSVHQSAITATEIRNQVK<br>KEMILAKRFFFIVFTDALCWIPIFVVKFLSLLQVEIPGTITSWVVIFILPINSAL<br>NPILYTLTTRPFKEMIHRFWYNYRQRKSMDSKGQKTYAPSFIWVEMWPL<br>QEMPPELMKPDLFTYPCEMSLISQSTRLNSYS |
| SEQ ID NO: 36<br>(DNA)<br>TEV-hRXFP1-2xhBG-120A<br>Sequence features:<br>Tobacco Etch Virus (TEV) 5' UTR: 37-190<br>Optimal Kozak sequence: 191-199<br>Human RXFP1 codon optimized, encoding amino acids Accession # NP_067647.2: 197-2467<br>2 stop codons: 2468-2473<br>2 copies of human beta-globin 3'UTR: 2492-2756<br>120 nucleotide polyA | GGAGGCCGGAGAATTGTAATACGACTCACTATAGGGAGACGCGTGTTAAATAA<br>CAAATCTCAACACAACATATACAAAACAAACGAATCTCAAGCAATCAAGCATTCT<br>ACTTCTATTGCAGCAATTTAAATCATTTCTTTTAAAGCAAAAGCAATTTTCTGAAA<br>ATTTTCACCATTTACGAACGATAGCCGCCACCATGACAAGCGGCAGCGTGTTCTT<br>CTACATCCTGATCTTCGGCAAGTACTTCAGCCACGGCGGAGGCCAGGACGTGAA<br>GTGTAGCCTGGGCTACTTCCCCTGCGGCAACATCACCAAGTGCCTGCCCCAGCT<br>GCTGCACTGCAACGGCGTGGACGATTGCGGCAACCAGGCCGACGAGGACAACT<br>GCGGCGACAACAATGGCTGGTCCCTGCAGTTCGATAAGTACTTCGCCTCCTACT<br>ACAAGATGACCAGCCAGTACCCCTTCGAGGCCGAGACACCTGAGTGCCTCGTGG<br>GCTCTGTGCCTGTGCAGTGTCTGTGCCAGGGCCTGGAACTGGACTGCGACGAG<br>ACAAACCTGAGAGCCGTGCCCAGCGTGTCCAGCAACGTGACAGCCATGAGCCT<br>GCAGTGGAACCTGATCCGGAAGCTGCCCCCCGACTGCTTCAAGAACTACCACGA<br>CCTGCAGAAGCTGTATCTGCAGAACAACAAGATCACCTCCATCAGCATCTACGCC<br>TTCCGGGGCCTGAACAGCCTGACCAAGCTGTACCTGAGCCACAACCGGATCACC<br>TTTCTGAAGCCCGGCGTGTTCGAGGACCTGCACAGACTGGAATGGCTGATCATC<br>GAGGACAATCACCTGAGCCGGATCAGCCCCCCCACCTTCTACGGCCTGAACTCC<br>CTGATCCTGCTGGTGCTGATGAACAACGTGCTGACCCGGCTGCCCGACAAGCCC<br>CTGTGTCAGCACATGCCCAGACTGCACTGGCTGGACCTGGAAGGCAACCACATC<br>CACAACCTGCGGAACCTGACCTTCATCAGCTGCAGCAACCTGACCGTGCTCGTG<br>ATGCGGAAGAACAAGATTAACCACCTGAACGAGAACACCTTCGCCCCCCTGCAG<br>AAACTGGACGAGCTGGATCTGGGCTCTAACAAGATCGAGAACCTGCCCCCTCTG |

TABLE 1-continued

| Exemplary RXFP1 Polynucleotide and Polypeptide Sequences | |
|---|---|
| SEQ ID NO: and features | Sequence |
| tail (SEQ ID NO: 59): 2764-2883 | ATCTTCAAGGACCTGAAAGAGCTGAGCCAGCTGAACCTGTCCTACAACCCCATC CAGAAGATCCAGGCCAACCAGTTCGACTACCTCGTGAAGCTGAAGTCCCTGTCC CTGGAAGGGATCGAGATCAGCAACATCCAGCAGCGGATGTTCCGGCCCCTGAT GAATCTGTCCCACATCTACTTCAAGAAGTTCCAGTACTGCGGCTACGCCCCCCAC GTGCGGAGCTGCAAGCCTAACACAGACGGCATCAGCAGCCTGGAAAACCTGCT GGCCTCCATCATCCAGCGGGTGTTCGTGTGGGTGGTGTCCGCCGTGACCTGCTT CGGCAATATCTTCGTGATCTGCATGCGGCCCTACATTCGGAGCGAGAACAAGCT GTATGCCATGAGCATCATCTCCCTGTGCTGCGCCGACTGCCTGATGGGCATCTAC CTGTTCGTGATCGGCGGCTTCGACCTGAAGTTCCGGGGCGAGTACAACAAGCAC GCCCAGCTGTGGATGGAAAGCACCCACTGCCAGCTCGTGGGCAGCCTGGCCAT CCTGAGCACTGAAGTGTCCGTGCTGCTGCTGACCTTCCTGACCCTGGAAAAGTA CATCTGCATCGTGTACCCTTTCAGATGCGTGCGGCCTGGCAAGTGCCGGACCAT CACAGTGCTGATCCTGATTTGGATCACCGGCTTCATCGTGGCCTTCATCCCCCTG AGCAACAAAGAGTTCTTCAAGAATTACTACGGCACCAATGGCGTGTGCTTCCCA CTGCACTCCGAGGACACAGAGAGCATCGGCGCCCAGATCTACAGCGTGGCCAT CTTCCTGGGCATCAATCTGGCCGCCTTCATCATCATCGTGTTCAGCTACGGCTCC ATGTTCTACTCCGTGCACCAGAGCGCCATCACCGCCACCGAGATCCGGAACCAA GTGAAGAAAGAGATGATCCTGGCCAAGCGCTTCTTCTTCATTGTGTTCACCGAC GCCCTGTGTTGGATTCCAATCTTCGTCGTGAAGTTCCTGAGCCTGCTGCAGGTG GAAATCCCCGGCACAATCACCAGCTGGGTCGTGATCTTCATCCTGCCCATCAACA GCGCCCTGAACCCTATCCTGTACACCCTGACCACCCGGCCCTTCAAAGAAATGAT CCACCGGTTCTGGTACAACTACCGGCAGAGAAAGAGCATGGACAGCAAGGGCC AGAAAACCTACGCCCCTAGCTTCATCTGGGTGGAAATGTGGCCACTGCAGGAAA TGCCTCCCGAACTGATGAAGCCCGACCTGTTCACCTACCCCTGCGAGATGAGCCT GATCTCCCAGAGCACCCGGCTGAACAGCTACTCCTGATAACGGACCGGCGATAG ATGAAGCTCGCTTTCTTGCTGTCCAATTTCTATTAAAGGTTCCTTTGTTCCCTAAG TCCAACTACTAAACTGGGGGATATTATGAAGGGCCTTGAGCATCTGGATTCTGC CTAATAAAAAACATTTATTTTCATTGCAGCTCGCTTTCTTGCTGTCCAATTTCTATT AAAGGTTCCTTTGTTCCCTAAGTCCAACTACTAAACTGGGGGATATTATGAAGG GCCTTGAGCATCTGGATTCTGCCTAATAAAAAACATTTATTTTCATTGCGGCCGC AAAAAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAAAAAA AAAAAAAAAAAAAAAA |
| SEQ ID NO: 4 (mRNA) TEV-hRXFP1-2xhBG-120A Sequence features: Tobacco Etch Virus (TEV) 5' UTR: 37-190 Optimal Kozak sequence: 191-199 Human RXFP1 codon optimized, encoding amino acids Accession # NP_067647.2: 197-2467 2 stop codons: 2468-2473 2 copies of human beta-globin 3'UTR: 2492-2756 120 nucleotide polyA tail (SEQ ID NO: 59): 2764-2883 | GGAGGCCGGAGAAUUGUAAUACGACUCACUAUAGGGAGACGCGUGUUAAA UAACAAAUCUCAACACAACAUAUACAAAACAAACGAAUCUCAAGCAAUCAAG CAUUCUACUUCUAUUGCAGCAAUUUAAAUCAUUUCUUUUAAAGCAAAAGCA AUUUUCUGAAAAUUUUCACCAUUUACGAACGAUAGCCGCCACCAUGACAAG CGGCAGCGUGUUCUUCUACAUCCUGAUCUUCGGCAAGUACUUCAGCCACGG CGGAGGCCAGGACGUGAAGUGUAGCCUGGGCUACUUCCCCUGCGGCAACAU CACCAAGUGCCUGCCCCAGCUGCUGCACUGCAACGGCGUGGACGAUUGCGG CAACCAGGCCGACGAGGACAACUGCGGCGACAACAAUGGCUGGUCCCUGCAG UUCGAUAAGUACUUCGCCUCCUACUACAAGAUGACCAGCCAGUACCCCUUCG AGGCCGAGACACCUGAGUGCCUCGUGGGCUCUGUGCCUGUGCAGUGUCUG UGCCAGGGCCUGGAACUGGACUGCGACGAGACAAACCUGAGAGCCGUGCCC AGCGUGUCCAGCAACGUGACAGCCAUGAGCCUGCAGUGGAACCUGAUCCGG AAGCUGCCCCCCGACUGCUUCAAGAACUACCACGACCUGCAGAAGCUGUAUC UGCAGAACAACAAGAUCACCUCCAUCAGCAUCUACGCCUUCCGGGGCCUGAA CAGCCUGACCAAGCUGUACCUGAGCCACAACCGGAUCACCUUUCUGAAGCCC GGCGUGUUCGAGGACCUGCACAGACUGGAAUGGCUGAUCAUCGAGGACAA UCACCUGAGCCGGAUCAGCCCCCCCACCUUCUACGGCCUGAACUCCCUGAUC CUGCUGGUGCUGAUGAACAACGUGCUGACCCGGCUGCCCGACAAGCCCCUG UGUCAGCACAUGCCCAGACUGCACUGGCUGGACCUGGAAGGCAACCACAUCC ACAACCUGCGGAACCUGACCUUCAUCAGCUGCAGCAACCUGACCGUGCUCGU GAUGCGGAAGAACAAGAUUAACCACCUGAACGAGAACACCUUCGCCCCCCUG CAGAAACUGGACGAGCUGGAUCUGGGCUCUAACAAGAUCGAGAACCUGCCC CCUCUGAUCUUCAAGGACCUGAAAGAGCUGAGCCAGCUGAACCUGUCCUAC AACCCCAUCCAGAAGAUCCAGGCCAACCAGUUCGACUACCUCGUGAAGCUGA AGUCCCUGUCCCUGGAAGGGAUCGAGAUCAGCAACAUCCAGCAGCGGAUGU UCCGGCCCCUGAUGAAUCUGUCCCACAUCUACUUCAAGAAGUUCCAGUACU GCGGCUACGCCCCCCACGUGCGGAGCUGCAAGCCUAACACAGACGGCAUCAG CAGCCUGGAAAACCUGCUGGCCUCCAUCAUCCAGCGGGUGUUCGUGUGGGU GGUGUCCGCCGUGACCUGCUUCGGCAAUAUCUUCGUGAUCUGCAUGCGGCC CUACAUUCGGAGCGAGAACAAGCUGUAUGCCAUGAGCAUCAUCUCCCUGUG CUGCGCCGACUGCCUGAUGGGCAUCUACCUGUUCGUGAUCGGCGGCUUCGA CCUGAAGUUCCGGGGCGAGUACAACAAGCACGCCCAGCUGUGGAUGGAAAG CACCCACUGCCAGCUCGUGGGCAGCCUGGCCAUCCUGAGCACUGAAGUGUCC GUGCUGCUGCUGACCUUCCUGACCCUGGAAAAGUACAUCUGCAUCGUGUAC CCUUUCAGAUGCGUGCGGCCUGGCAAGUGCCGGACCAUCACAGUGCUGAUC CUGAUUUGGAUCACCGGCUUCAUCGUGGCCUUCAUCCCCCUGAGCAACAAA GAGUUCUUCAAGAAUUACUACGGCACCAAUGGCGUGUGCUUCCCACUGCAC UCCGAGGACACAGAGAGCAUCGGCGCCCAGAUCUACAGCGUGGCCAUCUUCC UGGGCAUCAAUCUGGCCGCCUUCAUCAUCAUCGUGUUCAGCUACGGCUCCA UGUUCUACUCCGUGCACCAGAGCGCCAUCACCGCCACCGAGAUCCGGAACCA AGUGAAGAAAGAGAUGAUCCUGGCCAAGCGCUUCUUCUUCAUUGUGUUCA |

TABLE 1-continued

Exemplary RXFP1 Polynucleotide and Polypeptide Sequences

| SEQ ID NO: and features | Sequence |
|---|---|
| | CCGACGCCCUGUGUUGGAUUCCAAUCUUCGUCGUGAAGUUCCUGAGCCUGC UGCAGGUGGAAAUCCCCGGCACAAUCACCAGCUGGGUCGUGAUCUUCAUCC UGCCCAUCAACAGCGCCCUGAACCCUAUCCUGUACACCCUGACCACCCGGCCC UUCAAAGAAAUGAUCCACCGGUUCUGGUACAACUACCGGCAGAGAAAGAGC AUGGACAGCAAGGGCCAGAAAACCUACGCCCCUAGCUUCAUCUGGGUGGAA AUGUGGCCACUGCAGGAAAUGCCUCCCGAACUGAUGAAGCCCGACCUGUUC ACCUACCCCUGCGAGAUGAGCCUGAUCUCCCAGAGCACCCGGCUGAACAGCU ACUCCUGAUAACGGACCGGCGAUAGAUGAAGCUCGCUUUCUUGCUGUCCAA UUUCUAUUAAAGGUUCCUUUGUUCCCUAAGUCCAACUACUAAACUGGGGG AUAUUAUGAAGGGCCUUGAGCAUCUGGAUUCUGCCUAAUAAAAAACAUUU AUUUUCAUUGCAGCUCGCUUUCUUGCUGUCCAAUUUCUAUUAAAGGUUCC UUUGUUCCCUAAGUCCAACUACUAAACUGGGGGAUAUUAUGAAGGGCCUU GAGCAUCUGGAUUCUGCCUAAUAAAAAACAUUUAUUUUCAUUGCGGCCGCA AAAAAAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAAAAAA AAAAAAAAAAAAAAA |
| SEQ ID NO: 37 RXFP1 RNA coding sequence of SEQ ID NO: 4 above | AUGACAAGCGGCAGCGUGUUCUUCUACAUCCUGAUCUUCGGCAAGUACUUC AGCCACGGCGGAGGCCAGGACGUGAAGUGUAGCCUGGGCUACUUCCCCUGC GGCAACAUCACCAAGUGCCUGCCCCAGCUGCUGCACUGCAACGGCGUGGACG AUUGCGGCAACCAGGCCGACGAGGACAACUGCGGCGACAACAAUGGCUGGU CCCUGCAGUUCGAUAAGUACUUCGCCUCCUACUACAAGAUGACCAGCCAGU ACCCCUUCGAGGCCGAGACACCUGAGUGCCUCGUGGGCUCUGUGCCUGUGC AGUGUCUGUGCCAGGGCCUGGAACUGGACUGCGACGAGACAAACCUGAGAG CCGUGCCCAGCGUGUCCAGCAACGUGACAGCCAUGAGCCUGCAGUGGAACC UGAUCCGGAAGCUGCCCCCCGACUGCUUCAAGAACUACCACGACCUGCAGAA GCUGUAUCUGCAGAACAACAAGAUCACCUCCAUCAGCAUCUACGCCUUCCGG GGCCUGAACAGCCUGACCAAGCUGUACCUGAGCCACAACCGGAUCACCUUUC UGAAGCCCGGCGUGUUCGAGGACCUGCACAGACUGGAAUGGCUGAUCAUCG AGGACAAUCACCUGAGCCGGAUCAGCCCCCCCACCUUCUACGGCCUGAACUC CCUGAUCCUGCUGGUGCUGAUGAACAACGUGCUGACCCGGCUGCCCGACAA GCCCCUGUGUCAGCACAUGCCCAGACUGCACUGGCUGGACCUGGAAGGCAA CCACAUCCACAACCUGCGGAACCUGACCUUCAUCAGCUGCAGCAACCUGACC GUGCUCGUGAUGCGGAAGAACAAGAUUAACCACCUGAACGAGAACACCUUC GCCCCCCUGCAGAAACUGGACGAGCUGGAUCUGGGCUCUAACAAGAUCGAG AACCUGCCCCCUCUGAUCUUCAAGGACCUGAAAGAGCUGAGCCAGCUGAACC UGUCCUACAACCCCAUCCAGAAGAUCCAGGCCAACCAGUUCGACUACCUCGU GAAGCUGAAGUCCCUGUCCCUGGAAGGGAUCGAGAUCAGCAACAUCCAGCA GCGGAUGUUCCGGCCCCUGAUGAAUCUGUCCCACAUCUACUUCAAGAAGUU CCAGUACUGCGGCUACGCCCCCCACGUGCGGAGCUGCAAGCCUAACACAGAC GGCAUCAGCAGCCUGGAAAACCUGCUGGCCUCCAUCAUCCAGCGGGUGUUC GUGUGGGUGGUGUCCGCCGUGACCUGCUUCGGCAAUAUCUUCGUGAUCUG CAUGCGGCCCUACAUUCGGAGCGAGAACAAGCUGUAUGCCAUGAGCAUCAU CUCCCUGUGCUGCGCCGACUGCCUGAUGGGCAUCUACCUGUUCGUGAUCGG CGGCUUCGACCUGAAGUUCCGGGGCGAGUACAACAAGCACGCCCAGCUGUG GAUGGAAAGCACCCACUGCCAGCUCGUGGGCAGCCUGGCCAUCCUGAGCAC UGAAGUGUCCGUGCUGCUGCUGACCUUCCUGACCCUGGAAAAGUACAUCUG CAUCGUGUACCCUUUCAGAUGCGUGCGGCCUGGCAAGUGCCGGACCAUCAC AGUGCUGAUCCUGAUUUGGAUCACCGGCUUCAUCGUGGCCUUCAUCCCCCU GAGCAACAAAGAGUUCUUCAAGAAUUACUACGGCACCAAUGGCGUGUGCUU CCCACUGCACUCCGAGGACACAGAGAGCAUCGGCGCCCAGAUCUACAGCGUG GCCAUCUUCCUGGGCAUCAAUCUGGCCGCCUUCAUCAUCAUCGUGUUCAGC UACGGCUCCAUGUUCUACUCCGUGCACCAGAGCGCCAUCACCGCCACCGAGA UCCGGAACCAAGUGAAGAAAGAGAUGAUCCUGGCCAAGCGCUUCUUCUUCA UUGUGUUCACCGACGCCCUGUGUUGGAUUCCAAUCUUCGUCGUGAAGUUC CUGAGCCUGCUGCAGGUGGAAAUCCCCGGCACAAUCACCAGCUGGGUCGUG AUCUUCAUCCUGCCCAUCAACAGCGCCCUGAACCCUAUCCUGUACACCCUGA CCACCCGGCCCUUCAAAGAAAUGAUCCACCGGUUCUGGUACAACUACCGGCA GAGAAAGAGCAUGGACAGCAAGGGCCAGAAAACCUACGCCCCUAGCUUCAUC UGGGUGGAAAUGUGGCCACUGCAGGAAAUGCCUCCCGAACUGAUGAAGCCC GACCUGUUCACCUACCCCUGCGAGAUGAGCCUGAUCUCCCAGAGCACCCGGC UGAACAGCUACUCCUGAUAA |

II. SLC52A2

SLC52A2 (GPR172A) is a 445 amino acid multi-pass transmembrane protein predicted to have either 10 or 11 putative transmembrane helices. It has been shown to mediate the cellular uptake of riboflavin and has been reported to be a receptor for porcine endogenous retrovirus subgroup A. Certain genetic variants of SLC52A2 are associated with motor, sensory, and cranial neuronopathies.

For the generation of a human SLC52A2 mRNA, a native human nucleotide sequence for this protein's open reading frame (e.g., accession numbers NM_001253816.1/NP_001240745) was subjected to codon optimization using GeneArt®'s codon optimization algorithm for mice (see Table 2). In addition to changing codon sequences on the basis of mouse biases, sequences were altered to remove BamHI, RsrII, and BspQI restriction sites as these would be employed for subsequent subcloning and mRNA synthesis.

TABLE 2

Exemplary SLC52A2 Polynucleotide and Polypeptide Sequences

| SEQ ID NO: and features | Sequence |
|---|---|
| SEQ ID NO: 38<br>Native DNA sequence of<br>SLC52A2 corresponding to<br>Protein Accession #<br>NP_001240745 | GGGCGGGACTTCCGGTCGTGGGCCATGCCGGGGGCGGGCCCG<br>GAACCGCCACGGCTAGAAGAAGTCTTCACTTCCCAGGAGAGCCA<br>AAGCGTGTCTGGCCCTAGGTGGGAAAAGAACTGGCTGTGACCTT<br>TGCCCTGACCTGGAAGGGCCCAGCCTTGGGCTGAATGGCAGCA<br>CCCACGCCCGCCCGTCCGGTGCTGACCCACCTGCTGGTGGCTC<br>TCTTCGGCATGGGCTCCTGGGCTGCGGTCAATGGGATCTGGGTG<br>GAGCTACCTGTGGTGGTCAAAGAGCTTCCAGAGGGTTGGAGCCT<br>CCCCTCTTACGTCTCTGTGCTTGTGGCTCTGGGGAACCTGGGTC<br>TGCTGGTGGTGACCCTCTGGAGGAGGCTGGCCCCAGGAAAGGA<br>CGAGCAGGTCCCCATCCGGGTGGTGCAGGTGCTGGGCATGGTG<br>GGCACAGCCCTGCTGGCCTCTCTGTGGCACCATGTGGCCCCAGT<br>GGCAGGACAGTTGCATTCTGTGGCCTTCTTAGCACTGGCCTTTGT<br>GCTGGCACTGGCATGCTGTGCCTCGAATGTCACTTTCCTGCCCTT<br>CTTGAGCCACCTGCCACCTCGCTTCTTACGGTCATTCTTCCTGGG<br>TCAAGGCCTGAGTGCCCTGCTGCCCTGCGTGCTGGCCCTAGTGC<br>AGGGTGTGGGCCGCCTCGAGTGCCCGCCAGCCCCCATCAACGG<br>CACCCCTGGCCCCCCGCTCGACTTCCTTGAGCGTTTTCCCGCCA<br>GCACCTTCTTCTGGGCACTGACTGCCCTTCTGGTCGCTTCAGCTG<br>CTGCCTTCCAGGGTCTTCTGCTGCTGTTGCCGCCACCACCATCT<br>GTACCCACAGGGGAGTTAGGATCAGGCCTCCAGGTGGGAGCCC<br>CAGGAGCAGAGGAAGAGGTGGAAGAGTCCTCACCACTGCAAGA<br>GCCACCAAGCCAGGCAGCAGGCACCACCCCTGGTCCAGACCCT<br>AAGGCCTATCAGCTTCTATCAGCCCGCAGTGCCTGCCTGCTGGG<br>CCTGTTGGCCGCCACCAACGCGCTGACCAATGGCGTGCTGCCTG<br>CCGTGCAGAGCTTTTCCTGCTTACCCTACGGGCGTCTGGCCTAC<br>CACCTGGCTGTGGTGCTGGGCAGTGCTGCCAATCCCCTGGCCTG<br>CTTCCTGGCCATGGGTGTGCTGTGCAGGTCCTTGGCAGGGCTGG<br>GCGGCCTCTCTCTGCTGGGCGTGTTCTGTGGGGGCTACCTGATG<br>GCGCTGGCAGTCCTGAGCCCCTGCCCGCCCCTGGTGGGCACCT<br>CGGCGGGGGTGGTCCTCGTGGTGCTGTCGTGGGTGCTGTGTCT<br>TGGCGTGTTCTCCTACGTGAAGGTGGCAGCCAGCTCCCTGCTGC<br>ATGGCGGGGGCCGGCCGGCATTGCTGGCAGCCGGCGTGGCCAT<br>CCAGGTGGGCTCTCTGCTCGGCGCTGTTGCTATGTTCCCCCCGA<br>CCAGCATCTATCACGTGTTCCACAGCAGAAAGGACTGTGCAGAC<br>CCCTGTGACTCCTGAGCCTGGGCAGGTGGGGACCCCGCTCCCC<br>AACACCTGTCTTTCCCTCAATGCTGCCACCATGCCTGAGTGCCTG<br>CAGCCCAGGAGGCCCGCACACCGGTACACTCGTGGACACCTACA<br>CACTCCATAGGAGATCCTGGCTTTCCAGGGTGGGCAAGGGCAAG<br>GAGCAGGCTTGGAGCCAGGGACCAGTGGGGGCTGTAGGGTAAG<br>CCCCTGAGCCTGGGACCTACATGTGGTTTGCGTAATAAAACATTT<br>GTATTTAATGAGTTGGCATTAAAAAAAAAAAAAAA |
| SEQ ID NO: 5<br>Native mRNA sequence of<br>SLC52A2 corresponding to<br>Protein Accession #<br>NP_001240745 | GGGCGGGACUUCCGGUCGUGGGCCAUGCCGGGGGCGGGCCC<br>GGAACCGCCACGGCUAGAAGAAGUCUUCACUUCCCAGGAGAGC<br>CAAAGCGUGUCUGGCCCUAGGUGGGAAAAGAACUGGCUGUGAC<br>CUUUGCCCUGACCUGGAAGGGCCCAGCCUUGGGCUGAAUGGC<br>AGCACCCACGCCCGCCCGUCCGGUGCUGACCCACCUGCUGGU<br>GGCUCUCUUCGGCAUGGGCUCCUGGGCUGCGGUCAAUGGGAU<br>CUGGGUGGAGCUACCUGUGGUGGUCAAAGAGCUUCCAGAGGG<br>UUGGAGCCUCCCCUCUUACGUCUCUGUGCUUGUGGCUCUGGG<br>GAACCUGGGUCUGCUGGUGGUGACCCUCUGGAGGAGGCUGGC<br>CCCAGGAAAGGACGAGCAGGUCCCCAUCCGGGUGGUGCAGGU<br>GCUGGGCAUGGUGGGCACAGCCCUGCUGGCCUCUCUGUGGCA<br>CCAUGUGGCCCCAGUGGCAGGACAGUUGCAUUCUGUGGCCUU<br>CUUAGCACUGGCCUUUGUGCUGGCACUGGCAUGCUGUGCCUC<br>GAAUGUCACUUUCCUGCCCUUCUUGAGCCACCUGCCACCUCGC<br>UUCUUACGGUCAUUCUUCCUGGGUCAAGGCCUGAGUGCCCUG<br>CUGCCCUGCGUGCUGGCCCUAGUGCAGGGUGUGGGCCGCCUC<br>GAGUGCCCGCCAGCCCCCAUCAACGGCACCCCUGGCCCCCCGC<br>UCGACUUCCUUGAGCGUUUUCCCGCCAGCACCUUCUUCUGGGC<br>ACUGACUGCCCUUCUGGUCGCUUCAGCUGCUGCCUUCCAGGG<br>UCUUCUGCUGCUGUUGCCGCCACCACCAUCUGUACCCACAGGG<br>GAGUUAGGAUCAGGCCUCCAGGUGGGAGCCCCAGGAGCAGAG<br>GAAGAGGUGGAAGAGUCCUCACCACUGCAAGAGCCACCAAGCC<br>AGGCAGCAGGCACCACCCCUGGUCCAGACCCUAAGGCCUAUCA<br>GCUUCUAUCAGCCCGCAGUGCCUGCCUGCUGGGCCUGUUGGC<br>CGCCACCAACGCGCUGACCAAUGGCGUGCUGCCUGCCGUGCA<br>GAGCUUUUCCUGCUUACCCUACGGGCGUCUGGCCUACCACCUG<br>GCUGUGGUGCUGGGCAGUGCUGCCAAUCCCCUGGCCUGCUUC<br>CUGGCCAUGGGUGUGCUGUGCAGGUCCUUGGCAGGGCUGGGC<br>GGCCUCUCUCUGCUGGGCGUGUUCUGUGGGGGCUACCUGAUG<br>GCGCUGGCAGUCCUGAGCCCCUGCCCGCCCCUGGUGGGCACC<br>UCGGCGGGGGUGGUCCUCGUGGUGCUGUCGUGGGUGCUGUG<br>UCUUGGCGUGUUCUCCUACGUGAAGGUGGCAGCCAGCUCCCU<br>GCUGCAUGGCGGGGGCCGGCCGGCAUUGCUGGCAGCCGGCGU<br>GGCCAUCCAGGUGGGCUCUCUGCUCGGCGCUGUUGCUAUGUU |

TABLE 2-continued

Exemplary SLC52A2 Polynucleotide and Polypeptide Sequences

| SEQ ID NO: and features | Sequence |
|---|---|
| | CCCCCCGACCAGCAUCUAUCACGUGUUCCACAGCAGAAAGGAC<br>UGUGCAGACCCCUGUGACUCCUGAGCCUGGGCAGGUGGGGAC<br>CCCGCUCCCCAACACCUGUCUUUCCCUCAAUGCUGCCACCAUG<br>CCUGAGUGCCUGCAGCCCAGGAGGCCCGCACACCGGUACACUC<br>GUGGACACCUACACACUCCAUAGGAGAUCCUGGCUUUCCAGGG<br>UGGGCAAGGGCAAGGAGCAGGCUUGGAGCCAGGGACCAGUGG<br>GGGCUGUAGGGUAAGCCCCUGAGCCUGGGACCUACAUGUGGU<br>UUGCGUAAUAAAACAUUUGUAUUUAAUGAGUUGGCAUUAAAAAA<br>AAAAAAAAA<br>U = Uridine and/or pseudouridine |
| SEQ ID NO: 6<br>Translated human SLC52A2 from coding sequence (CDS) of the DNA construct of SEQ ID NO: 5 | MAAPTPARPVLTHLLVALFGMGSWAAVNGIWVELPVVVKELPEGWS<br>LPSYVSVLVALGNLGLLVVTLWRRLAPGKDEQVPIRVVQVLGMVGTA<br>LLASLWHHVAPVAGQLHSVAFLALAFVLALACCASNVTFLPFLSHLP<br>PRFLRSFFLGQGLSALLPCVLALVQGVGRLECPPAPINGTPGPPLDF<br>LERFPASTFFWALTALLVASAAAFQGLLLLLPPPPSVPTGELGSGLQ<br>VGAPGAEEEVEESSPLQEPPSQAAGTTPGPDPKAYQLLSARSACLL<br>GLLAATNALTNGVLPAVQSFSCLPYGRLAYHLAVVLGSAANPLACFL<br>AMGVLCRSLAGLGGLSLLGVFCGGYLMALAVLSPCPPLVGTSAGVV<br>LVVLSWVLCLGVFSYVKVAASSLLHGGGRPALLAAGVAIQVGSLLGA<br>VAMFPPTSIYHVFHSRKDCADPCDS |
| SEQ ID NO: 39 (DNA)<br>TEV-hSLC52A2-2xhBG-120A<br>Sequence features:<br>Tobacco Etch Virus (TEV) 5' UTR: 37-190<br>Optimal Kozak sequence: 191-199<br>Human SLC52A2 codon optimized, Protein Accession # NP_001240745: 197-751<br>1 stop codon: 752-754<br>2 copies of human beta-globin 3'UTR: 773-1038<br>120 nucleotide polyA tail (SEQ ID NO: 59): 1045-1164 | GGATCCGGAGGCCGGAGAATTGTAATACGACTCACTATAGGGAG<br>ACGCGTGTTAAATAACAAATCTCAACACAACATATACAAAACAAAC<br>GAATCTCAAGCAATCAAGCATTCTACTTCTATTGCAGCAATTTAAA<br>TCATTTCTTTTAAAGCAAAAGCAATTTTCTGAAAATTTTCACCATTT<br>ACGAACGATAGCCGCCACCATGGCAGCACCCACGCCCGCCCGT<br>CCGGTGCTGACCCACCTGCTGGTGGCTCTCTTCGGCATGGGCTC<br>CTGGGCTGCGGTCAATGGGATCTGGGTGGAGCTACCTGTGGTG<br>GTCAAAGAGCTTCCAGAGGGTTGGAGCCTCCCCTCTTACGTCTCT<br>GTGCTTGTGGCTCTGGGGAACCTGGGTCTGCTGGTGGTGACCCT<br>CTGGAGGAGGCTGGCCCCAGGAAAGGACGAGCAGGTCCCCATC<br>CGGGTGGTGCAGGTGCTGGGCATGGTGGGCACAGCCCTGCTGG<br>CCTCTCTGTGGCACCATGTGGCCCCAGTGGCAGGACAGTTGCAT<br>TCTGTGGCCTTCTTAGCACTGGCCTTTGTGCTGGCACTGGCATGC<br>TGTGCCTCGAATGTCACTTTCCTGCCCTTCTTGAGCCACCTGCCA<br>CCTCGCTTCTTACGGTCATTCTTCCTGGGTCAAGGCCTGAGTGCC<br>CTGCTGCCCTGCGTGCTGGCCCTAGTGCAGGGTGTGGGCCGCC<br>TCGAGTGCCCGCCAGCCCCCATCAACGGCACCCCTGGCCCCCC<br>GCTCGACTTCCTTGAGCGTTTTCCCGCCAGCACCTTCTTCTGGGC<br>ACTGACTGCCCTTCTGGTCGCTTCAGCTGCTGCCTTCCAGGGTCT<br>TCTGCTGCTGTTGCCGCCACCACCATCTGTACCCACAGGGGAGT<br>TAGGATCAGGCCTCCAGGTGGGAGCCCCAGGAGCAGAGGAAGA<br>GGTGGAAGAGTCCTCACCACTGCAAGAGCCACCAAGCCAGGCAG<br>CAGGCACCACCCCTGGTCCAGACCCTAAGGCCTATCAGCTTCTA<br>TCAGCCCGCAGTGCCTGCCTGCTGGGCCTGTTGGCCGCCACCAA<br>CGCGCTGACCAATGGCGTGCTGCCTGCCGTGCAGAGCTTTTCCT<br>GCTTACCCTACGGGCGTCTGGCCTACCACCTGGCTGTGGTGCTG<br>GGCAGTGCTGCCAATCCCCTGGCCTGCTTCCTGGCAATGGGTGT<br>GCTGTGCAGGTCCTTGGCAGGGCTGGGCGGCCTCTCTCTGCTG<br>GGCGTGTTCTGTGGGGGCTACCTGATGGCGCTGGCAGTCCTGA<br>GCCCCTGCCCGCCCCTGGTGGGCACCTCGGCGGGGGTGGTCCT<br>CGTGGTGCTGTCGTGGGTGCTGTGTCTTGGCGTGTTCTCCTACG<br>TGAAGGTGGCAGCCAGCTCCCTGCTGCATGGCGGGGGCCGGCC<br>GGCATTGCTGGCAGCCGGCGTGGCCATCCAGGTGGGCTCTCTG<br>CTCGGCGCTGTTGCTATGTTCCCCCCGACCAGCATCTATCACGT<br>GTTCCACAGCAGAAAGGACTGTGCAGACCCCTGTGACTCCTGAC<br>GGACCGGCGATAGATGAAGCTCGCTTTCTTGCTGTCCAATTTCTA<br>TTAAAGGTTCCTTTGTTCCCTAAGTCCAACTACTAAACTGGGGGA<br>TATTATGAAGGGCCTTGAGCATCTGGATTCTGCCTAATAAAAAAC<br>ATTTATTTTCATTGCAGCTCGCTTTCTTGCTGTCCAATTTCTATTAA<br>AGGTTCCTTTGTTCCCTAAGTCCAACTACTAAACTGGGGGATATT<br>ATGAAGGGCCTTGAGCATCTGGATTCTGCCTAATAAAAAACATTT<br>ATTTTCATTGCGGCCGCAAAAAAAAAAAAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA |
| SEQ ID NO: 7 (mRNA)<br>TEV-hSLC52A2-2xhBG-120A<br>Sequence features:<br>Tobacco Etch Virus (TEV) 5' UTR: 37-190<br>Optimal Kozak sequence: 191-199<br>Human SLC52A2 codon | GGGAGACGCGUGUUAAAUAACAAAUCUCAACACAACAUAUACAA<br>CAAUUUAAAUCAUUUCUUUUAAAGCAAAAGCAAUUUUCUGAAAA<br>UUUUCACCAUUUACGAACGAUAGCCGCCACCAUGGCAGCACCC<br>ACGCCCGCCCGUCCGGUGCUGACCCACCUGCUGGUGGCUCUC<br>UUCGGCAUGGGCUCCUGGGCUGCGGUCAAUGGGAUCUGGGUG<br>GAGCUACCUGUGGUGGUCAAAGAGCUUCCAGAGGGUUGGAGC<br>AACAAACGAAUCUCAAGCAAUCAAGCAUUCUACUUCUAUUGCAG<br>CUCCCCUCUUACGUCUCUGUGCUUGUGGCUCUGGGGAACCUG<br>GGUCUGCUGGUGGUGACCCUCUGGAGGAGGCUGGCCCCAGGA |

TABLE 2-continued

Exemplary SLC52A2 Polynucleotide and Polypeptide Sequences

| SEQ ID NO: and features | Sequence |
|---|---|
| optimized, Protein Accession # NP_001240745: 197-751<br>1 stop codon: 752-754<br>2 copies of human beta-globin 3'UTR: 773-1038<br>120 nucleotide polyA tail (SEQ ID NO: 59): 1045-1164 | AAGGACGAGCAGGUCCCCAUCCGGGUGGUGCAGGUGCUGGGC<br>AUGGUGGGCACAGCCCUGCUGGCCUCUCUGUGGCACCAUGUG<br>GCCCCAGUGGCAGGACAGUUGCAUUCUGUGGCCUUCUUAGCAC<br>UGGCCUUUGUGCUGGCACUGGCAUGCUGUGCCUCGAAUGUCA<br>CUUUCCUGCCCUUCUUGAGCCACCUGCCACCUCGCUUCUUACG<br>GUCAUUCUUCCUGGGUCAAGGCCUGAGUGCCCUGCUGCCCUG<br>CGUGCUGGCCCUAGUGCAGGGUGUGGGCCGCCUCGAGUGCCC<br>GCCAGCCCCCAUCAACGGCACCCCUGGCCCCCCGCUCGACUUC<br>CUUGAGCGUUUUCCCGCCAGCACCUUCUUCUGGGCACUGACUG<br>CCCUUCUGGUCGCUUCAGCUGCUGCCUUCCAGGGUCUUCUGC<br>UGCUGUUGCCGCCACCACCAUCUGUACCCACAGGGGAGUUAGG<br>AUCAGGCCUCCAGGUGGGAGCCCCAGGAGCAGAGGAAGAGGU<br>GGAAGAGUCCUCACCACUGCAAGAGCCACCAAGCCAGGCAGCA<br>GGCACCACCCCUGGUCCAGACCCUAAGGCCUAUCAGCUUCUAU<br>CAGCCCGCAGUGCCUGCCUGCUGGGCCUGUUGGCCGCCACCA<br>ACGCGCUGACCAAUGGCGUGCUGCCUGCCGUGCAGAGCUUUU<br>CCUGCUUACCCUACGGGCGUCUGGCCUACCACCUGGCUGUGG<br>UGCUGGGCAGUGCUGCCAAUCCCCUGGCCUGCUUCCUGGCAA<br>UGGGUGUGCUGUGCAGGUCCUUGGCAGGGCUGGGCGGCCUCU<br>CUCUGCUGGGCGUGUUCUGUGGGGGCUACCUGAUGGCGCUGG<br>CAGUCCUGAGCCCCUGCCCGCCCCUGGUGGGCACCUCGGCGG<br>GGGUGGUCCUCGUGGUGCUGUCGUGGGUGCUGUGUCUUGGC<br>GUGUUCUCCUACGUGAAGGUGGCAGCCAGCUCCCUGCUGCAU<br>GGCGGGGGCCGGCCGGCAUUGCUGGCAGCCGGCGUGGCCAUC<br>CAGGUGGGCUCUCUGCUCGGCGCUGUUGCUAUGUUCCCCCG<br>ACCAGCAUCUAUCACGUGUUCCACAGCAGAAAGGACUGUGCAG<br>ACCCCUGUGACUCCUGACGGACCGGCGAUAGAUGAAGCUCGCU<br>UUCUUGCUGUCCAAUUUCUAUUAAAGGUUCCUUUGUUCCCUAA<br>GUCCAACUACUAAACUGGGGGAUAUUAUGAAGGGCCUUGAGCA<br>UCUGGAUUCUGCCUAAUAAAAAACAUUUAUUUUCAUUGCAGCUC<br>GCUUUCUUGCUGUCCAAUUUCUAUUAAAGGUUCCUUUGUUCCC<br>UAAGUCCAACUACUAAACUGGGGGAUAUUAUGAAGGGCCUUGA<br>GCAUCUGGAUUCUGCCUAAUAAAAAACAUUUAUUUUCAUUGCG<br>GCCGCAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAA<br>U = Uridine and/or pseudouridine |
| SEQ ID NO: 40<br>Human SLC52A2 RNA coding region sequence of SEQ ID NO: 7 | AUGGCAGCACCCACGCCCGCCCGUCCGGUGCUGACCCACCUGC<br>UGGUGGCUCUCUUCGGCAUGGGCUCCUGGGCUGCGGUCAAUG<br>GGAUCUGGGUGGAGCUACCUGUGGUGGUCAAAGAGCUUCCAG<br>AGGGUUGGAGCCUCCCCUCUUACGUCUCUGUGCUUGUGGCUC<br>UGGGGAACCUGGGUCUGCUGGUGGUGACCCUCUGGAGGAGGC<br>UGGCCCCAGGAAAGGACGAGCAGGUCCCCAUCCGGGUGGUGC<br>AGGUGCUGGGCAUGGUGGGCACAGCCCUGCUGGCCUCUCUGU<br>GGCACCAUGUGGCCCCAGUGGCAGGACAGUUGCAUUCUGUGG<br>CCUUCUUAGCACUGGCCUUUGUGCUGGCACUGGCAUGCUGUG<br>CCUCGAAUGUCACUUUCCUGCCCUUCUUGAGCCACCUGCCACC<br>UCGCUUCUUACGGUCAUUCUUCCUGGGUCAAGGCCUGAGUGC<br>CCUGCUGCCCUGCGUGCUGGCCCUAGUGCAGGGUGUGGGCCG<br>CCUCGAGUGCCCGCCAGCCCCCAUCAACGGCACCCCUGGCCCC<br>CCGCUCGACUUCCUUGAGCGUUUUCCCGCCAGCACCUUCUUCU<br>GGGCACUGACUGCCCUUCUGGUCGCUUCAGCUGCUGCCUUCC<br>AGGGUCUUCUGCUGCUGUUGCCGCCACCACCAUCUGUACCCAC<br>AGGGGAGUUAGGAUCAGGCCUCCAGGUGGGAGCCCCAGGAGC<br>AGAGGAAGAGGUGGAAGAGUCCUCACCACUGCAAGAGCCACCA<br>AGCCAGGCAGCAGGCACCACCCCUGGUCCAGACCCUAAGGCCU<br>AUCAGCUUCUAUCAGCCCGCAGUGCCUGCCUGCUGGGCCUGU<br>UGGCCGCCACCAACGCGCUGACCAAUGGCGUGCUGCCUGCCG<br>UGCAGAGCUUUUCCUGCUUACCCUACGGGCGUCUGGCCUACCA<br>CCUGGCUGUGGUGCUGGGCAGUGCUGCCAAUCCCCUGGCCUG<br>CUUCCUGGCAAUGGGUGUGCUGUGCAGGUCCUUGGCAGGGCU<br>GGGCGGCCUCUCUCUGCUGGGCGUGUUCUGUGGGGGCUACCU<br>GAUGGCGCUGGCAGUCCUGAGCCCCUGCCCGCCCCUGGUGGG<br>CACCUCGGCGGGGGUGGUCCUCGUGGUGCUGUCGUGGGUGCU<br>GUGUCUUGGCGUGUUCUCCUACGUGAAGGUGGCAGCCAGCUC<br>CCUGCUGCAUGGCGGGGGCCGGCCGGCAUUGCUGGCAGCCGG<br>CGUGGCCAUCCAGGUGGGCUCUCUGCUCGGCGCUGUUGCUAU<br>GUUCCCCCCGACCAGCAUCUAUCACGUGUUCCACAGCAGAAAG<br>GACUGUGCAGACCCCUGUGACUCCUGA<br>U = Uridine and/or pseudouridine |

III. ANGPTL8

ANGPTL8 is a secreted protein, involved in lipid metabolism, which can be found in low ng/ml concentrations in human plasma. However, this protein is hard to express in heterologous systems in its native and soluble form. Furthermore, the biochemical function of this protein has not been described and thus there is no in vitro functional assay that could be used to measure the activity of recombinantly produced protein. Given the difficulty to generate and validate the quality of recombinant ANGPTL8 to use as an antigen, this protein was a good candidate for mRNA mediated immunization to generate monoclonal antibodies.

The full length coding sequence of human ANGPTL8 (e.g., accession number NP_061157) was codon optimized for expression in human cells and cloned into a vector that can sustain mRNA transcription by T7 polymerase and contains both 3 and 5' untranslated regions that help with mRNA stability and translatability (see Table 3 for sequence). mRNA was in vitro transcribed and encapsulated into lipid nanoparticles as described above.

TABLE 3

Exemplary ANGPTL8 Polynucleotide and Polypeptide Sequences

| SEQ ID NO: and features | Sequence |
|---|---|
| SEQ ID NO: 41<br>ANGPTL8 native DNA sequence corresponding to Protein Accession # NP_061157 | ATACCTTAGACCCTCAGTCATGCCAGTGCCTGCTCTGTGCCTGCT<br>CTGGGCCCTGGCAATGGTGACCCGGCCTGCCTCAGCGGCCCCC<br>ATGGGCGGCCCAGAACTGGCACAGCATGAGGAGCTGACCCTGC<br>TCTTCCATGGGACCCTGCAGCTGGGCCAGGCCCTCAACGGTGTG<br>TACAGGACCACGGAGGGACGGCTGACAAAGGCCAGGAACAGCC<br>TGGGTCTCTATGGCCGCACAATAGAACTCCTGGGGCAGGAGGTC<br>AGCCGGGGCCGGGATGCAGCCCAGGAACTTCGGGCAAGCCTGT<br>TGGAGACTCAGATGGAGGAGGATATTCTGCAGCTGCAGGCAGAG<br>GCCACAGCTGAGGTGCTGGGGGAGGTGGCCCAGGCACAGAAGG<br>TGCTACGGGACAGCGTGCAGCGGCTAGAAGTCCAGCTGAGGAG<br>CGCCTGGCTGGGCCCTGCCTACCGAGAATTTGAGGTCTTAAAGG<br>CTCACGCTGACAAGCAGAGCCACATCCTATGGGCCCTCACAGGC<br>CACGTGCAGCGGCAGAGGCGGGAGATGGTGGCACAGCAGCATC<br>GGCTGCGACAGATCCAGGAGAGACTCCACACAGCGGCGCTCCC<br>AGCCTGAATCTGCCTGGATGGAACTGAGGACCAATCATGCTGCA<br>AGGAACACTTCCACGCCCCGTGAGGCCCCTGTGCAGGGAGGAG<br>CTGCCTGTTCACTGGGATCAGCCAGGGCGCCGGGCCCCACTTCT<br>GAGCACAGAGCAGAGACAGACGCAGGCGGGGACAAAGGCAGAG<br>GATGTAGCCCCATTGGGGAGGGGTGGAGGAAGGACATGTACCCT<br>TTCATGCCTACACACCCCTCATTAAAGCAGAGTCGTGGCATCTCA<br>AAAAAAAAAAAAAAAA |
| SEQ ID NO: 8<br>ANGPTL8 native mRNA sequence of ANGPTL8 corresponding to Protein Accession # NP_061157 | AUACCUUAGACCCUCAGUCAUGCCAGUGCCUGCUCUGUGCCUG<br>CUCUGGGCCCUGGCAAUGGUGACCCGGCCUGCCUCAGCGGCC<br>CCCAUGGGCGGCCCAGAACUGGCACAGCAUGAGGAGCUGACCC<br>UGCUCUUCCAUGGGACCCUGCAGCUGGGCCAGGCCCUCAACG<br>GUGUGUACAGGACCACGGAGGGACGGCUGACAAAGGCCAGGAA<br>CAGCCUGGGUCUCUAUGGCCGCACAAUAGAACUCCUGGGGCAG<br>GAGGUCAGCCGGGGCCGGGAUGCAGCCCAGGAACUUCGGGCA<br>AGCCUGUUGGAGACUCAGAUGGAGGAGGAUAUUCUGCAGCUGC<br>AGGCAGAGGCCACAGCUGAGGUGCUGGGGGAGGUGGCCCAGG<br>CACAGAAGGUGCUACGGGACAGCGUGCAGCGGCUAGAAGUCCA<br>GCUGAGGAGCGCCUGGCUGGGCCCUGCCUACCGAGAAUUUGA<br>GGUCUUAAAGGCUCACGCUGACAAGCAGAGCCACAUCCUAUGG<br>GCCCUCACAGGCCACGUGCAGCGGCAGAGGCGGGAGAUGGUG<br>GCACAGCAGCAUCGGCUGCGACAGAUCCAGGAGAGACUCCACA<br>CAGCGGCGCUCCCAGCCUGAAUCUGCCUGGAUGGAACUGAGGA<br>CCAAUCAUGCUGCAAGGAACACUUCCACGCCCCGUGAGGCCCC<br>UGUGCAGGGAGGAGCUGCCUGUUCACUGGGAUCAGCCAGGGC<br>GCCGGGCCCCACUUCUGAGCACAGAGCAGAGACAGACGCAGGC<br>GGGGACAAAGGCAGAGGAUGUAGCCCCAUUGGGGAGGGGUGG<br>AGGAAGGACAUGUACCCUUUCAUGCCUACACACCCCUCAUUAAA<br>GCAGAGUCGUGGCAUCUCAAAAAAAAAAAAAAAAA<br>U = Uridine and/or pseudouridine |
| SEQ ID NO: 9<br>Translated human ANGPTL8 from coding sequence (CDS) of the DNA construct of SEQ ID NO: 8 | MPVPALCLLWALAMVTRPASAAPMGGPELAQHEELTLLFHGTLQLG<br>QALNGVYRTTEGRLTKARNSLGLYGRTIELLGQEVSRGRDAAQELR<br>ASLLETQMEEDILQLQAEATAEVLGEVAQAQKVLRDSVQRLEVQLRS<br>AWLGPAYREFEVLKAHADKQSHILWALTGHVQRQRREMVAQQHRL<br>RQIQERLHTAALPA |
| SEQ ID NO: 42<br>(DNA)<br>TEV-hANGPTL8-2xhBG-120A<br>Sequence features:<br>Tobacco Etch Virus (TEV) 5' UTR: 14-154<br>Optimal Kozak sequence: 155-163 | GGGATCCGGAGGCCGGAGAATTGTAATACGACTCACTATAGGGA<br>GACGCGTGTTAAATAACAAATCTCAACACAACATATACAAAACAAA<br>CGAATCTCAAGCAATCAAGCATTCTACTTCTATTGCAGCAATTTAA<br>ATCATTTCTTTTAAAGCAAAAGCAATTTTCTGAAAATTTTCACCATT<br>TACGAACGATAGCCGCCACCATGAAGACCTTCATCCTGCTGCTGT<br>GGGTGCTGCTGCTGTGGGTCATCTTCCTGCTGCCTGGCGCCACA<br>GCCGCTCCTATGGGAGGACCTGAACTGGCCCAGCACGAGGAACT<br>GACCCTGCTGTTTCACGGCACCCTGCAGCTGGGACAGGCCCTGA<br>ATGGCGTGTACAGAACCACCGAGGGCCGGCTGACCAAGGCCAG |

TABLE 3-continued

Exemplary ANGPTL8 Polynucleotide and Polypeptide Sequences

| SEQ ID NO: and features | Sequence |
| --- | --- |
| Ikk signal peptide: 204-275 Human ANGPTL8 codon optimized, encoding amino acids 22-198 of Protein Accession # NP_061157, Flag-6His-Avi tag: 807-899 1 stop codon: 900-902 2 copies of human beta-globin 3'UTR: 921-1186 120 nucleotide polyA tail (SEQ ID NO: 59): 1187-1306 | AAATAGCCTGGGCCTGTACGGCCGGACCATCGAACTGCTGGGGC AGGAAGTGTCCAGAGGCAGAGATGCCGCCCAGGAACTGAGAGC CAGCCTGCTGGAAACCCAGATGGAAGAGGACATCCTGCAGCTGC AGGCCGAGGCCACAGCTGAGGTGCTGGGAGAAGTGGCCCAGGC CCAGAAGGTGCTGAGAGACAGCGTGCAGCGGCTGGAAGTGCAG CTGAGATCTGCCTGGCTGGGCCCTGCCTACCGCGAGTTCGAAGT GCTGAAAGCCCACGCCGACAAGCAGAGCCACATCCTGTGGGCC CTGACAGGCCACGTGCAGAGACAGAGGCGGGAAATGGTGGCTC AGCAGCACAGACTGCGGCAGATCCAGGAACGGCTGCATACAGCT GCCCTGCCCGCCGACTACAAGGACGACGACGACAAGCACCACC ACCATCACCACGGCGGAGGCCTGAACGACATCTTCGAAGCCCAG AAAATCGAGTGGCACGAGTAACGGACCGGCGATAGATGAAGCTC GCTTTCTTGCTGTCCAATTTCTATTAAAGGTTCCTTTGTTCCCTAA GTCCAACTACTAAACTGGGGGATATTATGAAGGGCCTTGAGCATC TGGATTCTGCCTAATAAAAAACATTTATTTTCATTGCAGCTCGCTT TCTTGCTGTCCAATTTCTATTAAAGGTTCCTTTGTTCCCTAAGTCC AACTACTAAACTGGGGGATATTATGAAGGGCCTTGAGCATCTGGA TTCTGCCTAATAAAAAACATTTATTTTCATTGCAAAAAAAAAAAAAA AAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAA AAAAAAAAAAAA |
| SEQ ID NO: 10 (mRNA) TEV-hANGPTL8-2xhBG-120A Sequence features: Tobacco Etch Virus (TEV) 5' UTR: 14-154 Optimal Kozak sequence: 155-163 Ikk signal peptide: 204-275 Human ANGPTL8 codon optimized, encoding amino acids 22-198 of Protein Accession # NP_061157, Flag-6His-Avi tag: 807-899 1 stop codon: 900-902 2 copies of human beta-globin 3'UTR: 921-1186 120 nucleotide polyA tail (SEQ ID NO: 59): 1187-1306 | GGGAGACGCGUGUUAAAUAACAAAUCUCAACACAACAUAUACAA AACAAACGAAUCUCAAGCAAUCAAGCAUUCUACUUCUAUUGCAG CAAUUUAAAUCAUUUCUUUUAAAGCAAAAGCAAUUUUCUGAAAA UUUUCACCAUUUACGAACGAUAGCCGCCACCAUGAAGACCUUC AUCCUGCUGCUGUGGGUGCUGCUGCUGUGGGUCAUCUUCCUG CUGCCUGGCGCCACAGCCGCUCCUAUGGGAGGACCUGAACUG GCCCAGCACGAGGAACUGACCCUGCUGUUUCACGGCACCCUGC AGCUGGGACAGGCCCUGAAUGGCGUGUACAGAACCACCGAGGG CCGGCUGACCAAGGCCAGAAAUAGCCUGGGCCUGUACGGCCG GACCAUCGAACUGCUGGGGCAGGAAGUGUCCAGAGGCAGAGAU GCCGCCCAGGAACUGAGAGCCAGCCUGCUGGAAACCCAGAUGG AAGAGGACAUCCUGCAGCUGCAGGCCGAGGCCACAGCUGAGGU GCUGGGAGAAGUGGCCCAGGCCCAGAAGGUGCUGAGAGACAG CGUGCAGCGGCUGGAAGUGCAGCUGAGAUCUGCCUGGCUGGG CCCUGCCUACCGCGAGUUCGAAGUGCUGAAAGCCCACGCCGAC AAGCAGAGCCACAUCCUGUGGGCCCUGACAGGCCACGUGCAGA GACAGAGGCGGGAAAUGGUGGCUCAGCAGCACAGACUGCGGCA GAUCCAGGAACGGCUGCAUACAGCUGCCCUGCCCGCCGACUAC AAGGACGACGACGACAAGCACCACCACCAUCACCACGGCGGAG GCCUGAACGACAUCUUCGAAGCCCAGAAAAUCGAGUGGCACGA GUAACGGACCGGCGAUAGAUGAAGCUCGCUUUCUUGCUGUCCA AUUUCUAUUAAAGGUUCCUUUGUUCCCUAAGUCCAACUACUAAA CUGGGGGAUAUUAUGAAGGGCCUUGAGCAUCUGGAUUCUGCC UAAUAAAAAACAUUUAUUUUCAUUGCAGCUCGCUUUCUUGCUG UCCAAUUUCUAUUAAAGGUUCCUUUGUUCCCUAAGUCCAACUA CUAAACUGGGGGAUAUUAUGAAGGGCCUUGAGCAUCUGGAUUC UGCCUAAUAAAAAACAUUUAUUUUCAUUGCAAAAAAAAAAAAAAA AAAAAAAAAAAAAAAAAAAAAAAAAAAAAAAAAAAAAAAAAAAAAAAA AAAAAAAAAAAAAAAAAAAAAAAAAAAAAAAAAAAAAAAAAAAAAAAA AAAAAAAAAAA U = Uridine and/or pseudouridine |
| SEQ ID NO: 43 Human ANGPTL8 RNA coding sequence of SEQ ID NO: 10 | AUGAAGACCUUCAUCCUGCUGCUGUGGGUGCUGCUGCUGUGG GUCAUCUUCCUGCUGCCUGGCGCCACAGCCGCUCCUAUGGGA GGACCUGAACUGGCCCAGCACGAGGAACUGACCCUGCUGUUUC ACGGCACCCUGCAGCUGGGACAGGCCCUGAAUGGCGUGUACA GAACCACCGAGGGCCGGCUGACCAAGGCCAGAAAUAGCCUGGG CCUGUACGGCCGGACCAUCGAACUGCUGGGGCAGGAAGUGUC CAGAGGCAGAGAUGCCGCCCAGGAACUGAGAGCCAGCCUGCUG GAAACCCAGAUGGAAGAGGACAUCCUGCAGCUGCAGGCCGAGG CCACAGCUGAGGUGCUGGGAGAAGUGGCCCAGGCCCAGAAGG UGCUGAGAGACAGCGUGCAGCGGCUGGAAGUGCAGCUGAGAU CUGCCUGGCUGGGCCCUGCCUACCGCGAGUUCGAAGUGCUGA AAGCCCACGCCGACAAGCAGAGCCACAUCCUGUGGGCCCUGAC AGGCCACGUGCAGAGACAGAGGCGGGAAAUGGUGGCUCAGCA GCACAGACUGCGGCAGAUCCAGGAACGGCUGCAUACAGCUGCC CUGCCCGCCGACUACAAGGACGACGACGACAAGCACCACCACC AUCACCACGGCGGAGGCCUGAACGACAUCUUCGAAGCCCAGAA AAUCGAGUGGCACGAGUAA U = Uridine and/or pseudouridine |

IV. TSHR

The thyroid-stimulating hormone receptor (TSHR) is a G protein-coupled receptor, essential for thyroid growth and thyroid hormone production. It is also an autoantigen in Grave's disease. Prolonged activation of TSHR by TSHR-specific autoantibodies is one of the main cause underlying Graves' disease (Davies T F (2015) Expert Opin Ther Targets; 19:835-47).

TSHR has a large extracellular domain (ECD) and a transmembrane domain (TMD). ECD has eleven leucine-rich repeat domains (LRD), which contains the binding sites for TSH and many autoantibodies. TSHR goes through extensive post-translational modifications and can form homodimers and polymers. TSHR has low baseline constitutive activities. Its signaling is promiscuous, mediated by Gs, Gi/o, Gq/11 or G12/13. TSHR is 51% identical to luteinizing hormone, choriogonadotropin receptor (LHCGR) and 48% identical to follicle stimulating hormone receptor (FSHR).

In normal thyroids, TSH activates TSHR, regulating thyrocyte proliferation and thyroid hormone release. In Graves' disease, agonistic autoantibodies are generated in patients. They displace TSH and over-activate the receptor in an unregulated manner: thyroid is enlarged and T3 and T4 levels are elevated.

The full length coding sequence of human TSHR (e.g., Protein Accession No. NP_000360.2) was codon optimized for expression in human cells and cloned into a vector that can sustain mRNA transcription by T7 polymerase and contains both 3 and 5' untranslated regions that help with mRNA stability and translatability (see Table 4 for sequence). mRNA was in vitro transcribed and encapsulated into lipid nanoparticles as described above.

TABLE 4

Exemplary TSHR Polynucleotide and Polypeptide Sequences

| SEQ ID NO: and features | Sequence |
|---|---|
| SEQ ID NO: 44<br>TSHR native DNA<br>sequence<br>corresponding to<br>Protein Accession<br># NP_000360.2 | CCTCCTCCACAGTGGTGAGGTCACAGCCCCTTGGAGCCCTCCCTCTTCCCAC<br>CCCTCCCGCTCCCGGGTCTCCTTTGGCCTGGGGTAACCCGAGGTGCAGAGC<br>TGAGAATGAGGCGATTTCGGAGGATGGAGAAATAGCCCCGAGTCCCGTGGA<br>AAATGAGGCCGGCGGACTTGCTGCAGCTGGTGCTGCTGCTCGACCTGCCCA<br>GGGACCTGGGCGGAATGGGGTGTTCGTCTCCACCCTGCGAGTGCCATCAGG<br>AGGAGGACTTCAGAGTCACCTGCAAGGATATTCAACGCATCCCCAGCTTACC<br>GCCCAGTACGCAGACTCTGAAGCTTATTGAGACTCACCTGAGAACTATTCCAA<br>GTCATGCATTTTCTAATCTGCCCAATATTTCCAGAATCTACGTATCTATAGATG<br>TGACTCTGCAGCAGCTGGAATCACACTCCTTCTACAATTTGAGTAAAGTGACT<br>CACATAGAAATTCGGAATACCAGGAACTTAACTTACATAGACCCTGATGCCCT<br>CAAAGAGCTCCCCCTCCTAAAGTTCCTTGGCATTTTCAACACTGGACTTAAAA<br>TGTTCCCTGACCTGACCAAAGTTTATTCCACTGATATATTCTTTATACTTGAAA<br>TTACAGACAACCCTTACATGACGTCAATCCCTGTGAATGCTTTTCAGGGACTA<br>TGCAATGAAACCTTGACACTGAAGCTGTACAACAATGGCTTTACTTCAGTCCA<br>AGGATATGCTTTCAATGGGACAAAGCTGGATGCTGTTTACCTAAACAAGAATA<br>AATACCTGACAGTTATTGACAAAGATGCATTTGGAGGAGTATACAGTGGACCA<br>AGCTTGCTGGACGTGTCTCAAACCAGTGTCACTGCCCTTCCATCCAAAGGCC<br>TGGAGCACCTGAAGGAACTGATAGCAAGAAACACCTGGACTCTTAAGAAACT<br>TCCACTTTCCTTGAGTTTCCTTCACCTCACACGGGCTGACCTTTCTTACCCAA<br>GCCACTGCTGTGCTTTTAAGAATCAGAAGAAAATCAGAGGAATCCTTGAGTCC<br>TTGATGTGTAATGAGAGCAGTATGCAGAGCTTGCGCCAGAGAAAATCTGTGA<br>ATGCCTTGAATAGCCCCCTCCACCAGGAATATGAAGAGAATCTGGGTGACAG<br>CATTGTTGGGTACAAGGAAAAGTCCAAGTTCCAGGATACTCATAACAACGCTC<br>ATTATTACGTCTTCTTTGAAGAACAAGAGGATGAGATCATTGGTTTTGGCCAG<br>GAGCTCAAAAACCCCCAGGAAGAGACTCTACAAGCTTTTGACAGCCATTATGA<br>CTACACCATATGTGGGGACAGTGAAGACATGGTGTGTACCCCCAAGTCCGAT<br>GAGTTCAACCCGTGTGAAGACATAATGGGCTACAAGTTCCTGAGAATTGTGG<br>TGTGGTTCGTTAGTCTGCTGGCTCTCCTGGGCAATGTCTTTGTCCTGCTTATT<br>CTCCTCACCAGCCACTACAAACTGAACGTCCCCCGCTTTCTCATGTGCAACCT<br>GGCCTTTGCGGATTTCTGCATGGGGATGTACCTGCTCCTCATCGCCTCTGTA<br>GACCTCTACACTCACTCTGAGTACTACAACCATGCCATCGACTGGCAGACAG<br>GCCCTGGGTGCAACACGGCTGGTTTCTTCACTGTCTTTGCAAGCGAGTTATC<br>GGTGTATACGCTGACGGTCATCACCCTGGAGCGCTGGTATGCCATCACCTTC<br>GCCATGCGCCTGGACCGGAAGATCCGCCTCAGGCACGCATGTGCCATCATG<br>GTTGGGGGCTGGGTTTGCTGCTTCCTTCTCGCCCTGCTTCCTTTGGTGGGAA<br>TAAGTAGCTATGCCAAAGTCAGTATCTGCCTGCCCATGGACACCGAGACCCC<br>TCTTGCTCTGGCATATATTGTTTTTGTTCTGACGCTCAACATAGTTGCCTTCGT<br>CATCGTCTGCTGCTGTTATGTGAAGATCTACATCACAGTCCGAAATCCGCAGT<br>ACAACCCAGGGGACAAAGATACCAAAATTGCCAAGAGGATGGCTGTGTTGAT<br>CTTCACCGACTTCATATGCATGGCCCCAATCTCATTCTATGCTCTGTCAGCAA<br>TTCTGAACAAGCCTCTCATCACTGTTAGCAACTCCAAAATCTTGCTGGTACTC<br>TTCTATCCACTTAACTCCTGTGCCAATCCATTCCTCTATGCTATTTTCACCAAG<br>GCCTTCCAGAGGGATGTGTTCATCCTACTCAGCAAGTTTGGCATCTGTAAACG<br>CCAGGCTCAGGCATACCGGGGGCAGAGGGTTCCTCCAAAGAACAGCACTGA<br>TATTCAGGTTCAAAAGGTTACCCACGAGATGAGGCAGGGTCTCCACAACATG<br>GAAGATGTCTATGAACTGATTGAAAACTCCCATCTAACCCCAAAGAAGCAAGG<br>CCAAATCTCAGAAGAGTATATGCAAACGGTTTTGTAAGTTAACACTACACTACT<br>CACAATGGTAGGGGAACTTACAAAATAATAGTTTCTTGAATATGCATTCCAATC<br>CCATGACACCCCCAACACATAGCTGCCCTCACTCTTGTGCAGGCGATGTTTC<br>AATGTTTCATGGGGCAAGAGTTTATCTCTGGAGAGTGATTAGTATTAACCTAA<br>TCATTGCCCCCAAGAAGGAAGTTAGGCTACCAGCATATTTGAATGCCAGGTG<br>AAATCAAAATAATCTACACTATCTAGAAGACTTTCTTGATGCCAAGTCCAGAGA<br>TGTCATTGTGTAGGATGTTCAGTAAATATTAACTGAGCTATGTCAATATAGAGC |

TABLE 4-continued

| Exemplary TSHR Polynucleotide and Polypeptide Sequences | |
|---|---|
| SEQ ID NO: and features | Sequence |
| | TTCTCAGTTTTGTATAACATTTCATACTAAAGATTCAGCAAATGGAAAATGCTA |
| | TTAATTTGGTTGGTGACCACAAGATAAAATCAGTCCCACGTTGGCTCAGTTCA |
| | ACTAGATGTTCCCTGATACAAAGAGAACTTGATTTCCTTAAAACTGAAAAGCC |
| | AAACACAGCTAGCTGTCATACAAGAAACAGCTATTATGAGACATGAAGGAGG |
| | GTAAGAATTAGCTTTAAGTTTTGTTTTGCTTTGTTTTGTTTTTTAACTCAACCTA |
| | TTAATCATCTCTTCACAAGAATCCACCTGATGTGACCAAGCTATTATGTGTTGC |
| | CTGGAAAAACTGGCAAGATTTCAGCTTATGTGGCCTAGCAAACTAAGAATTGC |
| | TCTTCTTGGCCAGCCTCATAGCATAAAAGATGTGAACTCTAGGAAGTCTTTCT |
| | GAGTAGCAATAAGTGGGAATTATGGGCAGAGCACACTCAATCCCCTGTTGAT |
| | TAATAAAACAGGCTGGACACTAATTAACTATGGGACTTAAATCTGTAGAAATG |
| | AAGGAGTCCAATAGCTTCTTCCAATTTTAAAACTCTAGTACATCCCTTTCCCTC |
| | AAATATATATTTCTAAGATAAAGAGAAAGAAGAGCACTAAGTAAGTAGAATCTG |
| | TTTTTCCTATTTTGTAGGGCTGCTGACTCCTAGTCCTTGAAGCCTAGACACAT |
| | GACCCAGGAAATTTTTCCTTTGTTTCACTTTTGATTATGATGTCTGAGCCAAAA |
| | ATTCAATTAAGTAAACATACTCGCCTGGATCTGAATCATTCATTTAATTACTAG |
| | ATCTACCCAGCTGTTATATCAGGCCAAAAACAGATTCGTGTTTATATAAAAGA |
| | GTAAACGATGGTTGCAAATTTTGGCTATTTAGAGTTGCTACTTCACTATGAAGA |
| | GTCACTTCAAAACACTTCGCTTGTCTTTAGGATGATTTTTGCCATTTCCAGTC |
| | CACGGTATGATACTAAAGCTGTCAAGAGAGGTTTCTTCTTTTCTGAAACTGCC |
| | AGCTCTTTCCAGCCCTGTTGATCACTGGACATAAAGCTTCTTTTCCCCAATAAT |
| | TCTTCTTTACTTAAAATAGTCAGGATCTTTATCTACAGATGTACTCTCCAGGTT |
| | ACCTGTGATGATAGCCCCCTAATGTCCTGCTAGAAAAGTCTCCAAGCAGAGAT |
| | GACATTACTTCTGAATGCTCATAAACCACACCATGAAATAAAAGCTCTTTGTTG |
| | TTTTAAGATTGTGAAGTGTCGTTAATGGGTCCCCACAGATGGTCCCTGCTGGA |
| | CTCACCTGGAATCTCTCCACAGCCATACCCACTCATCACTATCATTGAGACCT |
| | GCACATCTTAATAGAAATATTATAAACATCGAAAATCATGACTTACCTAGAAGT |
| | TCGCTTGTAACTAATGAAATTAAACAAATGTGTTGCCTTTTGTCATGTGTTTCT |
| | CTCCTGTGACATTTCAAAATATCACATCTTGATAAATAATGTGTTTCATCTTGA |
| | ATAGCTGAACTAATTGCTTTGGAAACAGAGTCCTAGAAAAGTGACTTCAACAG |
| | AATTGTTACTAAAATTTGCACTCACAACATGAAATAAATTTTCTTCCTATGGAAT |
| | AATCGTGAAAAAAAAAA |
| SEQ ID NO: 14 | CCUCCUCCACAGUGGUGAGGUCACAGCCCCUUGGAGCCCUCCCCUCUUCCC |
| TSHR native | ACCCCUCCCGCUCCCGGGUCUCCUUUGGCCUGGGGUAACCCGAGGUGCAG |
| mRNA sequence | AGCUGAGAAUGAGGCGAUUUCGGAGGAUGGAGAAAUAGCCCCGAGUCCCG |
| corresponding to | UGGAAAAUGAGGCCGGCGGACUUGCUGCAGCUGGUGCUGCUGCUCGACCU |
| Protein Accession | GCCCAGGGACCUGGGCGGAAUGGGGUGUUCGUCUCCACCCUGCGAGUGC |
| # NP_000360.2 | CAUCAGGAGGAGGACUUCAGAGUCACCUGCAAGGAUAUUCAACGCAUCCCC |
| | AGCUUACCGCCCAGUACGCAGACUCUGAAGCUUAUUGAGACUCACCUGAGA |
| | ACUAUUCCAAGUCAUGCAUUUUCUAAUCUGCCCAAUAUUUCCAGAAUCUAC |
| | GUAUCUAUAGAUGUGACUCUGCAGCAGCUGGAAUCACACUCCUUCUACAAU |
| | UUGAGUAAAGUGACUCACAUAGAAAUUCGGAAUACCAGGAACUUAACUUAC |
| | AUAGACCCUGAUGCCCUCAAAGAGCUCCCCCUCCUAAAGUUCCUUGGCAUU |
| | UUCAACACUGGACUUAAAAUGUUCCCUGACCUGACCAAAGUUUAUUCCACU |
| | GAUAUAUUCUUUAUACUUGAAAUUACAGACAACCCUUACAUGACGUCAAUC |
| | CCUGUGAAUGCUUUUCAGGGACUAUGCAAUGAAACCUUGACACUGAAGCU |
| | GUACAACAAUGGCUUUACUUCAGUCCAAGGAUAUGCUUUCAAUGGGACAAA |
| | GCUGGAUGCUGUUUACCUAAACAAGAAUAAAUACCUGACAGUUAUUGACAA |
| | AGAUGCAUUUGGAGGAGUAUACAGUGGACCAAGCUUGCUGGACGUGUCUC |
| | AAACCAGUGUCACUGCCCUUCCAUCCAAAGGCCUGGAGCACCUGAAGGAAC |
| | UGAUAGCAAGAAACACCUGGACUCUUAAGAAACUUCCACUUUCCUUGAGUU |
| | UCCUUCACCUCACACGGGCUGACCUUUCUUACCCAAGCCACUGCUGUGCU |
| | UUUAAGAAUCAGAAGAAAAUCAGAGGAAUCCUUGAGUCCUUGAUGUGUAAU |
| | GAGAGCAGUAUGCAGAGCUUGCGCCAGAGAAAAUCUGUGAAUGCCUUGAA |
| | UAGCCCCCUCCACCAGGAAUAUGAAGAGAAUCUGGGUGACAGCAUUGUUG |
| | GGUACAAGGAAAAGUCCAAGUUCCAGGAUACUCAUAACAACGCUCAUUAUU |
| | ACGUCUUCUUUGAAGAACAAGAGGAUGAGAUCAUUGGUUUUGGCCAGGAG |
| | CUCAAAAACCCCCAGGAAGAGACUCUACAAGCUUUUGACAGCCAUUAUGAC |
| | UACACCAUAUGUGGGGACAGUGAAGACAUGGUGUGUACCCCCAAGUCCGA |
| | UGAGUUCAACCCGUGUGAAGACAUAAUGGGCUACAAGUUCCUGAGAAUUG |
| | UGGUGUGGUUCGUUAGUCUGCUGGCUCUCCUGGGCAAUGUCUUUGUCCU |
| | GCUUAUUCUCCUCACCAGCCACUACAAACUGAACGUCCCCCGCUUUCUCAU |
| | GUGCAACCUGGCCUUUGCGGAUUUCUGCAUGGGGAUGUACCUGCUCCUCA |
| | UCGCCUCUGUAGACCUCUACACUCACUCUGAGUACUACAACCAUGCCAUCG |
| | ACUGGCAGACAGGCCCUGGGUGCAACACGGCUGGUUUCUUCACUGUCUUU |
| | GCAAGCGAGUUAUCGGUGUAUACGCUGACGGUCAUCACCCUGGAGCGCUG |
| | GUAUGCCAUCACCUUCGCCAUGCGCCUGGACCGGAAGAUCCGCCUCAGGC |
| | ACGCAUGUGCCAUCAUGGUUGGGGGCUGGGUUUGCUGCUUCCUUCUCGC |
| | CCUGCUUCCUUUGGUGGGAAUAAGUAGCUAUGCCAAAGUCAGUAUCUGCC |
| | UGCCCAUGGACACCGAGACCCCUCUUGCUCUGGCAUAUAUUGUUUUUGUU |
| | CUGACGCUCAACAUAGUUGCCUUCGUCAUCGUCUGCUGCUGUUAUGUGAA |
| | GAUCUACAUCACAGUCCGAAAUCCGCAGUACAACCCAGGGGACAAAGAUAC |
| | CAAAAUUGCCAAGAGGAUGGCUGUGUUGAUCUUCACCGACUUCAUAUGCAU |
| | GGCCCCAAUCUCAUUCUAUGCUCUGUCAGCAAUUCUGAACAAGCCUCUCAU |
| | CACUGUUAGCAACUCCAAAAUCUUGCUGGUACUCUUCUAUCCACUUAACUC |

TABLE 4-continued

Exemplary TSHR Polynucleotide and Polypeptide Sequences

| SEQ ID NO: and features | Sequence |
| --- | --- |
| | CUGUGCCAAUCCAUUCCUCUAUGCUAUUUUCACCAAGGCCUUCCAGAGGG AUGUGUUCAUCCUACUCAGCAAGUUUGGCAUCUGUAAACGCCAGGCUCAG GCAUACCGGGGGCAGAGGGUUCCUCCAAAGAACAGCACUGAUAUUCAGGU UCAAAAGGUUACCCACGAGAUGAGGCAGGGUCUCCACAACAUGGAAGAUGU CUAUGAACUGAUUGAAAACUCCCAUCUAACCCCAAAGAAGCAAGGCCAAAU CUCAGAAGAGUAUAUGCAAACGGUUUUGUAAGUUAACACUACACUACUCAC AAUGGUAGGGGAACUUACAAAAUAAUAGUUUCUUGAAUAUGCAUUCCAAUC CCAUGACACCCCCAACACAUAGCUGCCCUCACUCUUGUGCAGGCGAUGUU UCAAUGUUUCAUGGGGCAAGAGUUUAUCUCUGGAGAGUGAUUAGUAUUAA CCUAAUCAUUGCCCCCAAGAAGGAAGUUAGGCUACCAGCAUAUUUGAAUGC CAGGUGAAAUCAAAAUAAUCUACACUAUCUAGAAGACUUUCUUGAUGCCAA GUCCAGAGAUGUCAUUGUGUAGGAUGUUCAGUAAAUAUUAACUGAGCUAU GUCAAUAUAGAGCUUCUCAGUUUUGUAUAACAUUUCAUACUAAAGAUUCAG CAAAUGGAAAAUGCUAUUAAUUUGGUUGGUGACCACAAGAUAAAAUCAGUC CCACGUUGGCUCAGUUCAACUAGAUGUUCCCUGAUACAAAGAGAACUUGAU UUCCUUAAAACUGAAAAGCCAAACACAGCUAGCUGUCAUACAAGAAACAGC UAUUAUGAGACAUGAAGGAGGGUAAGAAUUAGCUUUAAGUUUUGUUUUGC UUUGUUUUGUUUUUUAACUCAACCUAUUAAUCAUCUCUUCACAAGAAUCCA CCUGAUGUGACCAAGCUAUUAUGUGUUGCCUGGAAAAACUGGCAAGAUUU CAGCUUAUGUGGCCUAGCAAACUAAGAAUUGCUCUUCUUGGCCAGCCUCA UAGCAUAAAAGAUGUGAACUCUAGGAAGUCUUUCUGAGUAGCAAUAAGUGG GAAUUAUGGGCAGAGCACACUCAAUCCCCUGUUGAUUAAUAAAACAGGCUG GACACUAAUUAACUAUGGGACUUAAAUCUGUAGAAAUGAAGGAGUCCAAUA GCUUCUUCCAAUUUUAAAACUCUAGUACAUCCCUUUCCCUCAAAUAUAUAU UUCUAAGAUAAAGAGAAAGAAGAGCACUAAGUAAGUAGAAUCUGUUUUUCC UAUUUUGUAGGGCUGCUGACUCCUAGUCCUUGAAGCCUAGACACAUGACC CAGGAAAUUUUUCCUUUGUUUCACUUUUGAUUAUGAUGUCUGAGCCAAAAA UUCAAUUAAGUAAACAUACUCGCCUGGAUCUGAAUCAUUCAUUUAAUUACU AGAUCUACCCAGCUGUUAUAUCAGGCCAAAAACAGAUUCGUGUUUAUAUAA AAGAGUAAACGAUGGUUGCAAAUUUUGGCUAUUUAGAGUUGCUACUUCACU AUGAAGAGUCACUUCAAAACACUUCGCUUGUCUUUAGGGAUGAUUUUUGCC AUUUCCAGUCCACGGUAUGAUACUAAAGCUGUCAAGAGAGGUUUCUUCUUU UCUGAAACUGCCAGCUCUUUCCAGCCCUGUUGAUCACUGGACAUAAAGCUU CUUUUCCCCAAUAAUUCUUCUUUACUUAAAAUAGUCAGGAUCUUUAUCUAC AGAUGUACUCUCCAGGUUACCUGUGAUGAUAGCCCCCUAAUGUCCUGCUA GAAAAGUCUCCAAGCAGAGAUGACAUUACUUCUGAAUGCUCAUAAACCACA CCAUGAAAUAAAAGCUCUUUGUUGUUUUAAGAUUGUGAAGUGUCGUUAAUG GGUCCCCACAGAUGGUCCCUGCUGGACUCACCUGGAAUCUCUCCACAGCC AUACCCACUCAUCACUAUCAUUGAGACCUGCACAUCUUAAUAGAAAUAUUA UAAACAUCGAAAAUCAUGACUUACCUAGAAGUUCGCUUGUAACUAAUGAAA UUAAACAAAUGUGUUGCCUUUUGUCAUGUGUUUCUCUCCUGUGACAUUUC AAAAUAUCACAUCUUGAUAAAUAAUGUGUUUCAUCUUGAAUAGCUGAACUA AUUGCUUUGGAAACAGAGUCCUAGAAAAGUGACUUCAACAGAAUUGUUACU AAAAUUUGCACUCACAACAUGAAAUAAAUUUUCUUCCUAUGGAAUAAUCGU GAAAAAAAAAA<br>U = Uridine and/or pseudouridine |
| SEQ ID NO: 15 Translated human TSHR from coding sequence (CDS) of the mRNA construct of SEQ ID NO: 14 | MRPADLLQLVLLLDLPRDLGGMGCSSPPCECHQEEDFRVTCKDIQRIPSLPPSTQ TLKLIETHLRTIPSHAFSNLPNISRIYVSIDVTLQQLESHSFYNLSKVTHIEIRNTRNL TYIDPDALKELPLLKFLGIFNTGLKMFPDLTKVYSTDIFFILEITDNPYMTSIPVNAFQ GLCNETLTLKLYNNGFTSVQGYAFNGTKLDAVYLNKNKYLTVIDKDAFGGVYSGP SLLDVSQTSVTALPSKGLEHLKELIARNTWTLKKLPLSLSFLHLTRADLSYPSHCC AFKNQKKIRGILESLMCNESSMQSLRQRKSVNALNSPLHQEYEENLGDSIVGYKE KSKFQDTHNNAHYYVFFEEQEDEIIGFGQELKNPQEETLQAFDSHYDYTICGDSE DMVCTPKSDEFNPCEDIMGYKFLRIVVWFVSLLALLGNVFVLLILLTSHYKLNVPR FLMCNLAFADFCMGMYLLLIASVDLYTHSEYYNHAIDWQTGPGCNTAGFFTVFAS ELSVYTLTVITLERWYAITFAMRLDRKIRLRHACAIMVGGWVCCFLLALLPLVGISS YAKVSICLPMDTETPLALAYIVFVLTLNIVAFVIVCCCYVKIYITVRNPQYNPGDKDT KIAKRMAVLIFTDFICMAPISFYALSAILNKPLITVSNSKILLVLFYPLNSCANPFLYAI FTKAFQRDVFILLSKFGICKRQAQAYRGQRVPPKNSTDIQVQKVTHEMRQGLHN MEDVYELIENSHLTPKKQGQISEEYMQTVL |
| SEQ ID NO: 45 (DNA) TEV-hTSHR-2xhBG-120A Sequence features: Tobacco Etch Virus (TEV) 5' UTR: 37-190 Optimal Kozak sequence: 191-199 Human TSHR codon optimized, encoding amino | GGAGGCCGGAGAATTGTAATACGACTCACTATAGGGAGACGCGTGTTAAATA ACAAATCTCAACACAACATATACAAAACAAACGAATCTCAAGCAATCAAGCATT CTACTTCTATTGCAGCAATTTAAATCATTTCTTTTAAAGCAAAAGCAATTTTCTG AAAATTTTCACCATTTACGAACGATAGCCGCCACCATGAGGCCTGCCGACCT GCTGCAGCTGGTGCTGCTGCTGGACCTGCCTAGAGATCTGGGCGGCATGGG CTGTAGCAGCCCTCCATGCGAGTGCCACCAGGAAGAGGACTTCAGAGTGAC CTGCAAGGACATCCAGAGAATCCCCAGCCTGCCCCCCAGCACCCAGACCCT GAAGCTGATCGAGACACACCTGAGAACCATCCCTAGCCACGCCTTCAGCAAC CTGCCCAACATCAGCAGAATCTACGTGTCCATCGACGTGACCCTGCAGCAGC TGGAAAGCCACAGCTTCTACAACCTGAGCAAAGTGACCCACATCGAGATCAG AAACACCCGGAACCTGACCTACATCGACCCCGACGCCCTGAAAGAGCTGCC CCTGCTGAAGTTCCTGGGCATCTTCAACACCGGCCTGAAGATGTTCCCCGAC CTGACCAAGGTGTACTCTACCGACATCTTCTTCATCCTGGAAATCACCGACAA |

TABLE 4-continued

Exemplary TSHR Polynucleotide and Polypeptide Sequences

| SEQ ID NO: and features | Sequence |
|---|---|
| acids Accession #<br>NP_000360.2,<br>197-2488<br>2 stop codons:<br>2489-2495<br>2 copies of human<br>beta-globin 3'UTR:<br>2513-2776<br>120 nucleotide<br>polyA tail(SEQ ID<br>NO: 59):<br>2785-2904 | CCCCTACATGACCAGCATCCCCGTGAACGCCTTCCAGGGCCTGTGCAACGA<br>GACACTGACACTGAAGCTGTACAACAACGGCTTCACCAGCGTGCAGGGCTAC<br>GCCTTCAACGGCACAAAGCTGGACGCCGTGTACCTGAACAAGAACAAGTACC<br>TGACCGTGATCGACAAGGACGCCTTCGGCGGCGTGTACTCTGGACCTTCTCT<br>GCTGGACGTGTCCCAGACCAGCGTGACAGCCCTGCCTAGCAAGGGCCTGGA<br>ACACCTGAAAGAACTGATCGCCCGCAACACCTGGACTCTGAAGAAGCTGCCT<br>CTGAGCCTGAGCTTCCTGCACCTGACCAGAGCCGACCTGAGCTACCCAAGC<br>CACTGCTGCGCCTTCAAGAACCAGAAGAAGATCCGGGGAATCCTGGAATCCC<br>TGATGTGTAACGAGAGCAGCATGCAGAGCCTGAGACAGAGAAAGTCTGTGAA<br>CGCTCTGAACAGCCCCCTGCACCAGGAATACGAGGAAAACCTGGGCGACAG<br>CATCGTGGGCTACAAAGAGAAGTCCAAGTTCCAGGACACCCACAACAACGCC<br>CACTACTACGTGTTCTTCGAGGAACAGGAAGATGAGATCATCGGCTTCGGCC<br>AGGAACTGAAGAACCCTCAGGAAGAGACACTGCAGGCCTTCGACAGCCACTA<br>CGACTACACCATCTGCGGCGACAGCGAGGACATGGTGTGCACCCCTAAGAG<br>CGACGAGTTCAACCCCTGCGAGGATATTATGGGGTACAAGTTCCTGAGGATC<br>GTCGTGTGGTTCGTGTCCCTGCTGGCTCTGCTGGGCAACGTGTTCGTGCTGC<br>TGATCCTGCTGACCTCCCACTACAAGCTGAACGTGCCCAGATTCCTGATGTG<br>CAACCTGGCCTTCGCCGACTTCTGCATGGGCATGTACCTGCTGCTGATTGCC<br>AGCGTGGACCTGTACACCCACAGCGAGTACTACAACCACGCCATCGACTGGC<br>AGACCGGCCCTGGCTGTAACACCGCCGGCTTTTTCACCGTGTTCGCCAGCGA<br>GCTGAGCGTGTACACCCTGACAGTGATCACCCTGGAAAGGTGGTACGCCATC<br>ACCTTCGCCATGAGACTGGACAGAAAGATCAGACTGAGACACGCCTGCGCCA<br>TCATGGTGGGAGGCTGGGTGTGCTGTTTCCTGCTGGCCCTGCTGCCCCTCGT<br>GGGCATCAGCTCTTACGCCAAGGTGTCCATCTGCCTGCCCATGGACACCGAG<br>ACACCTCTGGCCCTGGCCTACATTGTGTTTGTGCTGACCCTGAACATCGTGG<br>CCTTCGTGATCGTGTGCTGCTGTTACGTGAAGATCTACATCACCGTGCGGAA<br>CCCCCAGTACAACCCCGGCGACAAGGATACCAAGATCGCCAAGAGAATGGC<br>CGTGCTGATCTTCACCGACTTCATCTGCATGGCCCCCATCAGCTTCTATGCCC<br>TGAGCGCCATTCTGAACAAGCCTCTGATCACCGTGTCCAACAGCAAAATCCT<br>GCTGGTGCTGTTCTACCCCCTGAACAGCTGCGCCAACCCCTTCCTGTACGCT<br>ATCTTCACCAAGGCCTTCCAGAGGGACGTGTTCATCCTGCTGTCTAAGTTCG<br>GCATCTGCAAGAGACAGGCCCAGGCCTACCGGGGCCAGAGAGTGCCTCCTA<br>AGAACTCCACAGACATCCAGGTGCAGAAAGTGACACACGACATGAGACAGGG<br>CCTGCACAACATGGAAGATGTGTACGAGCTGATTGAGAACAGCCACCTGACC<br>CCCAAGAAACAGGGACAGATCAGCGAAGAGTACATGCAGACCGTGCTGTGAT<br>AACGGACCGGCGATAGATGAAGCTCGCTTTCTTGCTGTCCAATTTCTATTAAA<br>GGTTCCTTTGTTCCCTAAGTCCAACTACTAAACTGGGGGATATTATGAAGGGC<br>CTTGAGCATCTGGATTCTGCCTAATAAAAAACATTTATTTTCATTGCAGCTCGC<br>TTTCTTGCTGTCCAATTTCTATTAAAGGTTCCTTTGTTCCCTAAGTCCAACTAC<br>TAAACTGGGGGATATTATGAAGGGCCTTGAGCATCTGGATTCTGCCTAATAAA<br>AAACATTTATTTTCATTGCGGCCGCAAAAAAAAAAAAAAAAAAAAAAAAAAAAA<br>AAAAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAA |
| SEQ ID NO: 16<br>(mRNA)<br>TEV-hTSHR-<br>2xhBG-120A<br>Sequence features:<br>Tobacco Etch Virus<br>(TEV) 5' UTR:<br>37-190<br>Optimal Kozak<br>sequence: 191-199<br>Human TSHR<br>codon optimized,<br>encoding amino<br>acids Accession #<br>NP_000360.2,<br>197-2488<br>2 stop codons:<br>2489-2495<br>2 copies of human<br>beta-globin 3'UTR:<br>2513-2776<br>120 nucleotide<br>polyA tail(SEQ ID<br>NO: 59):<br>2785-2904 | GGGAGACGCGUGUUAAAUAACAAAUCUCAACACAACAUAUACAAAACAAACG<br>AAUCUCAAGCAAUCAAGCAUUCUACUUCUAUUGCAGCAAUUUAAAUCAUUU<br>CUUUUAAAGCAAAAGCAAUUUUCUGAAAAUUUUCACCAUUUACGAACGAUA<br>GCCGCCACCAUGAGGCCUGCCGACCUGCUGCAGCUGGUGCUGCUGCUGG<br>ACCUGCCUAGAGAUCUGGGCGGCAUGGGCUGUAGCAGCCCUCCAUGCGAG<br>UGCCACCAGGAAGAGGACUUCAGAGUGACCUGCAAGGACAUCCAGAGAAUC<br>CCCAGCCUGCCCCCCAGCACCCAGACCCUGAAGCUGAUCGAGACACACCU<br>GAGAACCAUCCCUAGCCACGCCUUCAGCAACCUGCCCAACAUCAGCAGAAU<br>CUACGUGUCCAUCGACGUGACCCUGCAGCAGCUGGAAAGCCACAGCUUCU<br>ACAACCUGAGCAAAGUGACCCACAUCGAGAUCAGAAACACCCGGAACCUGA<br>CCUACAUCGACCCCGACGCCCUGAAAGAGCUGCCCCUGCUGAAGUUCCUG<br>GGCAUCUUCAACACCGGCCUGAAGAUGUUCCCCGACCUGACCAAGGUGUA<br>CUCUACCGACAUCUUCUUCAUCCUGGAAAUCACCGACAACCCCUACAUGAC<br>CAGCAUCCCCGUGAACGCCUUCCAGGGCCUGUGCAACGAGACACUGACAC<br>UGAAGCUGUACAACAACGGCUUCACCAGCGUGCAGGGCUACGCCUUCAAC<br>GGCACAAAGCUGGACGCCGUGUACCUGAACAAGAACAAGUACCUGACCGU<br>GAUCGACAAGGACGCCUUCGGCGGCGUGUACUCUGGACCUUCUCUGCUGG<br>ACGUGUCCCAGACCAGCGUGACAGCCCUGCCUAGCAAGGGCCUGGAACAC<br>CUGAAAGAACUGAUCGCCCGCAACACCUGGACUCUGAAGAAGCUGCCUCU<br>GAGCCUGAGCUUCCUGCACCUGACCAGAGCCGACCUGAGCUACCCAAGCC<br>ACUGCUGCGCCUUCAAGAACCAGAAGAAGAUCCGGGGAAUCCUGGAAUCC<br>CUGAUGUGUAACGAGAGCAGCAUGCAGAGCCUGAGACAGAGAAAGUCUGU<br>GAACGCUCUGAACAGCCCCCUGCACCAGGAAUACGAGGAAAACCUGGGCG<br>ACAGCAUCGUGGGCUACAAAGAGAAGUCCAAGUUCCAGGACACCCACAACA<br>ACGCCCACUACUACGUGUUCUUCGAGGAACAGGAAGAUGAGAUCAUCGGC<br>UUCGGCCAGGAACUGAAGAACCCUCAGGAAGAGACACUGCAGGCCUUCGA<br>CAGCCACUACGACUACACCAUCUGCGGCGACAGCGAGGACAUGGUGUGCA<br>CCCCUAAGAGCGACGAGUUCAACCCCUGCGAGGAUAUUAUGGGGUACAAG<br>UUCCUGAGGAUCGUCGUGUGGUUCGUGUCCCUGCUGGCUCUGCUGGGCA<br>ACGUGUUCGUGCUGCUGAUCCUGCUGACCUCCCACUACAAGCUGAACGUG<br>CCCAGAUUCCUGAUGUGCAACCUGGCCUUCGCCGACUUCUGCAUGGGCAU |

TABLE 4-continued

Exemplary TSHR Polynucleotide and Polypeptide Sequences

| SEQ ID NO: and features | Sequence |
|---|---|
| | GUACCUGCUGCUGAUUGCCAGCGUGGACCUGUACACCCACAGCGAGUACU<br>ACAACCACGCCAUCGACUGGCAGACCGGCCCUGGCUGUAACACCGCCGGC<br>UUUUUCACCGUGUUCGCCAGCGAGCUGAGCGUGUACACCCUGACAGUGAU<br>CACCCUGGAAAGGUGGUACGCCAUCACCUUCGCCAUGAGACUGGACAGAA<br>AGAUCAGACUGAGACACGCCUGCGCCAUCAUGGUGGGAGGCUGGGUGUGC<br>UGUUUCCUGCUGGCCCUGCUGCCCCUCGUGGGCAUCAGCUCUUACGCCAA<br>GGUGUCCAUCUGCCUGCCCAUGGACACCGAGACACCUCUGGCCCUGGCCU<br>ACAUUGUGUUUGUGCUGACCCUGAACAUCGUGGCCUUCGUGAUCGUGUGC<br>UGCUGUUACGUGAAGAUCUACAUCACCGUGCGGAACCCCCAGUACAACCCC<br>GGCGACAAGGAUACCAAGAUCGCCAAGAGAAUGGCCGUGCUGAUCUUCAC<br>CGACUUCAUCUGCAUGGCCCCCAUCAGCUUCUAUGCCCUGAGCGCCAUUC<br>UGAACAAGCCUCUGAUCACCGUGUCCAACAGCAAAAUCCUGCUGGUGCUG<br>UUCUACCCCCUGAACAGCUGCGCCAACCCCUUCCUGUACGCUAUCUUCACC<br>AAGGCCUUCCAGAGGGACGUGUUCAUCCUGCUGUCUAAGUUCGGCAUCUG<br>CAAGAGACAGGCCCAGGCCUACCGGGGCCAGAGAGUGCCUCCUAAGAACU<br>CCACAGACAUCCAGGUGCAGAAAGUGACACACGACAUGAGACAGGGCCUGC<br>ACAACAUGGAAGAUGUGUACGAGCUGAUUGAGAACAGCCACCUGACCCCCA<br>AGAAACAGGGACAGAUCAGCGAAGAGUACAUGCAGACCGUGCUGUGAUAAC<br>GGACCGGCGAUAGAUGAAGCUCGCUUUCUUGCUGUCCAAUUUCUAUUAAA<br>GGUUCCUUUGUUCCCUAAGUCCAACUACUAAACUGGGGGAUAUUAUGAAG<br>GGCCUUGAGCAUCUGGAUUCUGCCUAAUAAAAAACAUUUAUUUUCAUUGCA<br>GCUCGCUUUCUUGCUGUCCAAUUUCUAUUAAAGGUUCCUUUGUU<br>CCCUAAGUCCAACUACUAAACUGGGGGAUAUUAUGAAGGGCCUUGAGCAU<br>CUGGAUUCUGCCUAAUAAAAAACAUUUAUUUUCAUUGCGGCCGCAAAAAAA<br>AAAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAAA<br>AAAAA<br>U = Uridine and/or pseudouridine |
| SEQ ID NO: 46<br>TSHR RNA coding sequence of construct of SEQ ID NO: 16 | AUGAGGCCUGCCGACCUGCUGCAGCUGGUGCUGCUGCUGGACCUGCCUA<br>GAGAUCUGGGCGGCAUGGGCUGUAGCAGCCCUCCAUGCGAGUGCCACCA<br>GGAAGAGGACUUCAGAGUGACCUGCAAGGACAUCCAGAGAAUCCCCAGCC<br>UGCCCCCCAGCACCCAGACCCUGAAGCUGAUCGAGACACACCUGAGAACCA<br>UCCCUAGCCACGCCUUCAGCAACCUGCCCAACAUCAGCAGAAUCUACGUGU<br>CCAUCGACGUGACCCUGCAGCAGCUGGAAAGCCACAGCUUCUACAACCUG<br>AGCAAAGUGACCCACAUCGAGAUCAGAAACACCCGGAACCUGACCUACAUC<br>GACCCCGACGCCCUGAAAGAGCUGCCCCUGCUGAAGUUCCUGGGCAUCUU<br>CAACACCGGCCUGAAGAUGUUCCCCGACCUGACCAAGGUGUACUCUACCG<br>ACAUCUUCUUCAUCCUGGAAAUCACCGACAACCCCUACAUGACCAGCAUCC<br>CCGUGAACGCCUUCCAGGGCCUGUGCAACGAGACACUGACACUGAAGCUG<br>UACAACAACGGCUUCACCAGCGUGCAGGGCUACGCCUUCAACGGCACAAA<br>GCUGGACGCCGUGUACCUGAACAAGAACAAGUACCUGACCGUGAUCGACA<br>AGGACGCCUUCGGCGGCGUGUACUCUGGACCUUCUCUGCUGGACGUGUC<br>CCAGACCAGCGUGACAGCCCUGCCUAGCAAGGGCCUGGAACACCUGAAAG<br>AACUGAUCGCCCGCAACACCUGGACUCUGAAGAAGCUGCCUCUGAGCCUG<br>AGCUUCCUGCACCUGACCAGAGCCGACCUGAGCUACCCAAGCCACUGCUG<br>CGCCUUCAAGAACCAGAAGAAGAUCCGGGGAAUCCUGGAAUCCCUGAUGU<br>GUAACGAGAGCAGCAUGCAGAGCCUGAGACAGAGAAAGUCUGUGAACGCU<br>CUGAACAGCCCCCUGCACCAGGAAUACGAGGAAAACCUGGGCGACAGCAU<br>CGUGGGCUACAAAGAGAAGUCCAAGUUCCAGGACACCCACAACAACGCCCA<br>CUACUACGUGUUCUUCGAGGAACAGGAAGAUGAGAUCAUCGGCUUCGGCC<br>AGGAACUGAAGAACCCUCAGGAAGAGACACUGCAGGCCUUCGACAGCCAC<br>UACGACUACACCAUCUGCGGCGACAGCGAGGACAUGGUGUGCACCCCUAA<br>GAGCGACGAGUUCAACCCCUGCGAGGAUAUUAUGGGGUACAAGUUCCUGA<br>GGAUCGUCGUGUGGUUCGUGUCCCUGCUGGCUCUGCUGGGCAACGUGUU<br>CGUGCUGCUGAUCCUGCUGACCUCCCACUACAAGCUGAACGUGCCCAGAU<br>UCCUGAUGUGCAACCUGGCCUUCGCCGACUUCUGCAUGGGCAUGUACCUG<br>CUGCUGAUUGCCAGCGUGGACCUGUACACCCACAGCGAGUACUACAACCA<br>CGCCAUCGACUGGCAGACCGGCCCUGGCUGUAACACCGCCGGCUUUUUCA<br>CCGUGUUCGCCAGCGAGCUGAGCGUGUACACCCUGACAGUGAUCACCCUG<br>GAAAGGUGGUACGCCAUCACCUUCGCCAUGAGACUGGACAGAAAGAUCAG<br>ACUGAGACACGCCUGCGCCAUCAUGGUGGGAGGCUGGGUGUGCUGUUUC<br>CUGCUGGCCCUGCUGCCCCUCGUGGGCAUCAGCUCUUACGCCAAGGUGU<br>CCAUCUGCCUGCCCAUGGACACCGAGACACCUCUGGCCCUGGCCUACAUU<br>GUGUUUGUGCUGACCCUGAACAUCGUGGCCUUCGUGAUCGUGUGCUGCU<br>GUUACGUGAAGAUCUACAUCACCGUGCGGAACCCCCAGUACAACCCCGGC<br>GACAAGGAUACCAAGAUCGCCAAGAGAAUGGCCGUGCUGAUCUUCACCGA<br>CUUCAUCUGCAUGGCCCCCAUCAGCUUCUAUGCCCUGAGCGCCAUUCUGA<br>ACAAGCCUCUGAUCACCGUGUCCAACAGCAAAAUCCUGCUGGUGCUGUUC<br>UACCCCCUGAACAGCUGCGCCAACCCCUUCCUGUACGCUAUCUUCACCAA<br>GGCCUUCCAGAGGGACGUGUUCAUCCUGCUGUCUAAGUUCGGCAUCUGCA<br>AGAGACAGGCCCAGGCCUACCGGGGCCAGAGAGUGCCUCCUAAGAACUCC |

TABLE 4-continued

Exemplary TSHR Polynucleotide and Polypeptide Sequences

| SEQ ID NO: and features | Sequence |
|---|---|
| | ACAGACAUCCAGGUGCAGAAAGUGACACACGACAUGAGACAGGGCCUGCA<br>CAACAUGGAAGAUGUGUACGAGCUGAUUGAGAACAGCCACCUGACCCCCAA<br>GAAACAGGGACAGAUCAGCGAAGAGUACAUGCAGACCGUGCUGUGAUAA |

V. APJ

Apelin receptor, also referred to as APJ, angiotension-like-1 receptor, angiotension II-like-1 receptor, and the like, is the previously orphan G-protein-coupled receptor (GPCR) that is cognate for the endogenous ligand Apelin. The apelin/APJ pathway is widely expressed in the cardiovascular system and apelin has shown major beneficial cardiovascular effects in preclinical models. Acute apelin administration in humans causes peripheral and coronary vasodilatation and increases cardiac output (Circulation. 2010; 121:1818-1827). As a result, APJ agonism is emerging as an important therapeutic target for patients with heart failure. Activation of the apelin receptor APJ is thought to increase cardiac contractility and provide cardioprotection, without the liabilities of current therapies.

APJ is widely distributed not only in the heart but also in other organs and tissues including vessels, kidney, liver, adipose tissue and brain.

The full length coding sequence of human APJ (e.g., Protein Accession No. NP_005152.1) was codon optimized for expression in human cells and cloned into a vector that can sustain mRNA transcription by T7 polymerase and contains both 3 and 5' untranslated regions that help with mRNA stability and translatability (see Table 5 for sequence). mRNA was in vitro transcribed and encapsulated into lipid nanoparticles as described above.

TABLE 5

Exemplary APJ Polynucleotide and Polypeptide Sequences

| SEQ ID NO: and features | Sequence |
|---|---|
| SEQ ID NO: 47<br>APJ native DNA<br>sequence<br>corresponding to<br>Protein Accession #<br>NP_005152.1 | GGAAAGCCGACTTGCAAAACCACAGATAATGTTCAGCCCAGCACAGTAGG<br>GGTCAATTTGGTCCACTTGCTCAGTGACAAAAAGAAAAAAAAAGTGGGCT<br>GTCACTAAAGATTTTGACTCACAAGAGAGGGGCTGGTCTGGAGGTGGGA<br>GGAGGGAGTGACGAGTCAAGGAGGAGACAGGGACGCAGGAGGGTGCA<br>AGGAAGTGTCTTAACTGAGACGGGGGTAAGGCAAGAGAGGGTGGAGGA<br>AATTCTGCAGGAGACAGGCTTCCTCCAGGGTCTGGAGAACCCAGAGGCAG<br>CTCCTCCTGAGTGCTGGGAAGGACTCTGGGCATCTTCAGCCCTTCTTACTC<br>TCTGAGGCTCAAGCCAGAAATTCAGGCTGCTTGCAGAGTGGGTGACAGAG<br>CCACGGAGCTGGTGTCCCTGGGACCCTCTGCCCGTCTTCTCTCCACTCCCC<br>AGCATGGAGGAAGGTGGTGATTTTGACAACTACTATGGGGCAGACAACC<br>AGTCTGAGTGTGAGTACACAGACTGGAAATCCTCGGGGGCCCTCATCCCT<br>GCCATCTACATGTTGGTCTTCCTCCTGGGCACCACGGGCAACGGTCTGGTG<br>CTCTGGACCGTGTTTCGGAGCAGCCGGGAGAAGAGGCGCTCAGCTGATAT<br>CTTCATTGCTAGCCTGGCGGTGGCTGACCTGACCTTCGTGGTGACGCTGCC<br>CCTGTGGGCTACCTACACGTACCGGGACTATGACTGGCCCTTTGGGACCTT<br>CTTCTGCAAGCTCAGCAGCTACCTCATCTTCGTCAACATGTACGCCAGCGT<br>CTTCTGCCTCACCGGCCTCAGCTTCGACCGCTACCTGGCCATCGTGAGGCC<br>AGTGGCCAATGCTCGGCTGAGGCTGCGGGTCAGCGGGGCCGTGGCCACG<br>GCAGTTCTTTGGGTGCTGGCCGCCCTCCTGGCCATGCCTGTCATGGTGTTA<br>CGCACCACCGGGGACTTGGAGAACACCACTAAGGTGCAGTGCTACATGGA<br>CTACTCCATGGTGGCCACTGTGAGCTCAGAGTGGGCCTGGGAGGTGGGCC<br>TTGGGGTCTCGTCCACCACCGTGGGCTTTGTGGTGCCCTTCACCATCATGC<br>TGACCTGTTACTTCTTCATCGCCCAAACCATCGCTGGCCACTTCCGCAAGG<br>AACGCATCGAGGGCCTGCGGAAGCGGCGCCGGCTGCTCAGCATCATCGT<br>GGTGCTGGTGGTGACCTTTGCCCTGTGCTGGATGCCCTACCACCTGGTGA<br>AGACGCTGTACATGCTGGGCAGCCTGCTGCACTGGCCCTGTGACTTTGACC<br>TCTTCCTCATGAACATCTTCCCCTACTGCACCTGCATCAGCTACGTCAACAG<br>CTGCCTCAACCCCTTCCTCTATGCCTTTTTCGACCCCCGCTTCCGCCAGGCC<br>TGCACCTCCATGCTCTGCTGTGGCCAGAGCAGGTGCGCAGGCACCTCCCA<br>CAGCAGCAGTGGGGAGAAGTCAGCCAGCTACTCTTCGGGGCACAGCCAG<br>GGGCCCGGCCCCAACATGGGCAAGGGTGGAGAACAGATGCACGAGAAAT<br>CCATCCCCTACAGCCAGGAGACCCTTGTGGTTGACTAGGGCTGGGAGCAG<br>AGAGAAGCCTGGCGCCCTCGGCCCTCCCCGGCCTTTGCCCTTGCTTTCTGA<br>AAATCAGGTAGTGTGGCTACTCCTTGTCCTATGCACATCCTTTAACTGTCCC<br>CTGATTCTGCCCCGCCCTGTCCTCCTCTACTGCTTTATTCTTTCTCAGAGGTT<br>TGTGGTTTAGGGGAAAGAGACTGGGCTCTACAGACCTGACCCTGCACAAG<br>CCATTTAATCTCACTCAGCCTCAGTTTCTCCATTGGTATGAAATGGGGGAA<br>AGTCATATTGATCCTAAAATGTTGAAGCCTGAGTCTGGACGCAGTAAAAG<br>CTTGTTTCCCTCTGCTGCTTTCTTAGATCTGCAATCGTCTTTCCTCCCTTCTTT<br>CCTTGTAGTTTTTCCCCCACCACTCTCTGCAGCTGCCGCTCCTTATCCCTGCC<br>TTCTGGCACCAATCCCCTCCTACAGCTCGTCCCCCTCCCTCCATCCATCCTTC<br>TCCCCTGTCTACTTTCTTGTTCTGAAGGGCTACTAAGGGTTAAGGATCCCA<br>AAGCTTGCAGAGACTGACCCTGTTTAAGCTTTCTATCCTGTTTTCTGAGTGT<br>GAGGCAGGGAATGGGCTGGGGCCGGGGGTGGGCTGTGTGTCAGCAGAT<br>AATTAGTGCTCCAGCCCTTAGATCTGGGAGCTCCAGAGCTTGCCCTAAAAT |

TABLE 5-continued

Exemplary APJ Polynucleotide and Polypeptide Sequences

| SEQ ID NO: and features | Sequence |
|---|---|
| | TGGATCACTTCCCTGTCATTTTGGGCATTGGGGCTAGTGTGATTCCTGCAG<br>TTCCCCCATGGCACCATGACACTGACTAGATATGCTTTCTCCAAATTGTCCG<br>CAGACCCTTTCATCCTTCCTCTATTTTCTATGAGAATTGGAAGGCAGCAGG<br>GCTGATGAATGGATGTACTCCTTGGTTTCATTATGTGAGTGGGGAGTTGG<br>GAAGGGCAACTAGAGAGAGAGGATGGAGGGGTGTCTGCATTTAGTCCAG<br>ACACTGCTTGGCTCGCTCCCCGAGTCCTCCTGTTTCTGACTTCCTGCATAAC<br>TGTGAGCTGAAGGGTTTCCTCATCTCCCCATCTTACCCCATCATACTGATTT<br>CTTTCTTGGGCACTGGTGCTACTTGGTGCCAAGAATCATGTTGTTTGGGAT<br>GGAGATGCCTGCCTCTTGTCTGTGTGTGTTGTACTTATATGTCTATATGGAT<br>GAGCCTGGCATGAACAGCAGTGTGCCTGGGTCATTTGGACAAACCTCCTC<br>CCACCCCCCAATCCACTGCAACTCTGCTGTTCACACATTACCCTTGGCAGG<br>GGGTGGTGGGGGGCAGGGACACACTGAGGCAATGAAAAATGTAGAATA<br>AAAATGAGTCCACCCCCTACTGGATTTGGGGGCTCCAACGGCTGGTCCGT<br>GCTTTAGGAGCGAAGTTAATGTTTGCACCAGGCTTCCTGTAGGGAGATCC<br>CTCCCCAAAGCAGCTGGCGCCAAGGCTTGGGGGCGTCCTACTGAGCTGGG<br>TTCCTGCTCCTTCTTGGGCTCCATGAAGGAAGTAAGAGGCTAGTTGAGAG<br>CCTCCCTTGGCCCCTTTCCGGTGCCTCCCCGCCTGGCTTCAAATTTATGAGC<br>ATTGCCCTCATCGTCCTTTCTTGTTCCAGGGTCAGTGGCCCTCTTCCTAAGG<br>AGGCCTCCTGCTTGCCATGGGCCAAAAGGCACGGGGTGGGTTTTTTCTCTC<br>CCTACCCTCAGGATTGGACCTCTTGGCTTCTGCTGGATTGGGGATCTGGGA<br>ATAGGGACTGGAGCAAGTGTGCAGATAGCATGATGTCTACACTGCCAGAG<br>AGACCGTGAGGATGAAATTAATAGTGGGGCCTTTGTGAGCTAGAGGCTG<br>GGAGTGTCTATTCCGGGTTTTGTTCTTGGAGGACTATGAAAGTGAAGGAC<br>AAGACATGAGCGATGGAGATAAGAAAAGCCCAGCTTGATGTGAATGGAC<br>ATCTTGACCCTCCCTGGAATGACGCCAGCTCTGGGGGCAGAGGGAGGAG<br>GAGAGGGGAAGGGGCTCCTCACAGCCTAGTCTCCCCATCTTAAGATAGCA<br>TCTTTCACAGAGTCACCTCCTCTGCCCAGAGCTGTCCTCAAAGCATCCAGT<br>GAACACTGGAAGAGGCTTCTAGAAGGGAAGAAATTGTCCCTCTGAGGCC<br>GCCGTGGGTGACCTGCAGAGACTTCCTGCCTGGAACTCATCTGTGAACTG<br>GGACAGAAGCAGAGGAGGCTGCCTGCTGTGATACCCCCTTACCTCCCCCA<br>GTGCCTTCTTCAGAATATCTGCACTGTCTTCTGATCCTGTTAGTCACTGTGG<br>TTCATCAAATAAAACTGTTTGTGCAACTGTTGTGTCCAAA |
| SEQ ID NO: 17<br>APJ Native mRNA sequence corresponding to Protein Accession # NP_005152.1 | GGAAAGCCGACUUGCAAAACCACAGAUAAUGUUCAGCCCAGCACAGUA<br>GGGGUCAAUUUGGUCCACUUGCUCAGUGACAAAAAGAAAAAAAAAGU<br>GGGCUGUCACUAAAGAUUUUGACUCACAAGAGAGGGGCUGGUCUGGA<br>GGUGGGAGGAGGGAGUGACGAGUCAAGGAGGAGACAGGGACGCAGGA<br>GGGUGCAAGGAAGUGUCUUAACUGAGACGGGGGUAAGGCAAGAGAG<br>GGUGGAGGAAAUUCUGCAGGAGACAGGCUUCCUCCAGGGUCUGGAGA<br>ACCCAGAGGCAGCUCCUCCUGAGUGCUGGGAAGGACUCUGGGCAUCU<br>UCAGCCCUUCUUACUCUCUGAGGCUCAAGCCAGAAAUUCAGGCUGCUU<br>GCAGAGUGGGUGACAGAGCCACGGAGCUGGUGUCCCUGGGACCCUCU<br>GCCCGUCUUCUCUCCACUCCCCAGCAUGGAGGAAGGUGGUGAUUUUG<br>ACAACUACUAUGGGGCAGACAACCAGUCUGAGUGUGAGUACACAGACU<br>GGAAAUCCUCGGGGGCCCUCAUCCCUGCCAUCUACAUGUUGGUCUUCC<br>UCCUGGGCACCACGGGCAACGGUCUGGUGCUCUGGACCGUGUUUCGG<br>AGCAGCCGGGAGAAGAGGCGCUCAGCUGAUAUCUUCAUUGCUAGCCU<br>GGCGGUGGCUGACCUGACCUUCGUGGUGACGCUGCCCCUGUGGGCUA<br>CCUACACGUACCGGGACUAUGACUGGCCCUUUGGGACCUUCUUCUGCA<br>AGCUCAGCAGCUACCUCAUCUUCGUCAACAUGUACGCCAGCGUCUUCU<br>GCCUCACCGGCCUCAGCUUCGACCGCUACCUGGCCAUCGUGAGGCCAG<br>UGGCCAAUGCUCGGCUGAGGCUGCGGGUCAGCGGGGCCGUGGCCACG<br>GCAGUUCUUUGGGUGCUGGCCGCCCUCCUGGCCAUGCCUGUCAUGGU<br>GUUACGCACCACCGGGGACUUGGAGAACACCACUAAGGUGCAGUGCUA<br>CAUGGACUACUCCAUGGUGGCCACUGUGAGCUCAGAGUGGGCCUGGG<br>AGGUGGGCCUUGGGGUCUCGUCCACCACCGUGGGCUUUGUGGUGCCC<br>UUCACCAUCAUGCUGACCUGUUACUUCUUCAUCGCCCAAACCAUCGCU<br>GGCCACUUCCGCAAGGAACGCAUCGAGGGCCUGCGGAAGCGGCGCCGG<br>CUGCUCAGCAUCAUCGUGGUGCUGGUGGUGACCUUUGCCCUGUGCUG<br>GAUGCCCUACCACCUGGUGAAGACGCUGUACAUGCUGGGCAGCCUGCU<br>GCACUGGCCCUGUGACUUUGACCUCUUCCUCAUGAACAUCUUCCCCUA<br>CUGCACCUGCAUCAGCUACGUCAACAGCUGCCUCAACCCCUUCCUCUAU<br>GCCUUUUUCGACCCCCGCUUCCGCCAGGCCUGCACCUCCAUGCUCUGC<br>UGUGGCCAGAGCAGGUGCGCAGGCACCUCCCACAGCAGCAGUGGGGAG<br>AAGUCAGCCAGCUACUCUUCGGGGCACAGCCAGGGGCCCGGCCCCAAC<br>AUGGGCAAGGGUGGAGAACAGAUGCACGAGAAAUCCAUCCCCUACAGC<br>CAGGAGACCCUUGUGGUUGACUAGGGCUGGGAGCAGAGAGAAGCCUG<br>GCGCCCUCGGCCCUCCCCGGCCUUUGCCCUUGCUUUCUGAAAAUCAGG<br>UAGUGUGGCUACUCCUUGUCCUAUGCACAUCCUUUAACUGUCCCCUG<br>AUUCUGCCCCGCCCUGUCCUCCUCUACUGCUUUAUUCUUUCUCAGAGG<br>UUUGUGGUUUAGGGGAAAGAGACUGGGCUCUACAGACCUGACCCUGC<br>ACAAGCCAUUUAAUCUCACUCAGCCUCAGUUUCUCCAUUGGUAUGAAA<br>UGGGGGAAAGUCAUAUUGAUCCUAAAAUGUUGAAGCCUGAGUCUGGA<br>CGCAGUAAAAGCUUGUUUCCCUCUGCUGCUUUCUUAGAUCUGCAAUC<br>GUCUUUCCUCCCUUCUUUCCUUGUAGUUUUUCCCCCACCACUCUCUGC |

TABLE 5-continued

| Exemplary APJ Polynucleotide and Polypeptide Sequences | |
|---|---|
| SEQ ID NO: and features | Sequence |
| | AGCUGCCGCUCCUUAUCCCUGCCUUCUGGCACCAAUCCCCUCCUACAGC<br>UCGUCCCCCUCCCUCCAUCCAUCCUUCUCCCCUGUCUACUUUCUUGUU<br>CUGAAGGGCUACUAAGGGUUAAGGAUCCCAAAGCUUGCAGAGACUGA<br>CCCUGUUUAAGCUUUCUAUCCUGUUUUCUGAGUGUGAGGCAGGGAA<br>UGGGCUGGGGCCGGGGGUGGGCUGUGUGUCAGCAGAUAAUUAGUGC<br>UCCAGCCCUUAGAUCUGGGAGCUCCAGAGCUUGCCCUAAAAUUGGAUC<br>ACUUCCCUGUCAUUUUGGGCAUUGGGGCUAGUGUGAUUCCUGCAGU<br>UCCCCCAUGGCACCAUGACACUGACUAGAUAUGCUUUCUCCAAAUUGU<br>CCGCAGACCCUUUCAUCCUUCCUCUAUUUUCUAUGAGAAUUGGAAGG<br>CAGCAGGGCUGAUGAAUGGAUGUACUCCUUGGUUUCAUUAUGUGAG<br>UGGGGAGUUGGGAAGGGCAACUAGAGAGAGAGGAUGGAGGGGUGUC<br>UGCAUUUAGUCCAGACACUGCUUGGCUCGCUCCCCGAGUCCUCCUGUU<br>UCUGACUUCCUGCAUAACUGUGAGCUGAAGGGUUUCCUCAUCUCCCC<br>AUCUUACCCCAUCAUACUGAUUUCUUUCUUGGGCACUGGUGCUACUU<br>GGUGCCAAGAAUCAUGUUGUUUGGGAUGGAGAUGCCUGCCUCUUGU<br>CUGUGUGUGUUGUACUUAUAUGUCUAUAUGGAUGAGCCUGGCAUGA<br>ACAGCAGUGUGCCUGGGUCAUUUGGACAAACCUCCUCCCACCCCCCAA<br>UCCACUGCAACUCUGCUGUUCACACAUUACCCUUGGCAGGGGGUGGU<br>GGGGGGCAGGGACACACUGAGGCAAUGAAAAAUGUAGAAUAAAAAUG<br>AGUCCACCCCCUACUGGAUUUGGGGGCUCCAACGGCUGGUCCGUGCU<br>UUAGGAGCGAAGUUAAUGUUUGCACCAGGCUUCCUGUAGGGAGAUCC<br>CUCCCCAAAGCAGCUGGCGCCAAGGCUUGGGGGCGUCCUACUGAGCUG<br>GGUUCCUGCUCCUUCUUGGGCUCCAUGAAGGAAGUAAGAGGCUAGUU<br>GAGAGCCUCCCUUGGCCCCUUUCCGGUGCCUCCCCGCCUGGCUUCAAA<br>UUUAUGAGCAUUGCCCUCAUCGUCCUUUCUUGUUCCAGGGUCAGUGG<br>CCCUCUUCCUAAGGAGGCCUCCUGCUUGCCAUGGGCCAAAAGGCACGG<br>GGUGGGUUUUUUCUCUCCCUACCCUCAGGAUUGGACCUCUUGGCUUC<br>UGCUGGAUUGGGGAUCUGGGAAUAGGGACUGGAGCAAGUGUGCAGA<br>UAGCAUGAUGUCUACACUGCCAGAGAGACCGUGAGGAUGAAAUUAAU<br>AGUGGGGCCUUUGUGAGCUAGAGGCUGGGAGUGUCUAUUCCGGGUU<br>UUGUUCUUGGAGGACUAUGAAAGUGAAGGACAAGACAUGAGCGAUG<br>GAGAUAAGAAAAGCCCAGCUUGAUGUGAAUGGACAUCUUGACCCUCCC<br>UGGAAUGACGCCAGCUCUGGGGGCAGAGGGAGGAGGAGAGGGGAAG<br>GGGCUCCUCACAGCCUAGUCUCCCCAUCUUAAGAUAGCAUCUUUCACA<br>GAGUCACCUCCUCUGCCCAGAGCUGUCCUCAAAGCAUCCAGUGAACAC<br>UGGAAGAGGCUUCUAGAAGGGAAGAAAUUGUCCCUCUGAGGCCGCCG<br>UGGGUGACCUGCAGAGACUUCCUGCCUGGAACUCAUCUGUGAACUGG<br>GACAGAAGCAGAGGAGGCUGCCUGCUGUGAUACCCCCUUACCUCCCCC<br>AGUGCCUUCUUCAGAAUAUCUGCACUGUCUUCUGAUCCUGUUAGUCA<br>CUGUGGUUCAUCAAAUAAAACUGUUUGUGCAACUGUUGUGUCCAAA<br>U = Uridine and/or pseudouridine |
| SEQ ID NO: 18<br>Translated human APJ from coding sequence (CDS) of the DNA construct of SEQ ID NO: 47 | MEEGGDFDNYYGADNQSECEYTDWKSSGALIPAIYMLVFLLGTTGNGLVLW<br>TVFRSSREKRRSADIFIASLAVADLTFVVTLPLWATYTYRDYDWPFGTFFCKLSS<br>YLIFVNMYASVFCLTGLSFDRYLAIVRPVANARLRLRVSGAVATAVLWVLAALL<br>AMPVMVLRTTGDLENTTKVQCYMDYSMVATVSSEWAWEVGLGVSSTTVG<br>FVVPFTIMLTCYFFIAQTIAGHFRKERIEGLRKRRRLLSIIVVLVVTFALCWMPYH<br>LVKTLYMLGSLLHWPCDFDLFLMNIFPYCTCISYVNSCLNPFLYAFFDPRF<br>RQACTSMLCCGQSRCAGTSHSSSGEKSASYSSGHSQGPGPNMGK<br>GGEQMHEKSIPYSQETLVVD |
| SEQ ID NO: 48<br>(DNA)<br>TEV-hAPJ-2xhBG-120A<br>Sequence features:<br>Tobacco Etch Virus (TEV) 5' UTR: 37-190<br>Optimal Kozak sequence: 191-199<br>Human APJ codon optimized, encoding amino acids 1-380 of Protein Accession #NP_005152.1: 197-1336<br>1 stop codon: 1337-1349<br>2 copies of human beta-globin 3'UTR: 1358-1623<br>120 nucleotide polyA tail (SEQ ID NO: 59): 1630-1749 | GGAGGCCGGAGAATTGTAATACGACTCACTATAGGGAGACGCGTGTTAA<br>ATAACAAATCTCAACACAACATATACAAAACAAACGAATCTCAAGCAATC<br>AAGCATTCTACTTCTATTGCAGCAATTTAAATCATTTCTTTTAAAGC<br>AAAAGCAATTTTCTGAAAATTTTCACCATTTACGAACGATAGCCGC<br>CACCATGGAAGAGGGCGGCGACTTCGACAACTACTACGGCGCC<br>GACAACCAGAGCGAGTGCGAGTACACCGACTGGAAGTCCTCTGG<br>CGCCCTGATCCCCGCTATCTACATGCTGGTGTTTCTGCTGGGCA<br>CCACCGGCAACGGACTGGTGCTGTGGACCGTGTTCAGAAGCAG<br>CAGAGAGAAGCGGCGGAGCGCCGACATCTTTATCGCCAGCCTG<br>GCCGTGGCCGACCTGACCTTTGTCGTGACACTGCCTCTGTGGGC<br>CACCTACACCTACCGGGACTACGACTGGCCCTTCGGCACATTTTT<br>CTGCAAGCTGAGCAGCTACCTGATCTTCGTGAATATGTACGCCAG<br>CGTGTTCTGCCTGACCGGCCTGAGCTTCGACAGATACCTGGCCA<br>TCGTGCGGCCCGTGGCCAACGCTAGACTGCGGCTGAGAGTGTC<br>TGGCGCCGTGGCTACAGCTGTGCTGTGGGTGCTGGCTGCCCTG<br>CTGGCTATGCCTGTGATGGTGCTGAGAACCACCGGCGACCTGGA<br>AAACACCACCAAGGTGCAGTGCTACATGGACTACAGCATGGTGG<br>CCACAGTGTCCAGCGAGTGGGCCTGGGAAGTGGGACTGGGAGT<br>GTCTAGCACCACCGTGGGCTTCGTGGTGCCCTTCACCATTATGC<br>TGACCTGCTACTTCTTCATTGCCCAGACAATCGCCGGCCACTTCC<br>GGAAAGAGCGGATCGAGGGCCTGCGGAAGAGAAGGCGGCTGCT<br>GAGCATCATCGTGGTGCTGGTCGTGACCTTCGCCCTGTGCTGGA<br>TGCCTTACCACCTCGTGAAAACCCTGTATATGCTGGGCAGCCTG<br>CTGCACTGGCCCTGCGATTTCGACCTGTTCCTGATGAACATCTTC |

TABLE 5-continued

Exemplary APJ Polynucleotide and Polypeptide Sequences

| SEQ ID NO: and features | Sequence |
|---|---|
| | CCCTACTGCACCTGTATCAGCTACGTGAACAGCTGCCTGAACCC<br>CTTCCTGTACGCCTTCTTCGACCCCCGGTTCAGACAGGCCTGCA<br>CCTCCATGCTGTGCTGCGGCCAGTCTAGATGCGCCGGCACAAGC<br>CACAGCAGCAGCGGCGAGAAGTCTGCCAGCTACAGCTCTGGCC<br>ACAGCCAGGGCCCAGGCCCCAATATGGGAAAGGGCGGAGAGCA<br>GATGCACGAGAAGTCCATCCCTTACAGCCAGGAAACCCTGGTGG<br>TGGACTGACGGACCGGCGATAGATGAAGCTCGCTTTCTTGCTGT<br>CCAATTTCTATTAAAGGTTCCTTTGTTCCCTAAGTCCAACTACTAA<br>ACTGGGGGATATTATGAAGGGCCTTGAGCATCTGGATTCTGCCTA<br>ATAAAAAACATTTATTTTCATTGCAGCTCGCTTTCTTGCTGTCCAA<br>TTTCTATTAAAGGTTCCTTTGTTCCCTAAGTCCAACTACTAAACTG<br>GGGGATATTATGAAGGGCCTTGAGCATCTGGATTCTGCCTAATAA<br>AAAACATTTATTTTCATTGCGGCCGCAAAAAAAAAAAAAAAAAAAA<br>AAAAAAAAAAAAAAAAAAAAAAAAAAAAAAAAAAAAAAAAAAAAAA<br>AAAAAAAA |
| SEQ ID NO: 19<br>(mRNA)<br>TEV-hAPJ-2xhBG-<br>120A<br>Sequence features:<br>Tobacco Etch Virus<br>(TEV) 5' UTR: 37-190<br>Optimal Kozak<br>sequence: 191-199<br>Human APJ codon<br>optimized, encoding<br>amino acids 1-380 of<br>Protein Accession<br>#NP_005152.1:<br>197-1336<br>1 stop codon:<br>1337-1349<br>2 copies of human<br>beta-globin 3'UTR:<br>1358-1623<br>120 nucleotide polyA<br>tail (SEQ ID NO: 59):<br>1630-1749 | GGGAGACGCGUGUUAAAUAACAAAUCUCAACACAACAUAUACAA<br>AACAAACGAAUCUCAAGCAAUCAAGCAUUCUACUUCUAUUGCAG<br>CAAUUUAAAUCAUUUCUUUUAAAGCAAAAGCAAUUUUCUGAAAA<br>UUUUCACCAUUUACGAACGAUAGCCGCCACCAUGGAAGAGGGC<br>GGCGACUUCGACAACUACUACGGCGCCGACAACCAGAGCGAGU<br>GCGAGUACACCGACUGGAAGUCCUCUGGCGCCCUGAUCCCCG<br>CUAUCUACAUGCUGGUGUUUCUGCUGGGCACCACCGGCAACG<br>GACUGGUGCUGUGGACCGUGUUCAGAAGCAGCAGAGAGAAGC<br>GGCGGAGCGCCGACAUCUUUAUCGCCAGCCUGGCCGUGGCCG<br>ACCUGACCUUUGUCGUGACACUGCCUCUGUGGGCCACCUACAC<br>CUACCGGGACUACGACUGGCCCUUCGGCACAUUUUUCUGCAAG<br>CUGAGCAGCUACCUGAUCUUCGUGAAUAUGUACGCCAGCGUGU<br>UCUGCCUGACCGGCCUGAGCUUCGACAGAUACCUGGCCAUCG<br>UGCGGCCCGUGGCCAACGCUAGACUGCGGCUGAGAGUGUCUG<br>GCGCCGUGGCUACAGCUGUGCUGUGGGUGCUGGCUGCCCUGC<br>UGGCUAUGCCUGUGAUGGUGCUGAGAACCACCGGCGACCUGG<br>AAAACACCACCAAGGUGCAGUGCUACAUGGACUACAGCAUGGU<br>GGCCACAGUGUCCAGCGAGUGGGCCUGGGAAGUGGGACUGGG<br>AGUGUCUAGCACCACCGUGGGCUUCGUGGUGCCCUUCACCAU<br>UAUGCUGACCUGCUACUUCUUCAUUGCCCAGACAAUCGCCGGC<br>CACUUCCGGAAAGAGCGGAUCGAGGGCCUGCGGAAGAGAAGG<br>CGGCUGCUGAGCAUCAUCGUGGUGCUGGUCGUGACCUUCGCC<br>CUGUGCUGGAUGCCUUACCACCUCGUGAAAACCCUGUAUAUGC<br>UGGGCAGCCUGCUGCACUGGCCCUGCGAUUUCGACCUGUUCC<br>UGAUGAACAUCUUCCCCUACUGCACCUGUAUCAGCUACGUGAA<br>CAGCUGCCUGAACCCCUUCCUGUACGCCUUCUUCGACCCCCG<br>GUUCAGACAGGCCUGCACCUCCAUGCUGUGCUGCGGCCAGUC<br>UAGAUGCGCCGGCACAAGCCACAGCAGCAGCGGCGAGAAGUCU<br>GCCAGCUACAGCUCUGGCCACAGCCAGGGCCCAGGCCCCAAUA<br>UGGGAAAGGGCGGAGAGCAGAUGCACGAGAAGUCCAUCCCUUA<br>CAGCCAGGAAACCCUGGUGGUGGACUGACGGACCGGCGAUAG<br>AUGAAGCUCGCUUUCUUGCUGUCCAAUUUCUAUUAAAGGUUCC<br>UUUGUUCCCUAAGUCCAACUACUAAACUGGGGGAUAUUAUGAA<br>GGGCCUUGAGCAUCUGGAUUCUGCCUAAUAAAAAACAUUUAUU<br>UUCAUUGCAGCUCGCUUUCUUGCUGUCCAAUUUCUAUUAAAGG<br>UUCCUUUGUUCCCUAAGUCCAACUACUAAACUGGGGGAUAUUA<br>UGAAGGGCCUUGAGCAUCUGGAUUCUGCCUAAUAAAAAACAUU<br>UAUUUUCAUUGCGGCCGCAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAA<br>A<br>U = Uridine and/or pseudouridine |
| SEQ ID NO: 49<br>APJ RNA coding<br>sequence of<br>construct<br>of SEQ ID NO: 19 | AUGGAAGAGGGCGGCGACUUCGACAACUACUACGGCGCCGACA<br>ACCAGAGCGAGUGCGAGUACACCGACUGGAAGUCCUCUGGCG<br>CCCUGAUCCCCGCUAUCUACAUGCUGGUGUUUCUGCUGGGCA<br>CCACCGGCAACGGACUGGUGCUGUGGACCGUGUUCAGAAGCA<br>GCAGAGAGAAGCGGCGGAGCGCCGACAUCUUUAUCGCCAGCC<br>UGGCCGUGGCCGACCUGACCUUUGUCGUGACACUGCCUCUGU<br>GGGCCACCUACACCUACCGGGACUACGACUGGCCCUUCGGCA<br>CAUUUUUCUGCAAGCUGAGCAGCUACCUGAUCUUCGUGAAUAU<br>GUACGCCAGCGUGUUCUGCCUGACCGGCCUGAGCUUCGACAG<br>AUACCUGGCCAUCGUGCGGCCCGUGGCCAACGCUAGACUGCG<br>GCUGAGAGUGUCUGGCGCCGUGGCUACAGCUGUGCUGUGGGU<br>GCUGGCUGCCCUGCUGGCUAUGCCUGUGAUGGUGCUGAGAAC<br>CACCGGCGACCUGGAAAACACCACCAAGGUGCAGUGCUACAUG<br>GACUACAGCAUGGUGGCCACAGUGUCCAGCGAGUGGGCCUGG<br>GAAGUGGGACUGGGAGUGUCUAGCACCACCGUGGGCUUCGUG<br>GUGCCCUUCACCAUUAUGCUGACCUGCUACUUCUUCAUUGCCC |

TABLE 5-continued

| Exemplary APJ Polynucleotide and Polypeptide Sequences | |
|---|---|
| SEQ ID NO: and features | Sequence |
| | AGACAAUCGCCGGCCACUUCCGGAAAGAGCGGAUCGAGGGCC<br>UGCGGAAGAGAAGGCGGCUGCUGAGCAUCAUCGUGGUGCUGG<br>UCGUGACCUUCGCCCUGUGCUGGAUGCCUUACCACCUCGUGA<br>AAACCCUGUAUAUGCUGGGCAGCCUGCUGCACUGGCCCUGCG<br>AUUUCGACCUGUUCCUGAUGAACAUCUUCCCCUACUGCACCUG<br>UAUCAGCUACGUGAACAGCUGCCUGAACCCCUUCCUGUACGCC<br>UUCUUCGACCCCCGGUUCAGACAGGCCUGCACCUCCAUGCUG<br>UGCUGCGGCCAGUCUAGAUGCGCCGGCACAAGCCACAGCAGC<br>AGCGGCGAGAAGUCUGCCAGCUACAGCUCUGGCCACAGCCAG<br>GGCCCAGGCCCCAAUAUGGGAAAGGGCGGAGAGCAGAUGCAC<br>GAGAAGUCCAUCCCUUACAGCCAGGAAACCCUGGUGGUGGACU<br>GA |

VI. GP130

Glycoprotein 130 (GP130) is a 918 amino acid containing protein and is member of the type I single pass transmembrane protein receptor family. It is core component of the signal transduction complex used by many cytokines including interleukin 6, interleukin 11, ciliary neurotrophic factor, leukemia inhibitory factor, and oncostatin M. In the case of interleukin 6 (IL6), GP130 binds to the IL6/1L6R (alpha chain) complex, resulting in the formation of high-affinity 1L6 binding sites and initiation of signal transduction. GP130 contains five fibronectin type III domains and one Ig-like C2-type domain.

The full length coding sequence of human GP130 (e.g., Protein Accession No. NP_002175.2 or AAI17405) was codon optimized for expression in human cells and cloned into a vector that can sustain mRNA transcription by T7 polymerase and contains both 3 and 5' untranslated regions that help with mRNA stability and translatability (see Table 6 for sequence). mRNA was in vitro transcribed and encapsulated into lipid nanoparticles as described above.

TABLE 6

| Exemplary GP130 Polynucleotide and Polypeptide Sequences | |
|---|---|
| SEQ ID NO: and features | Sequence |
| SEQ ID NO: 50<br>GP130 native DNA sequence corresponding to Protein Accession # NP_002175.2 or AAI17405 | GAGCAGCCAAAAGGCCCGCGGAGTCGCGCTGGGCCGCCCCGGCGCA<br>GCTGAACCGGGGGCCGCGCCTGCCAGGCCGACGGGTCTGGCCCAGC<br>CTGGCGCCAAGGGGTTCGTGCGCTGTGGAGACGCGGAGGGTCGAGG<br>CGGCGCGGCCTGAGTGAAACCCAATGGAAAAAGCATGACATTTAGAAG<br>TAGAAGACTTAGCTTCAAATCCCTACTCCTTCACTTACTAATTTTGTGAT<br>TTGGAAATATCCGCGCAAGATGTTGACGTTGCAGACTTGGGTAGTGCA<br>AGCCTTGTTTATTTTCCTCACCACTGAATCTACAGGTGAACTTCTAGATC<br>CATGTGGTTATATCAGTCCTGAATCTCCAGTTGTACAACTTCATTCTAAT<br>TTCACTGCAGTTTGTGTGCTAAAGGAAAAATGTATGGATTATTTTCATGT<br>AAATGCTAATTACATTGTCTGGAAAACAAACCATTTTACTATTCCTAAGG<br>AGCAATATACTATCATAAACAGAACAGCATCCAGTGTCACCTTTACAGAT<br>ATAGCTTCATTAAATATTCAGCTCACTTGCAACATTCTTACATTCGGACA<br>GCTTGAACAGAATGTTTATGGAATCACAATAATTTCAGGCTTGCCTCCA<br>GAAAAACCTAAAAATTTGAGTTGCATTGTGAACGAGGGGAAGAAAATGA<br>GGTGTGAGTGGGATGGTGGAAGGGAAACACACTTGGAGACAAACTTCA<br>CTTTAAAATCTGAATGGGCAACACACAAGTTTGCTGATTGCAAAGCAAA<br>ACGTGACACCCCCACCTCATGCACTGTTGATTATTCTACTGTGTATTTTG<br>TCAACATTGAAGTCTGGGTAGAAGCAGAGAATGCCCTTGGGAAGGTTA<br>CATCAGATCATATCAATTTTGATCCTGTATATAAAGTGAAGCCCAATCCG<br>CCACATAATTTATCAGTGATCAACTCAGAGGAACTGTCTAGTATCTTAAA<br>ATTGACATGGACCAACCCAAGTATTAAGAGTGTTATAATACTAAAATATA<br>ACATTCAATATAGGACCAAAGATGCCTCAACTTGGAGCCAGATTCCTCC<br>TGAAGACACAGCATCCACCCGATCTTCATTCACTGTCCAAGACCTTAAA<br>CCTTTTACAGAATATGTGTTTAGGATTCGCTGTATGAAGGAAGATGGTA<br>AGGGATACTGGAGTGACTGGAGTGAAGAAGCAAGTGGGATCACCTATG<br>AAGATAGACCATCTAAAGCACCAAGTTTCTGGTATAAAATAGATCCATC<br>CCATACTCAAGGCTACAGAACTGTACAACTCGTGTGGAAGACATTGCCT<br>CCTTTTGAAGCCAATGGAAAAATCTTGGATTATGAAGTGACTCTCACAA |

TABLE 6-continued

Exemplary GP130 Polynucleotide and Polypeptide Sequences

| SEQ ID NO: and features | Sequence |
|---|---|
| | GATGGAAATCACATTTACAAAATTACACAGTTAATGCCACAAAACTGACA<br>GTAAATCTCACAAATGATCGCTATCTAGCAACCCTAACAGTAAGAAATCT<br>TGTTGGCAAATCAGATGCAGCTGTTTTAACTATCCCTGCCTGTGACTTT<br>CAAGCTACTCACCCTGTAATGGATCTTAAAGCATTCCCCAAAGATAACA<br>TGCTTTGGGTGGAATGGACTACTCCAAGGGAATCTGTAAAGAAATATAT<br>ACTTGAGTGGTGTGTGTTATCAGATAAAGCACCCTGTATCACAGACTGG<br>CAACAAGAAGATGGTACCGTGCATCGCACCTATTTAAGAGGGAACTTAG<br>CAGAGAGCAAATGCTATTTGATAACAGTTACTCCAGTATATGCTGATGG<br>ACCAGGAAGCCCTGAATCCATAAAGGCATACCTTAAACAAGCTCCACCT<br>TCCAAAGGACCTACTGTTCGGACAAAAAAAGTAGGGAAAAACGAAGCT<br>GTCTTAGAGTGGGACCAACTTCCTGTTGATGTTCAGAATGGATTTATCA<br>GAAATTATACTATATTTTATAGAACCATCATTGGAAATGAAACTGCTGTG<br>AATGTGGATTCTTCCCACACAGAATATACATTGTCCTCTTTGACTAGTGA<br>CACATTGTACATGGTACGAATGGCAGCATACACAGATGAAGGTGGGAA<br>GGATGGTCCAGAATTCACTTTTACTACCCCAAAGTTTGCTCAAGGAGAA<br>ATTGAAGCCATAGTCGTGCCTGTTTGCTTAGCATTCCTATTGACAACTCT<br>TCTGGGAGTGCTGTTCTGCTTTAATAAGCGAGACCTAATTAAAAAACAC<br>ATCTGGCCTAATGTTCCAGATCCTTCAAAGAGTCATATTGCCCAGTGGT<br>CACCTCACACTCCTCCAAGGCACAATTTTAATTCAAAAGATCAAATGTAT<br>TCAGATGGCAATTTCACTGATGTAAGTGTTGTGGAAATAGAAGCAAATG<br>ACAAAAAGCCTTTTCCAGAAGATCTGAAATCATTGGACCTGTTCAAAAA<br>GGAAAAAATTAATACTGAAGGACACAGCAGTGGTATTGGGGGGTCTTC<br>ATGCATGTCATCTTCTAGGCCAAGCATTTCTAGCAGTGATGAAAATGAA<br>TCTTCACAAAACACTTCGAGCACTGTCCAGTATTCTACCGTGGTACACA<br>GTGGCTACAGACACCAAGTTCCGTCAGTCCAAGTCTTCTCAAGATCCGA<br>GTCTACCCAGCCCTTGTTAGATTCAGAGGAGCGGCCAGAAGATCTACA<br>ATTAGTAGATCATGTAGATGGCGGTGATGGTATTTTGCCCAGGCAACAG<br>TACTTCAAACAGAACTGCAGTCAGCATGAATCCAGTCCAGATATTTCAC<br>ATTTTGAAAGGTCAAAGCAAGTTTCATCAGTCAATGAGGAAGATTTTGTT<br>AGACTTAAACAGCAGATTTCAGATCATATTTCACAATCCTGTGGATCTG<br>GGCAAATGAAAATGTTTCAGGAAGTTTCTGCAGCAGATGCTTTTGGTCC<br>AGGTACTGAGGGACAAGTAGAAAGATTTGAAACAGTTGGCATGGAGGC<br>TGCGACTGATGAAGGCATGCCTAAAAGTTACTTACCACAGACTGTACGG<br>CAAGGCGGCTACATGCCTCAGTGAAGGACTAGTAGTTCCTGCTACAAC<br>TTCAGCAGTACCTATAAAGTAAAGCTAAAATGATTTTATCTGTGAATTC |
| SEQ ID NO: 20<br>GP130 native mRNA sequence corresponding to Protein Accession # NP_002175.2 or AAI17405 | GAGCAGCCAAAAGGCCCGCGGAGUCGCGCUGGGCCGCCCCGGCGCA<br>GCUGAACCGGGGGCCGCGCCUGCCAGGCCGACGGGUCUGGCCCAGC<br>CUGGCGCCAAGGGGUUCGUGCGCUGUGGAGACGCGGAGGGUCGAG<br>GCGGCGCGGCCUGAGUGAAACCCAAUGGAAAAAGCAUGACAUUUAGA<br>AGUAGAAGACUUAGCUUCAAAUCCCUACUCCUUCACUUACUAAUUUU<br>GUGAUUUGGAAAUAUCCGCGCAAGAUGUUGACGUUGCAGACUUGGG<br>UAGUGCAAGCCUUGUUUAUUUUCCUCACCACUGAAUCUACAGGUGAA<br>CUUCUAGAUCCAUGUGGUUAUAUCAGUCCUGAAUCUCCAGUUGUACA<br>ACUUCAUUCUAAUUUCACUGCAGUUUGUGUGCUAAAGGAAAAAUGUA<br>UGGAUUAUUUUCAUGUAAAUGCUAAUUACAUUGUCUGGAAAACAAAC<br>CAUUUUACUAUUCCUAAGGAGCAAUAUACUAUCAUAAACAGAACAGCA<br>UCCAGUGUCACCUUUACAGAUAUAGCUUCAUUAAAUAUUCAGCUCAC<br>UUGCAACAUUCUUACAUUCGGACAGCUUGAACAGAAUGUUUAUGGAA<br>UCACAAUAAUUUCAGGCUUGCCUCCAGAAAAACCUAAAAAUUUGAGUU<br>GCAUUGUGAACGAGGGGAAGAAAAUGAGGUGUGAGUGGGAUGGUGG<br>AAGGGAAACACACUUGGAGACAAACUUCACUUUAAAAUCUGAAUGGG<br>CAACACACAAGUUUGCUGAUUGCAAAGCAAAACGUGACACCCCCACC<br>UCAUGCACUGUUGAUUAUUCUACUGUGUAUUUUGUCAACAUUGAAGU<br>CUGGGUAGAAGCAGAGAAUGCCCUUGGGAAGGUUACAUCAGAUCAUA<br>UCAAUUUUGAUCCUGUAUAUAAAGUGAAGCCCAAUCCGCCACAUAAU<br>UUAUCAGUGAUCAACUCAGAGGAACUGUCUAGUAUCUUAAAAUUGAC<br>AUGGACCAACCCAAGUAUUAAGAGUGUUAUAAUACUAAAAUAUAACAU<br>UCAAUAUAGGACCAAAGAUGCCUCAACUUGGAGCCAGAUUCCUCCUG<br>AAGACACAGCAUCCACCCGAUCUUCAUUCACUGUCCAAGACCUUAAA<br>CCUUUUACAGAAUAUGUGUUUAGGAUUCGCUGUAUGAAGGAAGAUGG<br>UAAGGGAUACUGGAGUGACUGGAGUGAAGAAGCAAGUGGGAUCACC<br>UAUGAAGAUAGACCAUCUAAAGCACCAAGUUUCUGGUAUAAAAUAGAU<br>CCAUCCCAUACUCAAGGCUACAGAACUGUACAACUCGUGUGGAAGAC<br>AUUGCCUCCUUUUGAAGCCAAUGGAAAAAUCUUGGAUUAUGAAGUGA<br>CUCUCACAAGAUGGAAAUCACAUUUACAAAAUUACACAGUUAAUGCCA<br>CAAAACUGACAGUAAAUCUCACAAAUGAUCGCUAUCUAGCAACCCUAA<br>CAGUAAGAAAUCUUGUUGGCAAAUCAGAUGCAGCUGUUUUAACUAUC<br>CCUGCCUGUGACUUUCAAGCUACUCACCCUGUAAUGGAUCUUAAAGC<br>AUUCCCCAAAGAUAACAUGCUUUGGGUGGAAUGGACUACUCCAAGGG<br>AAUCUGUAAAGAAAUAUAUACUUGAGUGGUGUGUGUUAUCAGAUAAA<br>GCACCCUGUAUCACAGACUGGCAACAAGAAGAUGGUACCGUGCAUCG<br>CACCUAUUUAAGAGGGAACUUAGCAGAGAGCAAAUGCUAUUUGAUAA<br>CAGUUACUCCAGUAUAUGCUGAUGGACCAGGAAGCCCUGAAUCCAUA<br>AAGGCAUACCUUAAACAAGCUCCACCUUCCAAAGGACCUACUGUUCG |

TABLE 6-continued

Exemplary GP130 Polynucleotide and Polypeptide Sequences

| SEQ ID NO: and features | Sequence |
|---|---|
| | GACAAAAAAAGUAGGGAAAAACGAAGCUGUCUUAGAGUGGGACCAAC<br>UUCCUGUUGAUGUUCAGAAUGGAUUUAUCAGAAAUUAUACUAUAUUU<br>UAUAGAACCAUCAUUGGAAAUGAAACUGCUGUGAAUGUGGAUUCUUC<br>CCACACAGAAUAUACAUUGUCCUCUUUGACUAGUGACACAUUGUACA<br>UGGUACGAAUGGCAGCAUACACAGAUGAAGGUGGGAAGGAUGGUCC<br>AGAAUUCACUUUUACUACCCCAAAGUUUGCUCAAGGAGAAAUUGAAG<br>CCAUAGUCGUGCCUGUUUGCUUAGCAUUCCUAUUGACAACUCUUCUG<br>GGAGUGCUGUUCUGCUUUAAUAAGCGAGACCUAAUUAAAAAACACAU<br>CUGGCCUAAUGUUCCAGAUCCUUCAAAGAGUCAUAUUGCCCAGUGGU<br>CACCUCACACUCCUCCAAGGCACAAUUUUAAUUCAAAAGAUCAAAUGU<br>AUUCAGAUGGCAAUUUCACUGAUGUAAGUGUUGUGGAAAUAGAAGCA<br>AAUGACAAAAAGCCUUUUCCAGAAGAUCUGAAAUCAUUGGACCUGUU<br>CAAAAAGGAAAAAAUUAAUACUGAAGGACACAGCAGUGGUAUUGGGG<br>GGUCUUCAUGCAUGUCAUCUUCUAGGCCAAGCAUUUCUAGCAGUGAU<br>GAAAAUGAAUCUUCACAAAACACUUCGAGCACUGUCCAGUAUUCUAC<br>CGUGGUACACAGUGGCUACAGACACCAAGUUCCGUCAGUCCAAGUCU<br>UCUCAAGAUCCGAGUCUACCCAGCCCUUGUUAGAUUCAGAGGAGCGG<br>CCAGAAGAUCUACAAUUAGUAGAUCAUGUAGAUGGCGGUGAUGGUAU<br>UUUGCCCAGGCAACAGUACUUCAAACAGAACUGCAGUCAGCAUGAAU<br>CCAGUCCAGAUAUUUCACAUUUUGAAAGGUCAAAGCAAGUUUCAUCA<br>GUCAAUGAGGAAGAUUUUGUUAGACUUAAACAGCAGAUUUCAGAUCA<br>UAUUUCACAAUCCUGUGGAUCUGGGCAAAUGAAAAUGUUUCAGGAAG<br>UUUCUGCAGCAGAUGCUUUUGGUCCAGGUACUGAGGGACAAGUAGA<br>AAGAUUUGAAACAGUUGGCAUGGAGGCUGCGACUGAUGAAGGCAUG<br>CCUAAAAGUUACUUACCACAGACUGUACGGCAAGGCGGCUACAUGCC<br>UCAGUGAAGGACUAGUAGUUCCUGCUACAACUUCAGCAGUACCUAUA<br>AAGUAAAGCUAAAAUGAUUUUAUCUGUGAAUUC<br>U = Uridine and/or pseudouridine |
| SEQ ID NO: 21<br>Translated human GP130 from coding sequence (CDS) of the DNA construct of SEQ ID NO: 20 | MLTLQTWLVQALFIFLTTESTGELLDPCGYISPESPVVQLHSNFTAVCVLKEKCMDYF<br>HVNANYIVWKTNHFTIPKEQYTIINRTASSVTFTDIASLNIQLTCNILTFGQLEQNVYGI<br>TIISGLPPEKPKNLSCIVNEGKKMRCEWDRGRETHLETNFTLKSEWATHKFADC<br>KAKRDTPTSCTVDYSTVYFVNIEVWVEAENALGKVTSDHINFDPVYKVKPN<br>PPHNLSVINSEELSSILKLTWTNPSIKSVIILKYNIQYRTKDASTWSQIPPEDT<br>ASTRSSFTVQDLKPFTEYVFRIRCMKEDGKGYWSDWSEEASGITYEDRPSKA<br>PSFWYKIDPSHTQGYRTVQLVWKTLPPFEANGKILDYEVTLTRWKSHLQNYTV<br>NATKLTVNLTNDRYVATLTVRNLVGKSDAAVLTIPACDFQATHPVMDLKAF<br>PKDNMLWVEWTTPRESVKKYILEWCVLSDKAPCITDWQQEDGTVHRTYL<br>RGNLAESKCYLITVTPVYADGPGSPESIKAYLKQAPPSKGPTVRTKKVGKN<br>EAVLEWDQLPVDVQNGFIRNYTIFYRTIIGNETAVNVDSSHTEYTLSSLTSD<br>TLYMVRMAAYTDEGGKDGPEFTFTTPKFAQGEIEAIVVPVCLAFLLTTLLGV<br>LFCFNKRDLIKKHIWPNVPDPSKSHIAQWSPHTPPRHNFNSKDQMYSDGN<br>FTDVSVVEIEANDKKPFPEDLKSLDLFKKEKINTEGHSSGIGGSSCMSSSRP<br>SISSSDENESSQNTSSTVQYSTVVHSGYRHQVPSVQVFSRSESTQPLLDS<br>EERPEDLQLVDHVDGGDGILPRQQYFKQNCSQHESSPDISHFERSKQVSS<br>VNEEDFVRLKQQISDHISQSCGSGQMKMFQEVSAADAFGPGTEGQVERF<br>ETVGMEAATDEGMPKSYLPQTVRQGGYMPQ |
| SEQ ID NO: 51<br>(DNA)<br>TEV-hGP130-2xhBG-120A<br>Sequence features:<br>Tobacco Etch Virus (TEV) 5' UTR: 37-190<br>Optimal Kozak sequence: 191-199<br>Human GP130 codon optimized, encoding amino acids Accession # XM_011543376: 226-29791 stop codon: 2980-2982<br>2 copies of human beta-globin 3'UTR: 2983-3245<br>120 nucleotide polyA tail (SEQ ID NO: 59): 3249-3368 | GATCCGGAGGCCGGAGAATTGTAATACGACTCACTATAGGGAGACGCGTGTTAA<br>ATAACAAATCTCAACACAACATATACAAAACAAACGAATCTCAAGCAATCAAGCA<br>TTCTACTTCTATTGCAGCAATTTAAATCATTTCTTTTAAAGCAAAAGCAATTTTCTG<br>AAAATTTTCACCATTTACGAACGATAGCCGCCACCGCATCGTGAACGAGGGCAAG<br>AAAATGCTGACCCTGCAGACCTGGCTGGTGCAGGCCCTGTTCATCTTCCTGACCA<br>CCGAGAGCACCGGCGAGCTGCTGGACCCTTGTGGCTACATCAGCCCCGAGAGCC<br>CTGTGGTGCAGCTGCATAGCAACTTCACCGCCGTGTGCGTGCTGAAAGAAAAGT<br>GCATGGACTACTTCCACGTGAACGCCAACTACATCGTGTGGAAAACAAACCACTT<br>CACCATCCCCAAAGAGCAGTACACCATCATCAACAGAACCGCCAGCAGCGTGACC<br>TTCACCGATATCGCCAGCCTGAACATCCAGCTGACCTGCAACATCCTGACCTTCGG<br>CCAGCTGGAACAGAACGTGTACGGCATCACAATCATCAGCGGCCTGCCCCCCGA<br>GAAGCCCAAGAACCTGAGCTGCATCGTGAACGAGGGCAAGAAAATGAGATGCG<br>AGTGGGACGGCGGCAGAGAGACACACCTGGAAACAAACTTCACCCTGAAGTCCG<br>AGTGGGCCACCCACAAGTTCGCCGACTGCAAGGCCAAGAGGGACACCCCCACCA<br>GCTGTACCGTGGACTACAGCACCGTGTACTTCGTGAACATCGAAGTGTGGGTGG<br>AAGCCGAGAACGCCCTGGGCAAAGTGACCAGCGACCACATCAACTTCGACCCTG<br>TGTACAAAGTGAAGCCCAACCCCCCCCACAACCTGAGCGTGATCAACAGCGAGG<br>AACTGAGCAGCATCCTGAAGCTGACATGGACCAACCCCAGCATCAAGTCCGTGAT<br>CATTCTGAAGTACAACATCCAGTACCGGACCAAGGACGCCAGCACCTGGTCCCAG<br>ATCCCTCCAGAGGACACCGCCTCCACCAGATCCAGCTTCACAGTGCAGGACCTGA<br>AGCCTTTCACCGAGTACGTGTTCAGGATTCGGTGCATGAAGGAAGATGGCAAGG<br>GCTACTGGAGCGATTGGAGCGAGGAAGCCAGCGGCATCACCTACGAGGACAGA<br>CCCTCTAAGGCCCCCAGCTTCTGGTACAAGATCGACCCCAGCCACACCCAGGGCT<br>ACAGAACCGTGCAGCTCGTGTGGAAAACCCTGCCCCCATTCGAGGCCAACGGCA<br>AGATCCTGGACTACGAAGTGACCCTGACCAGATGGAAGTCCCATCTGCAGAACTA<br>CACCGTGAACGCTACCAAGCTGACCGTGAACCTGACAAACGACAGATACCTGGC<br>CACCCTGACCGTGCGGAACCTCGTGGGCAAGTCTGATGCCGCCGTGCTGACCATC |

TABLE 6-continued

Exemplary GP130 Polynucleotide and Polypeptide Sequences

| SEQ ID NO: and features | Sequence |
|---|---|
| | CCCGCATGCGATTTTCAAGCCACCCACCCCGTGATGGATCTGAAGGCTTTCCCCA<br>AGGACAACATGCTGTGGGTGGAATGGACCACCCCCAGAGAAAGCGTGAAAAAG<br>TACATCCTGGAATGGTGTGTGCTGAGCGACAAGGCCCCCTGCATCACCGATTGGC<br>AGCAGGAAGATGGAACCGTGCACAGAACCTACCTGAGAGGCAACCTGGCCGAG<br>AGCAAGTGCTACCTGATCACCGTGACCCCCGTGTACGCTGACGGCCCTGGAAGCC<br>CTGAGAGCATCAAGGCCTACCTGAAGCAGGCCCCTCCCAGCAAGGGACCTACAG<br>TGCGGACCAAGAAAGTGGGCAAGAACGAGGCCGTGCTGGAATGGGACCAGCTG<br>CCTGTGGATGTGCAGAACGGCTTCATCAGAAACTACACCATCTTCTACAGGACCA<br>TCATCGGCAACGAGACAGCCGTGAACGTGGACAGCAGCCACACAGAGTACACCC<br>TGAGCAGCCTGACCTCCGACACCCTGTATATGGTGCGAATGGCCGCCTACACCGA<br>CGAGGGCGGAAAGGATGGCCCCGAGTTCACCTTCACCACACCTAAGTTCGCTCA<br>GGGCGAGATCGAGGCCATCGTGGTGCCTGTGTGTCTGGCTTTCCTGCTGACCACC<br>CTGCTGGGCGTGCTGTTCTGCTTCAACAAGCGGGACCTGATCAAGAAGCACATCT<br>GGCCCAACGTGCCCGACCCTAGCAAGAGCCATATCGCCCAGTGGTCCCCCCACAC<br>CCCCCCTAGACACAACTTCAACAGCAAGGACCAGATGTACAGCGACGGCAACTTT<br>ACAGACGTGTCCGTGGTGGAAATCGAGGCTAACGATAAGAAGCCCTTCCCAGAA<br>GATCTGAAGTCCCTGGATCTGTTCAAGAAAGAGAAGATCAACACAGAGGGCCAC<br>AGCTCCGGCATCGGCGGCAGCTCTTGTATGAGCAGCAGCAGACCTAGCATCAGC<br>AGCAGCGACGAGAACGAGAGCAGCCAGAACACCTCTAGCACCGTGCAGTACTCC<br>ACCGTGGTGCACAGCGGCTACAGACACCAGGTGCCAAGCGTGCAGGTGTTCAGC<br>AGAAGCGAGTCCACCCAGCCCCTGCTGGACAGCGAAGAGAGGCCTGAGGATCTG<br>CAGCTGGTGGACCATGTGGACGGCGGAGATGGCATCCTGCCCAGACAGCAGTAC<br>TTCAAGCAGAACTGCTCCCAGCACGAGTCCAGCCCCGACATCAGCCACTTCGAGA<br>GAAGCAAACAGGTGTCCAGCGTGAACGAAGAGGACTTCGTGCGGCTGAAGCAG<br>CAGATCAGCGATCACATCTCCCAGAGCTGCGGCAGCGGCCAGATGAAGATGTTC<br>CAGGAAGTGTCCGCCGCTGACGCCTTCGGACCTGGAACTGAGGGCCAGGTGGAA<br>AGATTCGAGACAGTGGGCATGGAAGCCGCCACAGACGAGGGCATGCCTAAGAG<br>CTACCTGCCCCAGACTGTGCGGCAGGGCGGCTACATGCCTCAGTGAAGCTCGCTT<br>TCTTGCTGTCCAATTTCTATTAAAGGTTCCTTTGTTCCCTAAGTCCAACTACTAAAC<br>TGGGGGATATTATGAAGGGCCTTGAGCATCTGGATTCTGCCTAATAAAAAACATT<br>TATTTTCATTGCAGCTCGCTTTCTTGCTGTCCAATTTCTATTAAAGGTTCCTTTGTTC<br>CCTAAGTCCAACTACTAAACTGGGGGATATTATGAAGGGCCTTGAGCATCTGGAT<br>TCTGCCTAATAAAAAACATTTATTTTCATTGCAAAAAAAAAAAAAAAAAAAAAAA<br>AAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA |
| SEQ ID NO: 22<br>(mRNA)<br>TEV-hGP130-2xhBG-<br>120A<br>Sequence features:<br>Tobacco Etch Virus<br>(TEV) 5' UTR: 37-190<br>Optimal Kozak<br>sequence: 191-199<br>Human GP130 codon<br>optimized, encoding<br>amino acids<br>Accession #<br>XM_011543376: 226-<br>29791 stop codon:<br>2980-2982<br>2 copies of human<br>beta-globin 3'UTR:<br>2983-3245<br>120 nucleotide polyA<br>tail (SEQ ID NO: 59):<br>3249-3368 | GGGAGACGCGUGUUAAAUAACAAAUCUCAACACAACAUAUACAAAACAAACG<br>AAUCUCAAGCAAUCAAGCAUUCUACUUCUAUUGCAGCAAUUUAAAUCAUUUC<br>UUUUAAAGCAAAAGCAAUUUUCUGAAAAUUUUCACCAUUUACGAACGAUAG<br>CCGCCACCGCAUCGUGAACGAGGGCAAGAAAAUGCUGACCCUGCAGACCUGG<br>CUGGUGCAGGCCCUGUUCAUCUUCCUGACCACCGAGAGCACCGGCGAGCUGC<br>UGGACCCUUGUGGCUACAUCAGCCCCGAGAGCCCUGUGGUGCAGCUGCAUAG<br>CAACUUCACCGCCGUGUGCGUGCUGAAAGAAAAGUGCAUGGACUACUUCCAC<br>GUGAACGCCAACUACAUCGUGUGGAAAACAAACCACUUCACCAUCCCCAAAGA<br>GCAGUACACCAUCAUCAACAGAACCGCCAGCAGCGUGACCUUCACCGAUAUCG<br>CCAGCCUGAACAUCCAGCUGACCUGCAACAUCCUGACCUUCGGCCAGCUGGAA<br>CAGAACGUGUACGGCAUCACAAUCAUCAGCGGCCUGCCCCCCGAGAAGCCCAA<br>GAACCUGAGCUGCAUCGUGAACGAGGGCAAGAAAAUGAGAUGCGAGUGGGA<br>CGGCGGCAGAGAGACACACCUGGAAACAAACUUCACCCUGAAGUCCGAGUGG<br>GCCACCCACAAGUUCGCCGACUGCAAGGCCAAGAGGGACACCCCCACCAGCUG<br>UACCGUGGACUACAGCACCGUGUACUUCGUGAACAUCGAAGUGUGGGUGGA<br>AGCCGAGAACGCCCUGGGCAAAGUGACCAGCGACCACAUCAACUUCGACCCUG<br>UGUACAAAGUGAAGCCCAACCCCCCCACAACCUGAGCGUGAUCAACAGCGAG<br>GAACUGAGCAGCAUCCUGAAGCUGACAUGGACCAACCCCAGCAUCAAGUCCG<br>UGAUCAUUCUGAAGUACAACAUCCAGUACCGGACCAAGGACGCCAGCACCUG<br>GUCCCAGAUCCCUCCAGAGGACACCGCCUCCACCAGAUCCAGCUUCACAGUGC<br>AGGACCUGAAGCCUUUCACCGAGUACGUGUUCAGGAUUCGGUGCAUGAAGG<br>AAGAUGGCAAGGGCUACUGGAGCGAUUGGAGCGAGGAAGCCAGCGGCAUCA<br>CCUACGAGGACAGACCCUCUAAGGCCCCCAGCUUCUGGUACAAGAUCGACCCC<br>AGCCACACCCAGGGCUACAGAACCGUGCAGCUCGUGUGGAAAACCCUGCCCCC<br>AUUCGAGGCCAACGGCAAGAUCCUGGACUACGAAGUGACCCUGACCAGAUGG<br>AAGUCCCAUCUGCAGAACUACACCGUGAACGCUACCAAGCUGACCGUGAACC<br>UGACAAACGACAGAUACCUGGCCACCCUGACCGUGCGGAACCUCGUGGGCAA<br>GUCUGAUGCCGCCGUGCUGACCAUCCCCGCAUGCGAUUUUCAAGCCACCCAC<br>CCCGUGAUGGAUCUGAAGGCUUUCCCCAAGGACAACAUGCUGUGGGUGGAA<br>UGGACCACCCCCAGAGAAAGCGUGAAAAAGUACAUCCUGGAAUGGUGUGUGC<br>UGAGCGACAAGGCCCCCUGCAUCACCGAUUGGCAGCAGGAAGAUGGAACCGU<br>GCACAGAACCUACCUGAGAGGCAACCUGGCCGAGAGCAAGUGCUACCUGAUC<br>ACCGUGACCCCCGUGUACGCUGACGGCCCUGGAAGCCCUGAGAGCAUCAAGG<br>CCUACCUGAAGCAGGCCCCUCCCAGCAAGGGACCUACAGUGCGGACCAAGAAA<br>GUGGGCAAGAACGAGGCCGUGCUGGAAUGGGACCAGCUGCCUGUGGAUGUG<br>CAGAACGGCUUCAUCAGAAACUACACCAUCUUCUACAGGACCAUCAUCGGCA<br>ACGAGACAGCCGUGAACGUGGACAGCAGCCACACAGAGUACACCCUGAGCAG<br>CCUGACCUCCGACACCCUGUAUAUGGUGCGAAUGGCCGCCUACACCGACGAG<br>GGCGGAAAGGAUGGCCCCGAGUUCACCUUCACCACACCUAAGUUCGCUCAGG |

TABLE 6-continued

Exemplary GP130 Polynucleotide and Polypeptide Sequences

| SEQ ID NO: and features | Sequence |
|---|---|
| | GCGAGAUCGAGGCCAUCGUGGUGCCUGUGUGUCUGGCUUUCCUGCUGACCA<br>CCCUGCUGGGCGUGCUGUUCUGCUUCAACAAGCGGGACCUGAUCAAGAAGCA<br>CAUCUGGCCCAACGUGCCCGACCCUAGCAAGAGCCAUAUCGCCCAGUGGUCCC<br>CCCACACCCCCCCUAGACACAACUUCAACAGCAAGGACCAGAUGUACAGCGAC<br>GGCAACUUUACAGACGUGUCCGUGGUGGAAAUCGAGGCUAACGAUAAGAAG<br>CCCUUCCCAGAAGAUCUGAAGUCCCUGGAUCUGUUCAAGAAAGAGAAGAUCA<br>ACACAGAGGGCCACAGCUCCGGCAUCGGCGGCAGCUCUUGUAUGAGCAGCAG<br>CAGACCUAGCAUCAGCAGCAGCGACGAGAACGAGAGCAGCCAGAACACCUCUA<br>GCACCGUGCAGUACUCCACCGUGGUGCACAGCGGCUACAGACACCAGGUGCC<br>AAGCGUGCAGGUGUUCAGCAGAAGCGAGUCCACCCAGCCCCUGCUGGACAGC<br>GAAGAGAGGCCUGAGGAUCUGCAGCUGGUGGACCAUGUGGACGGCGGAGAU<br>GGCAUCCUGCCCAGACAGCAGUACUUCAAGCAGAACUGCUCCCAGCACGAGU<br>CCAGCCCCGACAUCAGCCACUUCGAGAGAAGCAAACAGGUGUCCAGCGUGAAC<br>GAAGAGGACUUCGUGCGGCUGAAGCAGCAGAUCAGCGAUCACAUCUCCCAGA<br>GCUGCGGCAGCGGCCAGAUGAAGAUGUUCCAGGAAGUGUCCGCCGCUGACGC<br>CUUCGGACCUGGAACUGAGGGCCAGGUGGAAAGAUUCGAGACAGUGGGCAU<br>GGAAGCCGCCACAGACGAGGGCAUGCCUAAGAGCUACCUGCCCCAGACUGUG<br>CGGCAGGGCGGCUACAUGCCUCAGUGAAGCUCGCUUUCUUGCUGUCCAAUU<br>UCUAUUAAAGGUUCCUUUGUUCCCUAAGUCCAACUACUAAACUGGGGGAUA<br>UUAUGAAGGGCCUUGAGCAUCUGGAUUCUGCCUAAUAAAAAACAUUUAUUU<br>UCAUUGCAGCUCGCUUUCUUGCUGUCCAAUUUCUAUUAAAGGUUCCUUUGU<br>UCCCUAAGUCCAACUACUAAACUGGGGGAUAUUAUGAAGGGCCUUGAGCAU<br>CUGGAUUCUGCCUAAUAAAAAACAUUUAUUUUCAUUGCAAAAAAAAAAAAAA<br>AAAAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAA<br>U = URIDINE AND/OR PSEUDOURIDINE |
| SEQ ID NO: 52<br>GP130 RNA coding sequence of construct of SEQ ID NO: 22 | AUGCUGACCCUGCAGACCUGGCUGGUGCAGGCCCUGUUCAUCUUCCUGACCA<br>CCGAGAGCACCGGCGAGCUGCUGGACCCUUGUGGCUACAUCAGCCCCGAGAG<br>CCCUGUGGUGCAGCUGCAUAGCAACUUCACCGCCGUGUGCGUGCUGAAAGAA<br>AAGUGCAUGGACUACUUCCACGUGAACGCCAACUACAUCGUGUGGAAAACAA<br>ACCACUUCACCAUCCCCAAAGAGCAGUACACCAUCAUCAACAGAACCGCCAGC<br>AGCGUGACCUUCACCGAUAUCGCCAGCCUGAACAUCCAGCUGACCUGCAACA<br>UCCUGACCUUCGGCCAGCUGGAACAGAACGUGUACGGCAUCACAAUCAUCAG<br>CGGCCUGCCCCCCGAGAAGCCCAAGAACCUGAGCUGCAUCGUGAACGAGGGC<br>AAGAAAAUGAGAUGCGAGUGGGACGGCGGCAGAGAGACACACCUGGAAACAA<br>ACUUCACCCUGAAGUCCGAGUGGGCCACCCACAAGUUCGCCGACUGCAAGGC<br>CAAGAGGGACACCCCCACCAGCUGUACCGUGGACUACAGCACCGUGUACUUC<br>GUGAACAUCGAAGUGUGGGUGGAAGCCGAGAACGCCCUGGGCAAAGUGACC<br>AGCGACCACAUCAACUUCGACCCUGUGUACAAAGUGAAGCCCAACCCCCCCA<br>CAACCUGAGCGUGAUCAACAGCGAGGAACUGAGCAGCAUCCUGAAGCUGACA<br>UGGACCAACCCCAGCAUCAAGUCCGUGAUCAUUCUGAAGUACAACAUCCAGU<br>ACCGGACCAAGGACGCCAGCACCUGGUCCCAGAUCCCUCCAGAGGACACCGCC<br>UCCACCAGAUCCAGCUUCACAGUGCAGGACCUGAAGCCUUUCACCGAGUACG<br>UGUUCAGGAUUCGGUGCAUGAAGGAAGAUGGCAAGGGCUACUGGAGCGAU<br>UGGAGCGAGGAAGCCAGCGGCAUCACCUACGAGGACAGACCCUCUAAGGCCC<br>CCAGCUUCUGGUACAAGAUCGACCCCAGCCACACCCAGGGCUACAGAACCGUG<br>CAGCUCGUGUGGAAAACCCUGCCCCCAUUCGAGGCCAACGGCAAGAUCCUGG<br>ACUACGAAGUGACCCUGACCAGAUGGAAGUCCCAUCUGCAGAACUACACCGU<br>GAACGCUACCAAGCUGACCGUGAACCUGACAAACGACAGAUACCUGGCCACCC<br>UGACCGUGCGGAACCUCGUGGGCAAGUCUGAUGCCGCCGUGCUGACCAUCCC<br>CGCAUGCGAUUUUCAAGCCACCCACCCCGUGAUGGAUCUGAAGGCUUUCCCC<br>AAGGACAACAUGCUGUGGGUGGAAUGGACCACCCCCAGAGAAAGCGUGAAAA<br>AGUACAUCCUGGAAUGGUGUGUGCUGAGCGACAAGGCCCCCUGCAUCACCGA<br>UUGGCAGCAGGAAGAUGGAACCGUGCACAGAACCUACCUGAGAGGCAACCUG<br>GCCGAGAGCAAGUGCUACCUGAUCACCGUGACCCCCGUGUACGCUGACGGCC<br>CUGGAAGCCCUGAGAGCAUCAAGGCCUACCUGAAGCAGGCCCCUCCCAGCAAG<br>GGACCUACAGUGCGGACCAAGAAAGUGGGCAAGAACGAGGCCGUGCUGGAA<br>UGGGACCAGCUGCCUGUGGAUGUGCAGAACGGCUUCAUCAGAAACUACACCA<br>UCUUCUACAGGACCAUCAUCGGCAACGAGACAGCCGUGAACGUGGACAGCAG<br>CCACACAGAGUACACCCUGAGCAGCCUGACCUCCGACACCCUGUAUAUGGUGC<br>GAAUGGCCGCCUACACCGACGAGGGCGGAAAGGAUGGCCCCGAGUUCACCUU<br>CACCACACCUAAGUUCGCUCAGGGCGAGAUCGAGGCCAUCGUGGUGCCUGUG<br>UGUCUGGCUUUCCUGCUGACCACCCUGCUGGGCGUGCUGUUCUGCUUCAAC<br>AAGCGGGACCUGAUCAAGAAGCACAUCUGGCCCAACGUGCCCGACCCUAGCAA<br>GAGCCAUAUCGCCCAGUGGUCCCCCCACACCCCCCCUAGACACAACUUCAACA<br>GCAAGGACCAGAUGUACAGCGACGGCAACUUUACAGACGUGUCCGUGGUGG<br>AAAUCGAGGCUAACGAUAAGAAGCCCUUCCCAGAAGAUCUGAAGUCCCUGGA<br>UCUGUUCAAGAAAGAGAAGAUCAACACAGAGGGCCACAGCUCCGGCAUCGGC<br>GGCAGCUCUUGUAUGAGCAGCAGCAGACCUAGCAUCAGCAGCAGCGACGAGA<br>ACGAGAGCAGCCAGAACACCUCUAGCACCGUGCAGUACUCCACCGUGGUGCAC<br>AGCGGCUACAGACACCAGGUGCCAAGCGUGCAGGUGUUCAGCAGAAGCGAGU<br>CCACCCAGCCCCUGCUGGACAGCGAAGAGAGGCCUGAGGAUCUGCAGCUGGU<br>GGACCAUGUGGACGGCGGAGAUGGCAUCCUGCCCAGACAGCAGUACUUCAAG<br>CAGAACUGCUCCCAGCACGAGUCCAGCCCCGACAUCAGCCACUUCGAGAGAAG |

TABLE 6-continued

| Exemplary GP130 Polynucleotide and Polypeptide Sequences | |
|---|---|
| SEQ ID NO: and features | Sequence |
| | CAAACAGGUGUCCAGCGUGAACGAAGAGGACUUCGUGCGGCUGAAGCAGCAG AUCAGCGAUCACAUCUCCCAGAGCUGCGGCAGCGGCCAGAUGAAGAUGUUCC AGGAAGUGUCCGCCGCUGACGCCUUCGGACCUGGAACUGAGGGCCAGGUGG AAAGAUUCGAGACAGUGGGCAUGGAAGCCGCCACAGACGAGGGCAUGCCUAA GAGCUACCUGCCCCAGACUGUGCGGCAGGGCGGCUACAUGCCUCAGUGA |

VII. Galectin-3

Galectin-3 is a 26 kDa protein and is a member of the β-galactoside-binding lectin family. It contains a collagen-like N-terminal domain and a C-terminal carbohydrate recognition domain which confers the ability of galectin-3 to bind carbohydrates. Via its N-terminal domain, galectin-3 is able to form higher order oligomers. Galectin-3 has been suggested to play a role in cell attachment, differentiation, metastasis, embryogenesis, inflammation, and fibrosis.

The full length coding sequence of human galectin-3 (e.g., Protein Accession No. NP_002297) was codon optimized for expression in human cells and cloned into a vector that can sustain mRNA transcription by T7 polymerase and contains both 3 and 5' untranslated regions that help with mRNA stability and translatability (see Table 7 for sequence). mRNA was in vitro transcribed and encapsulated into lipid nanoparticles as described above.

TABLE 7

| Exemplary Galectin 3 Polynucleotide and Polypeptide Sequences | |
|---|---|
| SEQ ID NO: and features | Sequence |
| SEQ ID NO: 53 Galectin-3 native DNA sequence corresponding to Protein Accession # NP_002297 | GAGTATTTGAGGCTCGGAGCCACCGCCCCGCCGGCGCCCGCAGCACCTCCTCGCCAGCAG CCGTCCGGAGCCAGCCAACGAGCGGAAAATGGCAGACAATTTTTCGCTCCATGATGCGTT ATCTGGGTCTGGAAACCCAAACCCTCAAGGATGGCCTGGCGCATGGGGGAACCAGCCTG CTGGGGCAGGGGGCTACCCAGGGGCTTCCTATCCTGGGGCCTACCCCGGGCAGGCACCC CCAGGGGCTTATCCTGGACAGGCACCTCCAGGCGCCTACCCTGGAGCACCTGGAGCTTAT CCCGGAGCACCTGCACCTGGAGTCTACCCAGGGCCACCCAGCGGCCCTGGGGCCTACCCA TCTTCTGGACAGCCAAGTGCCACCGGAGCCTACCCTGCCACTGGCCCCTATGGCGCCCCTG CTGGGCCACTGATTGTGCCTTATAACCTGCCTTTGCCTGGGGGAGTGGTGCCTCGCATGCT GATAACAATTCTGGGCACGGTGAAGCCCAATGCAAACAGAATTGCTTTAGATTTCCAAAG AGGGAATGATGTTGCCTTCCACTTTAACCCACGCTTCAATGAGAACAACAGGAGAGTCATT GTTTGCAATACAAAGCTGGATAATAACTGGGGAAGGGAAGAAAGACAGTCGGTTTTCCCA TTTGAAAGTGGGAAACCATTCAAAATACAAGTACTGGTTGAACCTGACCACTTCAAGGTTG CAGTGAATGATGCTCACTTGTTGCAGTACAATCATCGGGTTAAAAAACTCAATGAAATCAG CAAACTGGGAATTTCTGGTGACATAGACCTCACCAGTGCTTCATATACCATGATATAATCT GAAAGGGGCAGATTAAAAAAAAAAAAAGAATCTAAACCTTACATGTGTAAAGGTTTCATG TTCACTGTGAGTGAAAATTTTTACATTCATCAATATCCCTCTTGTAAGTCATCTACTTAATAA ATATTACAGTGAATTACCTGTCTCAATATGTCAAAAAAAAAAAAAAAAAA |
| SEQ ID NO: 26 Native mRNA sequence corresponding to Protein Accession # NP_002297 | GAGUAUUUGAGGCUCGGAGCCACCGCCCCGCCGGCGCCCGCAGCAC CUCCUCGCCAGCAGCCGUCCGGAGCCAGCCAACGAGCGGAAAAUGG CAGACAAUUUUUCGCUCCAUGAUGCGUUAUCUGGGUCUGGAAACCCA AACCCUCAAGGAUGGCCUGGCGCAUGGGGGAACCAGCCUGCUGGGG CAGGGGGCUACCCAGGGGCUUCCUAUCCUGGGGCCUACCCCGGGCA GGCACCCCCAGGGGCUUAUCCUGGACAGGCACCUCCAGGCGCCUAC CCUGGAGCACCUGGAGCUUAUCCCGGAGCACCUGCACCUGGAGUCU ACCCAGGGCCACCCAGCGGCCCUGGGGCCUACCCAUCUUCUGGACA GCCAAGUGCCACCGGAGCCUACCCUGCCACUGGCCCCUAUGGCGCC CCUGCUGGGCCACUGAUUGUGCCUUAUAACCUGCCUUUGCCUGGGG GAGUGGUGCCUCGCAUGCUGAUAACAAUUCUGGGCACGGUGAAGCC CAAUGCAAACAGAAUUGCUUUAGAUUUCCAAAGAGGGAAUGAUGUUG CCUUCCACUUUAACCCACGCUUCAAUGAGAACAACAGGAGAGUCAUU GUUUGCAAUACAAAGCUGGAUAAUAACUGGGGAAGGGAAGAAAGACA GUCGGUUUUCCCAUUUGAAAGUGGGAAACCAUUCAAAAUACAAGUAC UGGUUGAACCUGACCACUUCAAGGUUGCAGUGAAUGAUGCUCACUUG UUGCAGUACAAUCAUCGGGUUAAAAAACUCAAUGAAAUCAGCAAACUG GGAAUUUCUGGUGACAUAGACCUCACCAGUGCUUCAUAUACCAUGAU AUAAUCUGAAAGGGGCAGAUUAAAAAAAAAAAAAGAAUCUAAACCUUA CAUGUGUAAAGGUUUCAUGUUCACUGUGAGUGAAAAUUUUUACAUUC AUCAAUAUCCCUCUUGUAAGUCAUCUACUUAAUAAAUAUUACAGUGAA UUACCUGUCUCAAUAUGUCAAAAAAAAAAAAAAAAAA U = Uridine and/or pseudouridine |

TABLE 7-continued

Exemplary Galectin 3 Polynucleotide and Polypeptide Sequences

| SEQ ID NO: and features | Sequence |
|---|---|
| SEQ ID NO: 27<br>Translated human galectin-3 from coding sequence (CDS) of the DNA construct of SEQ ID NO: 26 | MADNFSLHDALSGSGNPNPQGWPGAWGNQPAGAGGYPGASYPGAYPG<br>QAPPGAYPGQAPPGAYPGAPGAYPGAPAPGVYPGPPSGPGAYPSSGQP<br>SATGAYPATGPYGAPAGPLIVPYNLPLPGGVVPRMLITILGTVKPNANRIAL<br>DFQRGNDVAFHFNPRFNENNRRVIVCNTKLDNNWGREERQSVFPFESGK<br>PFKIQVLVEPDHFKVAVNDAHLLQYNHRVKKLNEISKLGISGDIDLTSASYT<br>MI |
| SEQ ID NO: 54<br>(DNA)<br>TEV-hGalectin-3-2xhBG-120A<br>Sequence features:<br>Tobacco Etch Virus (TEV) 5' UTR: 37-190<br>Optimal Kozak sequence: 191-199<br>Human Galectin-3 codon optimized, encoding amino acids Accession # NP_002297: 202-951<br>stop codon: 952-954.<br>2 copies of human beta-globin 3'UTR: 973-1238.<br>120 nucleotide polyA tail (SEQ ID NO: 59): 1245-1364. | GATCCGGAGGCCGGAGAATTGTAATACGACTCACTATAGGGAGACGCGTGTTAA<br>ATAACAAATCTCAACACAACATATACAAAACAAACGAATCTCAAGCAATCAAGCA<br>TTCTACTTCTATTGCAGCAATTTAAATCATTTCTTTTAAAGCAAAAGCAATTTTCTG<br>AAAATTTTCACCATTTACGAACGATAGCCGCCACCATGGCCGACAACTTCAGCCT<br>GCACGATGCCCTGAGCGGCAGCGGCAACCCTAATCCTCAGGGATGGCCTGGCGC<br>TTGGGGCAATCAGCCTGCTGGCGCTGGCGGATATCCTGGCGCATCTTACCCAGGC<br>GCTTACCCCGGACAGGCTCCTCCAGGCGCATATCCAGGCCAGGCACCTCCTGGG<br>GCTTATCCTGGGGCACCTGGCGCCTACCCTGGCGCTCCTGCTCCTGGCGTGTAC<br>CCTGGACCTCCTTCTGGACCCGGCGCATACCCTAGCTCTGGCCAGCCA<br>TCTGCTACCGGCGCCTATCCAGCCACAGGACCTTATGGCGCTCCAGCC<br>GGACCTCTGATCGTGCCCTACAACCTGCCTCTGCCTGGCGGCGTGGTG<br>CCCAGAATGCTGATCACAATCCTGGGCACCGTGAAGCCCAACGCCAAC<br>AGAATCGCCCTGGACTTCCAGAGGGGCAACGACGTGGCCTTCCACTTC<br>AACCCCAGATTCAACGAGAACAATCGGCGCGTGATCGTGTGCAACACC<br>AAGCTGGACAACAACTGGGGCAGAGAAGAAAGACAGAGCGTGTTCCCA<br>TTCGAGAGCGGCAAGCCATTCAAGATCCAGGTGCTGGTGGAACCCGAC<br>CACTTCAAGGTGGCCGTGAACGACGCCCATCTGCTGCAGTACAACCAC<br>AGAGTGAAGAAGCTGAACGAGATCAGCAAGCTGGGCATCAGCGGCGA<br>CATCGACCTGACCAGCGCCTCCTACACCATGATCTGACGGACCGGCGA<br>TAGATGAAGCTCGCTTTCTTGCTGTCCAATTTCTATTAAAGGTTCCTTTG<br>TTCCCTAAGTCCAACTACTAAACTGGGGGATATTATGAAGGGCCTTGAG<br>CATCTGGATTCTGCCTAATAAAAAACATTTATTTTCATTGCAGCTCGCTT<br>TCTTGCTGTCCAATTTCTATTAAAGGTTCCTTTGTTCCCTAAGTCCAACT<br>ACTAAACTGGGGGATATTATGAAGGGCCTTGAGCATCTGGATTCTGCCT<br>AATAAAAAACATTTATTTTCATTGCGGCCGCAAAAAAAAAAAAAAAAAAA<br>AAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAA |
| SEQ ID NO: 55<br>(mRNA)<br>TEV-hGalectin3-2xhBG-120A<br>Sequence features:<br>Tobacco Etch Virus (TEV) 5' UTR: 37-190<br>Optimal Kozak sequence: 191-199<br>Human Galectin-3 codon optimized, encoding amino acids Accession #<br>stop codon: 952-954.<br>2 copies of human beta-globin 3'UTR: 973-1238.<br>120 nucleotide polyA tail (SEQ ID NO: 59): 1245-1364. | GGGAGACGCGUGUUAAAUAACAAAUCUCAACACAACAUAUACAAAACA<br>AACGAAUCUCAAGCAAUCAAGCAUUCUACUUCUAUUGCAGCAAUUUAA<br>AUCAUUUCUUUUAAAGCAAAAGCAAUUUUCUGAAAAUUUUCACCAUUU<br>ACGAACGAUAGCCGCCACCAUGGCCGACAACUUCAGCCUGCACGAUG<br>CCCUGAGCGGCAGCGGCAACCCUAAUCCUCAGGGAUGGCCUGGCGC<br>UUGGGGCAAUCAGCCUGCUGGCGCUGGCGGAUAUCCUGGCGCAUCU<br>UACCCAGGCGCUUACCCCGGACAGGCUCCUCCAGGCGCAUAUCCAG<br>GCCAGGCACCUCCUGGGGCUUAUCCUGGGGCACCUGGCGCCUACCC<br>UGGCGCUCCUGCUCCUGGCGUGUACCCUGGACCUCCUUCUGGACCC<br>GGCGCAUACCCUAGCUCUGGCCAGCCAUCUGCUACCGGCGCCUAUC<br>CAGCCACAGGACCUUAUGGCGCUCCAGCCGGACCUCUGAUCGUGCC<br>CUACAACCUGCCUCUGCCUGGCGGCGUGGUGCCCAGAAUGCUGAUC<br>ACAAUCCUGGGCACCGUGAAGCCCAACGCCAACAGAAUCGCCCUGGA<br>CUUCCAGAGGGGCAACGACGUGGCCUUCCACUUCAACCCCAGAUUCA<br>ACGAGAACAAUCGGCGCGUGAUCGUGUGCAACACCAAGCUGGACAAC<br>AACUGGGGCAGAGAAGAAAGACAGAGCGUGUUCCCAUUCGAGAGCG<br>GCAAGCCAUUCAAGAUCCAGGUGCUGGUGGAACCCGACCACUUCAAG<br>GUGGCCGUGAACGACGCCCAUCUGCUGCAGUACAACCACAGAGUGAA<br>GAAGCUGAACGAGAUCAGCAAGCUGGGCAUCAGCGGCGACAUCGACC<br>UGACCAGCGCCUCCUACACCAUGAUCUGACGGACCGGCGAUAGAUGA<br>AGCUCGCUUUCUUGCUGUCCAAUUUCUAUUAAAGGUUCCUUUGUUCC<br>CUAAGUCCAACUACUAAACUGGGGGAUAUUAUGAAGGGCCUUGAGCA<br>UCUGGAUUCUGCCUAAUAAAAAACAUUUAUUUUCAUUGCAGCUCGCU<br>UUCUUGCUGUCCAAUUUCUAUUAAAGGUUCCUUUGUUCCCUAAGUCC<br>AACUACUAAACUGGGGGAUAUUAUGAAGGGCCUUGAGCAUCUGGAUU<br>CUGCCUAAUAAAAAACAUUUAUUUUCAUUGCGGCCGCAAAAAAAAAAA<br>AAAAAAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAA<br>AAAAAAA<br>U = URIDINE AND/OR PSEUDOURIDINE |
| SEQ ID NO: 56<br>Galectin 3 RNA coding sequence of construct of SEQ ID NO: 55 | AUGGCCGACAACUUCAGCCUGCACGAUGCCCUGAGCGGCAGCGGCA<br>ACCCUAAUCCUCAGGGAUGGCCUGGCGCUUGGGGCAAUCAGCCUGC<br>UGGCGCUGGCGGAUAUCCUGGCGCAUCUUACCCAGGCGCUUACCCC<br>GGACAGGCUCCUCCAGGCGCAUAUCCAGGCCAGGCACCUCCUGGGG<br>CUUAUCCUGGGGCACCUGGCGCCUACCCUGGCGCUCCUGCUCCUGG<br>CGUGUACCCUGGACCUCCUUCUGGACCCGGCGCAUACCCUAGCUCU<br>GGCCAGCCAUCUGCUACCGGCGCCUAUCCAGCCACAGGACCUUAUG |

TABLE 7-continued

| Exemplary Galectin 3 Polynucleotide and Polypeptide Sequences | |
|---|---|
| SEQ ID NO: and features | Sequence |
| | GCGCUCCAGCCGGACCUCUGAUCGUGCCCUACAACCUGCCUCUGCC UGGCGGCGUGGUGCCCAGAAUGCUGAUCACAAUCCUGGGCACCGUG AAGCCCAACGCCAACAGAAUCGCCCUGGACUUCCAGAGGGGCAACGA CGUGGCCUUCCACUUCAACCCCAGAUUCAACGAGAACAAUCGGCGCG UGAUCGUGUGCAACACCAAGCUGGACAACAACUGGGGCAGAGAAGAA AGACAGAGCGUGUUCCCAUUCGAGAGCGGCAAGCCAUUCAAGAUCCA GGUGCUGGUGGAACCCGACCACUUCAAGGUGGCCGUGAACGACGCC CAUCUGCUGCAGUACAACCACAGAGUGAAGAAGCUGAACGAGAUCAG CAAGCUGGGCAUCAGCGGCGACAUCGACCUGACCAGCGCCUCCUACA CCAUGAUCUGA<br>U = URIDINE AND/OR PSEUDOURIDINE |

V. Encapsulated Nucleic Acid Nanoparticles

The term "lipid nanoparticle" or "LNP" or "LNPs" refers to a particle that comprises a plurality of (i.e. more than one) lipid molecules physically associated (e.g., covalently or non-covalently) with each other by intermolecular forces. The lipid nanoparticles may be, e.g., microspheres (including unilamellar and multilamellar vesicles, e.g. liposomes), a dispersed phase in an emulsion, micelles or an internal phase in a suspension.

The term "lipid nanoparticle host" refers to a plurality of lipid molecules physically associated with each other by intermolecular forces/electrostatic interactions to encapsulate one or more nucleic acid molecules, such as an mRNA.

Certain embodiments provide an encapsulated nucleic acid nanoparticle composition comprising a pharmaceutically acceptable carrier and an encapsulated nucleic acid nanoparticle. The encapsulated nucleic acid nanoparticle includes a lipid nanoparticle host and a nucleic acid, e.g., polyribonucleotide such as mRNA that is encapsulated in the lipid nanoparticle host.

The term "pharmaceutically acceptable carrier" as used herein, means a non-toxic, inert diluent. Materials which can serve as pharmaceutically acceptable carriers include, but are not limited to, pyrogen-free water, deionized water, isotonic saline, Ringer's solution, and phosphate buffer solutions. In preferred embodiments, the encapsulated nucleic acid nanoparticle has an average size of about 40 to about 70 nm and a polydispersity index of less than about 0.1 as determined by dynamic light scattering, e.g., using a Malvern Zetasizer Nano ZS. The lipid nanoparticle host comprises a degradable cationic lipid, a lipidated polyethylene glycol, cholesterol, and 1,2-distearoyl-sn-glycero-3-phosphocholine components as described elsewhere herein.

Provided herein are methods of preparing an encapsulated nucleic acid nanoparticle composition comprising a cationic lipid and another lipid component. Another embodiment provides a method using a cationic lipid and a helper lipid, for example cholesterol. Another embodiment provides for a method using a cationic lipid, a helper lipid, for example cholesterol, and a neutral lipid, for example DSPC. Another embodiment of the present invention provides a method using a cationic lipid, a helper lipid, for example cholesterol, a neutral lipid, for example DSPC, and a stealth lipid, for example S010, S024, S027, S031, or S033. Another embodiment of the present invention provides for a method of encapsulating a nucleic acid in a lipid nanoparticle host where the nanoparticle comprises a cationic lipid, a helper lipid, for example cholesterol, a neutral lipid, for example DSPC, a stealth lipid, for example S010, S024, S027, S031, or S033, and the nucleic acid is, for example an RNA or DNA. Another embodiment of the present invention provides a method of using a cationic lipid, a helper lipid, for example cholesterol, a neutral lipid, for example DSPC, and a stealth lipid, for example S010, S024, S027, S031, or S033, where the nucleic acid is, for example, mRNA, mRNA or DNA.

In some embodiments, the lipid solution/stream(s) contain a cationic lipid compound, a helper lipid (cholesterol), an optional neutral lipid (DSPC) and a stealth lipid (e.g., S010, S024, S027, or S031). Where a formulation contains four lipid components, the molar ratios of the lipids may range from 20 to 70 mole percent for the cationic lipid with a target of 40 to 60, the mole percent of helper lipid ranges from 20 to 70 with a target of 30 to 50, the mole percent of neutral lipid ranges from 10 to 30, the mole percent of PEG lipid has a range from 1 to 6 with a target of 2 to 5.

In some embodiments, the lipid solution/stream(s) contain 30-60% of a compound of formula (III), 30-60% cholesterol/5-10% DSPC, and 1-5% PEG-DMG, S010, S011 or S024.

Another embodiment of the present disclosure provides a method of encapsulating a nucleic acid in a lipid nanoparticle host using a cationic lipid and a helper lipid, for example cholesterol, in a lipid molar ratio of about 40-55 cationic lipid/about 40-55 helper lipid. Another embodiment provides a method using a cationic lipid, a helper lipid, for example cholesterol, and a neutral lipid, for example DSPC in a lipid molar ratio of about 40-55 a cationic lipid/about 40-55 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-55 cationic lipid/about 40-55 helper lipid/about 5-15 neutral lipid/about 1-10 stealth lipid.

Another embodiment of the present disclosure provides a method of encapsulating a nucleic acid in a lipid nanoparticle host using a cationic lipid and a helper lipid, for example cholesterol, in a lipid molar ratio of about 40-50 cationic lipid/about 40-50 helper lipid. Another embodiment provides a method using a cationic lipid, a helper lipid, for example cholesterol, and a neutral lipid, for example DSPC in a lipid molar ratio of about 40-50 cationic lipid/about 40-50 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-50 cationic lipid/about 40-50 helper lipid/about 5-15 neutral lipid/about 1-5 stealth lipid.

Another embodiment of the present disclosure provides a method of encapsulating a nucleic acid in a lipid nanoparticle host using a cationic lipid and a helper lipid, for example cholesterol, in a lipid molar ratio of about 43-47 cationic lipid/about 43-47 helper lipid. Another embodiment provides a method using a cationic lipid, a helper lipid, for example cholesterol, and a neutral lipid, for example DSPC in a lipid molar ratio of about 43-47 cationic lipid/about 43-47 helper lipid/about 7-12 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 43-47 cationic lipid/about 43-47 helper lipid/about 7-12 neutral lipid/about 1-4 stealth lipid.

Another embodiment of the present disclosure provides a method of encapsulating a nucleic acid in a lipid nanoparticle host using a cationic lipid and a helper lipid, for example cholesterol, in a lipid molar ratio of about 45% cationic lipid and about 44% helper lipid. Another embodiment provides a method using a cationic lipid, a helper lipid, for example cholesterol, and a neutral lipid, for example DSPC in a lipid molar ratio of about 45% cationic lipid, about 44% helper lipid, and about 9% neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 45% cationic lipid, about 44% helper lipid, about 9% neutral lipid, and about 2% stealth lipid.

One embodiment of the present disclosure provides a method of preparing an encapsulated nucleic acid nanoparticle composition comprising a cationic lipid and another lipid component. Another embodiment provides a method using a compound of formula (I) and a helper lipid, for example cholesterol. Another embodiment provides for a method using a cationic lipid, a helper lipid, for example cholesterol, and a neutral lipid, for example DSPC. Another embodiment of the present disclosure provides a method using a cationic lipid, a helper lipid, for example cholesterol, a neutral lipid, for example DSPC, and a stealth lipid, for example S010, S024, S027, S031, or S033. Another embodiment of the present disclosure provides for a method of encapsulating a nucleic acid in a lipid nanoparticle host where the nanoparticle comprises a cationic lipid, a helper lipid, for example cholesterol, a neutral lipid, for example DSPC, a stealth lipid, for example S010, S024, S027, S031, or S033, and the nucleic acid is, for example an RNA or DNA. Another embodiment of the present disclosure provides a method of using cationic lipid, a helper lipid, for example cholesterol, a neutral lipid, for example DSPC, and a stealth lipid, for example S010, S024, S027, S031, or S033, where the nucleic acid is, for example, mRNA, mRNA or DNA.

Another embodiment of the present disclosure provides a method of encapsulating a nucleic acid in a lipid nanoparticle host using a cationic lipid and a helper lipid, for example cholesterol, in a lipid molar ratio of about 40-55 compound of formula (I)/about 40-55 helper lipid. Another embodiment provides a method using a cationic lipid, a helper lipid, for example cholesterol, and a neutral lipid, for example DSPC in a lipid molar ratio of about 40-55 cationic lipid/about 40-55 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-55 compound of formula (I)/about 40-55 helper lipid/about 5-15 neutral lipid/about 1-10 stealth lipid.

Another embodiment of the present disclosure provides a method of encapsulating a nucleic acid in a lipid nanoparticle host using a cationic lipid and a helper lipid, for example cholesterol, in a lipid molar ratio of about 40-50 cationic lipid/about 40-50 helper lipid. Another embodiment provides a method using a cationic lipid, a helper lipid, for example cholesterol, and a neutral lipid, for example DSPC in a lipid molar ratio of about 40-50 cationic lipid/about 40-50 helper lipid/about 5-15 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 40-50 cationic lipid/about 40-50 helper lipid/about 5-15 neutral lipid/about 1-5 stealth lipid.

Another embodiment of the present disclosure provides a method of encapsulating a nucleic acid in a lipid nanoparticle host using a cationic lipid and a helper lipid, for example cholesterol, in a lipid molar ratio of about 43-47 cationic lipid/about 43-47 helper lipid. Another embodiment provides a method using a cationic lipid, a helper lipid, for example cholesterol, and a neutral lipid, for example DSPC in a lipid molar ratio of about 43-47 cationic lipid/about 43-47 helper lipid/about 7-12 neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 43-47 cationic lipid/about 43-47 helper lipid/about 7-12 neutral lipid/about 1-4 stealth lipid.

Another embodiment of the present disclosure provides a method of encapsulating a nucleic acid in a lipid nanoparticle host using a cationic lipid and a helper lipid, for example cholesterol, in a lipid molar ratio of about 45% cationic lipid and about 44% helper lipid. Another embodiment provides a method using a cationic lipid, a helper lipid, for example cholesterol, and a neutral lipid, for example DSPC in a lipid molar ratio of about 45% cationic lipid, about 44% helper lipid, and about 9% neutral lipid. Another embodiment provides a method using a cationic lipid, a helper lipid, for example cholesterol, a neutral lipid, for example DSPC, and a stealth lipid, for example S010, S024, S027, S031, or S033 in a lipid molar ratio of about 45% cationic lipid, about 44% helper lipid, about 9% neutral lipid, and about 2% stealth lipid.

The ratio of lipids:nucleic acid (e.g. polyribonucleotide such as mRNA) in the processes of the disclosure may be approximately 15-20:1 (wt/wt). In certain embodiments, the ratio of lipids:nucleic acid is about 17-19:1. In other embodiments, the ratio of lipids:nucleic acid is about 18.5:1. In other embodiments, the ratio of lipids:nucleic acid is at least about 30:1, 25:1, 24:1, 23:1, 22:1, 21:1, 20:1, 19:1, 18:1, 17:1, 16:1, 15:1, 14:1, 13:1, 12:1, 11:1, or 10:1 (wt/wt).

In certain aspects, the nanoparticles produced by the processes of the disclosure have an average/mean diameter and a distribution of sizes around the average value. A narrower range of particle sizes corresponds to a more uniform distribution of particle sizes. Particle size may be determined at the time of collection of the nanoparticles, after an incubation time, or after fully processing (e.g., dilution, filtration, dialysis, etc.) a nanoparticle formulation. For example, particle size determination is typically done after a 60 min incubation period and/or after full sample processing. Average particle sizes are reported as either a Z-Average or a number average. Z-Averages are measured by dynamic light scattering on a Malvern Zetasizer. The nanoparticle sample is diluted in phosphate buffered saline (PBS) so that the count rate is approximately 200-400 kcts. The data is presented as a weighted average of the intensity measure. Dynamic light scattering also provides a polydispersity index (PDI) that quantifies the width of the particle size distribution. A larger PDI correlates with a larger particle size distribution and vice versa. Number averages, on the other hand, can be determined by measurement under a microscope.

In some embodiments, the encapsulated nucleic acid nanoparticles produced by the processes of the disclosure have an average diameter of about 30 to about 150 nm. In other embodiments, the particles have an average diameter of about 30 to about 40 nm. In other embodiments, the particles have an average diameter of about 40 to about 70 nm. In other embodiments, the particles have an average diameter of about 65 to about 80 nm. In other embodiments, the particles have a Z-average of about 50 to about 80 nm and/or a number average of about 40 to about 80 nm. In still other embodiments, the particles have a Z-average of about 50 to about 70 nm and/or a number average of about 40 to about 65 nm. In yet other embodiments, the particles have a Z-average of about 70 to about 80 nm and/or a number average of about 60 to about 80 nm. The particular size of the particles obtained may depend on the linear velocity of the nucleic acid and lipid streams, the use of an optional dilution step, and the particular nucleic acid or lipids used. Greater linear velocities and maintaining the organic solvent concentration in the first outlet solution<33% tend to produce smaller particle sizes.

In some embodiments, the encapsulated mRNA nanoparticles produced by the processes of the disclosure have an average diameter of about 30 to about 150 nm. In other embodiments, the particles have an average diameter of about 30 to about 40 nm. In other embodiments, the particles have an average diameter of about 40 to about 70 nm. In other embodiments, the particles have an average diameter of about 65 to about 80 nm. In other embodiments, the particles have a Z-average of about 50 to about 80 nm and/or a number average of about 40 to about 80 nm. In still other embodiments, the particles have a Z-average of about 50 to about 70 nm and/or a number average of about 40 to about 65 nm. In yet other embodiments, the particles have a Z-average of about 70 to about 80 nm and/or a number average of about 60 to about 80 nm. In still other embodiments, encapsulated mRNA nanoparticles produced by the processes of the disclosure may have average diameters of about 30, about 35, about 40, about 45, about 50, about 55, about 60, about 65, about 70, about 75, or about 80 nm. In still other embodiments, encapsulated mRNA nanoparticles produced by the processes of the disclosure may have average diameters of at least about 30, about 35, about 40, about 45, about 50, about 55, about 60, about 65, about 70, about 75, or about 80 nm. In still other embodiments, encapsulated mRNA nanoparticles produced by the processes of the disclosure may have average diameters of less than about 30, about 35, about 40, about 45, about 50, about 55, about 60, about 65, about 70, about 75, or about 80 nm.

Using dynamic light scattering (e.g., Malvern Zetasizer NanoZS), the polydispersity index (PDI) may range from 0 to 1.0. In certain embodiments, the PDI is less than about 0.2. In other embodiments, the PDI is less than about 0.1. In some embodiments, the PDI is less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2 or less than 0.1.

The processes of the present disclosure may be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, and/or process parameters. The various optimization techniques known to those of skill in the art pertaining to the above listed embodiments are considered as part of this invention.

Processes for Encapsulating a Nucleic Acid in a Lipid Nanoparticle Host

The following methods can be used to make lipid nanoparticles provided herein. Non-limiting methods of making lipid nanoparticles have been described, for example, see PCT International Patent Application Publication Nos. WO 2016/010840, WO2016/037053, WO2015/095346, WO2015/095340, WO2014/136086, and WO2011/076807, each of which is incorporated by reference herein in its entirety. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition provided herein typically comprises providing an aqueous solution, such as citrate buffer, comprising a nucleic acid in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration or dialysis step, and a dilution and/or concentration step. The incubation step comprises allowing the solution from the mixing step to stand in a vessel for about 0 to about 24 hours (preferably about 1 hour) at about room temperature and optionally protected from light. In one embodiment, a dilution step follows the incubation step. The dilution step may involve dilution with aqueous buffer (e.g. citrate buffer or pure water) e.g., using a pumping apparatus (e.g. a peristaltic pump). The filtration step may be ultrafiltration or dialysis. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent). Dialysis comprises solvent (buffer) exchange through a suitable membrane (e.g. 10,000 mwc snakeskin membrane).

In one embodiment, the mixing step provides a clear single phase. In one embodiment, after the mixing step, the organic solvent is removed to provide a suspension of particles, wherein the nucleic acid is encapsulated by the lipid(s).

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of nucleic acid and lipids. Suitable organic solvents include those described by Strickley, Pharmaceutical Res. (2004), 21, 201-230 for use as co-solvents for injectable formulations. For example, the organic solvent may be selected from one or more (e.g. two) of ethanol, propylene glycol, polyethylene glycol 300, polyethylene glycol 400, glycerin, dimethylacetamide (DMA), N-methyl-2-pyrrolidone (NMP), and dimethylsulfoxide (DMSO). In one embodiment, the organic solvent is ethanol.

There is herein disclosed an apparatus for making a composition of the present disclosure. The apparatus typically includes at least one reservoir for holding an aqueous solution comprising a nucleic acid and another one or more reservoirs for holding an organic lipid solution. The apparatus also typically includes a pump mechanism configured to pump the aqueous and the organic lipid solutions into a mixing region or mixing chamber. In some embodiments, the mixing region or mixing chamber comprises a cross coupling, or equivalent thereof, which allows the aqueous and organic fluid streams to combine as input into the cross connector and the resulting combined aqueous and organic solutions to exit out of the cross connector into a collection reservoir or equivalent thereof. In other embodiments, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof.

In certain embodiments, the concentration of nucleic acid in the one or more nucleic acid streams is about 0.1 to about 1.5 mg/mL and the concentration of lipids in the one or more lipid streams is about 10 to about 25 mg/mL. In other embodiments, the concentration of nucleic acid in the one or more nucleic acid streams is about 0.2 to about 0.9 mg/mL and the concentration of lipids in the one or more lipid streams is about 15 to about 20 mg/mL. In other embodiments, the concentration of nucleic acid in the one or more nucleic acid streams is from about 0.225, 0.3, 0.33, or 0.45 to about 0.675 mg/mL, and the concentration of lipids in the one or more lipid streams is about 16-18 mg/mL. In other embodiments, the concentration of nucleic acid in the one or more nucleic acid streams is about 0.225, 0.3, 0.33, 0.45, or 0.675 mg/mL and the concentration of lipids in the one or more lipid streams is about 16.7 mg/mL.

The lipid streams comprise a mixture of one or more lipids in an organic solvent. The one or more lipids may be a mixture of a cationic lipid, a neutral lipid, a helper lipid, and a stealth lipid, each of which may be present in about the same relative amounts as described elsewhere hereinabove for the final encapsulated nucleic acid nanoparticle. The organic solvent used in the lipid stream is one capable of solubilizing the lipids and that is also miscible with aqueous media. Suitable organic solvents include ethanol, propylene glycol, polyethylene glycol 300, polyethylene glycol 400, glycerin, dimethylacetamide (DMA), N-methyl-2-pyrrolidone (NMP), and dimethylsulfoxide (DMSO). In one aspect, the organic solvent comprises about 80% or more ethanol. In a particular aspect, the organic solvent comprises about 90% or more ethanol. In a specific aspect, the organic solvent is ethanol. In certain embodiments, the lipid stream comprises an optional buffer solution, such as a buffer solution of sodium citrate (e.g., 25 mM).

The nucleic acid stream comprises a mixture of a suitable nucleic acid in a first aqueous solution. The first aqueous solution may include no salts or at least one salt. For example, the first aqueous solution may include a suitable nucleic acid in deionized or distilled water without an added salt. In certain embodiments, the first aqueous solution is a first buffer solution that includes at least one salt such as, for example sodium chloride and/or sodium citrate. In the first aqueous solution, sodium chloride may be present in concentrations ranging from about 0 to about 300 mM. In certain embodiments, the concentration of sodium chloride is about 50, 66, 75, 100, or 150 mM. The first aqueous solution may include sodium citrate in a concentration of about 0 mM to about 100 mM. The first buffer solution preferably has a pH of about 4 to about 6.5, more preferably about 4.5-5.5. In some embodiments, the pH of the first buffer solution is about 5 and the sodium citrate concentration is about 25 mM. In other embodiments, the pH of the first buffer solution is about 6 and the concentration of sodium citrate is about 100 mM. In specific embodiments, the first buffer solution has a pH that is less than the pKa of the cationic lipid. For the embodiments of the disclosure that include no salt in the aqueous solution, the lipid stream includes the optional buffer solution. In the absence of a salt (e.g., sodium citrate) in either the nucleic acid stream or lipid stream, no encapsulation occurs.

Other possible buffers include, but are not limited to, sodium acetate/acetic acid, $Na_2HPO_4$/citric acid, potassium hydrogen phthalate/sodium hydroxide, disodium hydrogen phthalate/sodium dihydrogen orthophosphate, dipotassium hydrogen phthalate/potassium dihydrogen orthophosphate, potassium dihydrogen orthophosphate/sodium hydroxide.

In certain embodiments, the organic solvent comprises ethanol and the first outlet solution comprises about 20-25% ethanol, about 0.15-0.25 mg/mL nucleic acid, and about 3-4.5 mg/mL lipids. In other embodiments, the organic solvent comprises ethanol and the first outlet solution comprises about 20% ethanol, about 0.15-0.2 mg/mL nucleic acid, and about 3-3.5 mg/mL lipids. In yet other embodiments, the organic solvent comprises ethanol and the first outlet solution comprises about 20% ethanol, about 0.18 mg/mL nucleic acid, and about 3.3 mg/mL lipids. In other embodiments, the organic solvent comprises ethanol and the first outlet solution comprises about 25% ethanol, about 0.2-0.25 mg/mL nucleic acid, and about 4-4.5 mg/mL lipids. In still other embodiments, the organic solvent comprises ethanol and the first outlet solution comprises about 25% ethanol, about 0.23 mg/mL nucleic acid, and about 4.2 mg/mL lipids.

In some embodiments of the present disclosure, the concentrations of the nucleic acid and the lipids may both be lowered or raised together. For example, although it is generally desirable to keep concentrations as high as possible for a more efficient process, it is possible to lower the concentrations of the nucleic acid to about 0.045 mg/mL and the lipids to about 1.67 mg/mL. At still lower concentrations, however, particle aggregation tends to increase.

In certain embodiments, the concentration of nucleic acid in the one or more nucleic acid streams is about 0.1 to about 1.5 mg/mL and the concentration of lipids in the one or more lipid streams is about 10 to about 25 mg/mL. In other embodiments, the concentration of nucleic acid in the one or more nucleic acid streams is about 0.2 to about 0.9 mg/mL and the concentration of lipids in the one or more lipid streams is about 15 to about 20 mg/mL. In other embodiments, the concentration of nucleic acid in the one or more nucleic acid streams is from about 0.225, 0.3, 0.33, or 0.45 to about 0.675 mg/mL, and the concentration of lipids in the one or more lipid streams is about 16-18 mg/mL. In other embodiments, the concentration of nucleic acid in the one or more nucleic acid streams is about 0.225, 0.3, 0.33, 0.45, or 0.675 mg/mL and the concentration of lipids in the one or more lipid streams is about 16.7 mg/mL. Generally, higher nucleic acid concentrations require a correspondingly increased level of dilution from the dilution stream 50 to maintain the nucleic acid concentration in the first outlet stream 60 in a preferred range (e.g., about 0.15-0.25 mg/mL).

In particular embodiments, the mass ratio of lipids:nucleic acid is about 15-20:1 or about 17-19:1 and the concentration of the organic solvent in the outlet solution is about 20-25%. In other particular embodiments, the mass ratio of lipids: nucleic acid is about 18.5:1 and the concentration of the organic solvent in the outlet solution is about 25%.

In particular embodiments, the mass ratio of lipids:nucleic acid is about 17-19:1. In other particular embodiments, the mass ratio of lipids:nucleic acid is about 18.5:1.

In particular embodiments, the mass ratio of lipids:nucleic acid is about 15-20:1 or about 17-19:1 and the concentration of the organic solvent in the outlet solution is about 20-25%. In other particular embodiments, the mass ratio of lipids: nucleic acid is about 18.5:1 and the concentration of the organic solvent in the outlet solution is about 20% or 25%.

In particular embodiments, the mass ratio of lipids:nucleic acid is about 17-19:1. In other particular embodiments, the mass ratio of lipids:nucleic acid is about 18.5:1. In particular embodiments, the mass ratio of lipids:nucleic acid is about 15-20:1 or about 17-19:1 and the concentration of the organic solvent in the outlet solution is about 20-25%. In other particular embodiments, the mass ratio of lipids: nucleic acid is about 18.5:1 and the concentration of the organic solvent in the outlet solution is about 20%.

In particular embodiments, the mass ratio of lipids:nucleic acid is about 17-19:1. In other particular embodiments, the mass ratio of lipids:nucleic acid is about 18.5:1.

In certain aspects, the encapsulation rate is >60%. In certain aspects, the encapsulation rate is >65%. In certain aspects, the encapsulation rate is >70%. In some embodiments of the present disclosure, 75% or more of the nucleic acid is encapsulated. In other embodiments, 80% or 85% of the nucleic acid is encapsulated. In still other embodiments, 90% or more of the nucleic acid is encapsulated. In other embodiments about 91%, about 92%, about 93%, about 94%, about 95%, about 96%, about 97%, about 98%, about 99%, or about 100% of the nucleic acid is encapsulated.

In certain aspects, following formation of the encapsulated nucleic acid nanoparticles as described herein, the first outlet solution may be incubated for about 60 minutes at room temperature. After incubation, the solution may be mixed with a second dilution solvent to dilute the first outlet solution by about 2-fold to provide a second outlet solution. The second dilution solvent may be a third buffer solution or water. The dilution step may be carried out by mixing the incubated first outlet solution with the second dilution solvent (water), for example, in a T connector. The incubated first outlet solution and the second dilution solvent may be supplied to the T connector at any suitable flow rate or velocity, such as, for example, about 0.5 to 1 meter/second. Following the dilution step, the concentration of organic solvent in the second outlet solution is reduced by one-half relative to the first outlet solution. Thus, in some embodiments, the concentration of organic solvent (e.g., ethanol) in the second outlet solution is less than 16.5%. In other embodiments, the concentration of organic solvent (e.g., ethanol) in the second outlet solution is about 10-15%, about 10-12.5%, about 12.5%, or about 10%. The second outlet solution may be concentrated by tangential flow filtration and subjected to a 15× diafiltration with phosphate buffered saline (PBS) to remove the starting buffer and ethanol, which are replaced with PBS. After tangential flow filtration, the pool of concentrated encapsulated nucleic acid nanoparticles in PBS may be collected and sterile filtered. Encapsulated nucleic acid nanoparticles present in formulations produced by the foregoing additional process steps may be storage stable at 4° C. for greater than 6 months.

According to each of the embodiments disclosed herein, are further embodiments where the nucleic acid is a polyribonucleotide such as an mRNA. For example, according to the embodiments described herein are further embodiments where the nucleic stream is an mRNA stream comprising a mixture of one or more mRNA molecules in a buffer solution and having the linear velocities disclosed herein.

VI. Immunization of Animals

Host animals used for immunization encompass any species which can generate a humoral (antibody)-mediated immune response. Non-limiting examples of host animals, such as non-human animals, used for immunization include mouse, rat, rabbit, goat, sheep, camelid, horse, chicken, dog, cat, pig, donkey, cow, monkey and shark.

In a specific aspect of the present disclosure for generating human antibodies against a target protein, transgenic or transchromosomic mice carrying parts of the human immune system rather than the mouse immune system may be used as host animals immunized with the mRNA-LNP complexes described herein. Non-limiting examples of these transgenic and/or transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies can be raised by the mRNA-immunization methods provided herein using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used as host animals for the mRNA-immunization methods provided herein. For example, an alternative transgenic system referred to as the Xenomouse (Abgenix, Inc.) can be used. Such mice are described in, e.g., U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used as host animals for the mRNA-immunization methods provided herein. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used as host animals for the mRNA-immunization methods provided herein.

Following encapsulated mRNA-mediated immunization, antibody secreting cells (e.g., such as lymphocytes, bone marrow cells, plasma cells, or splenocytes) from host animals may be harvested and screened for antibodies generated against the protein target which contain the desired properties. This may be done through the use of hybridoma-based technology, direct screening of antibody producing B cells followed by cloning and recombinant antibody production, or the generation of a recombinant antibody library from B cells followed by expression and screening in a heterologous expression system such as phage or yeast display.

In a particular aspects, antibody secreting cells (e.g., such as lymphocytes, bone marrow cells, plasma cells, or splenocytes) from host animals are fused with fusion partner cells (e.g., immortal B cell cancer cells, for example, an immortalized myeloma cells), such as F0 cells (ATCC®, CRL-1646) and SP2/0 myeloma cells (ATCC®, CRL-1581). Cell fusion can be carried out by various methods, such as, electrofusion or chemical protocols, for example, using polyethylene glycol.

In the case of immunizations wherein mice are the host animal, hybridoma-based antibody generation followed by FACS or ELISA-based screening offers an effective antibody expression and screening platform. Circulating levels of target-specific antibodies (i.e. sera titers) can be monitored over the course of a hybridoma-based immunization campaign to evaluate the effectiveness of the humoral response. Given the high degree of target specificity that is associated with mRNA-based immunization, sera titers for integral or membrane proteins can be efficiently monitored by FACS using cells which overexpress the target protein. Titers for soluble proteins can also be assayed by ELISA. Depending upon sera titers, dosing can be adjusted to achieve levels that are deemed suitable for initiation of B cell isolation and myeloma fusion. Route of mRNA administration (e.g. intravenous, subcutaneous, intramuscular, etc.) can also be altered to vary the degree and perhaps diversity of the immune response. Intravenous administration of encapsulated mRNA has been found to be a particularly efficacious route for generating rapid target-specific titers.

One generalizable immunization schedule is outlined below, as an example:

Day 0: draw blood to establish baseline titers in immunologically naive mice

Day 1 ($1^{st}$ immunization): Inject 4 mice subcutaneously and 4 mice intravenously with 5-100 μg, e.g., 25-50 μg, of encapsulated mRNA.

Day 10: Withdraw blood to monitor sera titers.

Day 21 ($2^{nd}$ immunization): Inject 4 mice subcutaneously and 4 mice intravenously with 5-100 μg, e.g., 25-50 μg, of encapsulated mRNA.

Day 31: Withdraw blood to monitor sera titers.

Day 42 (Final immunization): Inject mice intravenously with 5-100 μg, e.g., 25-50 μg, of encapsulated mRNA.

Day 45: Harvest spleens for isolation of splenocytes and hybridoma fusion.

In certain aspects, a generalizable immunization schedule may include combinations of immunization with encapsulated mRNA and other conventional immunization methods, such as recombinant protein immunization or whole cell/whole cell extract immunization. For example, the $1^{st}$ immunization comprises immunization with encapsulated mRNA followed by a $2^{nd}$ immunization by conventional immunization methods, such as recombinant protein immunization or whole cell/whole cell extract immunization. In specific aspects, the number of days in between immunization, blood withdrawal to monitor sera titers, and subsequence rounds of immunizations may vary by 1, 2, 3, 4, 5, 6, or 7 days.

VIII. Antibody Production

Generation of Monoclonal Antibodies

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

Animal systems for preparing hybridomas include the murine, rat and rabbit systems. Hybridoma production in the mouse is a well established procedure. Immunization protocols are described herein and techniques for isolation of immunized splenocytes for fusion are known in the art. Fusion partners (e.g., murine myeloma cells) and fusion procedures are also known and have been described.

Chimeric or humanized antibodies of the present disclosure can be prepared based on the sequence of a non-human, e.g., murine, monoclonal antibody prepared as described herein. DNA encoding the heavy and light chain immunoglobulins can be obtained from the hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison, 1985, Science 229: 1202; Oi et al., 1986, BioTechniques 4:214; Gillies et al., 1989, J. Immunol.

In a certain aspects, the antibodies of the present disclosure are human monoclonal antibodies. Such human monoclonal antibodies can be generated using transgenic or transchromosomic mice carrying parts of the human immune system rather than the mouse system. These transgenic and/or transchromosomic mice include mice referred to herein as HuMAb mice and KM mice, respectively, and are collectively referred to herein as "human Ig mice."

Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

Antibodies or antigen-binding fragments produced using techniques such as those described herein can be isolated using standard, well known techniques. For example, antibodies or antigen-binding fragments can be suitably separated from, e.g., culture medium, ascites fluid, serum, cell lysate, synthesis reaction material or the like by conventional immunoglobulin purification procedures such as, for example, protein A-Sepharose, hydroxylapatite chromatography, gel electrophoresis, dialysis, or affinity chromatography.

EXAMPLES

The following examples are provided by way of illustration, and are not intended to be limiting of the present invention, unless specified.

Example 1

Encapsulated mRNA Production Workflow

Step One: Design of cDNA and Cloning into In-Vitro Transcription Vector

Design of the cDNA Construct

Native cDNA sequences may be used for the purposes of subcloning if it does not contain any consensus sites for the restriction enzymes used in the subcloning strategy or in the linearization of the final construct prior to transcription. In this particular example, the restriction enzymes used for subcloning are BamHI and RsrII, the restriction enzyme used for linearization is BspQI. However, any suitable restriction enzyme and corresponding restriction site can be used. For example, certain restriction sites that are not present in a particular cDNA encoding a target protein of interest can be selected for subcloning strategy and linearization.

The native cDNA sequence can also be codon optimized for expression in a non-human animal, such as mouse or rabbit, using conventional methods, for example, using the GeneOptimizer® software (ThermoFisher Scientific, Inc.). The process of codon optimization involves one or more of the following: (i) elimination of cryptic splice sites and RNA destabilizing sequence elements for increased RNA stability; (ii) addition of RNA stabilizing sequence elements; (iii) codon optimization and G/C content adaptation for a particular expression system; (iv) intron removal; and (v) avoidance of stable RNA secondary structures.

In specific aspects using the GeneOptimizer® software, codon optimization settings were adjusted to protect the 5'/3' restriction and exclude them from the rest of the molecule. BspQ1 consensus sequences (both forward [GCTCTTC] and reverse [GAAGAGC], as BspQ1 is not a palindromic sequence restriction enzyme) should also be excluded.

TABLE 8

Materials and Reagents for cloning of cDNA into transcription vector

| Reagent | Vendor | Catalog # |
|---|---|---|
| BspQ1 | New England Biolabs | R0712S |
| BamH1 | New England Biolabs | R0136S |
| RsrII | New England Biolabs | R0501S |
| Stbl3 competent cells | Life technologies | C7373-03 |
| Quick ligase | NEB | M220S |

Description of the Vector cDNA encoding a target protein (e.g., see Tables 1-7) was cloned into a vector designed to drive RNA polymerase-mediated transcription from a T7 RNA polymerase promoter. Immediately downstream of the T7 promoter is a sequence which encodes the 5' untranslated region (UTR) of the tobacco etch virus (TEV). This UTR has been shown to improve translational efficiency in eukaryotic cells. Downstream of the TEV UTR, the cDNA of the target protein is placed. A Kozak consensus sequence (ccgccacc) was inserted upstream of the initiator methionine/start codon to enhance translation. Two stop codons were placed at the end of the cDNA followed by a RsrII restriction site. Two tandem human beta-globin 3' UTRs follow the cDNA sequence. This element has been shown to enhance mRNA stability in cells. A C-terminal element of the transcriptionally-relevant components of the vector is a polyA tail. In specific embodiments, a polyA tail of an mRNA encoding a target protein or a fragment thereof is approximately 50 bps to 120 bps or 60 bps to 120 bps. In particular embodiments, a polyA tail of an mRNA encoding a target protein or a fragment thereof is approximately 60 bps or 120 bps. In certain embodiments a polyA tail of an mRNA encoding a target protein or a fragment thereof is approximately 70 bps, 80 bps, 90 bps, 100 bps, or 110 bps.

Cloning of cDNA into the In Vitro Transcription Vector

Digestion of the cDNA construct along with the vector with the restriction enzymes BamHI/RsrII generated compatible fragments that were purified by agarose gel electrophoresis, and the purified cDNA subsequently were ligated to the digested vector to yield the desired transcription vector construct.

The ligation mixture was transformed into stbl3 competent bacterial cells and plated onto ampicillin plates. The plates were incubated overnight at 37° C.

Prior to sequencing, colonies were triaged by digesting with the subcloning restriction enzymes to verify the appropriately sized insert and backbone. Colonies were also digested in parallel with RsrII and SapI (an isoschizimer of BspQ1 that cuts efficiently at 37° C.) to establish the integrity of the polyA tail. Plasmids from a sequence-verified clone were expanded and used for mRNA generation.

Step Two: Transcript Linearization, In Vitro Transcription and Capping

Circular plasmid DNA was prepared according to conventional methods. Purified plasmid DNA was digested with BspQI restriction endonuclease. Plasmid DNA was combined with the appropriate reaction buffer (Buffer 4, New England Biolabs, 10× stock) and BspQI enzyme (1,250 U per mg of DNA). The reaction was incubated at 50° C. for 2 hours and then placed on ice or at 4° C. A small sample of the reaction was run on a standard agarose electrophoresis gel to confirm complete linearization of the circular plasmid DNA. The linearized DNA template was purified by ethanol precipitation. DNA pellet from the ethanol precipitation step was dissolved using nuclease-free water to a concentration of >0.5 mg/ml.

In Vitro Transcription and Capping of Modified Synthetic mRNA

The modified synthetic mRNA of this EXAMPLE was generated by in vitro transcription (IVT), purified by lithium chloride (LiCl) purification, and then capped using a commercially available kit from New England Biolabs® (Beverly, Mass. USA). Materials and reagents are shown in TABLE 9.

TABLE 9

Materials and Reagents for In vitro Transcription Capping

| Reagent | Vendor | Catalog # |
|---|---|---|
| Nuclease-free water | | |
| Tris-HCl pH 8.0 | Life Technologies/ThermoFisher | AM9855G |
| $MgCl_2$ | Life Technologies/ThermoFisher | AM9530G |
| ATP, CTP, GTP, UTP | New England Biolabs | N0450L |
| Pseudouridine (Ψ) | TriLink Biotech | N-1019 |
| DTT | Sigma-Aldrich | 43816 |
| Spermidine | Sigma-Aldrich | 85558 |
| Linearized plasmid DNA | | |
| Pyrophosphatase | New England Biolabs | M2403L |
| RNase inhibitor | New England Biolabs | M0307L |
| T7 RNA polymerase | New England Biolabs | M0251L |
| DNase | New England Biolabs | M0303 |
| LiCl | Life Technologies/ThermoFisher | AM9480 |
| Vaccinia capping system | New England Biolabs | M2080S |
| mRNA cap 2'-O-methyltransferase | New England Biolabs | M0366S |

Transcription reactions are assembled, for example, as listed in TABLE 10, with care towards the use of RNase-free tubes, tips and practices.

TABLE 10

In vitro Transcription Reaction

| Reagent | Concentration | Notes |
|---|---|---|
| Nuclease-free water | Remaining volume | |
| Tris-HCl pH 8.0 (mM) | 40 | |
| $MgCl_2$ (mM) | 20 | |
| ATP, CTP, GTP, UTP (mM) | 4 | |
| Pseudouridine (mM) | 4 | To make 100% pseudouridine mRNA, do not include UTP in reaction. To make 100% unmodified mRNA, do not include pseudouridine in reaction |
| DTT (mM) | 10 | |
| Spermidine (mM) | 2 | Dilute 1M stock 1:10 in water |
| Linearized plasmid DNA (μg/μL) | 0.05 | |

TABLE 10-continued

In vitro Transcription Reaction

| Reagent | Concentration | Notes |
|---|---|---|
| Pyrophosphatase (U/μL) | 0.004 | |
| RNase inhibitor (U/μL) | 1 | |
| T7 RNA polymerase (U/μl) | 5 | |

The procedure in this EXAMPLE for making modified synthetic mRNA was carried out as follows:

1. The materials above were incubated for 2 hours at 30° C., while monitoring the temperature. The DNA template was digested by adding 0.04 U/μL DNase, and this reaction mixture was incubated for 30 minutes at 37° C.
2. LiCl was added to a final concentration of 2.81M, and the reaction mixture was mixed well and incubated for over an hour at −20° C. The mixture then was centrifuged at 4° C. for 15 minutes at a maximum speed of approximately 20,000×g (max speed). The supernatant was removed and the pellet was washed with 1 mL 70% ethanol. The preparation was centrifuged as described immediately above for 10 minutes. Then the supernatant was removed, and the remaining pellet was centrifuged again as described above for less than one minute.
3. The remaining ethanol was removed, and the pellet was resuspended in nuclease-free water. The concentration was measured and adjusted to approximately 1 μg/μL.
4. To the preparation, 10% volume of 3M sodium acetate pH 5.5 was added, and the preparation was mixed well. Then, 1 volume of room temperature isopropanol was added to the preparation, and mixed well. The preparation was incubated overnight at −20° C. Subsequently, the preparation was centrifuged at 4° C. for 15 minutes at a maximum speed of approximately 20,000×g (max speed), the supernatant was removed, and the remaining pellet was washed with 1 mL 70% ethanol. Again, the preparation was centrifuged as described immediately above for 10 minutes, followed by removal of the supernatant, and the centrifuge step was carried out again as described above for less than one minute.
5. The remaining ethanol was removed, and the pellet was resuspended in nuclease-free water. The concentration of the preparation was measured and adjusted to approximately 4 μg/μL.

The modified synthetic mRNA can then be stored at −80° C. until capping, and the concentration measured again upon thawing.

For capping, the procedure used was that of New England BioLabs. The synthetic mRNA and water mixture was heat denatured at 65° C. for 10 minutes, and then transferred to cold block to quench for 5 minutes. The stock solution of S-adenosyl methionine (SAM) (32 mM) was diluted 1:8 in water to 4 mM immediately before use, then the remaining reaction components were added in the order specified in TABLE 11.

TABLE 11

| Capping Reaction | | |
|---|---|---|
| Reagent | Stock concentration | Final concentration |
| mRNA (μg/μl) | | 0.5 |
| Water | | Remaining volume |
| 10× capping buffer (×) | 10× | 1× |
| GTP (mM) | 10 | 0.5 |
| SAM (mM) | 4 | 0.2 |
| RNase Inhibitor (U/μL) | 40 | 1 |
| Vaccinia capping enzyme (U/μL) | 10 | 0.5 |
| mRNA Cap 2'-O-Methyltransferase (U/μL) | 50 | 2.5 |

Then, the mixture was incubated for one hour at 37° C. The sample was purified by LiCl precipitation as described above, and then stored at −80° C.

Step Three: Determine mRNA Quality and Functionality

The synthetic mRNA were analyzed for quality and integrity using an Agilent 2100 Bioanalyzer after the initial in vitro transcription reaction and/or after the capping reaction. The Agilent 2100 BioAnalyzer is a nanofluidics device that preforms size fractionation and quantification of small samples of DNA, RNA, or Protein. The analysis was performed using an Agilent RNA 6000 Nano Kit (Cat. #5067-1511).

All of the kit reagents must be equilibrated to room temperature for 30 minutes prior to use. The synthetic mRNA sample and ladder from the kit were stored on ice.

Prepare Gel, Gel/Dye Mix, and Samples

A gel matrix (550 μL) was pipetted into a spin filter, and centrifuged at 1,500 g for 10 minutes at room temperature, then stored at 4° C. (for use within 1 month). Dye stock (1 μl) was added to a 65 μl aliquot of filtered gel matrix. The dye and gel matrix mix was vortexed and then centrifuged at 13,000 g for 10 minutes at room temperature (for use within 1 day). The mRNA samples and ladder and kit standard were heat denatured at 70° C. for 3-5 minutes to break apart any higher order structures, then quenched on ice prior to analysis.

Decontaminate Bioanalyzer Electrodes

The Bioanalyzer electrodes were decontaminated with 350 μl of RNaseZap electrode cleaner and nuclease-free water.

Load Gel/Dye Mix onto Chip

A new chip was placed on the priming station of the Bioanalyzer (platform at position C, clip at top position), and 9 μl of gel/dye mixture was added into a well.

Load Samples onto Chip

Figure 4:
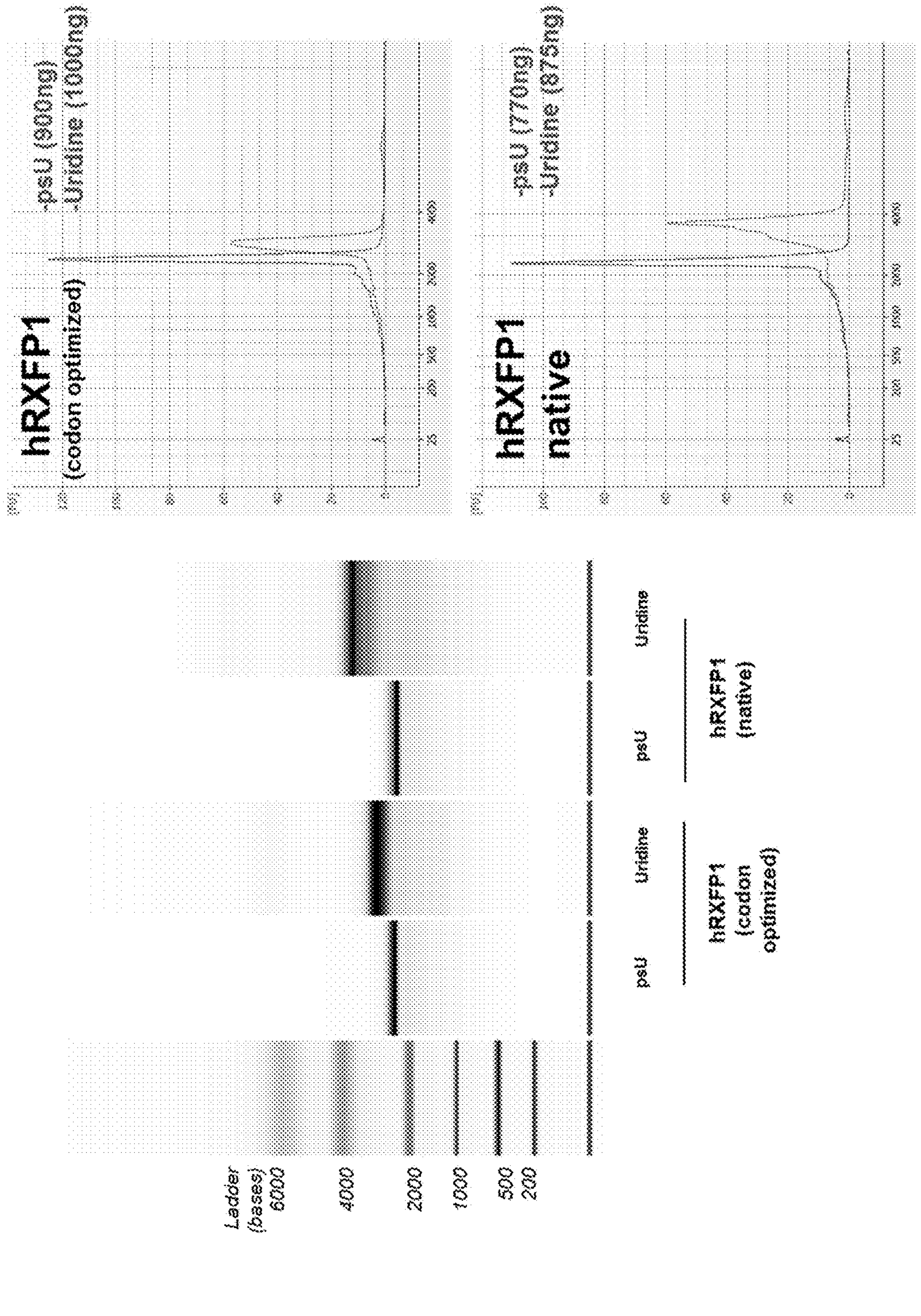
FIG. 4 shows bioanalyzer traces for purified human RXFP1 mRNA. Total amount of mRNA loaded per well is indicated. Samples synthesized using pseudouridine exhibit molecular weights that are closer to the predicted size (2687 bases) than transcripts synthesized with uridine.

A volume of 5 μl of marker was added to ladder well and sample wells, and a volume of 1 μl of mRNA sample (<1 μg) was added to sample wells. An IKA Vortexer was used to vortex for 1 minute at 2400 rpm. Then the samples were run on the Agilent 2100 Bioanalyzer using the mRNA assay method. See FIG. 4 for a sample bioanalyzer trace of mRNA prepared for human RXFP1 (both codon and non-codon optimized) synthesized using adenine, guanine, cytidine, and either uridine or pseudouridine.

Figure 5:
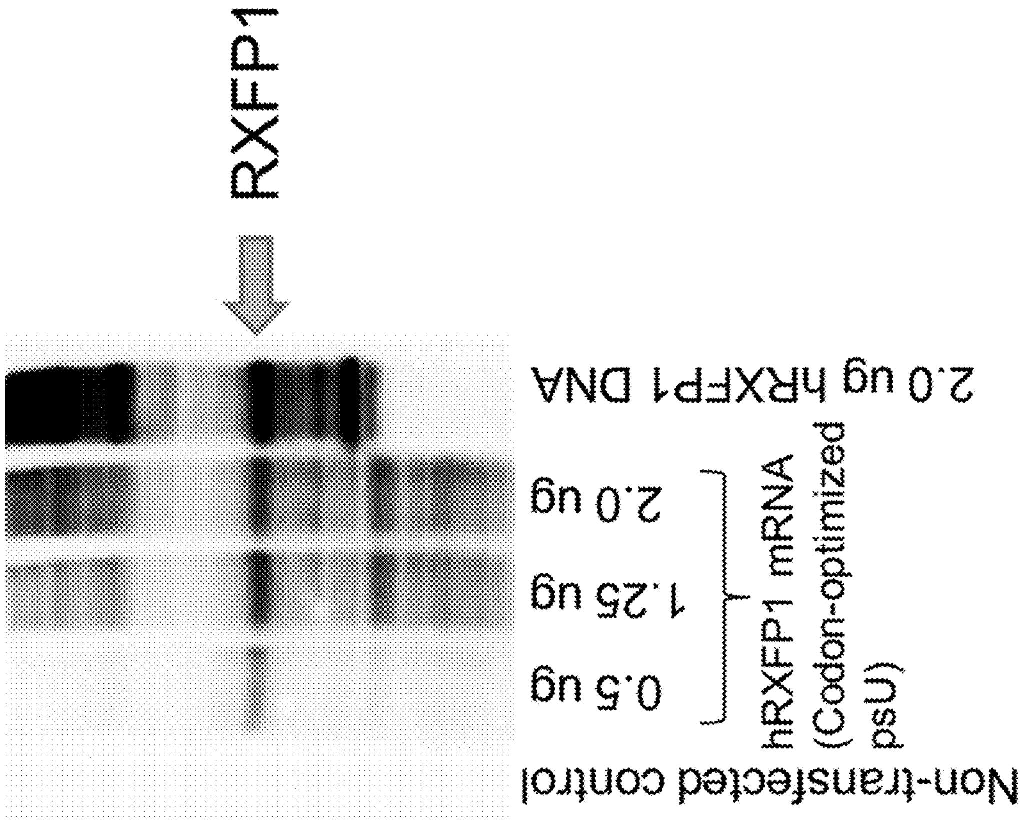
FIG. 5 depicts Western blotting of plasma membrane fractions prepared from HEK293 cells transiently transfected with increasing concentrations of human RXFP1 mRNA. As control comparators, non-transfected cells and cells transfected with a DNA plasmid encoding human RXFP1 were also loaded. Amount of nucleic acid used per transfected 6 well is indicated.

Transfection of mRNA into Cultured Mammalian Cells and Western Blot to Confirm Expression of Encoded Protein Translatability was assessed by in vitro transfection of the mRNA into cultured mammalian cells using Lipofectamine® 2000 reagent from Thermo Fisher Scientific. The transfected cells were then lysed 24 to 48 hours later, and the proteins in the lysates were resolved using polyacrylamide gel electrophoresis followed by immunoblot with antibodies specific to the protein encoded by the mRNA (see FIG. 5 for a sample Western blot illustrating confirmation of human RXFP1 expression from mRNA).

TABLE 12

| Materials for Packaging of Modified Synthetic mRNA | | |
|---|---|---|
| Item | Vendor | Catalog # |
| Cationic lipid | Novartis | Selected from Cationic Lipid A, Cationic Lipid B or Cationic Lipid C |
| 1,2-distearoyl-sn-glycero-3-phosphocholine (DSPC) | Corden | LP-R4-076 |
| Cholesterol | Sigma | C8667 |
| Lipidated Polyethylene Glycol (PEG lipid) | Novartis | S024 |
| Ethanol | Sigma | 459844 |
| Nuclease-free water | Life Technologies | 10977 |
| 100 mM citrate buffer, pH 6.0 | Teknova | Q2446 |
| Amicon Ultra-15 Centrifugal Filter unit, 30K MWCO | Millipore | UFC903024 |
| RNaseZap | Life Technologies | AM9780 |
| Syringe Pump | KD Scientific | KDS220 |
| 10× PBS | Lonza | S1226 |
| SnakeSkin dialysis tubing 10,000 MWCO | Thermo Scientific | 68100 |
| Minimate TFF system, 110 V | PALL Corporation | OAPMP110 |
| Minimate tangential flow filtration capsule, Omega 500K membrane | PALL Corporation | OA500C12 |
| Quant-iT Ribogreen RNA Assay Kit | Life Technologies | R11490 |
| TE buffer | Promega | V6231 |
| Triton X-100 | Sigma | T8787 |
| Zetasizer Nano ZS | Malvern | ZEN3600 |

Chemical structure Lipid A
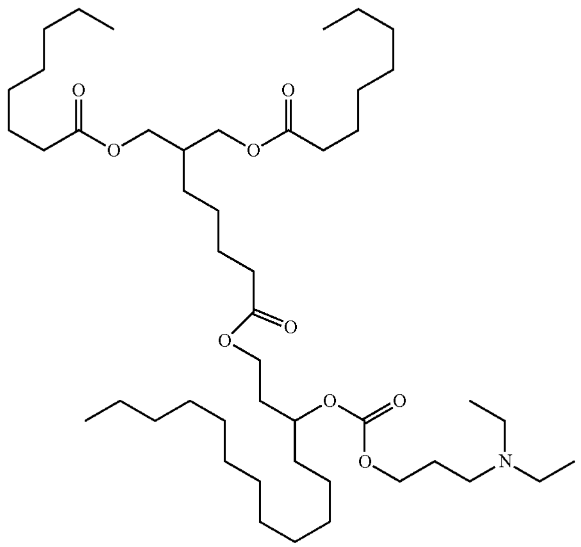
Molecular Formula: $C_{47}H_{89}NO_9$
Monoisotopic Mass: 811.6537
Chemical structure Lipid B
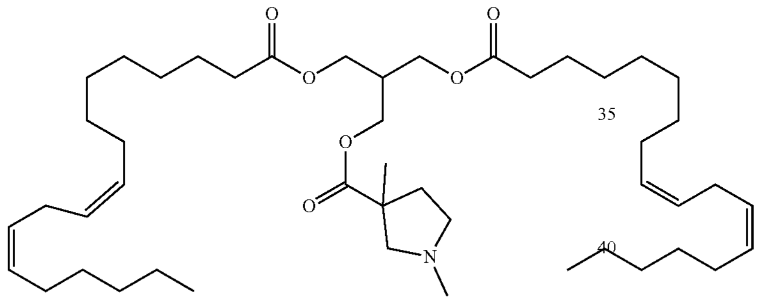
Molecular Formula: $C_{47}H_{81}NO_6$
Monoisotopic Mass: 755.6064
Chemical structure Lipid C
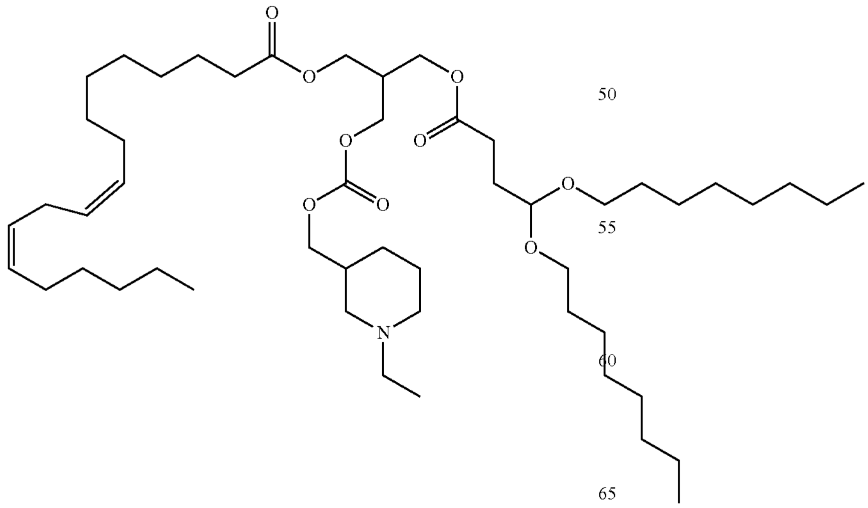

1. Modified synthetic mRNAs encoding target protein (e.g., see Tables 1-7) were packaged into lipid nanoparticles at a cationic lipid amine group to mRNA phosphate group (N:P) molar ratio=4:1, dialyzed, and concentrated. As an example, amounts are shown for the protocol resulting in ~2 mg packaged modified synthetic mRNA in a concentration of >0.4 mg/mL mRNA.
2. Using RNase-free reagents, tubes, tips, and practices, the lipid nanoparticle mixture reagents were weighed and mixed in a vial as described in TABLE 13.

TABLE 13

| Lipid Nanoparticle Mixture | |
|---|---|
| Reagent | Final concentration (mM) |
| Cationic lipid | 6 |
| DSPC | 1.5 |
| Cholesterol | 7.2 |
| PEG lipid | 0.3 |

3. Ethanol was added to the lipids, representing a 1.1× ratio of the volume needed, for ease of processing. The mixture was briefly sonicated and gently agitated for 5 minutes at 37° C. Subsequently, the mixture was incubated without agitation at 37° C. until ready for use.
4. The modified synthetic mRNA was exchanged from water into pH 6.0 buffer by loading mRNA solution onto Amicon Ultra-15 centrifugal device, and centrifuging for 15 minutes at 4,000 rpm at 4° C. The concentrated mRNA was resuspended in pH 6.0 citrate buffer and the mRNA concentration was measured.
5. The final modified synthetic mRNA concentration of 0.5 mg/mL in pH 6.0 citrate buffer was prepared in a rinsed scintillation vial (4 mg mRNA in 8 mL), and the final concentration of the mRNA solution was measured. The mRNA dilution was incubated at 37° C. until ready for use.
6. Three 10 ml syringes were prepared, with 8 mL of each: (a) lipid mixture; (b) mRNA solution; (c) citrate buffer. Syringes (a) and (b) were attached to the Luer fittings of the T-shaped junction. Briefly, a P727 T-mixer with 0.5 mm inner diameter attached to P652 adaptors (IDEX, Oak Harbor Wash. USA). Syringes (a) and (b) were attached to P658 Luer fittings (IDEX). The syringes (a) and (b) were connected to the T-mixer by PTFE 0.8 mm inner diameter tubing (#3200068, Dolomite, Royston, UK) with P938x nuts and ferrules (IDEX). Syringe (c) was attached to a Luer fitting connected to a final single tubing by P938x a nut and ferrule. The ends of the tubing were secured together over pre-rinsed beaker with stir bar and gently stirred.
7. The syringe pump settings were set to appropriate syringe manufacturer and size, and a volume (8 mL) and flow rate of 1.0 mL/min were entered. The pump was started, and the resulting material collected into RNase-free 50 mL plastic beaker with a stir bar. The suspension of lipid nanoparticles containing mRNA was transferred to dialysis tubing, 2-3 mL per bag and dialyzed into phosphate-buffered saline (PBS) at 4° C. overnight.
8. The divided material was pooled into one 15 mL conical tube. The lipid nanoparticle (LNP) suspension was concentrated using tangential flow filtration (TFF). Using fresh tubing to connect fresh 500K molecular weight cut-off capsule to the Minimate system, the TFF system was prepared by rinsing with 500 mL RNA-free water at a flow rate of 150 rpm.
9. The lipid nanoparticle/modified synthetic mRNA suspension was loaded into TFF unit reservoir and concentrated at a flow rate of 75 mL/min to 2-3 ml final volume.
10. The percent encapsulation of modified synthetic mRNA was determined using Quant-iT Ribogreen RNA Assay kit from Life Technologies (Grand Island N.Y. USA). The lipid nanoparticle/modified synthetic mRNA suspension was assayed by fluorescence measurement in buffer (mRNA outside the particle) and in buffer plus detergent (total mRNA). A 1000 ng/mL stock from the provided ribosomal RNA was prepared and used to generate a standard curve for the Ribogreen assay. For the assay, samples are prepared in TE buffer or TE plus Triton and the fluorescent reagent is added to each. The difference calculated is the mRNA inside the particle.

TABLE 14

| Standard Curve (Preparation for Duplicate Samples) | | |
|---|---|---|
| RNA concentration (ng/mL) | Volume 1000 ng/ml stock (μL) | Volume buffer (μL) |
| 0 | 0 | 250 |
| 20 | 5 | 245 |
| 100 | 25 | 225 |
| 500 | 125 | 125 |
| 1000 | 250 | 0 |

11. Samples were prepared in TE buffer and TE buffer+0.75% Triton X-100 with appropriate dilution so that reading is in the standard curve (400-600 fold). 100 μL standard/sample were added per well in a 96-well plate. The Ribogreen reagent was diluted 1:200 in TE buffer and 100 μL was added to each well.
12. The sample fluorescence was measured using a fluorescence microplate reader, excitation at 480 nm, emission at 520 nm. The fluorescence value of the reagent blank was subtracted from the fluorescence value for each RNA sample to generate a standard curve of fluorescence versus RNA concentration. The fluorescence value of the reagent blank was subtracted from that of each of the samples and the RNA concentration of the sample from the standard curve was determined. The percent encapsulation of the sample was determined by dividing the difference in concentrations between sample plus Triton and just sample by the sample plus Triton concentration. A 6-fold dilution of the lipid nanoparticle/modified synthetic suspension was made, and the diameter and polydispersity index determined using a Zetasizer Nano ZS instrument (Malvern Instruments, Ltd, Worcestershire, UK).

TABLE 15

| Example of encapsulation properties for RXFP1 formulation. | | | | | | | |
|---|---|---|---|---|---|---|---|
| Sample | Diameter Average (nm) | Poly dispersity Index | Encapsulation (%) | RNA concentration (ug/mL) | Total volume (mL) | Total amount (mg) | Yield (%) |
| RXFP1 | 112.6 | 0.053 | 93.5 | 1362.07 | 5.5 | 7.5 | 59.9 |

Example 2—Immunization Strategy for RXFP1

An overview of immunization strategies for a GPCR target protein, such as human RXFP1, is shown in Table 16.

TABLE 16

| Priming Immunization | Boosting Immunization | Final Boost |
|---|---|---|
| mRNA | mRNA | mRNA |
| mRNA | mRNA | Virus-like Particles |
| mRNA | Overexpressing Cells | mRNA |
| mRNA | Virus-like Particles | Virus-like Particles |
| Virus-like Particles | mRNA | Virus-like Particles |
| Overexpressing Cells | mRNA | |
| mRNA | Overexpressing Cells | |

Female BALB/c mice were immunized, via subcutaneous (s.c.) or intravenous (i.v.) route, with either 100 μg packaged human RXFP1 mRNA (e.g., see Table 1), $10^6$ cells/ml of Ba/F3 cells overexpressing hRXFP1, or 50 μg virus-like particles (VLPs) overexpressing human RXFP1 derived from either 300.19 or HEK293 cells. Titers were checked 10 days after the priming immunization (as seen in FIG. 1A). Boosting immunizations were delivered 21 days after the previous immunization.

A total of 207 hybridomas producing RXFP1-specific antibodies were obtained and further screened to identify 10 anti-RXFP1 monoclonal antibodies with high affinities that were in the pM and nM range.

Figure 1C:
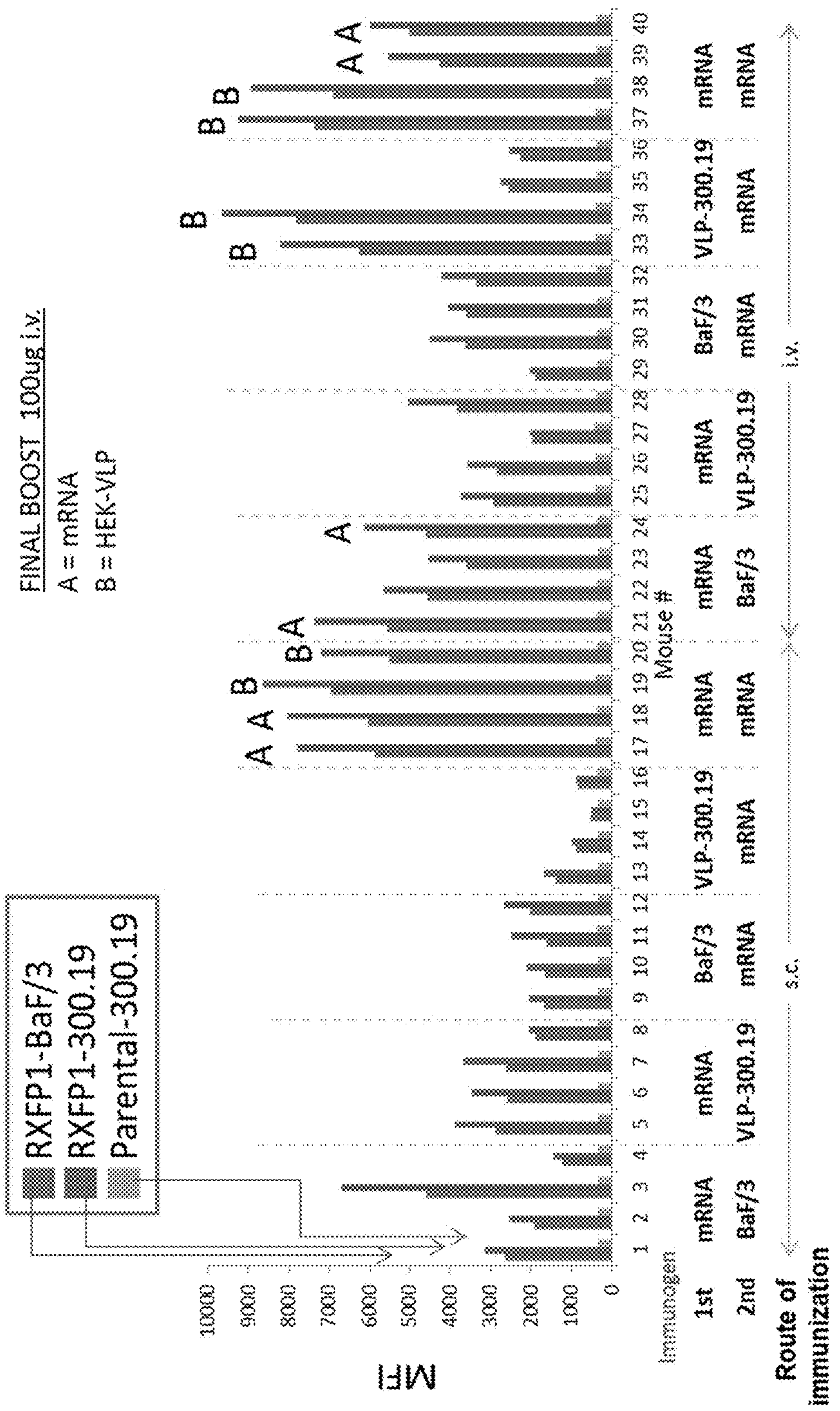

FIG. 1B shows that at 10 days post-immunization, immunization with virus-like particles or cells overexpressing RXFP1 (exemplary target protein immunogens) failed to elicit any significant antibody titer. Immunization with mRNA-LNPs, by contrast, produced titers that were between 2- and 12-fold above background. This data suggest that mRNA-LNP immunization confers a more robust immune response (e.g., higher antibody titer in sera) to the target protein immunogen than conventional methods, such as with virus-like particles or with cells overexpressing the target gene immunogen.

FIG. 10 shows antibody titers of animals (FIG. 1B) following the boosting immunization step (e.g., $2^{nd}$ administration of immunogen). Mice immunized (s.c.) with mRNA for both the $1^{st}$ and $2^{nd}$ immunizations exhibited higher antibody titers than mice immunized (s.c.) with mRNA for only one of the two immunizations (priming immunization and boosting immunization) and (s.c.) with VLPs or with cells overexpressing RXFP1 for one of the other immunizations. For immunization via i.v. administration, the difference in antibody titer for an immunization strategy with mRNA for both the priming and boosting immunizations and an immunization strategy with mRNA for only one of the two immunizations was less. On average the titer of all i.v. immunizations was higher than s.c. immunizations.

Figure 1D:
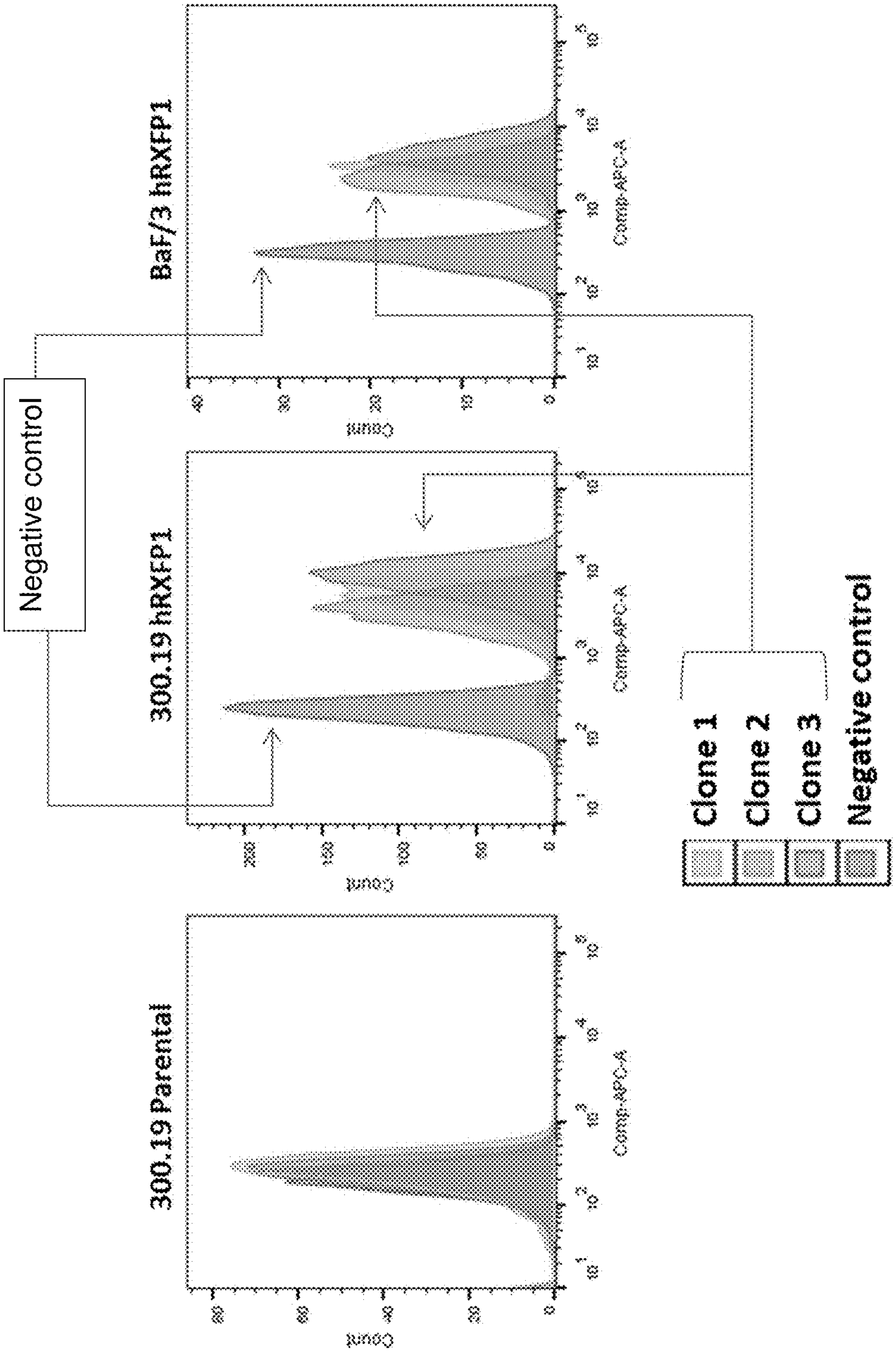

FIG. 1D shows FACS plots of three sample RXFP1-specific monoclonal hybridoma cultures obtained from mRNA-based immunization. Clones show minimal cross-reactivity to non-RXFP1 expressing cells (300.19 parental) and significant binding to cells overexpressing human RXFP1 (300.19 hRXFP1 and Ba/F3 hRXFP1).

Figure 2:
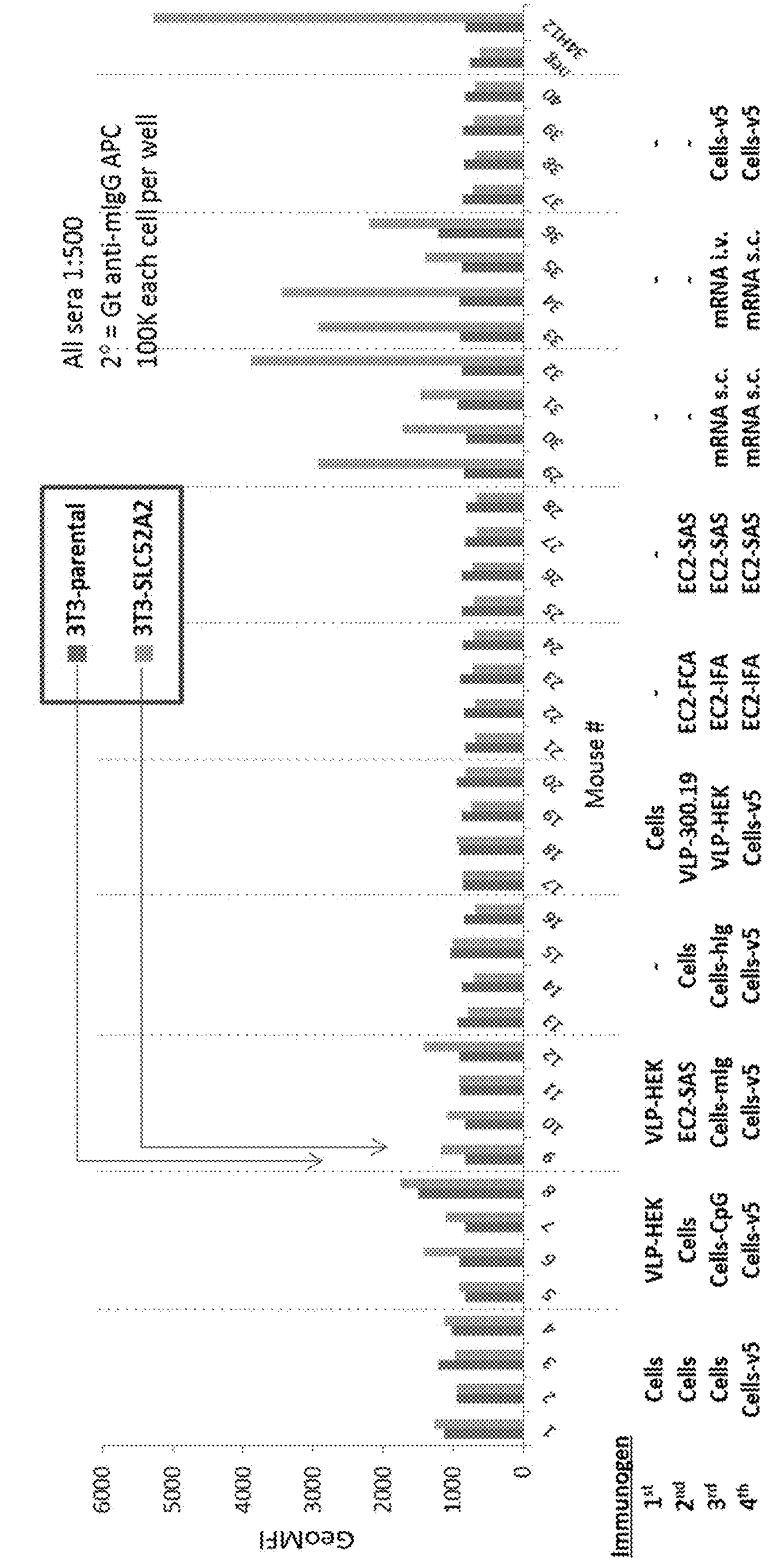
FIG. 2 depicts an exemplary SLC52A2 immunization strategy and resulting FACS-based sera response. Illustration of the immunization strategy employed for the generation of anti-SLC52A antibodies and the corresponding sera titers. Traditional immunogens, such as overexpressing cells, virus like particles, and peptides encoding extracellular loops (EC2) failed to elicit significant target specific titers. A total of 228 hybridomas capable of yielding SLC52A2 specific antibodies were generated from 8 fused mice.

FIG. 2 depicts immunization strategies for a multipass transmembrane protein, SLC52A2, and the resulting FACS-based sera response. Immunization with mRNA encoding SLC52A2 (e.g., see Table 2) for only two rounds was the only antigen able to elicit target-specific antibody titers; immunization with traditional antigens, such as overexpressing cells, VLPs, and peptides encoding extracellular loops (EC2), for two to four rounds, and in various combinations, failed to elicit target-specific titers. Because there were no detectable target-specific IgGs in the sera from mice immunized with these immunogen formats, hybridoma fusion was not initiated. Failure to detect target-specific IgGs in plasma from animals immunized with these traditional antigens suggest that SLC52A2 is a poorly immunogenic protein. In mice immunized with mRNA-LNPs, however, hybridoma fusion was initiated. A total of 228 hybridomas capable of yielding SLC52A2-specific antibodies were identified from a pool of 12,880 hybridoma wells, generally about one third (⅓) of these wells contain hybridomas (approximately over 4,290 hybridomas). Thus, the data presented in FIG. 2 suggest that the mRNA immunization methods described herein are surprisingly superior to traditional antigen formats for transmembrane proteins, e.g., multi-pass transmembrane proteins, for example SLC52A2, as it was the only means by which target specific sera titers could be produced.

Example 3—Immunization Strategy for ANGPTL8

An overview of immunization strategies for difficult-to-express target proteins, such as human ANGPTL8, is shown in Table 17. Examples of issues associated with recombinant expression of ANGPTL8 for raising specific antibodies include low yield, poor secretion, and aggregation. For instance, using standard expression protocols the resulting protein appeared to be more than 90% aggregated.

TABLE 17

| Priming Immunization | Boost | Final Boost |
|---|---|---|
| mRNA (iv) | mRNA (sc) | Fusion protein (iv) |
| mRNA (sc) | Fusion protein (sc) | mRNA (iv) |
| Fusion protein (sc) | Fusion protein (sc) | mRNA (iv) |

Female BALB/c mice were immunized with either 50 μg packaged human ANGPTL8 mRNA (e.g., see Table 3), or 50 μg of HSA-ANGPTL8 fusion protein. Titers were checked 10 days after the priming immunization and after the first boost. The first boosting immunizations were delivered 21 days after the priming immunization and the final boost 25 days after the first boost. Dosing mice with mRNA encoding human ANGPTL8 or with purified recombinant human ANGPTL8 protein resulted in roughly equally potent immune responses against human ANGPTL8 in mice. Hybridomas producing ANGPTL8-specific antibodies were generated, and high affinity ANGPTL8 antibodies were obtained from further screens. These results confirm that mRNA-LNP immunization methods provided herein are effective strategies for producing antibodies to difficult-to-express target proteins, such as human ANGPTL8.

Example 4—Immunization Strategy for Galectin-3

An overview of the immunization strategies for lectin-binding proteins, such as galectin-3, is shown in Table 18.

BALB/c mice were immunized with 2 mg/kg mRNA, complexed with LNPs, or 20 μg recombinant protein as indicated in Table 18. Plasma anti-galectin-3 IgG titers were assayed 7 days after the final boost, which was delivered at day 55.

Figure 3:
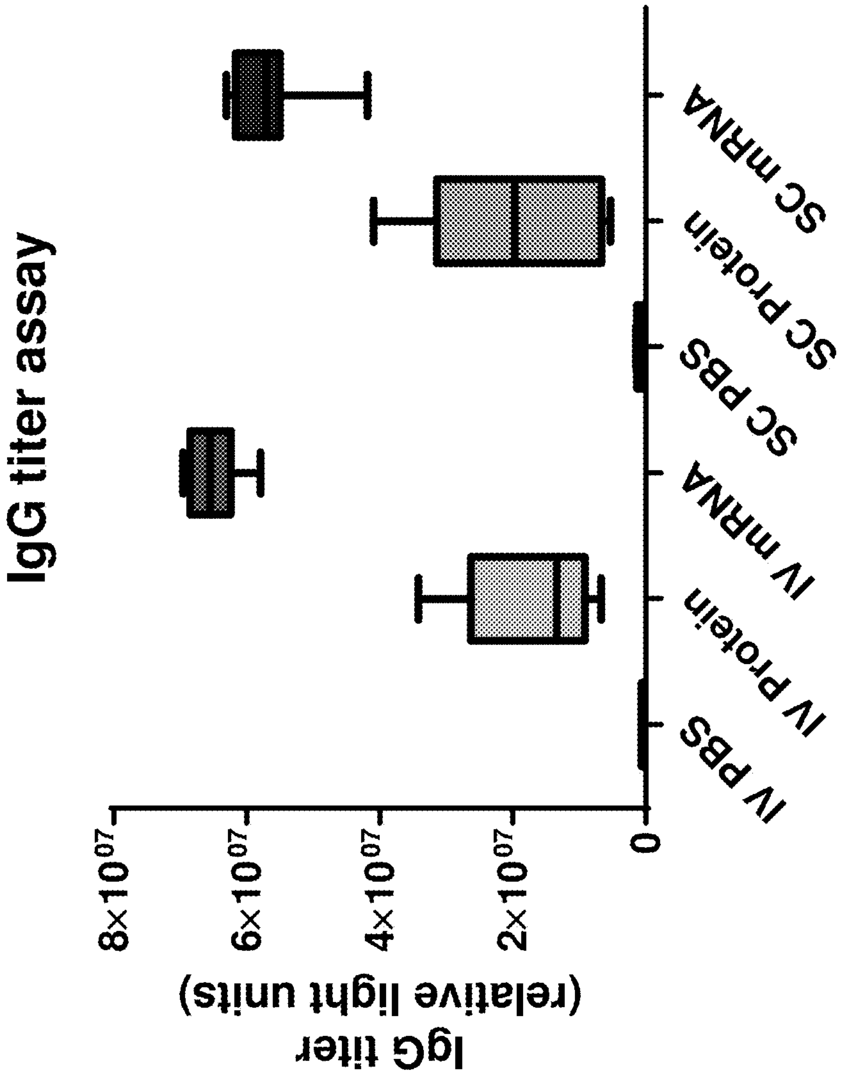
FIG. 3 depicts an exemplary Galectin-3 immunization strategy and resulting ELISA sera response.

FIG. 3 shows that the use of galectin-3 mRNA as a final boosting agent resulted in a significantly higher target-specific IgG titer than when purified recombinant protein (a traditional immunogen) was used. This effect was observed regardless of whether the antigens were delivered subcutaneously or intravenously.

Hybridomas producing galectin-3-specific antibodies were generated, and high affinity monoclonal anti-galectin-3 antibodies were obtained from further screens.

TABLE 18

| Priming Immunization (Day 0) | Boost (Day 7) | Final Boost (Day 55) |
|---|---|---|
| mRNA (I.V.) | mRNA (I.V.) | mRNA (I.V.) |
| mRNA (I.V.) | mRNA (I.V.) | Recombinant protein (I.V.) |
| mRNA (S.C.) | mRNA (S.C.) | mRNA (S.C.) |
| mRNA (S.C.) | mRNA (S.C.) | Recombinant protein (S.C.) |

Summary of the Hit Rates Attainable by mRNA-Mediated Immunization

Table 19 provides a target protein-specific summary of the total number of hybridoma wells (generally about one third (⅓) of these wells contain hybridomas) screened and the number of confirmed target-specific antibodies obtained from those hybridomas wells following the use of lipid-encapsulated mRNA as an immunogen.

Table 20 provides a comparison of mRNA-LNP immunization methods with other conventional methods of immunization by number of hybridomas producing target-specific antibodies. In general, these data suggest that mRNA-LNP immunization is an effective method for inducing an immune response to a target protein antigen and for obtaining a higher number/rate of target protein-specific antibodies. In particular, these results confirm that mRNA-LNP immunization is surprisingly more effective than conventional immunization methods for obtaining antibodies specific for transmembrane proteins, e.g., multi-pass transmembrane proteins, such as GPCRs, which are difficult to raise antibodies against, and for poorly immunogenic proteins (e.g., proteins which produce low or no detectable target-specific IgGs in plasma of animals immunized with traditional antigen).

TABLE 19

| Protein target | Type of protein | Number of hybridoma wells screened | Number of hybridomas producing target-specific antibodies |
|---|---|---|---|
| RXFP1 | Multi-pass Transmembrane protein/GPCR | 20240 | 207 |
| SLC52A2 | Multi-pass Transmembrane protein | 12880 | 228 |
| ANGPTL8 | Soluble protein | 22816 | 542 |
| TSHR | Transmembrane protein/GPCR | TBD | 130 |
| APJ | Transmembrane protein/GPCR | 22080 | 230 |
| GP130 | Single-pass Transmembrane protein | 23920 | 614 |

TABLE 20

Method of immunization and number of hybridomas producing target-specific antibodies

| Protein target | Type of protein | mRNA-LNP[1] | Whole cells only | Virus-like particles only | CDNA only | Protein/ peptide only |
|---|---|---|---|---|---|---|
| RXFP1 | GPCR/ multi-pass | 207 | 66 | ND | ND | ND |
| SLC52A2 | multi-pass | 228 | NST | NST | ND | NST |
| TSHR | GPCR/ multi-pass | 130 | ND | ND | 4[2] | 41[3] |
| APJ | GPCR/ multi-pass | 230 | 9 | 46 | 21 | ND |

[1]Immunization with mRNA-LNP alone or in combination with another antigen format (e.g., protein/peptide).

[2]Sanders et al. 2002 Thyroid stimulating monoclonal antibodies Thyroid 12(12): 1043-1050.

[3]Oda et al. 2000. Epitope analysis of the human thyrotropin (TSH) receptor using monoclonal antibodies. Thyroid 10(12): 1051-1059.

ND—Not determined; antigen format not tested

NST—No specific titers detected. Because no target-specific IgG titers were detectable in plasma, hybridoma generation was not initiated on these groups.

In general, successful generation of hybridomas producing antigen-specific antibodies have been achieved for at least 15 different targets utilizing mRNA-LNP immunization methods as exemplified herein. These results show that the mRNA immunization methods described herein are capable of eliciting an immune response against a wide range of antigens (e.g., transmembrane proteins, for example multi-pass transmembrane proteins, such as GPCRs) in host animals, and are effective methods for producing high affinity monoclonal antibodies, which can serve as parentals for generation of chimeric variants, humanized variants, and affinity matured variants.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and examples detail certain embodiments of the invention. It will be appreciated, however, that no matter how detailed the foregoing may appear in text, the invention may be practiced in many ways and the invention should be construed in accordance with the appended claims and any equivalents thereof.

The invention claimed is:

1. A method for producing monoclonal antibodies against a target protein, comprising the steps of: (a) mixing at least one cationic lipid with a messenger RNA (mRNA) coding for the target protein or a fragment thereof, thereby forming a cationic lipid-mRNA complex; (b) administering the lipid-mRNA complex to a non-human animal; and (c) obtaining antibodies that specifically bind to the target protein from the animal, wherein said mRNA of the complex comprises pseudouridine and one or more of the following: a consensus Kozak sequence; a 7-methylguanosine cap on the 5' end of the mRNA; a polyadenosine (polyA) tail found at the 3' terminus of the mRNA transcript; and 5'-and 3'-untranslated regions (UTRs).

2. The method of claim 1, wherein the target protein is a transmembrane protein.

3. The method of claim 2, wherein the transmembrane protein is selected from the following:

a G protein coupled receptor (GPCR);

(ii) a single pass transmembrane protein receptor;

(iii) a Tumor Necrosis Factor Receptor Superfamily (TNFRSF) member;

(iv) an interleukin (IL) receptor;

(v) an ion channel;

(vi) a solute carrier;

(vii) an immune receptor; and (viii) multi-pass transmembrane protein.

4. The method of claim 1, wherein the target protein is selected from the following:

ACKR1, ACKR2, ACKR3, ACKR4, ADCYAP1R1, ADGRA1, ADGRA2, ADGRA3, ADGRB1, ADGRB2, ADGRB3, ADGRD1, ADGRD2, ADGRE1, ADGRE2, ADGRE3, ADGRE4P, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADORA1, ADORA2A, ADORA2B, ADORA3, ADRA1A, ADRA1B, ADRA1D, ADRA2A, ADRA2B, ADRA2C, ADRB1, ADRB2, ADRB3, AGTR1, AGTR2, APLNR/APJ, ASGR1, ASGR2, AVPR1A, AVPR1B, AVPR2, BDKRB1, BDKRB2, BRS3, BRS3, C3AR1, C5AR1, C5AR2, CALCR, CALCRL, CASR, CCKAR, CCKBR, CCR1, CCR10, CCR2, CCR3, CCR4, CCR5, CCR6, CCR7, CCR8, CCR9, CCRL2, CELSR1, CELSR2, CELSR3, CHRM1, CHRM2, CHRM3, CHRM4, CHRM5, CMKLR1, CNR1, CNR2, CRHR1, CRHR2, CX3CR1, CXCR1, CXCR2, CXCR3, CXCR4, CXCR5, CXCR6, CYSLTR1, CYSLTR2, DRD1, DRD2, DRD3, DRD4, DRD5, EDNRA, EDNRB, F2R, F2RL1, F2RL2, F2RL3, FFAR1, FFAR2, FFAR3, FFAR4, FPR1, FPR2, FPR2, FPR3, FSHR, FZD1, FZD10, FZD2, FZD3, FZD4, FZD5, FZD6, FZD7, FZD8, FZD9, GABBR1, GABBR2, GALR1, GALR2, GALR3, GCGR, GHRHR, GHSR, GIPR, GLP1R, GLP2R, GNRHR, GNRHR2, GPBAR1, GPER1, GPR1, GPR4, GPR12, GPR15, GPR17, GPR18, GPR19, GPR20, GPR21, GPR22, GPR25, GPR26, GPR27, GPR3, GPR31, GPR32, GPR33, GPR34, GPR35, GPR37, GPR37L1, GPR39, GPR40, GPR42, GPR42, GPR45, GPR50, GPR52, GPR55, GPR6, GPR61, GPR62, GPR63, GPR65, GPR68, GPR75, GPR78, GPR79, GPR82, GPR83, GPR84, GPR85, GPR87, GPR88, GPR101, GPR107, GPR132, GPR135, GPR137, GPR139, GPR141, GPR142, GPR143, GPR146, GPR148, GPR149, GPR15, GPR150, GPR151, GPR152, GPR153, GPR156, GPR157, GPR158, GPR160, GPR161, GPR162, GPR171, GPR173, GPR174, GPR176, GPR179, GPR182, GPR183, GPRC5A, GPRC5B, GPRC5C, GPRC5D, GPRC6A, GRM1, GRM2, GRM3, GRM4, GRM5, GRM6, GRM7, GRM8, GRPR, HCAR1, HCAR2, HCAR3, HCRTR1, HCRTR2, HRH1, HRH2, HRH3, HRH4, HTR1A, HTR1B, HTR1D, HTR1E, HTR1F, HTR2A, HTR2B, HTR2C, HTR4, HTR5A, HTR5BP, HTR6, HTR7, KISS1R, LGR3, LGR4, LGR5, LGR6, LHCGR, LPAR1, LPAR2, LPAR3, LPAR4, LPAR5, LPAR6, LTB4R, LTB4R2, MAS1, MAS1L, MC1R, MC2R, MC3R, MC4R, MC5R, MCHR1, MCHR2, MLNR, MRGPRD, MRGPRE, MRGPRF, MRGPRG, MRGPRX1, MRGPRX2, MRGPRX3, MRGPRX4, MTNR1A, MTNR1B, NMBR, NMUR1, NMUR2, NPBWR1, NPBWR2, NPFFR1, NPFFR2, NPSR1, NPY1R, NPY2R, NPY4R, NPY5R, NPY6R, NTSR1, NTSR2, OPN3, OPN4, OPN5, OPRD1, OPRK1, OPRL1, OPRM1, OR51E1, OXER1, OXGR1, OXTR, P2RY1, P2RY10, P2RY11, P2RY12, P2RY13, P2RY14, P2RY2, P2RY4, P2RY6, P2RY8, PRLHR, PROKR1, PROKR2, PTAFR, PTGDR, PTGDR2, PTGER1, PTGER2, PTGER3, PTGER4, PTGFR, PTGIR, PTH1R, PTH2R, QRFPR, RXFP1, RXFP2, RXFP3, RXFP4, S1PR1, S1PR2, S1PR3, S1PR4, S1PR5, SCTR, SMO, SSTR1, SSTR2, SSTR3, SSTR4, SSTR5, SUCNR1, TAAR1, TAAR2, TAAR3, TAAR4P, TAAR5, TAAR6, TAAR8, TAAR9, TACR1, TACR2, TACR3, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R45, TAS2R46, TAS2R5, TAS2R50, TAS2R60, TAS2R7, TAS2R8, TAS2R9, TBXA2R, TPRA1, TRHR, TSHR, UTS2R, VIPR1, VIPR2, XCR1, TCR-a, TCR-13, CD3, ζ-chain accessory, CD4, CD8, SIGIRR, mannose receptor (MR), asialoglycoprotein receptor family (e.g., asialoglycoprotein receptor macrophage galactose-type lectin (MGL)), DC-SIGN (CLEC4L), langerin (CLEC4K), myeloid DAP12-associating lectin (MDL)-1 (CLEC5A), dectin 1/CLEC7A, DNGR1/CLEC9A, Myeloid C-type lectin-like receptor (MICL) (CLEC12A), CLEC2 (also called CLEC1B), CLEC12B, DCIR/CLEC4A, Dectin 2/CLEC6A, Blood DC antigen 2 (BDCA2) (CLEC4C), macrophage-inducible C-type lectin (CLEC4E), TLR1, TLR2, TLR3, TLR4, TLR5, TLR6, TLR7, TLR8, TLR9, TLR10, TLR11, TLR12, TLR13, FcγRI (CD64), FcγRIIA (CD32), FcγRIIB1 (CD32), FcγRIIB2 (CD32), FcγRIIIA (CD16a), FcγRIIIB (CD16b), FcαRI, FcαRII (CD23), FcαR1 (CD89), Fcα/μR, FcRn, CD27, CD40, OX40, GITR, CD137, PD-1, CTLA-4, PD-L1, TIGIT, T-cell immunoglobulin domain and mucin domain 3 (TIM3), V-domain Ig suppressor of T cell activation (VISTA), CD28, CD122, ICOS, A2AR, B7-H3, B7-H4, B and T lymphocyte attenuator (BTLA), Indoleamine 2,3-dioxygenase (IDO), killer-cell immunoglobulin-like receptor (KIR), lymphocyte activation gene-3 (LAG3), FAM159B, HLA-A, HLA-B, HLA-C, HLA-DPA1, HLA-DPB1, HLA-DQA1, HLA-DQB1, HLA-DRA, HLA-DRB1, gp130, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, IL-19 receptor, IL-20 receptor, IL-21 receptor, IL-22 receptor, IL-23 receptor, IL-24 receptor, IL-25 receptor, IL-26 receptor, IL-27 receptor, IL-28 receptor, IL-29 receptor, IL-30 receptor, IL-31 receptor, IL-32 receptor, IL-33 receptor, IL-35 receptor, IL-36 receptor, FGFR1, FGFR2, FGFR3, FGFR4, TNFRSF1A, TNFRSF1B, TNFRSF3, TNFRSF4, TNFRSF5, TNFRSF6, TNFRSF6B, TNFRSF7, TNFRSF8, TNFRSF9, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF16, TNFRSF17, TNFRSF18, TNFRSF19, TNFRSF21, TNFRSF25, TNFRSF27, SCN1A, SCN1B, SCN2A, SCN2B, SCN3A, SCN3B, SCN4A, SCN5A, SCN7A, SCN8A, SCN9A, SCN10A, SCN11A, CACNA1A, CACNA1B, CACNA1C, CACNA1D, CACNA1E, CACNA1F, CACNA1G, CACNA1H, CACNA1I, CACNA1S, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, MCOLN1, MCOLN2, MCOLN3, PKD1, PKD2, PKD2L1, PKD2L2, TRPV1, TRPV2, TRPV3, TRPV4, TRPV5, TRPV6, CATSPER1, CATSPER2, CATSPER3, CATSPER4, TPCN1, TPCN2, CNGA1, CNGA2, CNGA3, CNGA4, CNGB1, CNGB3, HCN1, HCN2, HCN3, HCN4, KCNMA1, KCNN1, KCNN2, KCNN3, KCNN4, KCNT1, KCNT2, KCNU1, KCNA1, KCNA2, KCNA3, KCNA4, KCNA5, KCNA6, KCNA7, KCNA10, KCNB1, KCNB2, KCNC1, KCNC2, KCNC3, KCNC4, KCND1, KCND2, KCND3, KCNF1, KCNG1, KCNC2, KCNC3, KCNG4, KCNH1, KCNH2, KCNH3, KCNH4, KCNH5, KCNH6, KCNH7, KCNH8, KCNQ1, KCNQ2, KCNQ3, KCNQ4, KCNQ5, KCNS1, KCNS2, KCNS3, KCNV1, KCNV2, KCNJ1, KCNJ2, KCNJ3, KCNJ4, KCNJ5, KCNJ6, KCNJ8, KCNJ9, KCNJ10, KCNJ11, KCNJ12, KCNJ13, KCNJ14, KCNJ15, KCNJ16, KCNJ18, KCNK1, KCNK2, KCNK3, KCNK4, KCNK5, KCNK6, KCNK7, KCNK9, KCNK10, KCNK12, KCNK13, KCNK15, KCNK16, KCNK17, KCNK18, HVCN1, HTR3A, HTR3B, HTR3C, HTR3D, HTR3E, CHRNA1, CHRNA2, CHRNA3, CHRNA4, CHRNA5, CHRNA6, CHRNA7, CHRNA9, CHRNA10, CHRNB1, CHRNB2, CHRNB3, CHRNB4, CHRND, CHRNE, CHRNG, GABRA1, GABRA2, GABRA3, GABRA4, GABRA5, GABRA6, GABRB1, GABRB2, GABRB3, GABRD, GABRE, GABRG1, GABRG2, GABRG3,GABRP, GABRQ, GABRR1, GABRR2, GABRR3, GRIA1, GRIA2, GRIA3, GRIA4, GRID1, GRID2, GRIK1, GRIK2, GRIK3, GRIK4, GRIK5, GRIN1, GRIN2A, GRIN2B, GRIN2C, GRIN2D, GRIN3A, GRIN3B, GLRA1, GLRA2, GLRA3, GLRA4, P2RX1, P2RX2, P2RX3, P2RX4, P2RX5, P2RX6, P2RX7, ZACN, ASIC1, ASIC2, ASIC3, ASIC4, AQP1, AQP2, AQP3, AQP4, AQP5, AQP6, AQP7, AQP8, AQP9, AQP10, AQP11, AQP12A, AQP12B, MIP, CLCN1, CLCN2, CLCN3, CLCN4, CLCN5, CLCN6, CLCN7, CLCNKA, CLCNKB, Cystic fibrosis transmembrane conductance regulator (CFTR), ANO1, ANO2, ANO3, ANO4, ANO5, ANO6, ANO7, ANO8, ANO9, ANO10, BEST1, BEST2, BEST3, BEST4, CLIC1, CLIC2, CLIC3, CLIC4, CLIC5, CLIC6, GJA1, GJA3, GJA4, GJA5, GJA6P, GJA8, GJA9, GJA10, GJB1, GJB2, GJB3, GJB4, GJB5, GJB6, GJB7, GJC1, GJC2, GJC3, GJD2, GJD3, GJD4, GJE1, ITPR1, ITPR2, ITPR3, PANX1, PANX2, PANX3, RYR1, RYR2, RYR3, NALCN, SCNN1A, SCNN1B, SCNN1D, SCNN1G, TEM16A, ADAMTS7, ANGPTL3, ANGPTL4, ANGPTL8, LPL, GDF15, galectin-1, galectin-2, galectin-3, galectin-4, galectin-7, galectin-8, galectin-9, galectin-10, galectin-12, galectin-13, matrix gla protein (MGP), PRNP, DGAT1, GPAT3, DMC1, BLM, BRCA2, members of the human endogenous retrovirus type K (HERV-K) family, ectonucleoside triphosphate diphosphohydrolase 1 (ENTPD1), ectonucleoside triphosphate diphosphohydrolase 2 (ENTPD2), SLC1A1, SLC1A2, SLC1A3, SLC1A4, SLC1A5, SLC1A6, SLC1A7, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, SLC2A14, SLC3A1, SLC3A2, SLC4A1, SLC4A2, SLC4A3, SLC4A4, SLC4A5, SLC4A6, SLC4A7, SLC4A8, SLC4A9, SLC4A10, SLC4A11, SLC5A1, SLC5A2, SLC5A3, SLC5A4, SLC5A5, SLC5A6, SLC5A7, SLC5A8, SLC5A9, SLC5A10, SLC5A11, SLC5A12, SLC6A1, SLC6A2, SLC6A3, SLC6A4, SLC6A5, SLC6A6, SLC6A7, SLC6A8, SLC6A9, SLC6A10, SLC6A11, SLC6A12, SLC6A13, SLC6A14, SLC6A15, SLC6A16, SLC6A17, SLC6A18, SLC6A19, SLC6A20, SLC7A5, SLC7A6, SLC7A7, SLC7A8, SLC7A9, SLC7A10, SLC7A11, SLC7A13, SLC7A14, SLC8A1, SLC8A2, SLC8A3, SLC9A1, SLC9A2, SLC9A3, SLC9A4, SLC9A5, SLC9A6, SLC9A7, SLC9A8, SLC9A9, SLC9A10, SLC9A11, SLC9B1, SLC9B2, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14, SLC17A1, SLC17A2, SLC17A3, SLC17A4, SLC17A5, SLC17A6, SLC17A7, SLC17A8, SLC17A9, SLC18A1, SLC18A2, SLC18A3, SLC19A1, SLC19A2, SLC19A3, SLC20A1, SLC20A2, SLCO1A2, SLCO1B1, SLCO1B3, SLCO1C1, SLCO2A1, SLCO2B1, SLCO3A1, SLCO4A1, SLCO4C1, SLCO5A1, SLCO6A1, SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A18A5, SLC22A19, SLC22A20, SLC22A23, SLC22A24, SLC22A25, SLC22A31, SLC23A1, SLC23A2, SLC23A3, SLC23A4, SLC24A1, SLC24A2, SLC24A3, SLC24A4, SLC24A5, SLC24A6, SLC25A1, SLC25A2, SLC25A3, SLC25A4, SLC25A5, SLC25A6, SLC25A7, SLC25A8, SLC25A9, SLC25A10, SLC25A11, SLC25A12, SLC25A13, SLC25A14, SLC25A15, SLC25A16, SLC25A17, SLC25A18, SLC25A19,SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37,SLC25A38, SLC25A39, SLC25A40, SLC25A41, SLC25A42, SLC25A43, SLC25A44, SLC25A45, SLC25A46, SLC26A1, SLC26A2, SLC26A3, SLC26A4, SLC26A5, SLC26A6, SLC26A7, SLC26A8, SLC26A9, SLC26A10, SLC26A11, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC30A1, SLC30A2, SLC30A3, SLC30A4, SLC30A5, SLC30A6, SLC30A7, SLC30A8, SLC30A9, SLC30A10, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E3, SLC35E4, SLC35F1, SLC35F2, SLC35F3, SLC35F4, SLC35F5, SLC35G1, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A2, SLC38A3, SLC38A4, SLC38A5, SLC38A6, SLC38A7, SLC38A8, SLC38A9, SLC38A10, SLC38A11, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14, SLC40A1, SLC41A1, SLC41A2, SLC41A3, RhAG, RhBG, RhCG, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, HCP-1, MFSD5, MFSD10, SLC50A1, OSTα, OSTβ, SLC52A1, SLC52A2, and SLC52A3.

5. The method of claim 1, wherein said administering is parenteral, intravenous, intramuscular, intranasal, or subcutaneous.

6. The method of claim 1, wherein said complex comprises an mRNA comprising the nucleic acid sequence of SEQ ID NO:4, or any one of SEQ ID NOs: 2, 4, and 37.

7. The method of claim 1, wherein said complex comprises an mRNA comprising the nucleic acid sequence of SEQ ID NO:7, or any one of SEQ ID NOs: 5, 7, and 40.

8. The method of claim 1, wherein said complex comprises an mRNA comprising the nucleic acid sequence of SEQ ID NO:10, or any one of SEQ ID NOs: 8, 10, and 43.

9. The method of claim 1, wherein said complex has a diameter of approximately 30-150 nm.

10. The method of claim 1, wherein the complex comprises helper lipids.

11. The method claim 1, wherein the complex comprises any combination of (i) cationic lipid, (ii) a helper lipid, (iii) a neutral lipid, and (iv) a stealth lipid.

12. The method of claim 11, wherein the cationic lipid is selected from the group consisting of: N,N-dioleyl-N,N-dimethylammonium chloride (DODAC), N,N-distearyl-N, N-dimethylammonium bromide (DDAB), N-(1-(2,3-dioleoyloxy) propyl)-N,N,N-trimethylammonium chloride (DOTAP), 1,2-Dioleoyl-3-Dimethylammonium -propane (DODAP), N-(1-(2,3-dioleyloxy)propyl) -N,N,N-trimethylammonium chloride (DOTMA), 1,2-Dioleoylcarbamyl -3-Dimethylammonium-propane (DOCDAP), 1,2-Dilineoyl-3-Dimethylammonium-propane (DLINDAP), dilauryl ($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl -hydroxyethyl ammonium bromide (DMRIE), 3-Dimethylamino-2-(Cholest-5-en -3-beta-oxybutan-4-oxy) -1-(cis,cis-9,12-octadecadienoxy) propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP).

13. The method of claim 1, wherein the animal is administered with 10 μg, 12.5 μg, 20 μg, 25 μg, 30 μg, 40 μg, 50 μg, 60 μg, 70 μg, 80 μg, 90 μg, 100 μg, 110 μg, 120 μg, 130 μg, 140 μg or 150 μg mRNA.

* * * * *

SEQUENCE LISTING

<160> NUMBER OF SEQ ID NOS: 60

<210> SEQ ID NO 1
<211> LENGTH: 9
<212> TYPE: DNA
<213> ORGANISM: Unknown
<220> FEATURE:
<223> OTHER INFORMATION: Description of Unknown:
Kozak sequence

<400> SEQUENCE: 1 gccaccatg 9

<210> SEQ ID NO 2
<211> LENGTH: 3874
<212> TYPE: RNA
<213> ORGANISM: Homo sapiens

<400> SEQUENCE: 2
gugcgugugu guaaagaagg agauuaggac auuuagagaa ggagggcggg gaggagagau 60
ccugagaaua gaaaggagga aagaaaaaaa gaggaaugga aagagacaga gaaaggaaau 120
gggaguggaa ggagggagga cugcuuugua acugcuaaga uugcagacag aaauagcaca 180
caaccacugu gagcuguaug cgauucagaa accaagacca aauuuugcuc acuuucauua 240
aucaguugcu cagauagaag gaaaugacau cugguucugu cuucuucuac aucuuaauuu 300
uuggaaaaua uuuuucucau gggggguggac aggaugucaa gugcucccuu ggcuauuucc 360
ccugugggaa caucacaaag ugcuugccuc agcuccugca cuguaacggu guggacgacu 420
gcgggaauca ggccgaugag gacaacugug gagacaacaa uggaugguc u cugcaauuug 480 acaaauauuu ugccaguuac uacaaaauga cuucccaaua uccuuuugag gcagaaacac 540
cugaauguuu ggucgguucu gugccagugc aaugucuuug ccaaggucug gagcuugacu 600
gugaugaaac caauuuacga gcuguuccau cgguuucuuc aaaugugacu gcaaugucac 660
uucaguggaa cuuaauaaga aagcuuccuc cugauugcuu caagaauuau caugaucuuc 720
agaagcugua ccugcaaaac aauaagauua cauccaucuc caucuaugcu uucagaggac 780
ugaauagccu uacuaaacug uaucucaguc auaacagaau aaccuuccug aagccgggug 840
uuuuugaaga ucuucacaga cuagaauggc ugauaauuga agauaaucac cucagucgaa 900
uuuccccacc aacauuuuau ggacuaaauu cucuuauucu cuuaguccug augaauaacg 960
uccucacccg uuuaccugau aaaccucucu gucaacacau gccaagacua cauuggcugg 1020
accuugaagg caaccauauc cauaauuuaa gaaauuugac uuuuauuucc ugcaguaauu 1080
uaacuguuuu agugaugagg aaaaacaaaa uuaaucacuu aaaugaaaau acuuuugcac 1140
cucuccagaa acuggaugaa uuggauuuag gaaguaauaa gauugaaaau cuuccaccgc 1200
uuauauucaa ggaccugaag gagcugucac aauugaaucu uuccuauaau ccaauccaga 1260
aaauucaagc aaaccaauuu gauuaucuug ucaaacucaa gucucucagc cuagaaggga 1320
uugaaauuuc aaauauccaa caaaggaugu uuagaccucu uaugaaucuc ucucacauau 1380
auuuuaagaa auuccaguac ugugggguaug caccacaugu ucgcagcugu aaaccaaaca 1440
cugauggaau uucaucucua gagaaucucu uggcaagcau uauucagaga guauuugucu 1500
ggguuguauc ugcaguuacc ugcuuuggaa acauuuuugu cauuugcaug cgaccuuaua 1560
ucaggucuga gaacaagcug uaugccaugu caaucauuuc ucucugcugu gccgacugcu 1620
uaaugggaau auauuuauuc gugaucggag gcuuugaccu aaaguuucgu ggagaauaca 1680

-continued

```
auaagcaugc gcagcugugg auggagagua cucauuguca gcuuguagga ucuuuggcca   1740

uucuguccac agaaguauca guuuuacugu uaacauuucu gacauuggaa aaauacaucu   1800

gcauugucua uccuuuuaga ugugugagac cuggaaaaug cagaacaauu acaguucuga   1860

uucucauuug gauuacuggu uuuauagugg cuuucauucc auugagcaau aaggaauuuu   1920

ucaaaaacua cuauggcacc aauggaguau gcuucccucu ucauucagaa gauacagaaa   1980

guauuggagc ccagauuuau ucaguggcaa uuuuucuugg uauuaauuug gccgcauuua   2040

ucaucauagu uuuuuccuau ggaagcaugu uuuauagugu ucaucaaagu gccauaacag   2100

caacugaaau acggaaucaa guuaaaaaag agaugauccu ugccaaacgu uuuuucuuua   2160

uaguauuuac ugaugcauua ugcuggauac ccauuuuugu agugaaauuu cuuucacugc   2220

uucagguaga aauaccaggu accauaaccu cuuggguagu gauuuuuauu cugcccauua   2280

acagugcuuu gaacccaauu cucuauacuc ugaccacaag accauuuaaa gaaaugauuc   2340

aucgguuuug guauaacuac agacaaagaa aaucuaugga cagcaaaggu cagaaaacau   2400

augcuccauc auucaucugg guggaaaugu ggccacugca ggagaugcca ccugaguuaa   2460

ugaagccgga ccuuuucaca uaccccugug aaaugucacu gauuucucaa ucaacgagac   2520

ucaauuccua uucaugacug acucugaaau ucauuucuuc gcagagaaua cuguggggu   2580

gcuucaugag ggauuuacug guaugaaaug aauaccacaa aauuaauuua uaauaauagc   2640

uaagauaaau auuuuacaag gacaugagga aaaauaaaaa ugacuaaugc ucuuacaaag   2700

ggaaguaauu auaucaauaa uguauauaua uuaguagaca uuuugcauaa gaaauuaaga   2760

gaaaucuacu ucaguaacau ucauucauuu uucuaacaug cauuuauuga guacccacua   2820

cuaugugcau agcauugcaa uauaguccug gaaguagaca gugcagaacc uuucaaucug   2880

uagauggugu uuaaugacaa aagacuauac aaaguccauc ugcaguuccu aguuuaaagu   2940

agagcuuuac cugucaugug caucagcaag aaucauaggc acuuuuaaau aaagguuuaa   3000

aguuuuggaa uacucagugu auuugcauca uagaaaaugu cugacuguuu gcaaaauaau   3060

auucuguuuu aagaauccau cuuaccucuc uuuaaguuuc cauacacuug agagccaaca   3120

caacauauuu auuacuaaaa agaugcuuug cuagaaacuc aaaaacagca cuucuuuugg   3180

cacuuccugc ccaguuuucu cuuugcuuua aaugaacauc aucauaugga auuggaauag   3240

gagaguauga guacggcaga gaaguggauc agaaaaacua gaaugaggau aaacauuuac   3300

auuaguggaa acuccugaaa uaaauccuug uauugucagu uaacugauuu ucaacaagga   3360

ugccaagaca aaaaggcuuu ucaacaaacc gugcuguuuu aagaacagac cuaaguggau   3420

uaauucaccc acuuuagaug ggugaauguu auggugugug aaauaucuca guaaagcagu   3480

uaaaaggaaa aagagcugga augcacugau ucaggaacuu aauuucagga aggaaagguc   3540

uguauguaca cauuucacuu uaagcagaaa aucuuucuuc aagaaaugac uuuacuuucu   3600

cuuugcacug ccagcacgug agauacuaac uuuuuaacua guuguucuuc ucuagucucu   3660

acguuauuag aauuuuuugc uuucauaaug ugaaaccuuu aagcaggaga agaaaauguu   3720

uucagauagu uucaaauaca ccaaaaaugu uugaaacaca aaaauacugg aaucaaacca   3780

uaaugcacuu auugaauaua uaguuguaua gauuuguucu gaaaauaaau uaucugaaau   3840

uuaacuauua aaaaaaaaaa aaaaaaaaaa aaaa                              3874
```

<210> SEQ ID NO 3
<211> LENGTH: 757
<212> TYPE: PRT
<213> ORGANISM: Homo sapiens

<400> SEQUENCE: 3

Met Thr Ser Gly Ser Val Phe Phe Tyr Ile Leu Ile Phe Gly Lys Tyr
1               5                   10                  15

Phe Ser His Gly Gly Gly Gln Asp Val Lys Cys Ser Leu Gly Tyr Phe
            20                  25                  30

Pro Cys Gly Asn Ile Thr Lys Cys Leu Pro Gln Leu Leu His Cys Asn
        35                  40                  45

Gly Val Asp Asp Cys Gly Asn Gln Ala Asp Glu Asp Asn Cys Gly Asp
    50                  55                  60

Asn Asn Gly Trp Ser Leu Gln Phe Asp Lys Tyr Phe Ala Ser Tyr Tyr
65                  70                  75                  80

Lys Met Thr Ser Gln Tyr Pro Phe Glu Ala Glu Thr Pro Glu Cys Leu
                85                  90                  95

Val Gly Ser Val Pro Val Gln Cys Leu Cys Gln Gly Leu Glu Leu Asp
            100                 105                 110

Cys Asp Glu Thr Asn Leu Arg Ala Val Pro Ser Val Ser Ser Asn Val
        115                 120                 125

Thr Ala Met Ser Leu Gln Trp Asn Leu Ile Arg Lys Leu Pro Pro Asp
    130                 135                 140

Cys Phe Lys Asn Tyr His Asp Leu Gln Lys Leu Tyr Leu Gln Asn Asn
145                 150                 155                 160

Lys Ile Thr Ser Ile Ser Ile Tyr Ala Phe Arg Gly Leu Asn Ser Leu
                165                 170                 175

Thr Lys Leu Tyr Leu Ser His Asn Arg Ile Thr Phe Leu Lys Pro Gly
            180                 185                 190

Val Phe Glu Asp Leu His Arg Leu Glu Trp Leu Ile Ile Glu Asp Asn
        195                 200                 205

His Leu Ser Arg Ile Ser Pro Pro Thr Phe Tyr Gly Leu Asn Ser Leu
    210                 215                 220

Ile Leu Leu Val Leu Met Asn Asn Val Leu Thr Arg Leu Pro Asp Lys
225                 230                 235                 240

Pro Leu Cys Gln His Met Pro Arg Leu His Trp Leu Asp Leu Glu Gly
                245                 250                 255

Asn His Ile His Asn Leu Arg Asn Leu Thr Phe Ile Ser Cys Ser Asn
            260                 265                 270

Leu Thr Val Leu Val Met Arg Lys Asn Lys Ile Asn His Leu Asn Glu
        275                 280                 285

Asn Thr Phe Ala Pro Leu Gln Lys Leu Asp Glu Leu Asp Leu Gly Ser
    290                 295                 300

Asn Lys Ile Glu Asn Leu Pro Pro Leu Ile Phe Lys Asp Leu Lys Glu
305                 310                 315                 320

Leu Ser Gln Leu Asn Leu Ser Tyr Asn Pro Ile Gln Lys Ile Gln Ala
                325                 330                 335

Asn Gln Phe Asp Tyr Leu Val Lys Leu Lys Ser Leu Ser Leu Glu Gly
            340                 345                 350

Ile Glu Ile Ser Asn Ile Gln Gln Arg Met Phe Arg Pro Leu Met Asn
        355                 360                 365

Leu Ser His Ile Tyr Phe Lys Lys Phe Gln Tyr Cys Gly Tyr Ala Pro
    370                 375                 380

His Val Arg Ser Cys Lys Pro Asn Thr Asp Gly Ile Ser Ser Leu Glu
385                 390                 395                 400

Asn Leu Leu Ala Ser Ile Ile Gln Arg Val Phe Val Trp Val Val Ser

```
                405                 410                 415

Ala Val Thr Cys Phe Gly Asn Ile Phe Val Ile Cys Met Arg Pro Tyr
            420                 425                 430

Ile Arg Ser Glu Asn Lys Leu Tyr Ala Met Ser Ile Ile Ser Leu Cys
        435                 440                 445

Cys Ala Asp Cys Leu Met Gly Ile Tyr Leu Phe Val Ile Gly Gly Phe
    450                 455                 460

Asp Leu Lys Phe Arg Gly Glu Tyr Asn Lys His Ala Gln Leu Trp Met
465                 470                 475                 480

Glu Ser Thr His Cys Gln Leu Val Gly Ser Leu Ala Ile Leu Ser Thr
                485                 490                 495

Glu Val Ser Val Leu Leu Leu Thr Phe Leu Thr Leu Glu Lys Tyr Ile
            500                 505                 510

Cys Ile Val Tyr Pro Phe Arg Cys Val Arg Pro Gly Lys Cys Arg Thr
        515                 520                 525

Ile Thr Val Leu Ile Leu Ile Trp Ile Thr Gly Phe Ile Val Ala Phe
    530                 535                 540

Ile Pro Leu Ser Asn Lys Glu Phe Phe Lys Asn Tyr Tyr Gly Thr Asn
545                 550                 555                 560

Gly Val Cys Phe Pro Leu His Ser Glu Asp Thr Glu Ser Ile Gly Ala
                565                 570                 575

Gln Ile Tyr Ser Val Ala Ile Phe Leu Gly Ile Asn Leu Ala Ala Phe
            580                 585                 590

Ile Ile Ile Val Phe Ser Tyr Gly Ser Met Phe Tyr Ser Val His Gln
        595                 600                 605

Ser Ala Ile Thr Ala Thr Glu Ile Arg Asn Gln Val Lys Lys Glu Met
    610                 615                 620

Ile Leu Ala Lys Arg Phe Phe Phe Ile Val Phe Thr Asp Ala Leu Cys
625                 630                 635                 640

Trp Ile Pro Ile Phe Val Val Lys Phe Leu Ser Leu Leu Gln Val Glu
                645                 650                 655

Ile Pro Gly Thr Ile Thr Ser Trp Val Val Ile Phe Ile Leu Pro Ile
            660                 665                 670

Asn Ser Ala Leu Asn Pro Ile Leu Tyr Thr Leu Thr Thr Arg Pro Phe
        675                 680                 685

Lys Glu Met Ile His Arg Phe Trp Tyr Asn Tyr Arg Gln Arg Lys Ser
    690                 695                 700

Met Asp Ser Lys Gly Gln Lys Thr Tyr Ala Pro Ser Phe Ile Trp Val
705                 710                 715                 720

Glu Met Trp Pro Leu Gln Glu Met Pro Pro Glu Leu Met Lys Pro Asp
                725                 730                 735

Leu Phe Thr Tyr Pro Cys Glu Met Ser Leu Ile Ser Gln Ser Thr Arg
            740                 745                 750

Leu Asn Ser Tyr Ser
        755
```

<210> SEQ ID NO 4
<211> LENGTH: 2883
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 4

-continued

```
ggaggccgga gaauuguaau acgacucacu auagggagac gcguguuaaa uaacaaaucu     60
caacacaaca uauacaaaac aaacgaaucu caagcaauca agcauucuac uucuauugca    120
gcaauuuaaa ucauuucuuu uaaagcaaaa gcaauuuucu gaaaauuuuc accauuuacg    180
aacgauagcc gccaccauga caagcggcag cguguucuuc uacauccuga ucuucggcaa    240
guacuucagc cacggcggag gccaggacgu gaaguguagc cugggcuacu uccccugcgg    300
caacaucacc aagugccugc cccagcugcu gcacugcaac ggcguggacg auugcggcaa    360
ccaggccgac gaggacaacu gcggcgacaa caauggcugg ucccugcagu ucgauaagua    420
cuucgccucc uacuacaaga ugaccagcca guaccccuuc gaggccgaga caccugagug    480
ccucgugggc ucugugccug ugcagugucu gugccagggc cuggaacugg acugcgacga    540
gacaaaccug agagccgugc ccagcguguc cagcaacgug acagccauga gccugcagug    600
gaaccugauc cggaagcugc cccccgacug cuucaagaac uaccacgacc ugcagaagcu    660
guaucugcag aacaacaaga ucaccuccau cagcaucuac gccuuccggg gccugaacag    720
ccugaccaag cuguaccuga gccacaaccg gaucaccuuu cugaagcccg gcguguucga    780
ggaccugcac agacuggaau ggcugaucau cgaggacaau caccugagcc ggaucagccc    840
ccccaccuuc uacggccuga acucccugau ccugcuggug cugaugaaca acgugcugac    900
ccggcugccc gacaagcccc ugugucagca caugcccaga cugcacuggc uggaccugga    960
aggcaaccac auccacaacc ugcggaaccu gaccuucauc agcugcagca accugaccgu   1020
gcucgugaug cggaagaaca agauuaacca ccugaacgag aacaccuucg cccccccugca   1080
gaaacuggac gagcuggauc ugggcucuaa caagaucgag aaccugcccc cucugaucuu   1140
caaggaccug aaagagcuga gccagcugaa ccuguccuac aaccccaucc agaagaucca   1200
ggccaaccag uucgacuacc ucgugaagcu gaagucccug ucccuggaag ggaucgagau   1260
cagcaacauc cagcagcgga uguuccggcc ccugaugaau cugucccaca ucuacuucaa   1320
gaaguuccag uacugcggcu acgcccccca cgugcggagc ugcaagccua acacagacgg   1380
caucagcagc cuggaaaacc ugcuggccuc caucauccag cggguguucg ugugggugguu   1440
guccgccgug accugcuucg gcaauaucuu cgugaucugc augcggcccu acauucggag   1500
cgagaacaag cuguaugcca ugagcaucau cucccugugc ugcgccgacu gccugauggg   1560
caucuaccug uucgugaucg gcggcuucga ccugaaguuc cggggcgagu acaacaagca   1620
cgcccagcug uggauggaaa gcacccacug ccagcucgug ggcagccugg ccauccugag   1680
cacugaagug uccgugcugc ugcugaccuu ccugacccug gaaaaguaca ucugcaucgu   1740
guacccuuuc agaugcgugc ggccuggcaa gugccggacc aucacagugc ugauccugau   1800
uuggaucacc ggcuucaucg uggccuucau cccccugagc aacaaagagu ucuucaagaa   1860
uuacuacggc accaauggcg ugugcuuccc acugcacucc gaggacacag agagcaucgg   1920
cgcccagauc uacagcgugg ccaucuuccu gggcaucaau cuggccgccu ucaucaucau   1980
cguguucagc uacggcucca uguucuacuc cgugcaccag agcgccauca ccgccaccga   2040
gauccggaac caagugaaga aagagaugau ccuggccaag cgcuucuucu ucauuguguu   2100
caccgacgcc cuguguugga uuccaaucuu cgucgugaag uuccugagcc ugcugcaggu   2160
ggaaaucccc ggcacaauca ccagcugggu cgugaucuuc auccugccca ucaacagcgc   2220
ccugaacccu auccuguaca cccugaccac ccggcccuuc aaagaaauga uccaccgguu   2280
cugguacaac uaccggcaga gaaagagcau ggacagcaag ggccagaaaa ccuacgcccc   2340
uagcuucauc ugggugggaaa uguggccacu gcaggaaaug ccucccgaac ugaugaagcc   2400
```

cgaccuguuc accuaccccu gcgagaugag ccugaucucc cagagcaccc ggcugaacag 2460
cuacuccuga uaacggaccg gcgauagaug aagcucgcuu ucuugcuguc caauuucuau 2520
uaaagguucc uuuguucccu aaguccaacu acuaaacugg gggauauuau gaagggccuu 2580
gagcaucugg auucugccua auaaaaaaca uuuauuuuca uugcagcucg cuuucuugcu 2640
guccaauuuc uauuaaaggu uccuuuguuc ccuaagucca acuacuaaac ugggggauau 2700
uaugaagggc cuugagcauc uggauucugc cuaauaaaaa acauuuauuu ucauugcggc 2760
cgcaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaa 2883

<210> SEQ ID NO 5
<211> LENGTH: 1786
<212> TYPE: RNA
<213> ORGANISM: Homo sapiens

<400> SEQUENCE: 5
gggcgggacu uccggucgug ggccaugccg ggggcgggcc cggaaccgcc acggcuagaa 60
gaagucuuca cuucccagga gagccaaagc gugucuggcc cuagguggga aaagaacugg 120
cugugaccuu ugcccugacc uggaagggcc cagccuuggg cugaauggca gcacccacgc 180
ccgcccgucc ggugcugacc caccugcugg uggcucucuu cggcaugggc uccugggcug 240
cggucaaugg gaucugggug gagcuaccug ugguggucaa agagcuucca gaggguugga 300
gccuccccuc uuacgucucu gugcuugugg cucuggggaa ccugggucug cuggugguga 360
cccucuggag gaggcuggcc ccaggaaagg acgagcaggu ccccauccgg gguggugcagg 420 ugcugggcau ggugggcaca gcccugcugg ccucucugug gcaccaugug gccccagugg 480
caggacaguu gcauucugug gccuucuuag cacuggccuu ugugcuggca cuggcaugcu 540
gugccucgaa ugucacuuuc cugcccuucu ugagccaccu gccaccucgc uucuuacggu 600
cauucuuccu gggucaaggc cugagugccc ugcugcccug cgugcuggcc cuagugcagg 660 guguggggccg ccucgagugc ccgccagccc ccaucaacgg caccccuggc cccccgcucg 720
acuuccuuga gcguuuuccc gccagcaccu ucuucugggc acugacugcc cuucuggucg 780
cuucagcugc ugccuuccag ggucuucugc ugcuguugcc gccaccacca ucuguaccca 840
caggggaguu aggaucaggc cuccaggugg gagccccagg agcagaggaa gagguggaag 900
aguccucacc acugcaagag ccaccaagcc aggcagcagg caccaccccu gguccagacc 960
cuaaggccua ucagcuucua ucagcccgca gugccugccu gcugggccug uuggccgcca 1020
ccaacgcgcu gaccaauggc gugcugccug ccgugcagag cuuuuccugc uuacccuacg 1080
ggcgucuggc cuaccaccug gcuguggugc ugggcagugc ugccaauccc cuggccugcu 1140
uccuggccau gggugugcug ugcaggucuu uggcagggcu gggcggccuc ucucugcugg 1200
gcguguucug ugggggcuac cugauggcgc uggcaguccu gagccccugc ccgccccugg 1260
ugggcaccuc ggcgggggug guccucgugg ugcugucgug ggugcugugu cuuggcgugu 1320
ucuccuacgu gaagguggca gccagcuccc ugcugcaugg cgggggccgg ccggcauugc 1380
uggcagccgg cguggccauc caggugggcu cucugcucgg cgcuguugcu auguuccccc 1440
cgaccagcau cuaucacgug uuccacagca gaaaggacug ugcagacccc ugugacuccu 1500
gagccugggc aggugggac cccgcucccc aacaccuguc uuucccucaa ugcugccacc 1560

-continued

```
augccugagu gccugcagcc caggaggccc gcacaccggu acacucgugg acaccuacac   1620

acuccauagg agauccuggc uuuccagggu gggcaagggc aaggagcagg cuuggagcca   1680

gggaccagug ggggcuguag gguaagcccc ugagccuggg accuacaugu gguuugcgua   1740

auaaaaacauu uguauuuaau gaguuggcau uaaaaaaaaa aaaaaa                 1786
```

<210> SEQ ID NO 6
<211> LENGTH: 445
<212> TYPE: PRT
<213> ORGANISM: Homo sapiens

<400> SEQUENCE: 6

```
Met Ala Ala Pro Thr Pro Ala Arg Pro Val Leu Thr His Leu Leu Val
1               5                   10                  15

Ala Leu Phe Gly Met Gly Ser Trp Ala Ala Val Asn Gly Ile Trp Val
            20                  25                  30

Glu Leu Pro Val Val Val Lys Glu Leu Pro Glu Gly Trp Ser Leu Pro
        35                  40                  45

Ser Tyr Val Ser Val Leu Val Ala Leu Gly Asn Leu Gly Leu Leu Val
    50                  55                  60

Val Thr Leu Trp Arg Arg Leu Ala Pro Gly Lys Asp Glu Gln Val Pro
65                  70                  75                  80

Ile Arg Val Val Gln Val Leu Gly Met Val Gly Thr Ala Leu Leu Ala
                85                  90                  95

Ser Leu Trp His His Val Ala Pro Val Ala Gly Gln Leu His Ser Val
            100                 105                 110

Ala Phe Leu Ala Leu Ala Phe Val Leu Ala Leu Ala Cys Cys Ala Ser
        115                 120                 125

Asn Val Thr Phe Leu Pro Phe Leu Ser His Leu Pro Pro Arg Phe Leu
    130                 135                 140

Arg Ser Phe Phe Leu Gly Gln Gly Leu Ser Ala Leu Leu Pro Cys Val
145                 150                 155                 160

Leu Ala Leu Val Gln Gly Val Gly Arg Leu Glu Cys Pro Pro Ala Pro
                165                 170                 175

Ile Asn Gly Thr Pro Gly Pro Pro Leu Asp Phe Leu Glu Arg Phe Pro
            180                 185                 190

Ala Ser Thr Phe Phe Trp Ala Leu Thr Ala Leu Leu Val Ala Ser Ala
        195                 200                 205

Ala Ala Phe Gln Gly Leu Leu Leu Leu Leu Pro Pro Pro Pro Ser Val
    210                 215                 220

Pro Thr Gly Glu Leu Gly Ser Gly Leu Gln Val Gly Ala Pro Gly Ala
225                 230                 235                 240

Glu Glu Glu Val Glu Glu Ser Ser Pro Leu Gln Glu Pro Pro Ser Gln
                245                 250                 255

Ala Ala Gly Thr Thr Pro Gly Pro Asp Pro Lys Ala Tyr Gln Leu Leu
            260                 265                 270

Ser Ala Arg Ser Ala Cys Leu Leu Gly Leu Leu Ala Ala Thr Asn Ala
        275                 280                 285

Leu Thr Asn Gly Val Leu Pro Ala Val Gln Ser Phe Ser Cys Leu Pro
    290                 295                 300

Tyr Gly Arg Leu Ala Tyr His Leu Ala Val Val Leu Gly Ser Ala Ala
305                 310                 315                 320

Asn Pro Leu Ala Cys Phe Leu Ala Met Gly Val Leu Cys Arg Ser Leu
                325                 330                 335
```

```
Ala Gly Leu Gly Gly Leu Ser Leu Leu Gly Val Phe Cys Gly Gly Tyr
            340                 345                 350

Leu Met Ala Leu Ala Val Leu Ser Pro Cys Pro Pro Leu Val Gly Thr
        355                 360                 365

Ser Ala Gly Val Val Leu Val Val Leu Ser Trp Val Leu Cys Leu Gly
    370                 375                 380

Val Phe Ser Tyr Val Lys Val Ala Ala Ser Ser Leu Leu His Gly Gly
385                 390                 395                 400

Gly Arg Pro Ala Leu Leu Ala Ala Gly Val Ala Ile Gln Val Gly Ser
                405                 410                 415

Leu Leu Gly Ala Val Ala Met Phe Pro Pro Thr Ser Ile Tyr His Val
            420                 425                 430

Phe His Ser Arg Lys Asp Cys Ala Asp Pro Cys Asp Ser
        435                 440                 445
```

<210> SEQ ID NO 7
<211> LENGTH: 1911
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 7

```
gggagacgcg uguuaaauaa caaaucucaa cacaacauau acaaaacaaa cgaaucucaa     60

gcaaucaagc auucuacuuc uauugcagca auuuaaauca uuucuuuuaa agcaaaagca    120

auuuucugaa aauuuucacc auuuacgaac gauagccgcc accauggcag cacccacgcc    180

cgcccguccg gugcugaccc accugcuggu ggcucucuuc ggcaugggcu ccugggcugc    240

ggucaauggg aucugggugg agcuaccugu gguggucaaa gagcuuccag aggguuggag    300

ccucccccucu uacgucucug ugcuugugggc ucuggggaac cugggucugc ugguggugac    360

ccucuggagg aggcuggccc caggaaagga cgagcagguc cccauccggg uggugcaggu    420

gcugggcaug gugggcacag cccugcuggc cucucugugg caccaugugg ccccaguggc    480

aggacaguug cauucugugg ccuucuuagc acuggccuuu gugcuggcac uggcaugcug    540

ugccucgaau gucacuuucc ugcccuucuu gagccaccug ccaccucgcu ucuuacgguc    600

auucuuccug ggucaaggcc ugagugcccu gcugcccugc gugcuggccc uagugcaggg    660

ugugggccgc cucgagugcc cgccagcccc caucaacggc accccuggcc ccccgcucga    720

cuuccuugag cguuuucccg ccagcaccuu cuucugggca cugacugccc uucuggucgc    780

uucagcugcu gccuuccagg gucuucugcu gcuguugccg ccaccaccau cuguacccac    840

aggggaguua ggaucaggcc uccaggugggg agccccagga gcagaggaag agguggaaga    900

guccucacca cugcaagagc caccaagcca ggcagcaggc accaccccug guccagaccc    960

uaaggccuau cagcuucuau cagcccgcag ugccugccug cugggccugu uggccgccac   1020

caacgcgcug accaauggcg ugcugccugc cgugcagagc uuuuccugcu uacccuacgg   1080

gcgucuggcc uaccaccugg cuguggugcu gggcagugcu gccaaucccc uggccugcuu   1140

ccuggcaaug ggugugcugu gcagguccuu ggcagggcug ggcggccucu cucugcuggg   1200

cguguucugu gggggcuacc ugauggcgcu ggcaguccug agccccugcc cgccccuggu   1260

gggcaccucg gcgggggugg uccucguggu gcugucgugg gugcugugucc uuggcguguu   1320

cuccuacgug aagguggcag ccagcucccu gcugcauggc gggggccggc cggcauugcu   1380

ggcagccggc guggccaucc aggugggcuc ucugcucggc gcuguugcua uguucccccc   1440
```

```
gaccagcauc uaucacgugu uccacagcag aaaggacugu gcagaccccu gugacuccug   1500

acggaccggc gauagaugaa gcucgcuuuc uugcugucca auuucuauua aagguuccuu   1560

uguucccuaa guccaacuac uaaacugggg gauauuauga agggccuuga gcaucuggau   1620

ucugccuaau aaaaaacauu uauuuucauu gcagcucgcu uucuugcugu ccaauuucua   1680

uuaaagguuc cuuuguuccc uaaguccaac uacuaaacug ggggauauua ugaagggccu   1740

ugagcaucug gauucugccu aauaaaaaac auuuauuuuc auugcggccg caaaaaaaaa   1800

aaaaaaaaaa aaaaaaaaaa aaaaaaaaaa aaaaaaaaaa aaaaaaaaaa aaaaaaaaaa   1860

aaaaaaaaaa aaaaaaaaaa aaaaaaaaaa aaaaaaaaaa aaaaaaaaaa a            1911


<210> SEQ ID NO 8
<211> LENGTH: 888
<212> TYPE: RNA
<213> ORGANISM: Homo sapiens

<400> SEQUENCE: 8

auaccuuaga cccucaguca ugccagugcc ugcucugugc cugcucuggg cccuggcaau     60

ggugacccgg ccugccucag cggcccccau gggcggccca gaacuggcac agcaugagga    120

gcugacccug cucuuccaug ggacccugca gcugggccag gcccucaacg guguguacag    180

gaccacggag ggacggcuga caaaggccag gaacagccug ggucucuaug gccgcacaau    240

agaacuccug ggcaggaggg ucagccgggg ccgggaugca gcccaggaac uucgggcaag    300

ccuguuggag acucagaugg aggaggauau ucugcagcug caggcagagg ccacagcuga    360

ggugcugggg gagguggccc aggcacagaa ggugcuacgg gacagcgugc agcggcuaga    420

aguccagcug aggagcgccu ggcugggccc ugccuaccga gaauuugagg ucuuaaaggc    480

ucacgcugac aagcagagcc acauccuaug ggcccucaca ggccacgugc agcggcagag    540

gcgggagaug guggcacagc agcaucggcu gcgacagauc caggagagac uccacacagc    600

ggcgcuccca gccugaaucu gccuggaugg aacugaggac caaucaugcu gcaaggaaca    660

cuuccacgcc ccgugaggcc ccugugcagg gaggagcugc cuguucacug ggaucagcca    720

gggcgccggg ccccacuucu gagcacagag cagagacaga cgcaggcggg gacaaaggca    780

gaggauguag ccccauuggg gaggggugga ggaaggacau guacccuuuc augccuacac    840

accccucauu aaagcagagu cguggcaucu caaaaaaaaa aaaaaaaa                 888


<210> SEQ ID NO 9
<211> LENGTH: 198
<212> TYPE: PRT
<213> ORGANISM: Homo sapiens

<400> SEQUENCE: 9

Met Pro Val Pro Ala Leu Cys Leu Leu Trp Ala Leu Ala Met Val Thr
1               5                   10                  15

Arg Pro Ala Ser Ala Ala Pro Met Gly Gly Pro Glu Leu Ala Gln His
            20                  25                  30

Glu Glu Leu Thr Leu Leu Phe His Gly Thr Leu Gln Leu Gly Gln Ala
        35                  40                  45

Leu Asn Gly Val Tyr Arg Thr Thr Glu Gly Arg Leu Thr Lys Ala Arg
    50                  55                  60

Asn Ser Leu Gly Leu Tyr Gly Arg Thr Ile Glu Leu Leu Gly Gln Glu
65                  70                  75                  80

Val Ser Arg Gly Arg Asp Ala Ala Gln Glu Leu Arg Ala Ser Leu Leu
```

-continued

```
                85                  90                  95

Glu Thr Gln Met Glu Glu Asp Ile Leu Gln Leu Gln Ala Glu Ala Thr
            100                 105                 110

Ala Glu Val Leu Gly Glu Val Ala Gln Ala Gln Lys Val Leu Arg Asp
        115                 120                 125

Ser Val Gln Arg Leu Glu Val Gln Leu Arg Ser Ala Trp Leu Gly Pro
    130                 135                 140

Ala Tyr Arg Glu Phe Glu Val Leu Lys Ala His Ala Asp Lys Gln Ser
145                 150                 155                 160

His Ile Leu Trp Ala Leu Thr Gly His Val Gln Arg Gln Arg Arg Glu
                165                 170                 175

Met Val Ala Gln Gln His Arg Leu Arg Gln Ile Gln Glu Arg Leu His
            180                 185                 190

Thr Ala Ala Leu Pro Ala
        195


<210> SEQ ID NO 10
<211> LENGTH: 1266
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

gggagacgcg uguuaaauaa caaaucucaa cacaacauau acaaaacaaa cgaaucucaa     60

gcaaucaagc auucuacuuc uauugcagca auuuaaauca uuucuuuuaa agcaaaagca    120

auuuucugaa aauuuucacc auuuacgaac gauagccgcc accaugaaga ccuucauccu    180

gcugcugugg gugcugcugc ugugggucau cuuccugcug ccuggcgcca cagccgcucc    240

uaugggagga ccugaacugg cccagcacga ggaacugacc cugcuguuuc acggcacccu    300

gcagcuggga caggcccuga auggcgugua cagaaccacc gagggccggc ugaccaaggc    360

cagaaauagc cugggccugu acggccggac caucgaacug cuggggcagg aaguguccag    420

aggcagagau gccgcccagg aacugagagc cagccugcug gaaacccaga uggaagagga    480

cauccugcag cugcaggccg aggccacagc ugaggugcug ggagaagugg cccaggccca    540

gaaggugcug agagacagcg ugcagcggcu ggaagugcag cugagaucug ccuggcuggg    600

cccugccuac cgcgaguucg aagugcugaa agcccacgcc gacaagcaga gccacauccu    660

gugggcccug acaggccacg ugcagagaca gaggcgggaa augguggcuc agcagcacag    720

acugcggcag auccaggaac ggcugcauac agcugcccug cccgccgacu acaaggacga    780

cgacgacaag caccaccacc aucaccacgg cggaggccug aacgacaucu ucgaagccca    840

gaaaaucgag uggcacgagu aacggaccgg cgauagauga agcucgcuuu cuugcugucc    900

aauuucuauu aaagguuccu uuguucccua aguccaacua cuaaacuggg ggauauuaug    960

aagggccuug agcaucugga uucugccuaa uaaaaaacau uuauuuucau ugcagcucgc   1020

uuucuugcug uccaauuucu auuaaagguu ccuuuguucc cuaaguccaa cuacuaaacu   1080

gggggauauu augaagggcc uugagcaucu ggauucugcc uaauaaaaaa cauuuauuuu   1140

cauugcaaaa aaaaaaaaaa aaaaaaaaaa aaaaaaaaaa aaaaaaaaaa aaaaaaaaaa   1200

aaaaaaaaaa aaaaaaaaaa aaaaaaaaaa aaaaaaaaaa aaaaaaaaaa aaaaaaaaaa   1260

aaaaaa                                                              1266
```

<210> SEQ ID NO 11
<211> LENGTH: 9
<212> TYPE: RNA
<213> ORGANISM: Unknown
<220> FEATURE:
<223> OTHER INFORMATION: Description of Unknown:
Kozak sequence

<400> SEQUENCE: 11 gccaccaug 9

<210> SEQ ID NO 12
<211> LENGTH: 13
<212> TYPE: RNA
<213> ORGANISM: Unknown
<220> FEATURE:
<223> OTHER INFORMATION: Description of Unknown:
Kozak sequence

<400> SEQUENCE: 12
gccgccrcca ugg 13

<210> SEQ ID NO 13
<211> LENGTH: 8
<212> TYPE: RNA
<213> ORGANISM: Unknown
<220> FEATURE:
<223> OTHER INFORMATION: Description of Unknown:
Kozak sequence
<220> FEATURE:
<221> NAME/KEY: modified_base
<222> LOCATION: (3)..(4)
<223> OTHER INFORMATION: a, g, c or u
<220> FEATURE:
<221> NAME/KEY: modified_base
<222> LOCATION: (8)..(8)
<223> OTHER INFORMATION: a, g, c or u

<400> SEQUENCE: 13 agnnaugn 8

<210> SEQ ID NO 14
<211> LENGTH: 4410
<212> TYPE: RNA
<213> ORGANISM: Homo sapiens

<400> SEQUENCE: 14
ccuccuccac aguggugagg ucacagcccc uuggagcccu cccucuuccc accccucccg 60
cucccggguc uccuuuggcc uggggguaacc cgaggugcag agcugagaau gaggcgauuu 120
cggaggaugg agaaauagcc ccgagucccg uggaaaauga ggccggcgga cuugcugcag 180
cuggugcugc ugcucgaccu gcccagggac cugggcggaa uggggguguuc gucuccaccc 240 ugcgagugcc aucaggagga ggacuucaga gucaccugca aggauauuca acgcaucccc 300
agcuuaccgc ccaguacgca gacucugaag cuuauugaga cucaccugag aacuauucca 360
agucaugcau uuucuaaucu gcccaauauu uccagaaucu acguaucuau agaugugacu 420
cugcagcagc uggaaucaca cuccuucuac aauuugagua aagugacuca cauagaaauu 480
cggaauacca ggaacuuaac uuacauagac ccugaugccc ucaaagagcu cccccuccua 540
aaguuccuug gcauuuucaa cacuggacuu aaaauguucc cugaccugac caaaguuuau 600
uccacugaua uauucuuuau acuugaaauu acagacaacc cuuacaugac gucaaucccu 660
gugaaugcuu uucagggacu augcaaugaa accuugacac ugaagcugua caacaauggc 720
uuuacuucag uccaaggaua ugcuuucaau gggacaaagc uggaugcugu uuaccuaaac 780

-continued

```
aagaauaaau accugacagu uauugacaaa gaugcauuug gaggaguaua caguggacca    840
agcuugcugg acgugucuca aaccaguguc acugcccuuc cauccaaagg ccuggagcac    900
cugaaggaac ugauagcaag aaacaccugg acucuuaaga aacuuccacu uuccuugagu    960
uuccuucacc ucacacgggc ugaccuuucu uacccaagcc acugcugugc uuuuaagaau   1020
cagaagaaaa ucagaggaau ccuugagucc uugaugugua augagagcag uaugcagagc   1080
uugcgccaga gaaaaucugu gaaugccuug aauagccccc uccaccagga auaugaagag   1140
aaucugggug acagcauugu uggguacaag gaaaagucca aguuccagga uacucauaac   1200
aacgcucauu auuacgucuu cuuugaagaa caagaggaug agaucauugg uuuuggccag   1260
gagcucaaaa acccccagga agagacucua caagcuuuug acagccauua ugacuacacc   1320
auauguggggg acagugaaga cauggugugu acccccaagu ccgaugaguu caacccgugu   1380
gaagacauaa ugggcuacaa guuccugaga auuguggugu gguucguuag ucugcuggcu   1440
cuccugggca augucuuugu ccugcuuauu cuccucacca gccacuacaa acugaacguc   1500
ccccgcuuuc ucaugugcaa ccuggccuuu gcggauuucu gcauggggau guaccugcuc   1560
cucaucgccu cuguagaccu cuacacucac ucugaguacu acaaccaugc caucgacugg   1620
cagacaggcc cugggugcaa cacggcuggu uucuucacug ucuuugcaag cgaguuaucg   1680
guguauacgc ugacggucau cacccuggag cgcugguaug ccaucaccuu cgccaugcgc   1740
cuggaccgga agauccgccu caggcacgca ugugccauca ugguuggggg cuggguuugc   1800
ugcuuccuuc ucgcccugcu uccuuuggug ggaauaagua gcuaugccaa agucaguauc   1860
ugccugccca uggacaccga gaccccucuu gcucuggcau auauuguuuu uguucugacg   1920
cucaacauag uugccuucgu caucgucugc ugcuguuaug ugaagaucua caucacaguc   1980
cgaaauccgc aguacaaccc aggggacaaa gauaccaaaa uugccaagag gauggcugug   2040
uugaucuuca ccgacuucau augcauggcc ccaaucucau ucuaugcucu gucagcaauu   2100
cugaacaagc cucucaucac uguuagcaac uccaaaaucu ugcugguacu cuucuaucca   2160
cuuaacuccu gugccaaucc auuccucuau gcuauuuuca ccaaggccuu ccagagggau   2220
guguucaucc uacucagcaa guuuggcauc uguaaacgcc aggcucaggc auaccggggg   2280
cagaggguuc cuccaaagaa cagcacugau auucagguuc aaaagguuac ccacgagaug   2340
aggcaggguc ucccacaacau ggaagauguc uaugaacuga uugaaaacuc ccaucuaacc   2400
ccaaagaagc aaggccaaau cucagaagag uauaugcaaa cgguuuugua aguuaacacu   2460
acacuacuca caaugguagg ggaacuuaca aaauaauagu uucuugaaua ugcauuccaa   2520
ucccaugaca cccccaacac auagcugccc ucacucuugu gcaggcgaug uuucaauguu   2580
ucauggggca agaguuuauc ucuggagagu gauuaguauu aaccuaauca uugcccccaa   2640
gaaggaaguu aggcuaccag cauauuugaa ugccagguga aaucaaaaua aucuacacua   2700
ucuagaagac uuucuugaug ccaaguccag agaugucauu guguaggaug uucaguaaau   2760
auuaacugag cuaugucaau auagagcuuc ucaguuuugu auaacauuuc auacuaaaga   2820
uucagcaaau ggaaaaugcu auuaauuugg uuggugacca caagauaaaa ucagucccac   2880
guuggcucag uucaacuaga uguucccuga uacaaagaga acuugauuuc cuuaaaacug   2940
aaaagccaaa cacagcuagc ugucauacaa gaaacagcua uuaugagaca ugaaggaggg   3000
uaagaauuag cuuuaaguuu uguuuugcuu uguuuuguuu uuuaacucaa ccuauuaauc   3060
aucucuucac aagaauccac cugaugugac caagcuauua uguguugccu ggaaaaacug   3120
```

```
gcaagauuuc agcuuaugug gccuagcaaa cuaagaauug cucuucuugg ccagccucau   3180

agcauaaaag augugaacuc uaggaagucu uucugaguag caauaagugg gaauuauggg   3240

cagagcacac ucaaucccu guugauuaau aaaacaggcu ggacacuaau uaacuauggg    3300

acuuaaaucu guagaaauga aggaguccaa uagcuucuuc caauuuuaaa acucuaguac   3360

aucccuuucc cucaaauaua uauuucuaag auaaagagaa agaagagcac uaaguaagua   3420

gaaucuguuu uuccuauuuu guagggcugc ugacuccuag uccuugaagc cuagacacau   3480

gacccaggaa auuuuuccuu uguuucacuu uugauuauga ugucugagcc aaaaauucaa   3540

uuaaguaaac auacucgccu ggaucugaau cauucauuua auuacuagau cuacccagcu   3600

guuauaucag gccaaaaaca gauucguguu uauauaaaag aguaaacgau gguugcaaau   3660

uuuggcuauu uagaguugcu acuucacuau gaagagucac uucaaaacac uucgcuuguc   3720

uuuagggaug auuuuugcca uuuccagucc acgguaugau acuaaagcug ucaagagagg   3780

uuucuucuuu ucugaaacug ccagcucuuu ccagcccugu ugaucacugg acauaaagcu   3840

ucuuuucccc aauaauucuu cuuuacuuaa aauagucagg aucuuuaucu acagauguac   3900

ucuccagguu accugugaug auagccccu aauguccugc uagaaaaguc uccaagcaga    3960

gaugacauua cuucugaaug cucauaaacc acaccaugaa auaaaagcuc uuuguuguuu   4020

uaagauugug aagugucguu aaugggucc cacagauggu cccugcugga cucaccugga    4080

aucucuccac agccauaccc acucaucacu aucauugaga ccugcacauc uuaauagaaa   4140

uauuauaaac aucgaaaauc augacuuacc uagaaguucg cuuguaacua augaaauuaa   4200

acaaaugugu ugccuuuugu cauguguuuc ucuccuguga cauuucaaaa uaucacaucu   4260

ugauaaauaa uguguuucau cuugaauagc ugaacuaauu gcuuuggaaa cagaguccua   4320

gaaaagugac uucaacagaa uuguuacuaa aauuugcacu cacaacauga aauaaauuuu   4380

cuuccuaugg aauaaucgug aaaaaaaaaa                                    4410
```

<210> SEQ ID NO 15
<211> LENGTH: 764
<212> TYPE: PRT
<213> ORGANISM: Homo sapiens

<400> SEQUENCE: 15

```
Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140
```

-continued

```
Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
```

-continued

```
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
        595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
        675                 680                 685

Val Phe Ile Leu Leu Ser Lys Phe Gly Ile Cys Lys Arg Gln Ala Gln
    690                 695                 700

Ala Tyr Arg Gly Gln Arg Val Pro Pro Lys Asn Ser Thr Asp Ile Gln
705                 710                 715                 720

Val Gln Lys Val Thr His Glu Met Arg Gln Gly Leu His Asn Met Glu
                725                 730                 735

Asp Val Tyr Glu Leu Ile Glu Asn Ser His Leu Thr Pro Lys Lys Gln
            740                 745                 750

Gly Gln Ile Ser Glu Glu Tyr Met Gln Thr Val Leu
        755                 760
```

```
<210> SEQ ID NO 16
<211> LENGTH: 2871
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16

gggagacgcg uguuaaauaa caaaucucaa cacaacauau acaaaacaaa cgaaucucaa      60

gcaaucaagc auucuacuuc uauugcagca auuuaaauca uuucuuuuaa agcaaaagca     120

auuuucugaa aauuuucacc auuuacgaac gauagccgcc accaugaggc cugccgaccu     180

gcugcagcug gugcugcugc uggaccugcc uagagaucug ggcggcaugg gcuguagcag     240

cccuccaugc gagugccacc aggaagagga cuucagagug accugcaagg acauccagag     300

aauccccagc cugcccccca gcacccagac ccugaagcug aucgagacac accugagaac     360

caucccuagc cacgccuuca gcaaccugcc caacaucagc agaaucuacg uguccaucga     420

cgugacccug cagcagcugg aaagccacag cuucuacaac cugagcaaag ugacccacau     480

cgagaucaga aacacccgga accugaccua caucgacccc gacgcccuga aagagcugcc     540

ccugcugaag uuccugggca ucuucaacac cggccugaag auguuccccg accugaccaa     600

gguguacucu accgacaucu ucuucauccu ggaaaucacc gacaaccccu acaugaccag     660

cauccccgug aacgccuucc agggccugug caacgagaca cugacacuga agcuguacaa     720

caacggcuuc accagcgugc agggcuacgc cuucaacggc acaaagcugg acgccgugua     780

ccugaacaag aacaaguacc ugaccgugau cgacaaggac gccuucggcg gcguguacuc     840

uggaccuucu cugcuggacg ugucccagac cagcgugaca gcccugccua gcaagggccu     900
```

ggaacaccug aaagaacuga ucgcccgcaa caccuggacu cugaagaagc ugccucugag 960
ccugagcuuc cugcaccuga ccagagccga ccugagcuac ccaagccacu gcugcgccuu 1020
caagaaccag aagaagaucc ggggaauccu ggaaucccug auguguaacg agagcagcau 1080
gcagagccug agacagagaa agucugugaa cgcucugaac agccccccugc accaggaaua 1140 cgaggaaaac cugggcgaca gcaucguggg cuacaaagag aaguccaagu uccaggacac 1200
ccacaacaac gcccacuacu acguguucuu cgaggaacag gaagaugaga ucaucggcuu 1260
cggccaggaa cugaagaacc cucaggaaga gacacugcag gccuucgaca gccacuacga 1320
cuacaccauc ugcggcgaca gcgaggacau ggugugcacc ccuaagagcg acgaguucaa 1380
ccccugcgag gauauuaugg gguacaaguu ccugaggauc gucguguggu ucgugucccu 1440
gcuggcucug cugggcaacg uguucgugcu gcugauccug cugaccuccc acuacaagcu 1500
gaacgugccc agauuccuga ugugcaaccu ggccuucgcc gacuucugca ugggcaugua 1560
ccugcugcug auugccagcg uggaccugua cacccacagc gaguacuaca accacgccau 1620
cgacuggcag accggcccug gcuguaacac cgccggcuuu uucaccgugu ucgccagcga 1680
gcugagcgug uacacccuga cagugaucac ccuggaaagg ugguacgcca ucaccuucgc 1740
caugagacug gacagaaaga ucagacugag acacgccugc gccaucaugg ugggaggcug 1800
ggugugcugu uuccugcugg cccugcugcc ccucgugggc aucagcucuu acgccaaggu 1860
guccaucugc cugcccaugg acaccgagac accucuggcc cuggccuaca uuguguuugu 1920
gcugacccug aacaucgugg ccuucgugau cgugugcugc uguuacguga agaucuacau 1980
caccgugcgg aacccccagu acaaccccgg cgacaaggau accaagaucg ccaagagaau 2040
ggccgugcug aucuucaccg acuucaucug cauggccccc aucagcuucu augcccugag 2100
cgccauucug aacaagccuc ugaucaccgu guccaacagc aaaauccugc uggugcuguu 2160
cuacccccug aacagcugcg ccaacccccuu ccuguacgcu aucuucacca aggccuucca 2220
gagggacgug uucauccugc ugucuaaguu cggcaucugc aagagacagg cccaggccua 2280
ccggggccag agagugccuc cuaagaacuc cacagacauc caggugcaga aagugacaca 2340
cgacaugaga cagggccugc acaacaugga agauguguac gagcugauug agaacagcca 2400
ccugaccccc aagaaacagg gacagaucag cgaagaguac augcagaccg ugcugugaua 2460
acggaccggc gauagaugaa gcucgcuuuc uugcugucca auuucuauua aagguuccuu 2520
uguucccuaa guccaacuac uaaacugggg gauauuauga agggccuuga gcaucuggau 2580
ucugccuaau aaaaaacauu uauuuucauu gcagcucgcu uucuugcugu ccaauuucua 2640
uuaaagguuc cuuuguuccc uaaguccaac uacuaaacug ggggauauua ugaagggccu 2700
ugagcaucug gauucugccu aauaaaaaac auuuauuuuc auugcggccg caaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa a 2871

<210> SEQ ID NO 17
<211> LENGTH: 3877
<212> TYPE: RNA
<213> ORGANISM: Homo sapiens

<400> SEQUENCE: 17
ggaaagccga cuugcaaaac cacagauaau guucagccca gcacaguagg ggucaauuug 60
guccacuugc ucagugacaa aaagaaaaaa aaagugggcu gucacuaaag auuuugacuc 120
acaagagagg ggcuggucug gaggugggag gagggaguga cgagucaagg aggagacagg 180

```
gacgcaggag ggugcaagga agugucuuaa cugagacggg gguaaggcaa gagagggugg    240
aggaaauucu gcaggagaca ggcuuccucc agggucugga gaacccagag gcagcuccuc    300
cugagugcug ggaaggacuc ugggcaucuu cagcccuucu uacucucuga ggcucaagcc    360
agaaauucag gcugcuugca gaguggguga cagagccacg gagcuggugu cccugggacc    420
cucugcccgu cuucucucca cuccccagca uggaggaagg uggugauuuu gacaacuacu    480
auggggcaga caaccagucu gagugugagu acacagacug gaaauccucg ggggcccuca    540
ucccugccau cuacauguug gucuuccucc ugggcaccac gggcaacggu cuggugcucu    600
ggaccguguu ucggagcagc cgggagaaga ggcgcucagc ugauaucuuc auugcuagcc    660
uggcggugge ugaccugacc uucgugguga cgcugcccu gugggcuacc uacacguacc    720
gggacuauga cuggcccuuu gggaccuucu ucugcaagcu cagcagcuac cucaucuucg    780
ucaacaugua cgccagcguc uucugccuca ccggccucag cuucgaccgc uaccuggcca    840
ucgugaggcc aguggccaau gcucggcuga ggcugcgggu cagcggggcc guggccacgg    900
caguucuuug ggugcuggcc gcccuccugg ccaugccugu cauggguguua cgcaccaccg    960
gggacuugga gaacaccacu aaggugcagu gcuacaugga cuacuccaug guggccacug   1020
ugagcucaga gugggccugg gaggugggcc uugggggucuc guccaccacc gugggcuuug   1080
uggugcccuu caccaucaug cugaccuguu acuucuucau cgcccaaacc aucgcuggcc   1140
acuuccgcaa ggaacgcauc gagggccugc ggaagcggcg ccggcugcuc agcaucaucg   1200
uggugcuggu ggugaccuuu gcccugugcu ggaugcccua ccaccuggug aagacgcugu   1260
acaugcuggg cagccugcug cacuggcccu gugacuuuga ccucuuccuc augaacaucu   1320
uccccuacug caccugcauc agcuacguca acagcugccu caaccccuuc cucuaugccu   1380
uuuucgaccc ccgcuuccgc caggccugca ccuccaugcu cugcuguggc cagagcaggu   1440
gcgcaggcac cucccacagc agcagugggg agaagucagc cagcuacucu ucggggcaca   1500
gccaggggcc cggccccaac augggcaagg guggagaaca gaugcacgag aaauccaucc   1560
ccuacagcca ggagacccuu gugguugacu agggcuggga gcagagagaa gccuggcgcc   1620
cucggcccuc cccggccuuu gcccuugcuu ucugaaaauc agguagugug gcuacuccuu   1680
guccuaugca cauccuuuaa cuguccccug auucugcccc gcccuguccu ccucuacugc   1740
uuuauucuuu cucagagguu ugugguuuag gggaaagaga cugggcucua cagaccugac   1800
ccugcacaag ccauuuaauc ucacucagcc ucaguuucuc cauugguaug aaaugggga   1860
aagucauauu gauccuaaaa uguugaagcc ugagucugga cgcaguaaaa gcuuguuucc   1920
cucugcugcu uucuuagauc ugcaaucguc uuuccucccu ucuuuccuug uaguuuuucc   1980
cccaccacuc ucugcagcug ccgcuccuua ucccugccuu cuggcaccaa uccccuccua   2040
cagcucgucc cccucccucc auccauccuu cuccccuguc uacuuucuug uucugaaggg   2100
cuacuaaggg uuaaggaucc caaagcuugc agagacugac ccuguuuaag cuuucuaucc   2160
uguuuucuga gugugaggca gggaaugggc uggggccggg ggugggcugu gugucagcag   2220
auaauuagug cuccagcccu uagaucuggg agcuccagag cuugcccuaa aauuggauca   2280
cuucccuguc auuuugggca uuggggcuag ugugauuccu gcaguucccc cauggcacca   2340
ugacacugac uagauaugcu uucuccaaau uguccgcaga cccuuucauc cuuccucuau   2400
uuucuaugag aauuggaagg cagcagggcu gaugaaugga uguacuccuu gguuucauua   2460
ugugaguggg gaguugggaa gggcaacuag agagagagga uggagggug ucugcauuua   2520
```

```
guccagacac ugcuuggcuc gcuccccgag uccuccuguu ucugacuucc ugcauaacug   2580

ugagcugaag gguuuccuca ucuccccauc uuaccccauc auacugauuu cuuucuuggg   2640

cacuggugcu acuuggugcc aagaaucaug uuguuuggga uggagaugcc ugccucuugu   2700

cugugugugu uguacuuaua ugucuauaug gaugagccug gcaugaacag cagugugccu   2760

gggucauuug gacaaaccuc cucccacccc ccaauccacu gcaacucugc uguucacaca   2820

uuacccuugg caggggggugg ugggggggcag ggacacacug aggcaaugaa aaauguagaa   2880

uaaaaaugag uccacccccu acuggauuug ggggcuccaa cggcuggucc gugcuuuagg   2940

agcgaaguua auguuugcac caggcuuccu guagggagau cccuccccaa agcagcuggc   3000

gccaaggcuu gggggcgucc uacugagcug gguuccugcu ccuucuuggg cuccaugaag   3060

gaaguaagag gcuaguugag agccucccuu ggccccuuuc cggugccucc ccgccuggcu   3120

ucaaauuuau gagcauugcc cucaucgucc uuucuuguuc cagggucagu ggcccucuuc   3180

cuaaggaggc cuccugcuug ccaugggcca aaaggcacgg ggugggguuu uucucucccu   3240

acccucagga uuggaccucu uggcuucugc uggauugggg aucugggaau agggacugga   3300

gcaagugugc agauagcaug augucuacac ugccagagag accgugagga ugaaauuaau   3360

aguggggccu uugugagcua gaggcuggga gugucuauuc cggguuuugu ucuuggagga   3420

cuaugaaagu gaaggacaag acaugagcga uggagauaag aaaagcccag cuugauguga   3480

auggacaucu ugacccuccc uggaaugacg ccagcucugg gggcagaggg aggaggagag   3540

gggaaggggc uccucacagc cuagucuccc caucuuaaga uagcaucuuu cacagaguca   3600

ccuccucugc ccagagcugu ccucaaagca uccagugaac acuggaagag gcuucuagaa   3660

gggaagaaau uguccccucug aggccgccgu gggugaccug cagagacuuc cugccuggaa   3720

cucaucugug aacugggaca gaagcagagg aggcugccug cugugauacc cccuuaccuc   3780

ccccagugcc uucuucagaa uaucugcacu gucuucugau ccuguuaguc acugugguuc   3840

aucaaauaaa acuguuugug caacuguugu guccaaa                            3877
```

<210> SEQ ID NO 18
<211> LENGTH: 380
<212> TYPE: PRT
<213> ORGANISM: Homo sapiens

<400> SEQUENCE: 18

```
Met Glu Glu Gly Gly Asp Phe Asp Asn Tyr Tyr Gly Ala Asp Asn Gln
1               5                   10                  15

Ser Glu Cys Glu Tyr Thr Asp Trp Lys Ser Ser Gly Ala Leu Ile Pro
            20                  25                  30

Ala Ile Tyr Met Leu Val Phe Leu Leu Gly Thr Thr Gly Asn Gly Leu
        35                  40                  45

Val Leu Trp Thr Val Phe Arg Ser Ser Arg Glu Lys Arg Arg Ser Ala
    50                  55                  60

Asp Ile Phe Ile Ala Ser Leu Ala Val Ala Asp Leu Thr Phe Val Val
65                  70                  75                  80

Thr Leu Pro Leu Trp Ala Thr Tyr Thr Tyr Arg Asp Tyr Asp Trp Pro
                85                  90                  95

Phe Gly Thr Phe Phe Cys Lys Leu Ser Ser Tyr Leu Ile Phe Val Asn
            100                 105                 110

Met Tyr Ala Ser Val Phe Cys Leu Thr Gly Leu Ser Phe Asp Arg Tyr
        115                 120                 125

Leu Ala Ile Val Arg Pro Val Ala Asn Ala Arg Leu Arg Leu Arg Val
```

```
    130                 135                 140

Ser Gly Ala Val Ala Thr Ala Val Leu Trp Val Leu Ala Ala Leu Leu
145                 150                 155                 160

Ala Met Pro Val Met Val Leu Arg Thr Thr Gly Asp Leu Glu Asn Thr
                165                 170                 175

Thr Lys Val Gln Cys Tyr Met Asp Tyr Ser Met Val Ala Thr Val Ser
            180                 185                 190

Ser Glu Trp Ala Trp Glu Val Gly Leu Gly Val Ser Ser Thr Thr Val
        195                 200                 205

Gly Phe Val Val Pro Phe Thr Ile Met Leu Thr Cys Tyr Phe Phe Ile
    210                 215                 220

Ala Gln Thr Ile Ala Gly His Phe Arg Lys Glu Arg Ile Glu Gly Leu
225                 230                 235                 240

Arg Lys Arg Arg Arg Leu Leu Ser Ile Ile Val Val Leu Val Val Thr
                245                 250                 255

Phe Ala Leu Cys Trp Met Pro Tyr His Leu Val Lys Thr Leu Tyr Met
            260                 265                 270

Leu Gly Ser Leu Leu His Trp Pro Cys Asp Phe Asp Leu Phe Leu Met
        275                 280                 285

Asn Ile Phe Pro Tyr Cys Thr Cys Ile Ser Tyr Val Asn Ser Cys Leu
    290                 295                 300

Asn Pro Phe Leu Tyr Ala Phe Phe Asp Pro Arg Phe Arg Gln Ala Cys
305                 310                 315                 320

Thr Ser Met Leu Cys Cys Gly Gln Ser Arg Cys Ala Gly Thr Ser His
                325                 330                 335

Ser Ser Ser Gly Glu Lys Ser Ala Ser Tyr Ser Ser Gly His Ser Gln
            340                 345                 350

Gly Pro Gly Pro Asn Met Gly Lys Gly Gly Glu Gln Met His Glu Lys
        355                 360                 365

Ser Ile Pro Tyr Ser Gln Glu Thr Leu Val Val Asp
    370                 375                 380
```

<210> SEQ ID NO 19
<211> LENGTH: 1716
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19

```
gggagacgcg uguuaaauaa caaaucucaa cacaacauau acaaaacaaa cgaaucucaa     60

gcaaucaagc auucuacuuc uauugcagca auuuaaauca uuucuuuuaa agcaaaagca    120

auuuucugaa aauuuucacc auuuacgaac gauagccgcc accauggaag agggcggcga    180

cuucgacaac uacuacggcg ccgacaacca gagcgagugc gaguacaccg acuggaaguc    240

cucuggcgcc cugauccccg cuaucuacau gcugguguuu cugcugggca ccaccggcaa    300

cggacuggug cuguggaccg uguucagaag cagcagagag aagcggcgga gcgccgacau    360

cuuuaucgcc agccuggccg uggccgaccu gaccuuuguc gugacacugc cucugugggc    420

caccuacacc uaccgggacu acgacuggcc cuucggcaca uuuuucugca agcugagcag    480

cuaccugauc uucgugaaua uguacgccag cguguucugc cugaccggcc ugagcuucga    540

cagauaccug gccaucgugc ggcccguggc caacgcuaga cugcggcuga gagugucugg    600

cgccguggcu acagcugugc ugugggugcu ggcugcccug cuggcuaugc cugugauggu    660
```

```
gcugagaacc accggcgacc uggaaaacac caccaaggug cagugcuaca uggacuacag    720

cauggugggcc acagugucca gcgagugggc cugggaagug ggacugggag ugucuagcac    780

caccgugggc uucguggugc ccuucaccau uaugcugacc ugcuacuucu ucauugccca    840

gacaaucgcc ggccacuucc ggaaagagcg gaucgagggc cugcggaaga gaaggcggcu    900

gcugagcauc aucguggugc uggucgugac cuucgcccug ugcuggaugc cuuaccaccu    960

cgugaaaacc cuguauaugc ugggcagccu gcugcacugg cccugcgauu ucgaccuguu   1020

ccugaugaac aucuuccccu acugcaccug uaucagcuac gugaacagcu gccugaaccc   1080

cuuccuguac gccuucuucg acccccgguu cagacaggcc ugcaccucca ugcugugcug   1140

cggccagucu agaugcgccg gcacaagcca cagcagcagc ggcgagaagu cugccagcua   1200

cagcucuggc cacagccagg gcccaggccc caauauggga aagggcggag agcagaugca   1260

cgagaagucc aucccuuaca gccaggaaac ccugguggug gacugacgga ccggcgauag   1320

augaagcucg cuuucuugcu guccaauuuc uauuaaaggu uccuuuguuc ccuaagucca   1380

acuacuaaac ugggggauau uaugaagggc cuugagcauc uggauucugc cuaauaaaaa   1440

acauuuauuu ucauugcagc ucgcuuucuu gcuguccaau uucuauuaaa gguuccuuug   1500

uucccuaagu ccaacuacua aacuggggga uauuaugaag ggccuugagc aucuggauuc   1560

ugccuaauaa aaaacauuua uuuucauugc ggccgcaaaa aaaaaaaaaa aaaaaaaaaa   1620

aaaaaaaaaa aaaaaaaaaa aaaaaaaaaa aaaaaaaaaa aaaaaaaaaa aaaaaaaaaa   1680

aaaaaaaaaa aaaaaaaaaa aaaaaaaaaa aaaaaa                             1716


<210> SEQ ID NO 20
<211> LENGTH: 3085
<212> TYPE: RNA
<213> ORGANISM: Homo sapiens

<400> SEQUENCE: 20

gagcagccaa aaggcccgcg gagucgcgcu gggccgcccc ggcgcagcug aaccgggggc     60

cgcgccugcc aggccgacgg gucuggccca gccuggcgcc aaggggguucg ugcgcugugg   120

agacgcggag ggucgaggcg gcgcggccug agugaaaccc aauggaaaaa gcaugacauu    180

uagaaguaga agacuuagcu ucaaaucccu acuccuucac uuacuaauuu ugugauuugg    240

aaauauccgc gcaagauguu gacguugcag acuuggguag ugcaagccuu guuuauuuuc    300

cucaccacug aaucuacagg ugaacuucua gauccaugug guuauaucag uccugaaucu    360

ccaguuguac aacuucauuc uaauuucacu gcaguuugug ugcuaaagga aaaauguaug    420

gauuauuuuc auguaaaugc uaauuacauu gucuggaaaa caaaccauuu uacuauuccu    480

aaggagcaau auacuaucau aaacagaaca gcauccagug ucaccuuuac agauauagcu    540

ucauuaaaua uucagcucac uugcaacauu cuuacauucg gacagcuuga acagaauguu    600

uauggaauca caauaauuuc aggcuugccu ccagaaaaac cuaaaaauuu gaguugcauu    660

gugaacgagg ggaagaaaau gaggugugag ugggauggug gaagggaaac acacuuggag    720

acaaacuuca cuuuaaaauc ugaaugggca acacacaagu uugcugauug caaagcaaaa    780

cgugacaccc ccaccucaug cacuguugau uauucuacug uguauuuugu caacauugaa    840

gucugguag aagcagagaa ugcccuuggg aagguuacau cagaucauau caauuuugau     900

ccuguauaua aagugaagcc caauccgcca cauaauuuau cagugaucaa cucagaggaa    960

cugucuagua ucuuaaaauu gacauggacc aacccaagua uuaagagugu uauaauacua   1020
```

aaauauaaca uucaauauag gaccaaagau gccucaacuu ggagccagau uccuccugaa 1080
gacacagcau ccacccgauc uucauucacu guccaagacc uuaaaccuuu uacagaauau 1140
guguuuagga uucgcuguau gaaggaagau gguaagggau acuggaguga cuggagugaa 1200
gaagcaagug ggaucaccua ugaagauaga ccaucuaaag caccaaguuu cugguauaaa 1260
auagauccau cccauacuca aggcuacaga acuguacaac ucguguggaa gacauugccu 1320
ccuuuugaag ccaauggaaa aaucuuggau uaugaaguga cucucacaag auggaaauca 1380
cauuuacaaa auuacacagu uaaugccaca aaacugacag uaaaucucac aaaugaucgc 1440
uaucuagcaa cccuaacagu aagaaaucuu guuggcaaau cagaugcagc uguuuuaacu 1500
aucccugccu gugacuuuca agcuacucac ccuguaaugg aucuuaaagc auuccccaaa 1560
gauaacaugc uuugggugga auggacuacu ccaagggaau cuguaaagaa auauauacuu 1620
gaguggugug uguuaucaga uaaagcaccc uguaucacag acuggcaaca agaagauggu 1680
accgugcauc gcaccuauuu aagagggaac uuagcagaga gcaaaugcua uuugauaaca 1740
guuacuccag uauaugcuga uggaccagga agcccugaau ccauaaaggc auaccuuaaa 1800
caagcuccac cuuccaaagg accuacuguu cggacaaaaa aaguagggaa aaacgaagcu 1860
gucuuagagu gggaccaacu uccuguugau guucagaaug gauuuaucag aaauuauacu 1920
auauuuuaua gaaccaucau uggaaaugaa acugcuguga auguggauuc uucccacaca 1980
gaauauacau uguccucuuu gacuagugac acauuguaca ugguacgaau ggcagcauac 2040
acagaugaag gugggaagga ugguccagaa uucacuuuua cuaccccaaa guuugcucaa 2100
ggagaaauug aagccauagu cgugccuguu ugcuuagcau uccuauugac aacucuucug 2160
ggagugcugu ucugcuuuaa uaagcgagac cuaauuaaaa aacacaucug gccuaauguu 2220
ccagauccuu caaagaguca uauugcccag uggucaccuc acacuccucc aaggcacaau 2280
uuuaauucaa aagaucaaau guauucagau ggcaauuuca cugauguaag uguuguggaa 2340
auagaagcaa augacaaaaa gccuuuucca gaagaucuga aaucauugga ccuguucaaa 2400
aaggaaaaaa uuaauacuga aggacacagc agugguauug gggggucuuc augcauguca 2460
ucuucuaggc caagcauuuc uagcagugau gaaaaugaau cuucacaaaa cacuucgagc 2520
acuguccagu auucuaccgu gguacacagu ggcuacagac accaaguucc gucaguccaa 2580
gucuucucaa gauccgaguc uacccagccc uuguuagauu cagaggagcg gccagaagau 2640
cuacaauuag uagaucaugu agauggcggu gaugguauuu ugcccaggca acaguacuuc 2700
aaacagaacu gcagucagca ugaauccagu ccagauauuu cacauuuuga aaggucaaag 2760
caaguuucau cagucaauga ggaagauuuu guuagacuua aacagcagau uucagaucau 2820
auuucacaau ccuguggauc ugggcaaaug aaaauguuuc aggaaguuuc ugcagcagau 2880
gcuuuugguc cagguacuga gggacaagua gaaagauuug aaacaguugg cauggaggcu 2940
gcgacugaug aaggcaugcc uaaaaguuac uuaccacaga cuguacggca aggcggcuac 3000
augccucagu gaaggacuag uaguuccugc uacaacuuca gcaguaccua uaaaguaaag 3060
cuaaaaugau uuuaucugug aauuc 3085

<210> SEQ ID NO 21
<211> LENGTH: 918
<212> TYPE: PRT
<213> ORGANISM: Homo sapiens

<400> SEQUENCE: 21

Met Leu Thr Leu Gln Thr Trp Leu Val Gln Ala Leu Phe Ile Phe Leu

-continued

```
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Val Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430
```

-continued

```
Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
    610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
    690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
    770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
        835                 840                 845
```

-continued

```
Lys Gln Gln Ile Ser Asp His Ile Ser Gln Ser Cys Gly Ser Gly Gln
    850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
            900                 905                 910

Gly Gly Tyr Met Pro Gln
        915


<210> SEQ ID NO 22
<211> LENGTH: 3329
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 22

gggagacgcg uguuaaauaa caaaucucaa cacaacauau acaaaacaaa cgaaucucaa     60

gcaaucaagc auucuacuuc uauugcagca auuuaaauca uuucuuuuaa agcaaaagca    120

auuuucugaa aauuuucacc auuuacgaac gauagccgcc accgcaucgu gaacgagggc    180

aagaaaaugc ugacccugca gaccuggcug gugcaggccc uguucaucuu ccugaccacc    240

gagagcaccg gcgagcugcu ggacccuugu ggcuacauca gccccgagag cccuguggug    300

cagcugcaua gcaacuucac cgccgugugc gugcugaaag aaaagugcau ggacuacuuc    360

cacgugaacg ccaacuacau cgucuggaaa acaaaccacu ucaccauccc caaagagcag    420

uacaccauca ucaacagaac cgccagcagc gugaccuuca ccgauaucgc cagccugaac    480

auccagcuga ccugcaacau ccugaccuuc ggccagcugg aacagaacgu guacggcauc    540

acaaucauca gcggccugcc ccccgagaag cccaagaacc ugagcugcau cgugaacgag    600

ggcaagaaaa ugagaugcga gugggacggc ggcagagaga cacaccugga aacaaacuuc    660

acccugaagu ccgagugggc cacccacaag uucgccgacu gcaaggccaa gagggacacc    720

cccaccagcu guaccgugga cuacagcacc guguacuucg ugaacaucga agugugggug    780

gaagccgaga acgcccuggg caaagugacc agcgaccaca ucaacuucga cccuguguac    840

aaagugaagc ccaacccccc ccacaaccug agcgugauca acagcgagga acugagcagc    900

auccugaagc ugacauggac caaccccagc aucaaguccg ugaucauucu gaaguacaac    960

auccaguacc ggaccaagga cgccagcacc ugguccgaga ucccuccaga ggacaccgcc   1020

uccaccagau ccagcuucac agugcaggac cugaagccuu ucaccgagua cguguucagg   1080

auucggugca ugaaggaaga uggcaagggc uacuggagcg auuggagcga ggaagccagc   1140

ggcaucaccu acgaggacag acccucuaag gcccccagcu ucugguacaa gaucgacccc   1200

agccacaccc agggcuacag aaccgugcag cucgugugga aaacccugcc cccauucgag   1260

gccaacggca agauccugga cuacgaagug acccugacca gauggaaguc ccaucugcag   1320

aacuacaccg ugaacgcuac caagcugacc gugaaccuga caaacgacag auaccuggcc   1380

acccugaccg ugcggaaccu cgugggcaag ucugaugccg ccgugcugac cauccccgca   1440

ugcgauuuuc aagccaccca ccccgugaug gaucugaagg cuuuccccaa ggacaacaug   1500

cugugggugg aauggaccac ccccagagaa agcgugaaaa aguacauccu ggaauggugu   1560

gugcugagcg acaaggcccc cugcaucacc gauuggcagc aggaagaugg aaccgugcac   1620
```

```
agaaccuacc ugagaggcaa ccuggccgag agcaagugcu accugaucac cgugaccccc   1680

guguacgcug acggcccugg aagcccugag agcaucaagg ccuaccugaa gcaggccccu   1740

cccagcaagg gaccuacagu gcggaccaag aaagugggca agaacgaggc cgugcuggaa   1800

ugggaccagc ugccugugga ugugcagaac ggcuucauca gaaacuacac caucuucuac   1860

aggaccauca ucggcaacga gacagccgug aacguggaca gcagccacac agaguacacc   1920

cugagcagcc ugaccuccga cacccuguau auggugcgaa uggccgccua caccgacgag   1980

ggcggaaagg auggccccga guucaccuuc accacaccua aguucgcuca gggcgagauc   2040

gaggccaucg uggugccugu gugucuggcu uuccugcuga ccacccugcu gggcgugcug   2100

uucugcuuca acaagcggga ccugaucaag aagcacaucu ggcccaacgu gcccgacccu   2160

agcaagagcc auaucgccca gugguccccc cacacccccc cuagacacaa cuucaacagc   2220

aaggaccaga uguacagcga cggcaacuuu acagacgugu ccguggugga aaucgaggcu   2280

aacgauaaga agcccuuccc agaagaucug aagucccugg aucuguucaa gaaagagaag   2340

aucaacacag agggccacag cuccggcauc ggcggcagcu cuuguaugag cagcagcaga   2400

ccuagcauca gcagcagcga cgagaacgag agcagccaga acaccucuag caccgugcag   2460

uacuccaccg uggugcacag cggcuacaga caccaggugc caagcgugca gguguucagc   2520

agaagcgagu ccacccagcc ccugcuggac agcgaagaga ggccugagga ucugcagcug   2580

guggaccaug uggacggcgg agauggcauc cugcccagac agcaguacuu caagcagaac   2640

ugcucccagc acgaguccag ccccgacauc agccacuucg agagaagcaa acagguguucc   2700

agcgugaacg aagaggacuu cgugcggcug aagcagcaga ucagcgauca caucucccag   2760

agcugcggca gcggccagau gaagauguuc caggaagugu ccgccgcuga cgccuucgga   2820

ccuggaacug agggccaggu ggaaagauuc gagacagugg gcauggaagc cgccacagac   2880

gagggcaugc cuaagagcua ccugccccag acugugcggc agggcggcua caugccucag   2940

ugaagcucgc uuucuugcug uccaauuucu auuaaagguu ccuuuguucc cuaaguccaa   3000

cuacuaaacu gggggauauu augaagggcc uugagcaucu ggauucugcc uaauaaaaaa   3060

cauuuauuuu cauugcagcu cgcuuucuug cuguccaauu ucuauuaaag guuccuuugu   3120

ucccuaaguc caacuacuaa acugggggau auuaugaagg gccuugagca ucuggauucu   3180

gccuaauaaa aaacauuuau uuucauugca aaaaaaaaaa aaaaaaaaaa aaaaaaaaaa   3240

aaaaaaaaaa aaaaaaaaaa aaaaaaaaaa aaaaaaaaaa aaaaaaaaaa aaaaaaaaaa   3300

aaaaaaaaaa aaaaaaaaaa aaaaaaaaa                                     3329
```

<210> SEQ ID NO 23
<211> LENGTH: 7
<212> TYPE: RNA
<213> ORGANISM: Unknown
<220> FEATURE:
<223> OTHER INFORMATION: Description of Unknown:
      Kozak sequence
<220> FEATURE:
<221> NAME/KEY: modified_base
<222> LOCATION: (2)..(3)
<223> OTHER INFORMATION: a, g, c or u

<400> SEQUENCE: 23 annaugg 7

<210> SEQ ID NO 24
<211> LENGTH: 7

<212> TYPE: RNA
<213> ORGANISM: Unknown
<220> FEATURE:
<223> OTHER INFORMATION: Description of Unknown:
Kozak sequence

<400> SEQUENCE: 24 accaugg 7

<210> SEQ ID NO 25
<211> LENGTH: 10
<212> TYPE: RNA
<213> ORGANISM: Unknown
<220> FEATURE:
<223> OTHER INFORMATION: Description of Unknown:
Kozak sequence

<400> SEQUENCE: 25
gacaccaugg 10

<210> SEQ ID NO 26
<211> LENGTH: 1017
<212> TYPE: RNA
<213> ORGANISM: Homo sapiens

<400> SEQUENCE: 26
gaguauuuga ggcucggagc caccgccccg ccggcgcccg cagcaccucc ucgccagcag 60
ccguccggag ccagccaacg agcggaaaau ggcagacaau uuuucgcucc augaugcguu 120
aucugggucu ggaaacccaa acccucaagg auggccuggc gcaugggga accagccugc 180 uggggcaggg ggcuacccag gggcuuccua uccuggggcc uaccccgggc aggcaccccc 240
aggggcuuau ccuggacagg caccuccagg cgccuacccu ggagcaccug gagcuuaucc 300
cggagcaccu gcaccuggag ucuacccagg gccacccagc ggcccugggg ccuacccauc 360
uucuggacag ccaagugcca ccggagccua cccugccacu ggccccuaug gcgccccugc 420
ugggccacug auugugccuu auaaccugcc uuugccuggg ggaguggugc cucgcaugcu 480
gauaacaauu cugggcacgg ugaagcccaa ugcaaacaga auugcuuuag auuuccaaag 540
agggaaugau guugccuucc acuuuaaccc acgcuucaau gagaacaaca ggagagucau 600
uguuugcaau acaaagcugg auaauaacug gggaagggaa gaaagacagu cgguuuuccc 660
auuugaaagu gggaaaccau ucaaaauaca aguacugguu gaaccugacc acuucaaggu 720
ugcagugaau gaugcucacu uguugcagua caaucaucgg guuaaaaaac ucaaugaaau 780
cagcaaacug ggaauuucug gugacauaga ccucaccagu gcuucauaua ccaugauaua 840
aucugaaagg ggcagauuaa aaaaaaaaaa agaaucuaaa ccuuacaugu guaaagguuu 900
cauguucacu gugagugaaa auuuuuacau ucaucaauau cccucuugua agucaucuac 960
uuaauaaaua uuacagugaa uuaccugucu caauauguca aaaaaaaaaa aaaaaaa 1017

<210> SEQ ID NO 27
<211> LENGTH: 250
<212> TYPE: PRT
<213> ORGANISM: Homo sapiens

<400> SEQUENCE: 27

Met Ala Asp Asn Phe Ser Leu His Asp Ala Leu Ser Gly Ser Gly Asn
1 5 10 15

Pro Asn Pro Gln Gly Trp Pro Gly Ala Trp Gly Asn Gln Pro Ala Gly
20 25 30

-continued

```
Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250
```

<210> SEQ ID NO 28
<211> LENGTH: 11
<212> TYPE: DNA
<213> ORGANISM: Unknown
<220> FEATURE:
<223> OTHER INFORMATION: Description of Unknown:
Kozak sequence

<400> SEQUENCE: 28
aaaaaatgtc t 11

<210> SEQ ID NO 29
<211> LENGTH: 12
<212> TYPE: DNA
<213> ORGANISM: Unknown
<220> FEATURE:
<223> OTHER INFORMATION: Description of Unknown:
Kozak sequence
<220> FEATURE:
<221> NAME/KEY: modified_base
<222> LOCATION: (11)..(11)
<223> OTHER INFORMATION: a, g, c or t

<400> SEQUENCE: 29
aaaaaaatgr na 12

<210> SEQ ID NO 30
<211> LENGTH: 12
<212> TYPE: DNA
<213> ORGANISM: Unknown
<220> FEATURE:
<223> OTHER INFORMATION: Description of Unknown:

Kozak sequence
<220> FEATURE:
<221> NAME/KEY: modified_base
<222> LOCATION: (1)..(1)
<223> OTHER INFORMATION: a, g, c or t

<400> SEQUENCE: 30
ntaaaaatgr ct 12

<210> SEQ ID NO 31
<211> LENGTH: 12
<212> TYPE: DNA
<213> ORGANISM: Unknown
<220> FEATURE:
<223> OTHER INFORMATION: Description of Unknown:
Kozak sequence
<220> FEATURE:
<221> NAME/KEY: modified_base
<222> LOCATION: (12)..(12)
<223> OTHER INFORMATION: a, g, c or t

<400> SEQUENCE: 31
taaaaaatga an 12

<210> SEQ ID NO 32
<211> LENGTH: 10
<212> TYPE: DNA
<213> ORGANISM: Unknown
<220> FEATURE:
<223> OTHER INFORMATION: Description of Unknown:
Kozak sequence
<220> FEATURE:
<221> NAME/KEY: modified_base
<222> LOCATION: (2)..(2)
<223> OTHER INFORMATION: a, g, c or t

<400> SEQUENCE: 32 gncaaaatgg 10

<210> SEQ ID NO 33
<211> LENGTH: 11
<212> TYPE: DNA
<213> ORGANISM: Unknown
<220> FEATURE:
<223> OTHER INFORMATION: Description of Unknown:
Kozak sequence
<220> FEATURE:
<221> NAME/KEY: modified_base
<222> LOCATION: (1)..(3)
<223> OTHER INFORMATION: a, g, c or t
<220> FEATURE:
<221> NAME/KEY: modified_base
<222> LOCATION: (5)..(6)
<223> OTHER INFORMATION: a, g, c or t
<220> FEATURE:
<221> NAME/KEY: modified_base
<222> LOCATION: (10)..(10)
<223> OTHER INFORMATION: a, g, c or t

<400> SEQUENCE: 33
nnnannatgn c 11

<210> SEQ ID NO 34
<211> LENGTH: 9
<212> TYPE: DNA
<213> ORGANISM: Unknown
<220> FEATURE:
<223> OTHER INFORMATION: Description of Unknown:
Kozak sequence

<400> SEQUENCE: 34 aacaatggc 9

<210> SEQ ID NO 35
<211> LENGTH: 3874
<212> TYPE: DNA
<213> ORGANISM: Homo sapiens

<400> SEQUENCE: 35
gtgcgtgtgt gtaaagaagg agattaggac atttagagaa ggagggcggg gaggagagat 60
cctgagaata gaaaggagga aagaaaaaaa gaggaatgga aagagacaga gaaaggaaat 120
gggagtggaa ggagggagga ctgctttgta actgctaaga ttgcagacag aaatagcaca 180
caaccactgt gagctgtatg cgattcagaa accaagacca aattttgctc actttcatta 240
atcagttgct cagatagaag gaaatgacat ctggttctgt cttcttctac atcttaattt 300
ttggaaaata tttttctcat gggggtggac aggatgtcaa gtgctccctt ggctatttcc 360
cctgtgggaa catcacaaag tgcttgcctc agctcctgca ctgtaacggt gtggacgact 420
gcgggaatca ggccgatgag gacaactgtg gagacaacaa tggatggtct ctgcaatttg 480
acaaatattt tgccagttac tacaaaatga cttcccaata tcctttttgag gcagaaacac 540 ctgaatgttt ggtcggttct gtgccagtgc aatgtctttg ccaaggtctg gagcttgact 600
gtgatgaaac caatttacga gctgttccat cggtttcttc aaatgtgact gcaatgtcac 660
ttcagtggaa cttaataaga aagcttcctc ctgattgctt caagaattat catgatcttc 720
agaagctgta cctgcaaaac aataagatta catccatctc catctatgct ttcagaggac 780
tgaatagcct tactaaactg tatctcagtc ataacagaat aaccttcctg aagccgggtg 840
tttttgaaga tcttcacaga ctagaatggc tgataattga agataatcac ctcagtcgaa 900
tttccccacc aacattttat ggactaaatt ctcttattct cttagtcctg atgaataacg 960
tcctcacccg tttacctgat aaacctctct gtcaacacat gccaagacta cattggctgg 1020
accttgaagg caaccatatc cataatttaa gaaatttgac ttttatttcc tgcagtaatt 1080
taactgtttt agtgatgagg aaaaacaaaa ttaatcactt aaatgaaaat acttttgcac 1140
ctctccagaa actggatgaa ttggatttag gaagtaataa gattgaaaat cttccaccgc 1200
ttatattcaa ggacctgaag gagctgtcac aattgaatct ttcctataat ccaatccaga 1260
aaattcaagc aaaccaattt gattatcttg tcaaactcaa gtctctcagc ctagaaggga 1320
ttgaaatttc aaatatccaa caaaggatgt ttagacctct tatgaatctc tctcacatat 1380
attttaagaa attccagtac tgtgggtatg caccacatgt tcgcagctgt aaaccaaaca 1440
ctgatggaat ttcatctcta gagaatctct tggcaagcat tattcagaga gtatttgtct 1500
gggttgtatc tgcagttacc tgctttggaa acatttttgt catttgcatg cgaccttata 1560
tcaggtctga gaacaagctg tatgccatgt caatcatttc tctctgctgt gccgactgct 1620
taatgggaat atatttattc gtgatcggag gctttgacct aaagtttcgt ggagaataca 1680
ataagcatgc gcagctgtgg atggagagta ctcattgtca gcttgtagga tctttggcca 1740
ttctgtccac agaagtatca gttttactgt taacatttct gacattggaa aaatacatct 1800
gcattgtcta tccttttaga tgtgtgagac ctggaaaatg cagaacaatt acagttctga 1860
ttctcatttg gattactggt tttatagtgg ctttcattcc attgagcaat aaggaatttt 1920
tcaaaaacta ctatggcacc aatggagtat gcttccctct tcattcagaa gatacagaaa 1980
gtattggagc ccagatttat tcagtggcaa tttttcttgg tattaatttg gccgcattta 2040

-continued

```
tcatcatagt tttttcctat ggaagcatgt tttatagtgt tcatcaaagt gccataacag   2100

caactgaaat acggaatcaa gttaaaaaag agatgatcct tgccaaacgt tttttcttta   2160

tagtatttac tgatgcatta tgctggatac ccatttttgt agtgaaattt ctttcactgc   2220

ttcaggtaga aataccaggt accataacct cttgggtagt gatttttatt ctgcccatta   2280

acagtgcttt gaacccaatt ctctatactc tgaccacaag accatttaaa gaaatgattc   2340

atcggttttg gtataactac agacaaagaa aatctatgga cagcaaaggt cagaaaacat   2400

atgctccatc attcatctgg gtggaaatgt ggccactgca ggagatgcca cctgagttaa   2460

tgaagccgga cctttcaca taccccctgtg aaatgtcact gatttctcaa tcaacgagac   2520

tcaattccta ttcatgactg actctgaaat tcatttcttc gcagagaata ctgtgggggt   2580

gcttcatgag ggatttactg gtatgaaatg aataccacaa aattaattta taataatagc   2640

taagataaat attttacaag gacatgagga aaaataaaaa tgactaatgc tcttacaaag   2700

ggaagtaatt atatcaataa tgtatatata ttagtagaca ttttgcataa gaaattaaga   2760

gaaatctact tcagtaacat tcattcattt ttctaacatg catttattga gtacccacta   2820

ctatgtgcat agcattgcaa tatagtcctg gaagtagaca gtgcagaacc tttcaatctg   2880

tagatggtgt ttaatgacaa aagactatac aaagtccatc tgcagttcct agtttaaagt   2940

agagctttac ctgtcatgtg catcagcaag aatcataggc acttttaaat aaaggtttaa   3000

agttttggaa tactcagtgt atttgcatca tagaaaatgt ctgactgttt gcaaaataat   3060

attctgtttt aagaatccat cttacctctc tttaagtttc catacacttg agagccaaca   3120

caacatattt attactaaaa agatgctttg ctagaaactc aaaaacagca cttcttttgg   3180

cacttcctgc ccagttttct ctttgcttta aatgaacatc atcatatgga attggaatag   3240

gagagtatga gtacggcaga gaagtggatc agaaaaacta gaatgaggat aaacatttac   3300

attagtggaa actcctgaaa taaatccttg tattgtcagt taactgattt tcaacaagga   3360

tgccaagaca aaaaggcttt tcaacaaacc gtgctgtttt aagaacagac ctaagtggtt   3420

taattcaccc actttagatg ggtgaatgtt atggtgtgtg aaatatctca gtaaagcagt   3480

taaaaggaaa aagagctgga atgcactgat tcaggaactt aatttcagga aggaaaggtc   3540

tgtatgtaca catttcactt taagcagaaa atctttcttc aagaaatgac tttactttct   3600

ctttgcactg ccagcacgtg agatactaac tttttaacta gttgttcttc tctagtctct   3660

acgttattag aatttttttgc tttcataatg tgaaaccttt aagcaggaga agaaaatgtt   3720

ttcagatagt ttcaaataca ccaaaaatgt ttgaaacaca aaaatactgg aatcaaacca   3780

taatgcactt attgaatata tagttgtata gatttgttct gaaaataaat tatctgaaat   3840

ttaactatta aaaaaaaaaa aaaaaaaaaa aaaa                               3874
```

<210> SEQ ID NO 36
<211> LENGTH: 2883
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
ggaggccgga gaattgtaat acgactcact atagggagac gcgtgttaaa taacaaatct     60

caacacaaca tatacaaaac aaacgaatct caagcaatca agcattctac ttctattgca    120

gcaatttaaa tcatttcttt taaagcaaaa gcaattttct gaaaattttc accatttacg    180
```

-continued

```
aacgatagcc gccaccatga caagcggcag cgtgttcttc tacatcctga tcttcggcaa    240
gtacttcagc cacggcggag gccaggacgt gaagtgtagc ctgggctact tcccctgcgg    300
caacatcacc aagtgcctgc cccagctgct gcactgcaac ggcgtggacg attgcggcaa    360
ccaggccgac gaggacaact gcggcgacaa caatggctgg tccctgcagt tcgataagta    420
cttcgcctcc tactacaaga tgaccagcca gtaccccttc gaggccgaga cacctgagtg    480
cctcgtgggc tctgtgcctg tgcagtgtct gtgccagggc ctggaactgg actgcgacga    540
gacaaacctg agagccgtgc ccagcgtgtc cagcaacgtg acagccatga gcctgcagtg    600
gaacctgatc cggaagctgc cccccgactg cttcaagaac taccacgacc tgcagaagct    660
gtatctgcag aacaacaaga tcacctccat cagcatctac gccttccggg gcctgaacag    720
cctgaccaag ctgtacctga gccacaaccg gatcaccttt ctgaagcccg gcgtgttcga    780
ggacctgcac agactggaat ggctgatcat cgaggacaat cacctgagcc ggatcagccc    840
ccccaccttc tacggcctga actccctgat cctgctggtg ctgatgaaca acgtgctgac    900
ccggctgccc gacaagcccc tgtgtcagca catgcccaga ctgcactggc tggacctgga    960
aggcaaccac atccacaacc tgcggaacct gaccttcatc agctgcagca acctgaccgt   1020
gctcgtgatg cggaagaaca agattaacca cctgaacgag aacaccttcg ccccccctgca   1080
gaaactggac gagctggatc tgggctctaa caagatcgag aacctgcccc ctctgatctt   1140
caaggacctg aaagagctga gccagctgaa cctgtcctac aaccccatcc agaagatcca   1200
ggccaaccag ttcgactacc tcgtgaagct gaagtccctg tccctggaag ggatcgagat   1260
cagcaacatc cagcagcgga tgttccggcc cctgatgaat ctgtcccaca tctacttcaa   1320
gaagttccag tactgcggct acgcccccca cgtgcggagc tgcaagccta acacagacgg   1380
catcagcagc ctggaaaacc tgctggcctc catcatccag cgggtgttcg tgtgggtggt   1440
gtccgccgtg acctgcttcg gcaatatctt cgtgatctgc atgcggccct acattcggag   1500
cgagaacaag ctgtatgcca tgagcatcat ctccctgtgc tgcgccgact gcctgatggg   1560
catctacctg ttcgtgatcg gcggcttcga cctgaagttc cggggcgagt acaacaagca   1620
cgcccagctg tggatggaaa gcacccactg ccagctcgtg ggcagcctgg ccatcctgag   1680
cactgaagtg tccgtgctgc tgctgacctt cctgaccctg gaaaagtaca tctgcatcgt   1740
gtaccctttc agatgcgtgc ggcctggcaa gtgccggacc atcacagtgc tgatcctgat   1800
ttggatcacc ggcttcatcg tggccttcat cccccctgagc aacaaagagt tcttcaagaa   1860
ttactacggc accaatggcg tgtgcttccc actgcactcc gaggacacag agagcatcgg   1920
cgcccagatc tacagcgtgg ccatcttcct gggcatcaat ctggccgcct tcatcatcat   1980
cgtgttcagc tacggctcca tgttctactc cgtgcaccag agcgccatca ccgccaccga   2040
gatccggaac caagtgaaga aagagatgat cctggccaag cgcttcttct tcattgtgtt   2100
caccgacgcc ctgtgttgga ttccaatctt cgtcgtgaag ttcctgagcc tgctgcaggt   2160
ggaaatcccc ggcacaatca ccagctgggt cgtgatcttc atcctgccca tcaacagcgc   2220
cctgaaccct atcctgtaca ccctgaccac ccggcccttc aaagaaatga tccaccggtt   2280
ctggtacaac taccggcaga gaaagagcat ggacagcaag ggccagaaaa cctacgcccc   2340
tagcttcatc tgggtggaaa tgtggccact gcaggaaatg cctcccgaac tgatgaagcc   2400
cgacctgttc acctacccct gcgagatgag cctgatctcc cagagcaccc ggctgaacag   2460
ctactcctga taacggaccg gcgatagatg aagctcgctt tcttgctgtc caatttctat   2520
taaaggttcc tttgttccct aagtccaact actaaactgg gggatattat gaagggcctt   2580
```

-continued

```
gagcatctgg attctgccta ataaaaaaca tttattttca ttgcagctcg ctttcttgct   2640

gtccaatttc tattaaaggt tcctttgttc cctaagtcca actactaaac tgggggatat   2700

tatgaagggc cttgagcatc tggattctgc ctaataaaaa acatttattt tcattgcggc   2760

cgcaaaaaaa aaaaaaaaaa aaaaaaaaaa aaaaaaaaaa aaaaaaaaaa aaaaaaaaaa   2820

aaaaaaaaaa aaaaaaaaaa aaaaaaaaaa aaaaaaaaaa aaaaaaaaaa aaaaaaaaaa   2880

aaa                                                                 2883
```

```
<210> SEQ ID NO 37
<211> LENGTH: 2277
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 37

augacaagcg gcagcguguu cuucuacauc cugaucuucg gcaaguacuu cagccacggc     60

ggaggccagg acgugaagug uagccugggc uacuuccccu gcggcaacau caccaagugc    120

cugccccagc ugcugcacug caacggcgug gacgauugcg gcaaccaggc cgacgaggac    180

aacugcggcg acaacaaugg cugguccug caguucgaua aguacuucgc cuccuacuac    240

aagaugacca gccaguaccc cuucgaggcc gagacaccug agugccucgu gggcucugug    300

ccugugcagu gucugugcca gggccuggaa cuggacugcg acgagacaaa ccugagagcc    360

gugcccagcg uguccagcaa cgugacagcc augagccugc aguggaaccu gauccggaag    420

cugcccccg acugcuucaa gaacuaccac gaccugcaga agcuguaucu gcagaacaac    480

aagaucaccu ccaucagcau cuacgccuuc cggggccuga acagccugac caagcuguac    540

cugagccaca accggaucac cuuucugaag cccggcgugu ucgaggaccu gcacagacug    600

gaauggcuga ucaucgagga caaucaccug agccggauca gcccccccac cuucuacggc    660

cugaacuccc ugauccugcu ggugcugaug aacaacgugc ugacccggcu gcccgacaag    720

ccccugugu agcacaugcc cagacugcac uggcuggacc uggaaggcaa ccacauccac    780

aaccugcgga accugaccuu caucagcugc agcaaccuga ccgugcucgu gaugcggaag    840

aacaagauua accaccugaa cgagaacacc uucgcccccc ugcagaaacu ggacgagcug    900

gaucugggcu cuaacaagau cgagaaccug cccccucuga ucuucaagga ccugaaagag    960

cugagccagc ugaaccuguc cuacaacccc auccagaaga uccaggccaa ccaguucgac   1020

uaccucguga agcugaaguc ccugucccug gaagggaucg agaucagcaa cauccagcag   1080

cggauguucc ggccccugau gaaucugucc cacaucuacu ucaagaaguu ccaguacugc   1140

ggcuacgccc cccacgugcg gagcugcaag ccuaacacag acggcaucag cagccuggaa   1200

aaccugcugg ccuccaucau ccagcgggug uucgugugg uggugucgc cgugaccugc   1260

uucggcaaua ucuucgugau cugcaugcgg cccuacauuc ggagcgagaa caagcuguau   1320

gccaugagca ucaucucccu gugcugcgcc gacugccuga ugggcaucua ccuguucgug   1380

aucggcggcu ucgaccugaa guuccggggc gaguacaaca agcacgccca gcuguggaug   1440

gaaagcaccc acugccagcu cgugggcagc cuggccaucc ugagcacuga aguguccgug   1500

cugcugcuga ccuuccugac ccuggaaaag uacaucugca ucguguaccc uuucagaugc   1560

gugcggccug gcaagugccg gaccaucaca gugcugaucc ugauuuggau caccggcuuc   1620

aucguggccu ucaucccccu gagcaacaaa gaguucuuca agaauuacua cggcaccaau   1680
```

ggcgugugcu ucccacugca cuccgaggac acagagagca ucggcgccca gaucuacagc 1740
guggccaucu uccugggcau caaucuggcc gccuucauca ucaucguguu cagcuacggc 1800
uccauguucu acuccgugca ccagagcgcc aucaccgcca ccgagauccg gaaccaagug 1860
aagaaagaga ugauccuggc caagcgcuuc uucuucauug uguucaccga cgcccugugu 1920
uggauuccaa ucuucgucgu gaaguuccug agccugcugc agguggaaau ccccggcaca 1980
aucaccagcu gggucgugau cuucauccug cccaucaaca gcgcccugaa cccuauccug 2040
uacacccuga ccacccggcc cuucaaagaa augauccacc gguucuggua caacuaccgg 2100
cagagaaaga gcauggacag caagggccag aaaaccuacg ccccuagcuu caucugggug 2160
gaaauguggc cacugcagga aaugccuccc gaacugauga agcccgaccu guucaccuac 2220
cccugcgaga ugagccugau cucccagagc acccggcuga acagcuacuc cugauaa 2277

<210> SEQ ID NO 38
<211> LENGTH: 1786
<212> TYPE: DNA
<213> ORGANISM: Homo sapiens

<400> SEQUENCE: 38
gggcgggact tccggtcgtg ggccatgccg ggggcgggcc cggaaccgcc acggctagaa 60
gaagtcttca cttcccagga gagccaaagc gtgtctggcc ctaggtggga aaagaactgg 120
ctgtgacctt tgccctgacc tggaagggcc cagccttggg ctgaatggca gcacccacgc 180
ccgcccgtcc ggtgctgacc cacctgctgg tggctctctt cggcatgggc tcctgggctg 240
cggtcaatgg gatctgggtg gagctacctg tggtggtcaa agagcttcca gagggttgga 300
gcctcccctc ttacgtctct gtgcttgtgg ctctggggaa cctgggtctg ctggtggtga 360
ccctctggag gaggctggcc ccaggaaagg acgagcaggt ccccatccgg gtggtgcagg 420
tgctgggcat ggtgggcaca gccctgctgg cctctctgtg gcaccatgtg gccccagtgg 480
caggacagtt gcattctgtg gccttcttag cactggcctt tgtgctggca ctggcatgct 540
gtgcctcgaa tgtcactttc ctgcccttct tgagccacct gccacctcgc ttcttacggt 600
cattcttcct gggtcaaggc ctgagtgccc tgctgccctg cgtgctggcc ctagtgcagg 660
gtgtgggccg cctcgagtgc ccgccagccc ccatcaacgg cacccctggc cccccgctcg 720
acttccttga gcgttttccc gccagcacct tcttctgggc actgactgcc cttctggtcg 780
cttcagctgc tgccttccag ggtcttctgc tgctgttgcc gccaccacca tctgtaccca 840
caggggagtt aggatcaggc ctccaggtgg gagccccagg agcagaggaa gaggtggaag 900
agtcctcacc actgcaagag ccaccaagcc aggcagcagg caccacccct ggtccagacc 960
ctaaggccta tcagcttcta tcagcccgca gtgcctgcct gctgggcctg ttggccgcca 1020
ccaacgcgct gaccaatggc gtgctgcctg ccgtgcagag cttttcctgc ttaccctacg 1080
ggcgtctggc ctaccacctg gctgtggtgc tgggcagtgc tgccaatccc ctggcctgct 1140
tcctggccat gggtgtgctg tgcaggtcct tggcagggct gggcggcctc tctctgctgg 1200
gcgtgttctg tgggggctac ctgatggcgc tggcagtcct gagcccctgc ccgcccctgg 1260
tgggcacctc ggcgggggtg gtcctcgtgg tgctgtcgtg ggtgctgtgt cttggcgtgt 1320
tctcctacgt gaaggtggca gccagctccc tgctgcatgg cgggggccgg ccggcattgc 1380
tggcagccgg cgtggccatc caggtgggct ctctgctcgg cgctgttgct atgttccccc 1440
cgaccagcat ctatcacgtg ttccacagca gaaaggactg tgcagacccc tgtgactcct 1500

-continued

```
gagcctgggc aggtggggac cccgctcccc aacacctgtc tttccctcaa tgctgccacc   1560

atgcctgagt gcctgcagcc caggaggccc gcacaccggt acactcgtgg acacctacac   1620

actccatagg agatcctggc tttccagggt gggcaagggc aaggagcagg cttggagcca   1680

gggaccagtg ggggctgtag ggtaagcccc tgagcctggg acctacatgt ggtttgcgta   1740

ataaaacatt tgtatttaat gagttggcat taaaaaaaaa aaaaaa                  1786


<210> SEQ ID NO 39
<211> LENGTH: 1950
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

ggatccggag gccggagaat tgtaatacga ctcactatag ggagacgcgt gttaaataac     60

aaatctcaac acaacatata caaaacaaac gaatctcaag caatcaagca ttctacttct    120

attgcagcaa tttaaatcat ttcttttaaa gcaaaagcaa ttttctgaaa attttcacca    180

tttacgaacg atagccgcca ccatggcagc acccacgccc gcccgtccgg tgctgaccca    240

cctgctggtg gctctcttcg gcatgggctc ctgggctgcg gtcaatggga tctgggtgga    300

gctacctgtg gtggtcaaag agcttccaga gggttggagc ctccccctctt acgtctctgt    360

gcttgtggct ctggggaacc tgggtctgct ggtggtgacc ctctggagga ggctggcccc    420

aggaaaggac gagcaggtcc ccatccgggt ggtgcaggtg ctgggcatgg tgggcacagc    480

cctgctggcc tctctgtggc accatgtggc cccagtggca ggacagttgc attctgtggc    540

cttcttagca ctggcctttg tgctggcact ggcatgctgt gcctcgaatg tcactttcct    600

gcccttcttg agccacctgc cacctcgctt cttacggtca ttcttcctgg gtcaaggcct    660

gagtgccctg ctgccctgcg tgctggccct agtgcagggt gtgggccgcc tcgagtgccc    720

gccagccccc atcaacggca cccctggccc cccgctcgac ttccttgagc gttttcccgc    780

cagcaccttc ttctgggcac tgactgccct tctggtcgct tcagctgctg ccttccaggg    840

tcttctgctg ctgttgccgc caccaccatc tgtacccaca ggggagttag gatcaggcct    900

ccaggtggga gccccaggag cagaggaaga ggtggaagag tcctcaccac tgcaagagcc    960

accaagccag gcagcaggca ccacccctgg tccagaccct aaggcctatc agcttctatc   1020

agcccgcagt gcctgcctgc tgggcctgtt ggccgccacc aacgcgctga ccaatggcgt   1080

gctgcctgcc gtgcagagct ttcctgctt accctacggg cgtctggcct accacctggc   1140

tgtggtgctg ggcagtgctg ccaatcccct ggcctgcttc ctggcaatgg gtgtgctgtg   1200

caggtccttg gcagggctgg gcggcctctc tctgctgggc gtgttctgtg gggggctacct   1260

gatggcgctg gcagtcctga gcccctgccc gcccctggtg ggcacctcgg cgggggtggt   1320

cctcgtggtg ctgtcgtggg tgctgtgtct tggcgtgttc tcctacgtga aggtggcagc   1380

cagctccctg ctgcatggcg gggccggcc ggcattgctg gcagccggcg tggccatcca   1440

ggtgggctct ctgctcggcg ctgttgctat gttcccccccg accagcatct atcacgtgtt   1500

ccacagcaga aaggactgtg cagacccctg tgactcctga cggaccggcg atagatgaag   1560

ctcgctttct tgctgtccaa tttctattaa aggttccttt gttccctaag tccaactact   1620

aaactggggg atattatgaa gggccttgag catctggatt ctgcctaata aaaaacattt   1680

attttcattg cagctcgctt tcttgctgtc caatttctat taaaggttcc tttgttccct   1740
```

aagtccaact actaaactgg gggatattat gaagggcctt gagcatctgg attctgccta 1800
ataaaaaaca tttattttca ttgcggccgc aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa 1950

<210> SEQ ID NO 40
<211> LENGTH: 1338
<212> TYPE: RNA
<213> ORGANISM: Homo sapiens

<400> SEQUENCE: 40
auggcagcac ccacgcccgc ccguccggug cugacccacc ugcugguggc ucucuucggc 60
augggcuccu gggcugcggu caaugggauc uggguggagc uaccuguggu ggucaaagag 120
cuuccagagg guuggagccu ccccucuuac gucucugugc uuguggcucu ggggaaccug 180
ggucugcugg uggugacccu cuggaggagg cuggccccag gaaaggacga gcagguccccc 240 auccgggugg ugcaggugcu gggcauggug ggcacagccc ugcuggccuc ucuguggcac 300
cauguggccc caguggcagg acaguugcau ucuguggccu ucuuagcacu ggccuuugug 360
cuggcacugg caugcugugc cucgaauguc acuuuccugc ccuucuugag ccaccugcca 420
ccucgcuucu uacggucauu cuuccugggu caaggccuga gugcccugcu gcccugcgug 480
cuggcccuag ugcagggugu gggccgccuc gagugcccgc cagcccccau caacggcacc 540
ccuggccccc cgcucgacuu ccuugagcgu uuucccgcca gcaccuucuu cugggcacug 600
acugcccuuc uggucgcuuc agcugcugcc uuccaggguc uucugcugcu guugccgcca 660
ccaccaucug uacccacagg ggaguuagga ucaggccucc aggugggagc cccaggagca 720
gaggaagagg uggaagaguc cucaccacug caagagccac caagccaggc agcaggcacc 780
accccugguc cagacccuaa ggccuaucag cuucuaucag cccgcagugc cugccugcug 840
ggccuguugg ccgccaccaa cgcgcugacc aauggcgugc ugccugccgu gcagagcuuu 900
uccugcuuac ccuacgggcg ucuggccuac caccuggcug uggugcuggg cagugcugcc 960
aauccccugg ccugcuuccu ggcaaugggu gugcugugca gguccuuggc agggcugggc 1020
ggccucucuc ugcugggcgu guucuguggg ggcuaccuga uggcgcuggc aguccugagc 1080
cccugcccgc cccugguggg caccucggcg gggguggucc ucguggugcu gucgugggug 1140
cugugucuug gcguguucuc cuacgugaag guggcagcca gcucccugcu gcauggcggg 1200
ggccggccgg cauugcuggc agccggcgug gccauccagg ugggcucucu gcucggcgcu 1260
guugcuaugu ucccccgac cagcaucuau cacguguucc acagcagaaa ggacugugca 1320
gaccccugug acuccuga 1338

<210> SEQ ID NO 41
<211> LENGTH: 888
<212> TYPE: DNA
<213> ORGANISM: Homo sapiens

<400> SEQUENCE: 41
ataccttaga ccctcagtca tgccagtgcc tgctctgtgc ctgctctggg ccctggcaat 60
ggtgacccgg cctgcctcag cggcccccat gggcggccca gaactggcac agcatgagga 120
gctgaccctg ctcttccatg ggaccctgca gctgggccag gccctcaacg gtgtgtacag 180
gaccacggag ggacggctga caaaggccag gaacagcctg ggtctctatg gccgcacaat 240
agaactcctg ggcaggaggg tcagccgggg ccgggatgca gcccaggaac ttcgggcaag 300
cctgttggag actcagatgg aggaggatat tctgcagctg caggcagagg ccacagctga 360
ggtgctgggg gaggtggccc aggcacagaa ggtgctacgg gacagcgtgc agcggctaga 420
agtccagctg aggagcgcct ggctgggccc tgcctaccga gaatttgagg tcttaaaggc 480
tcacgctgac aagcagagcc acatcctatg ggccctcaca ggccacgtgc agcggcagag 540
gcgggagatg gtggcacagc agcatcggct gcgacagatc caggagagac tccacacagc 600
ggcgctccca gcctgaatct gcctggatgg aactgaggac caatcatgct gcaaggaaca 660
cttccacgcc ccgtgaggcc cctgtgcagg gaggagctgc ctgttcactg ggatcagcca 720
gggcgccggg ccccacttct gagcacagag cagagacaga cgcaggcggg gacaaaggca 780
gaggatgtag ccccattggg gaggggtgga ggaaggacat gtaccctttc atgcctacac 840
acccctcatt aaagcagagt cgtggcatct caaaaaaaaa aaaaaaaa 888

<210> SEQ ID NO 42
<211> LENGTH: 1306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
gggatccgga ggccggagaa ttgtaatacg actcactata gggagacgcg tgttaaataa 60
caaatctcaa cacaacatat acaaaacaaa cgaatctcaa gcaatcaagc attctacttc 120
tattgcagca atttaaatca tttcttttaa agcaaaagca attttctgaa aattttcacc 180
atttacgaac gatagccgcc accatgaaga ccttcatcct gctgctgtgg gtgctgctgc 240
tgtgggtcat cttcctgctg cctggcgcca cagccgctcc tatgggagga cctgaactgg 300
cccagcacga ggaactgacc ctgctgtttc acggcaccct gcagctggga caggccctga 360
atggcgtgta cagaaccacc gagggccggc tgaccaaggc cagaaatagc ctgggcctgt 420
acggccggac catcgaactg ctggggcagg aagtgtccag aggcagagat gccgcccagg 480
aactgagagc cagcctgctg gaaacccaga tggaagagga catcctgcag ctgcaggccg 540
aggccacagc tgaggtgctg ggagaagtgg cccaggccca gaaggtgctg agagacagcg 600
tgcagcggct ggaagtgcag ctgagatctg cctggctggg ccctgcctac cgcgagttcg 660
aagtgctgaa agcccacgcc gacaagcaga gccacatcct gtgggccctg acaggccacg 720
tgcagagaca gaggcgggaa atggtggctc agcagcacag actgcggcag atccaggaac 780
ggctgcatac agctgccctg cccgccgact acaaggacga cgacgacaag caccaccacc 840
atcaccacgg cggaggcctg aacgacatct tcgaagccca gaaaatcgag tggcacgagt 900
aacggaccgg cgatagatga agctcgcttt cttgctgtcc aatttctatt aaaggttcct 960
ttgttcccta agtccaacta ctaaactggg ggatattatg aagggccttg agcatctgga 1020
ttctgcctaa taaaaaacat ttattttcat tgcagctcgc tttcttgctg tccaatttct 1080
attaaaggtt cctttgttcc ctaagtccaa ctactaaact gggggatatt atgaagggcc 1140
ttgagcatct ggattctgcc taataaaaaa catttatttt cattgcaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaa 1306

<210> SEQ ID NO 43
<211> LENGTH: 699

-continued

<212> TYPE: RNA
<213> ORGANISM: Homo sapiens

<400> SEQUENCE: 43
augaagaccu ucauccugcu gcugugggug cugcugcugu gggucaucuu ccugcugccu 60
ggcgccacag ccgcuccuau gggaggaccu gaacuggccc agcacgagga acugacccug 120
cuguuucacg gcacccugca gcugggacag gcccugaaug gcguguacag aaccaccgag 180
ggccggcuga ccaaggccag aaauagccug ggccuguacg gccggaccau cgaacugcug 240
gggcaggaag uguccagagg cagagaugcc gcccaggaac ugagagccag ccugcuggaa 300
acccagaugg aagaggacau ccugcagcug caggccgagg ccacagcuga ggugcuggga 360
gaaguggccc aggcccagaa ggugcugaga gacagcgugc agcggcugga agugcagcug 420
agaucugccu ggcugggccc ugccuaccgc gaguucgaag ugcugaaagc ccacgccgac 480
aagcagagcc acauccugug ggcccugaca ggccacgugc agagacagag gcgggaaaug 540
guggcucagc agcacagacu gcggcagauc caggaacggc ugcauacagc ugcccugccc 600
gccgacuaca aggacgacga cgacaagcac caccaccauc accacggcgg aggccugaac 660
gacaucuucg aagcccagaa aaucgagugg cacgaguaa 699

<210> SEQ ID NO 44
<211> LENGTH: 4410
<212> TYPE: DNA
<213> ORGANISM: Homo sapiens

<400> SEQUENCE: 44
cctcctccac agtggtgagg tcacagcccc ttggagccct ccctcttccc acccctcccg 60
ctcccgggtc tcctttggcc tggggtaacc cgaggtgcag agctgagaat gaggcgattt 120
cggaggatgg agaaatagcc ccgagtcccg tggaaaatga ggccggcgga cttgctgcag 180
ctggtgctgc tgctcgacct gcccagggac ctgggcggaa tggggtgttc gtctccaccc 240
tgcgagtgcc atcaggagga ggacttcaga gtcacctgca aggatattca acgcatcccc 300
agcttaccgc ccagtacgca gactctgaag cttattgaga ctcacctgag aactattcca 360
agtcatgcat tttctaatct gcccaatatt tccagaatct acgtatctat agatgtgact 420
ctgcagcagc tggaatcaca ctccttctac aatttgagta aagtgactca catagaaatt 480
cggaatacca ggaacttaac ttacatagac cctgatgccc tcaaagagct ccccctccta 540
aagttccttg gcattttcaa cactggactt aaaatgttcc ctgacctgac caaagtttat 600
tccactgata tattctttat acttgaaatt acagacaacc cttacatgac gtcaatccct 660
gtgaatgctt ttcagggact atgcaatgaa accttgacac tgaagctgta caacaatggc 720
tttacttcag tccaaggata tgctttcaat gggacaaagc tggatgctgt ttacctaaac 780
aagaataaat acctgacagt tattgacaaa gatgcatttg gaggagtata cagtggacca 840
agcttgctgg acgtgtctca aaccagtgtc actgcccttc catccaaagg cctggagcac 900
ctgaaggaac tgatagcaag aaacacctgg actcttaaga aacttccact ttccttgagt 960
ttccttcacc tcacacgggc tgacctttct tacccaagcc actgctgtgc ttttaagaat 1020
cagaagaaaa tcagaggaat ccttgagtcc ttgatgtgta atgagagcag tatgcagagc 1080
ttgcgccaga gaaaatctgt gaatgccttg aatagccccc tccaccagga atatgaagag 1140
aatctgggtg acagcattgt tgggtacaag gaaaagtcca agttccagga tactcataac 1200
aacgctcatt attacgtctt ctttgaagaa caagaggatg agatcattgg ttttggccag 1260

-continued

```
gagctcaaaa acccccagga agagactcta caagcttttg acagccatta tgactacacc   1320
atatgtgggg acagtgaaga catggtgtgt acccccaagt ccgatgagtt caacccgtgt   1380
gaagacataa tgggctacaa gttcctgaga attgtggtgt ggttcgttag tctgctggct   1440
ctcctgggca atgtctttgt cctgcttatt ctcctcacca gccactacaa actgaacgtc   1500
ccccgctttc tcatgtgcaa cctggccttt gcggatttct gcatggggat gtacctgctc   1560
ctcatcgcct ctgtagacct ctacactcac tctgagtact acaaccatgc catcgactgg   1620
cagacaggcc ctgggtgcaa cacggctggt ttcttcactg tctttgcaag cgagttatcg   1680
gtgtatacgc tgacggtcat caccctggag cgctggtatg ccatcacctt cgccatgcgc   1740
ctggaccgga agatccgcct caggcacgca tgtgccatca tggttggggg ctgggtttgc   1800
tgcttccttc tcgccctgct tcctttggtg ggaataagta gctatgccaa agtcagtatc   1860
tgcctgccca tggacaccga gacccctctt gctctggcat atattgtttt tgttctgacg   1920
ctcaacatag ttgccttcgt catcgtctgc tgctgttatg tgaagatcta catcacagtc   1980
cgaaatccgc agtacaaccc aggggacaaa gataccaaaa ttgccaagag gatggctgtg   2040
ttgatcttca ccgacttcat atgcatggcc ccaatctcat tctatgctct gtcagcaatt   2100
ctgaacaagc ctctcatcac tgttagcaac tccaaaatct tgctggtact cttctatcca   2160
cttaactcct gtgccaatcc attcctctat gctattttca ccaaggcctt ccagagggat   2220
gtgttcatcc tactcagcaa gtttggcatc tgtaaacgcc aggctcaggc ataccggggg   2280
cagagggttc ctccaaagaa cagcactgat attcaggttc aaaaggttac ccacgagatg   2340
aggcagggtc tccacaacat ggaagatgtc tatgaactga ttgaaaactc ccatctaacc   2400
ccaaagaagc aaggccaaat ctcagaagag tatatgcaaa cggttttgta agttaacact   2460
acactactca caatggtagg ggaacttaca aaataatagt ttcttgaata tgcattccaa   2520
tcccatgaca cccccaacac atagctgccc tcactcttgt gcaggcgatg tttcaatgtt   2580
tcatggggca agagtttatc tctggagagt gattagtatt aacctaatca ttgcccccaa   2640
gaaggaagtt aggctaccag catatttgaa tgccaggtga aatcaaaata atctacacta   2700
tctagaagac tttcttgatg ccaagtccag agatgtcatt gtgtaggatg ttcagtaaat   2760
attaactgag ctatgtcaat atagagcttc tcagttttgt ataacatttc atactaaaga   2820
ttcagcaaat ggaaaatgct attaatttgg ttggtgacca caagataaaa tcagtcccac   2880
gttggctcag ttcaactaga tgttccctga tacaaagaga acttgatttc cttaaaactg   2940
aaaagccaaa cacagctagc tgtcatacaa gaaacagcta ttatgagaca tgaaggaggg   3000
taagaattag ctttaagttt tgttttgctt tgttttgttt tttaactcaa cctattaatc   3060
atctcttcac aagaatccac ctgatgtgac caagctatta tgtgttgcct ggaaaaactg   3120
gcaagatttc agcttatgtg gcctagcaaa ctaagaattg ctcttcttgg ccagcctcat   3180
agcataaaag atgtgaactc taggaagtct ttctgagtag caataagtgg gaattatggg   3240
cagagcacac tcaatcccct gttgattaat aaaacaggct ggacactaat taactatggg   3300
acttaaatct gtagaaatga aggagtccaa tagcttcttc caattttaaa actctagtac   3360
atccctttcc ctcaaatata tatttctaag ataaagagaa agaagagcac taagtaagta   3420
gaatctgttt ttcctatttt gtagggctgc tgactcctag tccttgaagc ctagacacat   3480
gacccaggaa atttttcctt tgtttcactt ttgattatga tgtctgagcc aaaaattcaa   3540
ttaagtaaac atactcgcct ggatctgaat cattcattta attactagat ctacccagct   3600
gttatatcag gccaaaaaca gattcgtgtt tatataaaag agtaaacgat ggttgcaaat   3660
```

```
tttggctatt tagagttgct acttcactat gaagagtcac ttcaaaacac ttcgcttgtc   3720

tttagggatg atttttgcca tttccagtcc acggtatgat actaaagctg tcaagagagg   3780

tttcttcttt tctgaaactg ccagctcttt ccagccctgt tgatcactgg acataaagct   3840

tcttttcccc aataattctt ctttacttaa aatagtcagg atctttatct acagatgtac   3900

tctccaggtt acctgtgatg atagccccct aatgtcctgc tagaaaagtc tccaagcaga   3960

gatgacatta cttctgaatg ctcataaacc acaccatgaa ataaaagctc tttgttgttt   4020

taagattgtg aagtgtcgtt aatgggtccc cacagatggt ccctgctgga ctcacctgga   4080

atctctccac agccataccc actcatcact atcattgaga cctgcacatc ttaatagaaa   4140

tattataaac atcgaaaatc atgacttacc tagaagttcg cttgtaacta atgaaattaa   4200

acaaatgtgt tgccttttgt catgtgtttc tctcctgtga catttcaaaa tatcacatct   4260

tgataaataa tgtgtttcat cttgaatagc tgaactaatt gctttggaaa cagagtccta   4320

gaaaagtgac ttcaacagaa ttgttactaa aatttgcact cacaacatga aataaatttt   4380

cttcctatgg aataatcgtg aaaaaaaaaa                                    4410


<210> SEQ ID NO 45
<211> LENGTH: 2904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

ggaggccgga gaattgtaat acgactcact atagggagac gcgtgttaaa taacaaatct     60

caacacaaca tatacaaaac aaacgaatct caagcaatca agcattctac ttctattgca    120

gcaatttaaa tcatttcttt taaagcaaaa gcaattttct gaaaattttc accatttacg    180

aacgatagcc gccaccatga ggcctgccga cctgctgcag ctggtgctgc tgctggacct    240

gcctagagat ctgggcggca tgggctgtag cagccctcca tgcgagtgcc accaggaaga    300

ggacttcaga gtgacctgca aggacatcca gagaatcccc agcctgcccc ccagcaccca    360

gaccctgaag ctgatcgaga cacacctgag aaccatccct agccacgcct tcagcaacct    420

gcccaacatc agcagaatct acgtgtccat cgacgtgacc ctgcagcagc tggaaagcca    480

cagcttctac aacctgagca aagtgaccca catcgagatc agaaacaccc ggaacctgac    540

ctacatcgac cccgacgccc tgaaagagct gcccctgctg aagttcctgg gcatcttcaa    600

caccggcctg aagatgttcc ccgacctgac caaggtgtac tctaccgaca tcttcttcat    660

cctggaaatc accgacaacc cctacatgac cagcatcccc gtgaacgcct tccagggcct    720

gtgcaacgag acactgacac tgaagctgta caacaacggc ttcaccagcg tgcagggcta    780

cgccttcaac ggcacaaagc tggacgccgt gtacctgaac aagaacaagt acctgaccgt    840

gatcgacaag gacgccttcg gcggcgtgta ctctggacct tctctgctgg acgtgtccca    900

gaccagcgtg acagccctgc ctagcaaggg cctggaacac ctgaaagaac tgatcgcccg    960

caacacctgg actctgaaga agctgcctct gagcctgagc ttcctgcacc tgaccagagc   1020

cgacctgagc tacccaagcc actgctgcgc cttcaagaac cagaagaaga tccggggaat   1080

cctggaatcc ctgatgtgta acgagagcag catgcagagc ctgagacaga gaaagtctgt   1140

gaacgctctg aacagccccc tgcaccagga atacgaggaa aacctgggcg acagcatcgt   1200

gggctacaaa gagaagtcca agttccagga cacccacaac aacgcccact actacgtgtt   1260
```

cttcgaggaa caggaagatg agatcatcgg cttcggccag gaactgaaga accctcagga 1320
agagacactg caggccttcg acagccacta cgactacacc atctgcggcg acagcgagga 1380
catggtgtgc accccctaaga gcgacgagtt caacccctgc gaggatatta tggggtacaa 1440
gttcctgagg atcgtcgtgt ggttcgtgtc cctgctggct ctgctgggca acgtgttcgt 1500
gctgctgatc ctgctgacct cccactacaa gctgaacgtg cccagattcc tgatgtgcaa 1560
cctggccttc gccgacttct gcatgggcat gtacctgctg ctgattgcca gcgtggacct 1620
gtacacccac agcgagtact acaaccacgc catcgactgg cagaccggcc ctggctgtaa 1680
caccgccggc tttttcaccg tgttcgccag cgagctgagc gtgtacaccc tgacagtgat 1740
caccctggaa aggtggtacg ccatcacctt cgccatgaga ctggacagaa agatcagact 1800
gagacacgcc tgcgccatca tggtgggagg ctgggtgtgc tgtttcctgc tggccctgct 1860
gcccctcgtg ggcatcagct cttacgccaa ggtgtccatc tgcctgccca tggacaccga 1920
gacacctctg gccctggcct acattgtgtt tgtgctgacc ctgaacatcg tggccttcgt 1980
gatcgtgtgc tgctgttacg tgaagatcta catcaccgtg cggaaccccc agtacaaccc 2040
cggcgacaag gataccaaga tcgccaagag aatggccgtg ctgatcttca ccgacttcat 2100
ctgcatggcc cccatcagct tctatgccct gagcgccatt ctgaacaagc ctctgatcac 2160
cgtgtccaac agcaaaatcc tgctggtgct gttctacccc ctgaacagct gcgccaaccc 2220
cttcctgtac gctatcttca ccaaggcctt ccagagggac gtgttcatcc tgctgtctaa 2280
gttcggcatc tgcaagagac aggcccaggc ctaccggggc cagagagtgc ctcctaagaa 2340
ctccacagac atccaggtgc agaaagtgac acacgacatg agacagggcc tgcacaacat 2400
ggaagatgtg tacgagctga ttgagaacag ccacctgacc cccaagaaac agggacagat 2460
cagcgaagag tacatgcaga ccgtgctgtg ataacggacc ggcgatagat gaagctcgct 2520
ttcttgctgt ccaatttcta ttaaaggttc ctttgttccc taagtccaac tactaaactg 2580
ggggatatta tgaagggcct tgagcatctg gattctgcct aataaaaaac atttattttc 2640
attgcagctc gctttcttgc tgtccaattt ctattaaagg ttcctttgtt ccctaagtcc 2700
aactactaaa ctgggggata ttatgaaggg ccttgagcat ctggattctg cctaataaaa 2760
aacatttatt ttcattgcgg ccgcaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaa 2904

<210> SEQ ID NO 46
<211> LENGTH: 2298
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 46
augaggccug ccgaccugcu gcagcuggug cugcugcugg accugccuag agaucugggc 60
ggcaugggcu guagcagccc uccaugcgag ugccaccagg aagaggacuu cagagugacc 120
ugcaaggaca uccagagaau ccccagccug cccccccagca cccagacccu gaagcugauc 180
gagacacacc ugagaaccau cccuagccac gccuucagca accugcccaa caucagcaga 240
aucuacgugu ccaucgacgu gacccugcag cagcuggaaa gccacagcuu cuacaaccug 300
agcaaaguga cccacaucga gaucagaaac acccggaacc ugaccuacau cgaccccgac 360
gcccugaaag agcugccccu gcugaaguuc cugggcaucu ucaacaccgg ccugaagaug 420
uuccccgacc ugaccaaggu guacucuacc gacaucuucu ucauccugga aaucaccgac 480
aaccccuaca ugaccagcau ccccgugaac gccuuccagg gccugugcaa cgagacacug 540
acacugaagc uguacaacaa cggcuucacc agcgugcagg gcuacgccuu caacggcaca 600
aagcuggacg ccguguaccu gaacaagaac aaguaccuga ccgugaucga caaggacgcc 660
uucggcggcg uguacucugg accuucucug cuggacgugu cccagaccag cgugacagcc 720
cugccuagca agggccugga acaccugaaa gaacugaucg cccgcaacac cuggacucug 780
aagaagcugc cucugagccu gagcuuccug caccugacca gagccgaccu gagcuaccca 840
agccacugcu gcgccuucaa gaaccagaag aagauccggg gaauccugga aucccugaug 900
uguaacgaga gcagcaugca gagccugaga cagagaaagu cugugaacgc ucugaacagc 960
ccccugcacc aggaauacga ggaaaaccug ggcgacagca ucgugggcua caaagagaag 1020
uccaaguucc aggacaccca caacaacgcc cacuacuacg uguucuucga ggaacaggaa 1080
gaugagauca ucggcuucgg ccaggaacug aagaacccuc aggaagagac acugcaggcc 1140
uucgacagcc acuacgacua caccaucugc ggcgacagcg aggacauggu gugcaccccu 1200
aagagcgacg aguucaaccc cugcgaggau auuaaggggu acaaguuccu gaggaucguc 1260
gugugguucg ugucccugcu ggcucugcug ggcaacgugu ucgugcugcu gauccugcug 1320
accucccacu acaagcugaa cgugcccaga uuccugaugu gcaaccuggc cuucgccgac 1380
uucugcaugg gcauguaccu gcugcugauu gccagcgugg accuguacac ccacagcgag 1440
uacuacaacc acgccaucga cuggcagacc ggcccuggcu guaacaccgc cggcuuuuuc 1500
accguguucg ccagcgagcu gagcguguac acccugacag ugaucacccu ggaaaggugg 1560
uacgccauca ccuucgccau gagacuggac agaaagauca gacugagaca cgccugcgcc 1620 aucaugguggg gaggcugggu gugcuguuuc cugcuggccc ugcugccccu cgugggcauc 1680
agcucuuacg ccaaggugc caucugccug cccauggaca ccgagacacc ucuggcccug 1740
gccuacauug uguuugugcu gacccugaac aucguggccu ucgugaucgu gugcugcugu 1800
uacgugaaga ucuacaucac cgugcggaac ccccaguaca accccggcga caaggauacc 1860
aagaucgcca agagaauggc cgugcugauc uucaccgacu ucaucugcau ggcccccauc 1920
agcuucuaug cccugagcgc cauucugaac aagccucuga ucaccguguc caacagcaaa 1980
auccugcugg ugcuguucua cccccugaac agcugcgcca accccuuccu guacgcuauc 2040
uucaccaagg ccuuccagag ggacguguuc auccugcugu cuaaguucgg caucugcaag 2100
agacaggccc aggccuaccg gggccagaga gugccuccua agaacuccac agacauccag 2160
gugcagaaag ugacacacga caugagacag ggccugcaca acauggaaga uguguacgag 2220
cugauugaga acagccaccu gacccccaag aaacagggac agaucagcga agaguacaug 2280
cagaccgugc ugugauaa 2298

<210> SEQ ID NO 47
<211> LENGTH: 3877
<212> TYPE: DNA
<213> ORGANISM: Homo sapiens

<400> SEQUENCE: 47
ggaaagccga cttgcaaaac cacagataat gttcagccca gcacagtagg ggtcaatttg 60
gtccacttgc tcagtgacaa aaagaaaaaa aaagtgggct gtcactaaag attttgactc 120

-continued

```
acaagagagg ggctggtctg gaggtgggag gagggagtga cgagtcaagg aggagacagg    180
gacgcaggag ggtgcaagga agtgtcttaa ctgagacggg ggtaaggcaa gagagggtgg    240
aggaaattct gcaggagaca ggcttcctcc agggtctgga gaacccagag gcagctcctc    300
ctgagtgctg ggaaggactc tgggcatctt cagcccttct tactctctga ggctcaagcc    360
agaaattcag gctgcttgca gagtgggtga cagagccacg gagctggtgt ccctgggacc    420
ctctgcccgt cttctctcca ctccccagca tggaggaagg tggtgatttt gacaactact    480
atggggcaga caaccagtct gagtgtgagt acacagactg gaaatcctcg gggggccctca    540
tccctgccat ctacatgttg gtcttcctcc tgggcaccac gggcaacggt ctggtgctct    600
ggaccgtgtt tcggagcagc cgggagaaga ggcgctcagc tgatatcttc attgctagcc    660
tggcggtggc tgacctgacc ttcgtggtga cgctgcccct gtgggctacc tacacgtacc    720
gggactatga ctggcccttt gggaccttct tctgcaagct cagcagctac ctcatcttcg    780
tcaacatgta cgccagcgtc ttctgcctca ccggcctcag cttcgaccgc tacctggcca    840
tcgtgaggcc agtggccaat gctcggctga ggctgcgggt cagcggggcc gtggccacgg    900
cagttctttg ggtgctggcc gccctcctgg ccatgcctgt catggtgtta cgcaccaccg    960
gggacttgga gaacaccact aaggtgcagt gctacatgga ctactccatg gtggccactg   1020
tgagctcaga gtgggcctgg gaggtgggcc ttggggtctc gtccaccacc gtgggctttg   1080
tggtgccctt caccatcatg ctgacctgtt acttcttcat cgcccaaacc atcgctggcc   1140
acttccgcaa ggaacgcatc gagggcctgc ggaagcggcg ccggctgctc agcatcatcg   1200
tggtgctggt ggtgaccttt gccctgtgct ggatgcccta ccacctggtg aagacgctgt   1260
acatgctggg cagcctgctg cactggccct gtgactttga cctcttcctc atgaacatct   1320
tcccctactg cacctgcatc agctacgtca acagctgcct caacccccttc ctctatgcct   1380
ttttcgaccc ccgcttccgc caggcctgca cctccatgct ctgctgtggc cagagcaggt   1440
gcgcaggcac ctcccacagc agcagtgggg agaagtcagc cagctactct tcggggcaca   1500
gccaggggcc cggccccaac atgggcaagg gtggagaaca gatgcacgag aaatccatcc   1560
cctacagcca ggagaccctt gtggttgact agggctggga gcagagagaa gcctggcgcc   1620
ctcggccctc cccggccttt gcccttgctt tctgaaaatc aggtagtgtg gctactcctt   1680
gtcctatgca catcctttaa ctgtcccctg attctgcccc gccctgtcct cctctactgc   1740
tttattcttt ctcagaggtt tgtggtttag gggaaagaga ctgggctcta cagacctgac   1800
cctgcacaag ccatttaatc tcactcagcc tcagtttctc cattggtatg aaatgggggga   1860
aagtcatatt gatcctaaaa tgttgaagcc tgagtctgga cgcagtaaaa gcttgtttcc   1920
ctctgctgct ttcttagatc tgcaatcgtc tttcctccct tctttccttg tagtttttcc   1980
cccaccactc tctgcagctg ccgctcctta tccctgcctt ctggcaccaa tcccctccta   2040
cagctcgtcc ccctccctcc atccatcctt ctcccctgtc tactttcttg ttctgaaggg   2100
ctactaaggg ttaaggatcc caaagcttgc agagactgac cctgtttaag ctttctatcc   2160
tgttttctga gtgtgaggca gggaatgggc tggggccggg ggtgggctgt gtgtcagcag   2220
ataattagtg ctccagccct tagatctggg agctccagag cttgccctaa aattggatca   2280
cttccctgtc attttgggca ttggggctag tgtgattcct gcagttcccc catggcacca   2340
tgacactgac tagatatgct ttctccaaat tgtccgcaga ccctttcatc cttcctctat   2400
tttctatgag aattggaagg cagcagggct gatgaatgga tgtactcctt ggtttcatta   2460
tgtgagtggg gagttgggaa gggcaactag agagagagga tggaggggtg tctgcattta   2520
```

gtccagacac tgcttggctc gctccccgag tcctcctgtt tctgacttcc tgcataactg 2580
tgagctgaag ggtttcctca tctccccatc ttaccccatc atactgattt ctttcttggg 2640
cactggtgct acttggtgcc aagaatcatg ttgtttggga tggagatgcc tgcctcttgt 2700
ctgtgtgtgt tgtacttata tgtctatatg gatgagcctg gcatgaacag cagtgtgcct 2760
gggtcatttg gacaaacctc ctcccacccc ccaatccact gcaactctgc tgttcacaca 2820
ttacccttgg cagggggtgg tggggggcag ggacacactg aggcaatgaa aaatgtagaa 2880
taaaaatgag tccacccccct actggatttg ggggctccaa cggctggtcc gtgctttagg 2940
agcgaagtta atgtttgcac caggcttcct gtagggagat ccctccccaa agcagctggc 3000
gccaaggctt gggggcgtcc tactgagctg ggttcctgct ccttcttggg ctccatgaag 3060
gaagtaagag gctagttgag agcctccctt ggcccctttc cggtgcctcc ccgcctggct 3120
tcaaatttat gagcattgcc ctcatcgtcc tttcttgttc cagggtcagt ggccctcttc 3180
ctaaggaggc ctcctgcttg ccatgggcca aaaggcacgg ggtgggtttt ttctctccct 3240
accctcagga ttggacctct tggcttctgc tggattgggg atctgggaat agggactgga 3300
gcaagtgtgc agatagcatg atgtctacac tgccagagag accgtgagga tgaaattaat 3360
agtggggcct ttgtgagcta gaggctggga gtgtctattc cgggttttgt tcttggagga 3420
ctatgaaagt gaaggacaag acatgagcga tggagataag aaaagcccag cttgatgtga 3480
atggacatct tgaccctccc tggaatgacg ccagctctgg gggcagaggg aggaggagag 3540
gggaaggggc tcctcacagc ctagtctccc catcttaaga tagcatcttt cacagagtca 3600
cctcctctgc ccagagctgt cctcaaagca tccagtgaac actggaagag gcttctagaa 3660
gggaagaaat tgtccctctg aggccgccgt gggtgacctg cagagacttc ctgcctggaa 3720
ctcatctgtg aactgggaca gaagcagagg aggctgcctg ctgtgatacc cccttacctc 3780
ccccagtgcc ttcttcagaa tatctgcact gtcttctgat cctgttagtc actgtggttc 3840
atcaaataaa actgtttgtg caactgttgt gtccaaa 3877

<210> SEQ ID NO 48
<211> LENGTH: 1749
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48
ggaggccgga gaattgtaat acgactcact atagggagac gcgtgttaaa taacaaatct 60
caacacaaca tatacaaaac aaacgaatct caagcaatca agcattctac ttctattgca 120
gcaatttaaa tcatttcttt taaagcaaaa gcaattttct gaaaattttc accatttacg 180
aacgatagcc gccaccatgg aagagggcgg cgacttcgac aactactacg gcgccgacaa 240
ccagagcgag tgcgagtaca ccgactggaa gtcctctggc gccctgatcc ccgctatcta 300
catgctggtg tttctgctgg gcaccaccgg caacggactg gtgctgtgga ccgtgttcag 360
aagcagcaga gagaagcggc ggagcgccga catctttatc gccagcctgg ccgtggccga 420
cctgaccttt gtcgtgacac tgcctctgtg ggccacctac acctaccggg actacgactg 480
gcccttcggc acatttttct gcaagctgag cagctacctg atcttcgtga atatgtacgc 540
cagcgtgttc tgcctgaccg gcctgagctt cgacagatac ctggccatcg tgcggcccgt 600
ggccaacgct agactgcggc tgagagtgtc tggcgccgtg gctacagctg tgctgtgggt 660
gctggctgcc ctgctggcta tgcctgtgat ggtgctgaga accaccggcg acctggaaaa 720
caccaccaag gtgcagtgct acatggacta cagcatggtg gccacagtgt ccagcgagtg 780
ggcctgggaa gtgggactgg gagtgtctag caccaccgtg ggcttcgtgg tgcccttcac 840
cattatgctg acctgctact tcttcattgc ccagacaatc gccggccact tccggaaaga 900
gcggatcgag ggcctgcgga agagaaggcg gctgctgagc atcatcgtgg tgctggtcgt 960
gaccttcgcc ctgtgctgga tgccttacca cctcgtgaaa accctgtata tgctgggcag 1020
cctgctgcac tggccctgcg atttcgacct gttcctgatg aacatcttcc cctactgcac 1080
ctgtatcagc tacgtgaaca gctgcctgaa cccccttcctg tacgccttct tcgacccccg 1140
gttcagacag gcctgcacct ccatgctgtg ctgcggccag tctagatgcg ccggcacaag 1200
ccacagcagc agcggcgaga agtctgccag ctacagctct ggccacagcc agggcccagg 1260
ccccaatatg ggaaagggcg gagagcagat gcacgagaag tccatccctt acagccagga 1320
aaccctggtg gtggactgac ggaccggcga tagatgaagc tcgctttctt gctgtccaat 1380
ttctattaaa ggttcctttg ttccctaagt ccaactacta aactgggggga tattatgaag 1440 ggccttgagc atctggattc tgcctaataa aaaacattta ttttcattgc agctcgcttt 1500
cttgctgtcc aatttctatt aaaggttcct ttgttcccta agtccaacta ctaaactggg 1560
ggatattatg aagggccttg agcatctgga ttctgcctaa taaaaaacat ttattttcat 1620
tgcggccgca aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaa 1749

<210> SEQ ID NO 49
<211> LENGTH: 1143
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 49
auggaagagg gcggcgacuu cgacaacuac uacggcgccg acaaccagag cgagugcgag 60
uacaccgacu ggaaguccuc uggcgcccug aucccccgcua ucuacaugcu gguguuucug 120
cugggcacca ccggcaacgg acuggugcug uggaccgugu ucagaagcag cagagagaag 180
cggcggagcg ccgacaucuu uaucgccagc cuggccgugg ccgaccugac cuuugucgug 240
acacugccuc ugugggccac cuacaccuac cgggacuacg acuggcccuu cggcacauuu 300
uucugcaagc ugagcagcua ccugaucuuc gugaauaugu acgccagcgu guucugccug 360
accggccuga gcuucgacag auaccuggcc aucgugcggc ccguggccaa cgcuagacug 420
cggcugagag ugucuggcgc cguggcuaca gcugugcugu gggugcuggc ugcccugcug 480
gcuaugccug ugauggugcu gagaaccacc ggcgaccugg aaaacaccac caaggugcag 540
ugcuacaugg acuacagcau gguggccaca guguccagcg agugggccug ggaaguggga 600
cugggagugu cuagcaccac cgugggcuuc guggugcccu ucaccauuau gcugaccugc 660
uacuucuuca uugcccagac aaucgccggc cacuuccgga aagagcggau cgagggccug 720
cggaagagaa ggcggcugcu gagcaucauc guggugcugg ucgugaccuu cgcccugugc 780
uggaugccuu accaccucgu gaaaacccug uauaugcugg gcagccugcu gcacuggccc 840
ugcgauuucg accuguuccu gaugaacauc uuccccuacu gcaccuguau cagcuacgug 900
aacagcugcc ugaaccccuu ccuguacgcc uucuucgacc cccgguucag acaggccugc 960
accuccaugc ugugcugcgg ccagucuaga ugcgccggca caagccacag cagcagcggc 1020
gagaagucug ccagcuacag cucuggccac agccagggcc caggccccaa uaugggaaag 1080
ggcggagagc agaugcacga gaaguccauc ccuuacagcc aggaaacccu gguggugac 1140 uga 1143

<210> SEQ ID NO 50
<211> LENGTH: 3085
<212> TYPE: DNA
<213> ORGANISM: Homo sapiens

<400> SEQUENCE: 50
gagcagccaa aaggcccgcg gagtcgcgct gggccgcccc ggcgcagctg aaccgggggc 60
cgcgcctgcc aggccgacgg gtctggccca gcctggcgcc aaggggttcg tgcgctgtgg 120
agacgcggag ggtcgaggcg gcgcggcctg agtgaaaccc aatggaaaaa gcatgacatt 180
tagaagtaga agacttagct tcaaatccct actccttcac ttactaattt tgtgatttgg 240
aaatatccgc gcaagatgtt gacgttgcag acttgggtag tgcaagcctt gtttattttc 300
ctcaccactg aatctacagg tgaacttcta gatccatgtg gttatatcag tcctgaatct 360
ccagttgtac aacttcattc taatttcact gcagtttgtg tgctaaagga aaaatgtatg 420
gattattttc atgtaaatgc taattacatt gtctggaaaa caaaccattt tactattcct 480
aaggagcaat atactatcat aaacagaaca gcatccagtg tcacctttac agatatagct 540
tcattaaata ttcagctcac ttgcaacatt cttacattcg gacagcttga acagaatgtt 600
tatggaatca caataatttc aggcttgcct ccagaaaaac ctaaaaattt gagttgcatt 660
gtgaacgagg ggaagaaaat gaggtgtgag tgggatggtg gaagggaaac acacttggag 720
acaaacttca ctttaaaatc tgaatgggca acacacaagt ttgctgattg caaagcaaaa 780
cgtgacaccc ccacctcatg cactgttgat tattctactg tgtattttgt caacattgaa 840
gtctgggtag aagcagagaa tgcccttggg aaggttacat cagatcatat caattttgat 900
cctgtatata aagtgaagcc caatccgcca cataatttat cagtgatcaa ctcagaggaa 960
ctgtctagta tcttaaaatt gacatggacc aacccaagta ttaagagtgt tataatacta 1020
aaatataaca ttcaatatag gaccaaagat gcctcaactt ggagccagat tcctcctgaa 1080
gacacagcat ccacccgatc ttcattcact gtccaagacc ttaaaccttt tacagaatat 1140
gtgtttagga ttcgctgtat gaaggaagat ggtaagggat actggagtga ctggagtgaa 1200
gaagcaagtg ggatcaccta tgaagataga ccatctaaag caccaagttt ctggtataaa 1260
atagatccat cccatactca aggctacaga actgtacaac tcgtgtggaa gacattgcct 1320
ccttttgaag ccaatggaaa aatcttggat tatgaagtga ctctcacaag atggaaatca 1380
catttacaaa attacacagt taatgccaca aaactgacag taaatctcac aaatgatcgc 1440
tatctagcaa ccctaacagt aagaaatctt gttggcaaat cagatgcagc tgttttaact 1500
atccctgcct gtgactttca agctactcac cctgtaatgg atcttaaagc attccccaaa 1560
gataacatgc tttgggtgga atggactact ccaagggaat ctgtaaagaa atatatactt 1620
gagtggtgtg tgttatcaga taaagcaccc tgtatcacag actggcaaca agaagatggt 1680
accgtgcatc gcacctattt aagagggaac ttagcagaga gcaaatgcta tttgataaca 1740
gttactccag tatatgctga tggaccagga agccctgaat ccataaaggc ataccttaaa 1800

```
caagctccac cttccaaagg acctactgtt cggacaaaaa aagtagggaa aaacgaagct   1860

gtcttagagt gggaccaact tcctgttgat gttcagaatg gatttatcag aaattatact   1920

atattttata gaaccatcat tggaaatgaa actgctgtga atgtggattc ttcccacaca   1980

gaatatacat tgtcctcttt gactagtgac acattgtaca tggtacgaat ggcagcatac   2040

acagatgaag gtgggaagga tggtccagaa ttcactttta ctaccccaaa gtttgctcaa   2100

ggagaaattg aagccatagt cgtgcctgtt tgcttagcat tcctattgac aactcttctg   2160

ggagtgctgt tctgctttaa taagcgagac ctaattaaaa aacacatctg gcctaatgtt   2220

ccagatcctt caaagagtca tattgcccag tggtcacctc acactcctcc aaggcacaat   2280

tttaattcaa aagatcaaat gtattcagat ggcaatttca ctgatgtaag tgttgtggaa   2340

atagaagcaa atgacaaaaa gcctttttcca gaagatctga aatcattgga cctgttcaaa   2400

aaggaaaaaa ttaatactga aggacacagc agtggtattg gggggtcttc atgcatgtca   2460

tcttctaggc caagcatttc tagcagtgat gaaaatgaat cttcacaaaa cacttcgagc   2520

actgtccagt attctaccgt ggtacacagt ggctacagac accaagttcc gtcagtccaa   2580

gtcttctcaa gatccgagtc tacccagccc ttgttagatt cagaggagcg gccagaagat   2640

ctacaattag tagatcatgt agatggcggt gatggtattt tgcccaggca acagtacttc   2700

aaacagaact gcagtcagca tgaatccagt ccagatattt cacattttga aaggtcaaag   2760

caagtttcat cagtcaatga ggaagatttt gttagactta aacagcagat ttcagatcat   2820

atttcacaat cctgtggatc tgggcaaatg aaaatgtttc aggaagtttc tgcagcagat   2880

gcttttggtc caggtactga gggacaagta gaaagatttg aaacagttgg catggaggct   2940

gcgactgatg aaggcatgcc taaaagttac ttaccacaga ctgtacggca aggcggctac   3000

atgcctcagt gaaggactag tagttcctgc tacaacttca gcagtaccta taaagtaaag   3060

ctaaaatgat tttatctgtg aattc                                         3085
```

```
<210> SEQ ID NO 51
<211> LENGTH: 3367
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
```

```
gatccggagg ccggagaatt gtaatacgac tcactatagg gagacgcgtg ttaaataaca     60

aatctcaaca caacatatac aaaacaaacg aatctcaagc aatcaagcat tctacttcta    120

ttgcagcaat ttaaatcatt tcttttaaag caaaagcaat tttctgaaaa ttttcaccat    180

ttacgaacga tagccgccac cgcatcgtga acgagggcaa gaaaatgctg accctgcaga    240

cctggctggt gcaggccctg ttcatcttcc tgaccaccga gagcaccggc gagctgctgg    300

acccttgtgg ctacatcagc cccgagagcc ctgtggtgca gctgcatagc aacttcaccg    360

ccgtgtgcgt gctgaaagaa aagtgcatgg actacttcca cgtgaacgcc aactacatcg    420

tgtggaaaac aaaccacttc accatcccca aagagcagta caccatcatc aacagaaccg    480

ccagcagcgt gaccttcacc gatatcgcca gcctgaacat ccagctgacc tgcaacatcc    540

tgaccttcgg ccagctggaa cagaacgtgt acggcatcac aatcatcagc ggcctgcccc    600

ccgagaagcc caagaacctg agctgcatcg tgaacgaggg caagaaaatg agatgcgagt    660

gggacggcgg cagagagaca cacctggaaa caaacttcac cctgaagtcc gagtgggcca    720
```

-continued

```
cccacaagtt cgccgactgc aaggccaaga gggacacccc caccagctgt accgtggact    780
acagcaccgt gtacttcgtg aacatcgaag tgtgggtgga agccgagaac gccctgggca    840
aagtgaccag cgaccacatc aacttcgacc ctgtgtacaa agtgaagccc aacccccccc    900
acaacctgag cgtgatcaac agcgaggaac tgagcagcat cctgaagctg acatggacca    960
accccagcat caagtccgtg atcattctga agtacaacat ccagtaccgg accaaggacg   1020
ccagcacctg gtcccagatc cctccagagg acaccgcctc caccagatcc agcttcacag   1080
tgcaggacct gaagcctttc accgagtacg tgttcaggat tcggtgcatg aaggaagatg   1140
gcaagggcta ctggagcgat tggagcgagg aagccagcgg catcacctac gaggacagac   1200
cctctaaggc ccccagcttc tggtacaaga tcgaccccag ccacacccag ggctacagaa   1260
ccgtgcagct cgtgtggaaa accctgcccc cattcgaggc caacggcaag atcctggact   1320
acgaagtgac cctgaccaga tggaagtccc atctgcagaa ctacaccgtg aacgctacca   1380
agctgaccgt gaacctgaca aacgacagat acctggccac cctgaccgtg cggaacctcg   1440
tgggcaagtc tgatgccgcc gtgctgacca tccccgcatg cgattttcaa gccacccacc   1500
ccgtgatgga tctgaaggct ttccccaagg acaacatgct gtgggtggaa tggaccaccc   1560
ccagagaaag cgtgaaaaag tacatcctgg aatggtgtgt gctgagcgac aaggccccct   1620
gcatcaccga ttggcagcag gaagatggaa ccgtgcacag aacctacctg agaggcaacc   1680
tggccgagag caagtgctac ctgatcaccg tgacccccgt gtacgctgac ggccctggaa   1740
gccctgagag catcaaggcc tacctgaagc aggcccctcc cagcaaggga cctacagtgc   1800
ggaccaagaa agtgggcaag aacgaggccg tgctggaatg ggaccagctg cctgtggatg   1860
tgcagaacgg cttcatcaga aactacacca tcttctacag gaccatcatc ggcaacgaga   1920
cagccgtgaa cgtggacagc agccacacag agtacaccct gagcagcctg acctccgaca   1980
ccctgtatat ggtgcgaatg gccgcctaca ccgacgaggg cggaaaggat ggccccgagt   2040
tcaccttcac cacacctaag ttcgctcagg gcgagatcga ggccatcgtg gtgcctgtgt   2100
gtctggcttt cctgctgacc accctgctgg gcgtgctgtt ctgcttcaac aagcgggacc   2160
tgatcaagaa gcacatctgg cccaacgtgc ccgaccctag caagagccat atcgcccagt   2220
ggtcccccca caccccccct agacacaact tcaacagcaa ggaccagatg tacagcgacg   2280
gcaactttac agacgtgtcc gtggtggaaa tcgaggctaa cgataagaag cccttcccag   2340
aagatctgaa gtccctggat ctgttcaaga aagagaagat caacacagag ggccacagct   2400
ccggcatcgg cggcagctct tgtatgagca gcagcagacc tagcatcagc agcagcgacg   2460
agaacgagag cagccagaac acctctagca ccgtgcagta ctccaccgtg gtgcacagcg   2520
gctacagaca ccaggtgcca agcgtgcagg tgttcagcag aagcgagtcc acccagcccc   2580
tgctggacag cgaagagagg cctgaggatc tgcagctggt ggaccatgtg gacggcggag   2640
atggcatcct gcccagacag cagtacttca agcagaactg ctcccagcac gagtccagcc   2700
ccgacatcag ccacttcgag agaagcaaac aggtgtccag cgtgaacgaa gaggacttcg   2760
tgcggctgaa gcagcagatc agcgatcaca tctcccagag ctgcggcagc ggccagatga   2820
agatgttcca ggaagtgtcc gccgctgacg ccttcggacc tggaactgag ggccaggtgg   2880
aaagattcga gacagtgggc atggaagccg ccacagacga gggcatgcct aagagctacc   2940
tgccccagac tgtgcggcag ggcggctaca tgcctcagtg aagctcgctt tcttgctgtc   3000
caatttctat taaaggttcc tttgttccct aagtccaact actaaactgg gggatattat   3060
gaagggcctt gagcatctgg attctgccta ataaaaaaca tttattttca ttgcagctcg   3120
```

```
ctttcttgct gtccaatttc tattaaaggt tcctttgttc cctaagtcca actactaaac   3180

tgggggatat tatgaagggc cttgagcatc tggattctgc ctaataaaaa acatttattt   3240

tcattgcaaa aaaaaaaaaa aaaaaaaaaa aaaaaaaaaa aaaaaaaaaa aaaaaaaaaa   3300

aaaaaaaaaa aaaaaaaaaa aaaaaaaaaa aaaaaaaaaa aaaaaaaaaa aaaaaaaaaa   3360

aaaaaaa                                                             3367


<210> SEQ ID NO 52
<211> LENGTH: 2757
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 52

augcugaccc ugcagaccug gcuggugcag gcccuguuca ucuuccugac caccgagagc     60

accggcgagc ugcuggaccc uuguggcuac aucagccccg agagcccugu ggugcagcug    120

cauagcaacu ucaccgccgu gugcgugcug aaagaaaagu gcauggacua cuuccacgug    180

aacgccaacu acaucgugug gaaaacaaac cacuucacca uccccaaaga gcaguacacc    240

aucaucaaca gaaccgccag cagcgugacc uucaccgaua ucgccagccu gaacauccag    300

cugaccugca acauccugac cuucggccag cuggaacaga acguguacgg caucacaauc    360

aucagcggcc ugcccccega gaagcccaag aaccugagcu gcaucgugaa cgagggcaag    420

aaaaugagau gcgaguggga cggcggcaga gagacacacc uggaaacaaa cuucacccug    480

aaguccgagu gggccaccca caaguucgcc gacugcaagg ccaagaggga cacccccacc    540

agcuguaccg uggacuacag caccguguac uucgugaaca ucgaagugug gguggaagcc    600

gagaacgccc ugggcaaagu gaccagcgac cacaucaacu ucgacccugu guacaaagug    660

aagcccaacc cccccacaa ccugagcgug aucaacagcg aggaacugag cagcauccug    720

aagcugacau ggaccaaccc cagcaucaag uccgugauca uucugaagua caacauccag    780

uaccggacca aggacgccag caccuggucc cagaucccuc cagaggacac cgccuccacc    840

agauccagcu ucacagugca ggaccugaag ccuuucaccg aguacguguu caggauucgg    900

ugcaugaagg aagauggcaa gggcuacugg agcgauugga gcgaggaagc cagcggcauc    960

accuacgagg acagacccuc uaaggccccc agcuucuggu acaagaucga ccccagccac   1020

acccagggcu acagaaccgu gcagcucgug uggaaaaccc ugcccccauu cgaggccaac   1080

ggcaagaucc uggacuacga agugacccug accagaugga agucccaucu gcagaacuac   1140

accgugaacg cuaccaagcu gaccgugaac cugacaaacg acagauaccu ggccacccug   1200

accgugcgga accucguggg caagucugau gccgccgugc ugaccauccc cgcaugcgau   1260

uuucaagcca cccaccccgu gauggaucug aaggcuuucc ccaaggacaa caugcugugg   1320

guggaaugga ccacccccag agaaagcgug aaaaaguaca uccuggaaug gugugugcug   1380

agcgacaagg cccccugcau caccgauugg cagcaggaag auggaaccgu gcacagaacc   1440

uaccugagag gcaaccuggc cgagagcaag ugcuaccuga ucaccgugac ccccguguac   1500

gcugacggcc cuggaagccc ugagagcauc aaggccuacc ugaagcaggc cccucccagc   1560

aagggaccua cagugcggac caagaaagug ggcaagaacg aggccgugcu ggaaugggac   1620

cagcugccug uggaugugca gaacggcuuc aucagaaacu acaccaucuu cuacaggacc   1680

aucaucggca acgagacagc cgugaacgug gacagcagcc acacagagua cacccugagc   1740
```

agccugaccu ccgacacccu guauauggug cgaauggccg ccuacaccga cgagggcgga 1800
aaggauggcc ccgaguucac cuucaccaca ccuaaguucg cucagggcga gaucgaggcc 1860 aucgguggugc cugugugucu ggcuuuccug cugaccaccc ugcugggcgu gcuguucugc 1920
uucaacaagc gggaccugau caagaagcac aucuggccca acgugcccga cccuagcaag 1980
agccauaucg cccagugguc cccccacacc cccccuagac acaacuucaa cagcaaggac 2040
cagauguaca gcgacggcaa cuuuacagac guguccgugg uggaaaucga ggcuaacgau 2100
aagaagcccu ucccagaaga ucugaagucc cuggaucugu ucaagaaaga gaagaucaac 2160
acagagggcc acagcuccgg caucggcggc agcucuugua ugagcagcag cagaccuagc 2220
aucagcagca gcgacgagaa cgagagcagc cagaacaccu cuagcaccgu gcaguacucc 2280 accgugggugc acagcggcua cagacaccag gugccaagcg ugcaggugu cagcagaagc 2340 gaguccaccc agccccugcu ggacagcgaa gagaggccug aggaucugca gcugguggac 2400
cauguggacg gcggagaugg cauccugccc agacagcagu acuucaagca gaacugcucc 2460
cagcacgagu ccagccccga caucagccac uucgagagaa gcaaacaggu guccagcgug 2520
aacgaagagg acuucgugcg gcugaagcag cagaucagcg aucacaucuc ccagagcugc 2580
ggcagcggcc agaugaagau guuccaggaa guguccgccg cugacgccuu cggaccugga 2640
acugagggcc agguggaaag auucgagaca gugggcaugg aagccgccac agacgagggc 2700
augccuaaga gcuaccugcc ccagacugug cggcagggcg gcuacaugcc ucaguga 2757

<210> SEQ ID NO 53
<211> LENGTH: 1017
<212> TYPE: DNA
<213> ORGANISM: Homo sapiens

<400> SEQUENCE: 53
gagtatttga ggctcggagc caccgccccg ccggcgcccg cagcacctcc tcgccagcag 60
ccgtccggag ccagccaacg agcggaaaat ggcagacaat ttttcgctcc atgatgcgtt 120
atctgggtct ggaaacccaa accctcaagg atggcctggc gcatggggga accagcctgc 180
tggggcaggg ggctacccag gggcttccta tcctggggcc taccccgggc aggcaccccc 240
aggggcttat cctggacagg cacctccagg cgcctaccct ggagcacctg gagcttatcc 300
cggagcacct gcacctggag tctacccagg gccacccagc ggccctgggg cctacccatc 360
ttctggacag ccaagtgcca ccggagccta ccctgccact ggcccctatg gcgcccctgc 420
tgggccactg attgtgcctt ataacctgcc tttgcctggg ggagtggtgc ctcgcatgct 480
gataacaatt ctgggcacgg tgaagcccaa tgcaaacaga attgctttag atttccaaag 540
agggaatgat gttgccttcc actttaaccc acgcttcaat gagaacaaca ggagagtcat 600
tgtttgcaat acaaagctgg ataataactg gggaagggaa gaaagacagt cggttttccc 660
atttgaaagt gggaaaccat tcaaaataca agtactggtt gaacctgacc acttcaaggt 720
tgcagtgaat gatgctcact tgttgcagta caatcatcgg gttaaaaaac tcaatgaaat 780
cagcaaactg ggaatttctg gtgacataga cctcaccagt gcttcatata ccatgatata 840
atctgaaagg ggcagattaa aaaaaaaaaa agaatctaaa ccttacatgt gtaaaggttt 900
catgttcact gtgagtgaaa atttttacat tcatcaatat ccctcttgta agtcatctac 960
ttaataaata ttacagtgaa ttacctgtct caatatgtca aaaaaaaaaa aaaaaaa 1017

<210> SEQ ID NO 54

<211> LENGTH: 1364
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gatccggagg ccggagaatt gtaatacgac tcactatagg gagacgcgtg ttaaataaca 60
aatctcaaca caacatatac aaaacaaacg aatctcaagc aatcaagcat tctacttcta 120
ttgcagcaat ttaaatcatt tcttttaaag caaaagcaat tttctgaaaa ttttcaccat 180
ttacgaacga tagccgccac catggccgac aacttcagcc tgcacgatgc cctgagcggc 240
agcggcaacc ctaatcctca gggatggcct ggcgcttggg gcaatcagcc tgctggcgct 300
ggcggatatc ctggcgcatc ttacccaggc gcttaccccg gacaggctcc tccaggcgca 360
tatccaggcc aggcacctcc tggggcttat cctggggcac ctggcgccta ccctggcgct 420
cctgctcctg gcgtgtaccc tggacctcct tctggacccg gcgcataccc tagctctggc 480
cagccatctg ctaccggcgc ctatccagcc acaggacctt atggcgctcc agccggacct 540
ctgatcgtgc cctacaacct gcctctgcct ggcggcgtgg tgcccagaat gctgatcaca 600
atcctgggca ccgtgaagcc caacgccaac agaatcgccc tggacttcca gaggggcaac 660
gacgtggcct tccacttcaa ccccagattc aacgagaaca atcggcgcgt gatcgtgtgc 720
aacaccaagc tggacaacaa ctggggcaga gaagaaagac agagcgtgtt cccattcgag 780
agcggcaagc cattcaagat ccaggtgctg gtggaacccg accacttcaa ggtggccgtg 840
aacgacgccc atctgctgca gtacaaccac agagtgaaga agctgaacga gatcagcaag 900
ctgggcatca gcggcgacat cgacctgacc agcgcctcct acaccatgat ctgacggacc 960
ggcgatagat gaagctcgct ttcttgctgt ccaatttcta ttaaaggttc ctttgttccc 1020
taagtccaac tactaaactg gggatatta tgaagggcct tgagcatctg gattctgcct 1080
aataaaaaac atttattttc attgcagctc gctttcttgc tgtccaattt ctattaaagg 1140
ttcctttgtt ccctaagtcc aactactaaa ctgggggata ttatgaaggg ccttgagcat 1200
ctggattctg cctaataaaa aacatttatt ttcattgcgg ccgcaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaa 1364

<210> SEQ ID NO 55
<211> LENGTH: 1326
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 55
gggagacgcg uguuaaauaa caaaucucaa cacaacauau acaaaacaaa cgaaucucaa 60
gcaaucaagc auucuacuuc uauugcagca auuuaaauca uuucuuuuaa agcaaaagca 120
auuuucugaa aauuuucacc auuuacgaac gauagccgcc accauggccg acaacuucag 180
ccugcacgau gcccugagcg gcagcggcaa cccuaauccu cagggauggc cuggcgcuug 240
gggcaaucag ccugcuggcg cuggcggaua uccuggcgca ucuuacccag gcgcuuaccc 300
cggacaggcu ccuccaggcg cauauccagg ccaggcaccu ccuggggcuu auccuggggc 360
accuggcgcc uacccuggcg cuccugcucc uggcguguac ccuggaccuc cuucuggacc 420

-continued

```
cggcgcauac ccuagcucug gccagccauc ugcuaccggc gccuauccag ccacaggacc    480

uuauggcgcu ccagccggac cucugaucgu gcccuacaac cugccucugc cuggcggcgu    540

ggugcccaga augcugauca caauccuggg caccgugaag cccaacgcca acagaaucgc    600

ccuggacuuc cagaggggca acgacguggc cuuccacuuc aaccccagau ucaacgagaa    660

caaucggcgc gugaucgugu gcaacaccaa gcuggacaac aacuggggca gagaagaaag    720

acagagcgug uucccauucg agagcggcaa gccauucaag auccaggugc ugguggaacc    780

cgaccacuuc aagguggccg ugaacgacgc ccaucugcug caguacaacc acagagugaa    840

gaagcugaac gagaucagca agcugggcau cagcggcgac aucgaccuga ccagcgccuc    900

cuacaccaug aucugacgga ccggcgauag augaagcucg cuuucuugcu guccaauuuc    960

uauuaaaggu uccuuuguuc ccuaagucca acuacuaaac ugggggauau uaugaagggc   1020

cuugagcauc uggauucugc cuaauaaaaa acauuuauuu ucauugcagc ucgcuuucuu   1080

gcuguccaau uucuauuaaa gguuccuuug uucccuaagu ccaacuacua aacuggggga   1140

uauuaugaag ggccuugagc aucuggauuc ugccuaauaa aaaacauuua uuuucauugc   1200

ggccgcaaaa aaaaaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaa                                                              1326
```

```
<210> SEQ ID NO 56
<211> LENGTH: 753
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 56

auggccgaca acuucagccu gcacgaugcc cugagcggca gcggcaaccc uaauccucag     60

ggauggccug gcgcuugggg caaucagccu gcuggcgcug gcggauaucc uggcgcaucu    120

uacccaggcg cuuaccccgg acaggcuccu ccaggcgcau auccaggcca ggcaccuccu    180

ggggcuuauc cuggggcacc uggcgccuac ccuggcgcuc cugcuccugg cguguacccu    240

ggaccuccuu cuggacccgg cgcauacccu agcucuggcc agccaucugc uaccggcgcc    300

uauccagcca caggaccuua uggcgcucca gccggaccuc ugaucgugcc cuacaaccug    360

ccucugccug gcggcguggu gcccagaaug cugaucacaa uccugggcac cgugaagccc    420

aacgccaaca gaaucgcccu ggacuuccag aggggcaacg acguggccuu ccacuucaac    480

cccagauuca acgagaacaa ucggcgcgug aucgugugca acaccaagcu ggacaacaac    540

uggggcagag aagaaagaca gagcguguuc ccauucgaga gcggcaagcc auucaagauc    600

caggugcugg uggaacccga ccacuucaag guggccguga acgacgccca ucugcugcag    660

uacaaccaca gagugaagaa gcugaacgag aucagcaagc ugggcaucag cggcgacauc    720

gaccugacca gcgccuccua caccaugauc uga                                 753


<210> SEQ ID NO 57
<211> LENGTH: 10
<212> TYPE: DNA
<213> ORGANISM: Unknown
<220> FEATURE:
<223> OTHER INFORMATION: Description of Unknown:
      Kozak sequence
```

<400> SEQUENCE: 57 gccrccatgg 10

<210> SEQ ID NO 58
<211> LENGTH: 8
<212> TYPE: DNA
<213> ORGANISM: Unknown
<220> FEATURE:
<223> OTHER INFORMATION: Description of Unknown:
Kozak sequence

<400> SEQUENCE: 58 caaacatg 8

<210> SEQ ID NO 59
<211> LENGTH: 120
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: See specification as filed for detailed
description of substitutions and preferred embodiments

<400> SEQUENCE: 59
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120

<210> SEQ ID NO 60
<211> LENGTH: 500
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: misc_feature
<222> LOCATION: (1)..(500)
<223> OTHER INFORMATION: This sequence may encompass between 1 and 500
nucleotides
<220> FEATURE:
<223> OTHER INFORMATION: See specification as filed for detailed
description of substitutions and preferred embodiments

<400> SEQUENCE: 60
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa 500